United States Patent
Cohen et al.

(10) Patent No.: US 10,500,003 B2
(45) Date of Patent: Dec. 10, 2019

(54) CONTROL OF DEVICE INCLUDING MECHANICAL ARMS

(71) Applicant: Memic Innovative Surgery Ltd., Or-Yehuda (IL)

(72) Inventors: Dvir Cohen, Ramot-Menashe (IL); Eli Shapira, Sde Warburg (IL)

(73) Assignee: Memic Innovative Surgery Ltd., Or-Yehuda (IL)

( * ) Notice: Subject to any disclaimer, the term of this patent is extended or adjusted under 35 U.S.C. 154(b) by 0 days.

(21) Appl. No.: 16/271,915

(22) Filed: Feb. 11, 2019

(65) Prior Publication Data
US 2019/0167363 A1 Jun. 6, 2019

Related U.S. Application Data

(63) Continuation of application No. 16/121,704, filed on Sep. 5, 2018, which is a continuation of application
(Continued)

(51) Int. Cl.
*A61B 34/30* (2016.01)
*A61B 90/50* (2016.01)
(Continued)

(52) U.S. Cl.
CPC ........... *A61B 34/30* (2016.02); *A61B 1/05* (2013.01); *A61B 1/303* (2013.01); *A61B 17/29* (2013.01);
(Continued)

(58) Field of Classification Search
CPC ..... A61B 34/30; A61B 90/50; A61B 18/1492; A61B 34/35; A61B 34/76; A61B 34/77; A61B 17/320016; A61B 17/29; A61B 90/57; A61B 90/37; A61B 17/3201; A61B 90/06; A61B 34/74; A61B 1/303;
(Continued)

(56) References Cited

U.S. PATENT DOCUMENTS 2,165,478 A 7/1939 Gross
3,913,573 A 10/1975 Gutnick
(Continued)

FOREIGN PATENT DOCUMENTS

CN 102465957 5/2012
JP 2006-516910 7/2006
(Continued)

OTHER PUBLICATIONS

Notice of Allowance dated Jul. 3, 2019 From the US Patent and Trademark Office Re. U.S. Appl. No. 16/271,922. (26 pages).
(Continued)

*Primary Examiner* — Jason Holloway

(57) ABSTRACT

A method of initializing the layout of one or more robotic arms controllable by an input object, comprising: entering a paused mode, in which control of movement of the robotic arms by the input object is paused; measuring an input object initialization layout, defined by the layout of at least one segment of the input object; actuating at least a portion of the robotic arms to match the input object initialization layout; and entering a controlled mode, in which movements of the input object control the robotic arms.

22 Claims, 66 Drawing Sheets

Related U.S. Application Data

No. 15/418,891, filed on Jan. 30, 2017, now Pat. No. 10,070,930, which is a continuation of application No. PCT/IL2015/050891, filed on Sep. 4, 2015, said application No. 15/418,891 is a continuation of application No. PCT/IL2015/050892, filed on Sep. 4, 2015, said application No. 15/418,891 is a continuation of application No. PCT/IL2015/050893, filed on Sep. 4, 2015.

(60) Provisional application No. 62/045,756, filed on Sep. 4, 2014, provisional application No. 62/045,802, filed on Sep. 4, 2014.

(51) Int. Cl.

| | | |
|---|---|---|
| *A61B 18/14* | (2006.01) | |
| *A61B 34/35* | (2016.01) | |
| *A61B 34/00* | (2016.01) | |
| *A61B 90/00* | (2016.01) | |
| *A61B 90/57* | (2016.01) | |
| *A61B 17/29* | (2006.01) | |
| *A61B 17/32* | (2006.01) | |
| *A61B 17/3201* | (2006.01) | |
| *B25J 9/06* | (2006.01) | |
| *B25J 9/16* | (2006.01) | |
| *B25J 9/00* | (2006.01) | |
| *B25J 13/06* | (2006.01) | |
| *B25J 13/08* | (2006.01) | |
| *A61B 1/05* | (2006.01) | |
| *A61B 1/303* | (2006.01) | |
| *A61B 17/00* | (2006.01) | |

(52) U.S. Cl.
CPC .. *A61B 17/3201* (2013.01); *A61B 17/320016* (2013.01); *A61B 18/1492* (2013.01); *A61B 34/35* (2016.02); *A61B 34/74* (2016.02); *A61B 34/76* (2016.02); *A61B 34/77* (2016.02); *A61B 90/06* (2016.02); *A61B 90/37* (2016.02); *A61B 90/50* (2016.02); *A61B 90/57* (2016.02); *B25J 9/0084* (2013.01); *B25J 9/065* (2013.01); *B25J 9/1674* (2013.01); *B25J 13/065* (2013.01); *B25J 13/088* (2013.01); *A61B 17/00234* (2013.01); *A61B 90/361* (2016.02); *A61B 2017/00115* (2013.01); *A61B 2017/00207* (2013.01); *A61B 2017/00309* (2013.01); *A61B 2017/00314* (2013.01); *A61B 2017/00991* (2013.01); *A61B 2034/301* (2016.02); *A61B 2034/306* (2016.02); *A61B 2034/742* (2016.02); *A61B 2034/743* (2016.02); *A61B 2034/744* (2016.02); *A61B 2090/067* (2016.02); *A61B 2090/374* (2016.02); *A61B 2090/378* (2016.02); *A61B 2090/3762* (2016.02); *A61B 2090/571* (2016.02); *G05B 2219/45117* (2013.01)

(58) Field of Classification Search
CPC ............ A61B 1/05; A61B 2017/00309; A61B 2090/067; A61B 2034/301; A61B 2017/00115; A61B 17/00234; A61B 90/361; A61B 2090/571; A61B 2034/743; A61B 2034/742; A61B 2017/00991; A61B 2090/3762; A61B 2090/374; A61B 2034/306; A61B 2034/744; A61B 2090/378; A61B 2017/00314; A61B 2017/00207; B25J 9/0084; B25J 9/065; B25J 9/1674; B25J 13/088; B25J 13/065; G05B 2219/45117
See application file for complete search history.

(56) References Cited

U.S. PATENT DOCUMENTS

| | | |
|---|---|---|
| 4,054,131 A | 10/1977 | Kessel |
| 4,364,535 A | 12/1982 | Itoh et al. |
| 5,597,146 A | 1/1997 | Putman |
| 5,624,398 A | 4/1997 | Smith et al. |
| 5,810,716 A | 9/1998 | Mukherjee et al. |
| 5,876,325 A | 3/1999 | Mizuno et al. |
| 6,168,611 B1 | 1/2001 | Rizvi |
| 6,231,565 B1 | 5/2001 | Tovey et al. |
| 6,331,181 B1 | 12/2001 | Tierney et al. |
| 6,425,865 B1 | 7/2002 | Salcudean et al. |
| 7,008,362 B2 | 3/2006 | Fitzgibbon |
| 7,371,210 B2 | 5/2008 | Brock et al. |
| 7,833,156 B2 | 11/2010 | Williams et al. |
| 7,918,845 B2 | 4/2011 | Saadat et al. |
| 8,224,485 B2 | 7/2012 | Unsworth |
| 8,347,754 B1 | 1/2013 | Veltri et al. |
| 8,518,024 B2 | 8/2013 | Williams et al. |
| 9,033,998 B1 | 5/2015 | Schaible et al. |
| 9,662,176 B2 | 4/2017 | Cooper et al. |
| 2001/0021854 A1 | 9/2001 | Donnez et al. |
| 2002/0087048 A1 | 7/2002 | Brock et al. |
| 2003/0004610 A1 | 1/2003 | Niemeyer et al. |
| 2003/0109780 A1 | 6/2003 | Coste-Maniere et al. |
| 2003/0109857 A1 | 6/2003 | Sanchez et al. |
| 2004/0128026 A1* | 7/2004 | Harris .................... B25J 9/1689 700/245 |
| 2004/0138525 A1 | 7/2004 | Saadat et al. |
| 2004/0236316 A1 | 11/2004 | Danitz et al. |
| 2005/0059960 A1 | 3/2005 | Simaan et al. |
| 2005/0096694 A1 | 5/2005 | Lee |
| 2005/0272977 A1 | 12/2005 | Saadat et al. |
| 2006/0095022 A1 | 5/2006 | Moll et al. |
| 2006/0142657 A1* | 6/2006 | Quaid .................... G06F 19/00 600/424 |
| 2006/0206101 A1 | 9/2006 | Lee |
| 2006/0241414 A1 | 10/2006 | Nowlin et al. |
| 2007/0156019 A1 | 7/2007 | Larkin et al. |
| 2007/0221700 A1 | 9/2007 | Ortiz et al. |
| 2007/0287992 A1 | 12/2007 | Diolaiti et al. |
| 2008/0064921 A1 | 3/2008 | Larkin et al. |
| 2008/0065108 A1 | 3/2008 | Diolaiti |
| 2008/0119868 A1 | 5/2008 | Sharp et al. |
| 2008/0125869 A1 | 5/2008 | Paz et al. |
| 2009/0000626 A1* | 1/2009 | Quaid .................... G06F 19/00 128/898 |
| 2009/0012531 A1* | 1/2009 | Quaid .................... G06F 19/00 606/130 |
| 2009/0171373 A1 | 7/2009 | Farritor et al. |
| 2010/0016659 A1 | 1/2010 | Weitzner |
| 2010/0170361 A1 | 7/2010 | Bennett et al. |
| 2010/0191278 A1 | 7/2010 | Lee et al. |
| 2010/0274087 A1 | 10/2010 | Diolaiti et al. |
| 2010/0292558 A1 | 11/2010 | Saadat et al. |
| 2010/0318100 A1 | 12/2010 | Okamoto et al. |
| 2011/0022052 A1 | 1/2011 | Jorgensen |
| 2011/0046441 A1 | 2/2011 | Wiltshire et al. |
| 2011/0082462 A1* | 4/2011 | Suarez .................... A61B 34/20 606/99 |
| 2011/0082468 A1* | 4/2011 | Hagag .................... A61B 34/20 606/130 |
| 2011/0105843 A1 | 5/2011 | Mueller |
| 2011/0118748 A1 | 5/2011 | Itkowitz |
| 2011/0264136 A1 | 10/2011 | Choi et al. |
| 2011/0276038 A1 | 11/2011 | McIntyre et al. |
| 2011/0277775 A1 | 11/2011 | Holop et al. |
| 2012/0010629 A1 | 1/2012 | Mire et al. |
| 2012/0059392 A1 | 3/2012 | Diolaiti |
| 2012/0123207 A1 | 5/2012 | Vargas |
| 2012/0253131 A1 | 10/2012 | Malkowski et al. |

(56) References Cited

U.S. PATENT DOCUMENTS

| | | | |
|---|---|---|---|
| 2013/0006267 A1* | 1/2013 | Odermatt | B25J 9/1628 606/130 |
| 2013/0018303 A1 | 1/2013 | Webster et al. | |
| 2013/0035697 A1 | 2/2013 | Ogawa et al. | |
| 2013/0172904 A1* | 7/2013 | Ikits | G06T 17/10 606/130 |
| 2013/0296882 A1 | 11/2013 | Kim et al. | |
| 2014/0039517 A1* | 2/2014 | Bowling | B25J 13/00 606/130 |
| 2014/0046340 A1 | 2/2014 | Wilson et al. | |
| 2014/0062113 A1 | 3/2014 | Kovarik et al. | |
| 2014/0114293 A1 | 4/2014 | Jeong et al. | |
| 2014/0222198 A1 | 8/2014 | Emami et al. | |
| 2014/0276943 A1* | 9/2014 | Bowling | A61B 17/16 606/130 |
| 2014/0330432 A1 | 11/2014 | Simaan et al. | |
| 2015/0038981 A1 | 2/2015 | Kilroy et al. | |
| 2015/0230697 A1 | 8/2015 | Phee et al. | |
| 2016/0128790 A1 | 5/2016 | Ogawa et al. | |
| 2016/0135909 A1 | 5/2016 | Ogawa et al. | |
| 2016/0135911 A1 | 5/2016 | Yanagihara et al. | |
| 2016/0144504 A1* | 5/2016 | Kuth | B25J 13/003 700/255 |
| 2016/0166343 A1 | 6/2016 | Poon et al. | |
| 2017/0071587 A1 | 3/2017 | Harshman et al. | |
| 2017/0071687 A1 | 3/2017 | Cohen et al. | |
| 2017/0071688 A1 | 3/2017 | Cohen et al. | |
| 2017/0095299 A1 | 4/2017 | Hendrick et al. | |
| 2017/0112581 A1 | 4/2017 | Cohen et al. | |
| 2017/0112583 A1 | 4/2017 | Cohen et al. | |
| 2017/0119483 A1 | 5/2017 | Cohen et al. | |
| 2017/0135776 A1 | 5/2017 | Cohen et al. | |
| 2017/0165002 A1 | 6/2017 | Sharma et al. | |
| 2017/0231701 A1 | 8/2017 | Cohen et al. | |
| 2017/0239005 A1 | 8/2017 | Cohen et al. | |
| 2017/0258538 A1 | 9/2017 | Cohen et al. | |
| 2017/0258539 A1 | 9/2017 | Cohen et al. | |
| 2017/0274533 A1 | 9/2017 | Berghofer et al. | |
| 2017/0296170 A1 | 10/2017 | Shelton, IV et al. | |
| 2018/0256265 A1 | 9/2018 | Cohen et al. | |
| 2018/0256266 A1 | 9/2018 | Cohen et al. | |
| 2018/0256267 A1 | 9/2018 | Cohen et al. | |
| 2018/0256268 A1 | 9/2018 | Cohen et al. | |
| 2019/0000574 A1 | 1/2019 | Dvir et al. | |
| 2019/0167364 A1 | 6/2019 | Cohen et al. | |

FOREIGN PATENT DOCUMENTS

| | | |
|---|---|---|
| JP | 2007-509698 | 4/2007 |
| JP | 2013-126464 | 6/2013 |
| WO | WO 88/04544 | 6/1988 |
| WO | WO 2010/096580 | 8/2010 |
| WO | WO 2013/116869 | 8/2013 |
| WO | WO 2015/019675 | 2/2015 |
| WO | WO 2016/035084 | 3/2016 |
| WO | WO 2016/035086 | 3/2016 |
| WO | WO 2016/035085 | 8/2016 |
| WO | WO 2017/037723 | 3/2017 |

OTHER PUBLICATIONS

Translation Dated Apr. 22, 2019 of Decision of Rejection dated Apr. 10, 2019 From the State Intellectual Property Office of the People's Republic of China Re. Application No. 201580052098.8. (4 Pages).
Communication Pursuant to Article 94(3) EPC dated Apr. 8, 2019 From the European Patent Office Re. Application No. 15838126.9. (15 Pages).
Decision of Rejection dated Apr. 10, 2019 From the State Intellectual Property Office of the People's Republic of China Re. Application No. 201580052098.8. (3 Pages).
Applicant-Initiated Interview Summary dated Apr. 24, 2019 From the US Patent and Trademark Office Re. U.S. Appl. No. 15/358,331. (3 Pages).
Advisory Action Before the Filing of an Appeal Brief dated Feb. 13, 2019 From the US Patent and Trademark Office Re. U.S. Appl. No. 15/454,116. (4 pages).
Advisory Action Before the Filing of an Appeal Brief dated Jul. 13, 2018 From the US Patent and Trademark Office Re. U.S. Appl. No. 15/454,123. (3 pages).
Advisory Action Before the Filing of an Appeal Brief dated Jan. 24, 2019 From the US Patent and Trademark Office Re. U.S. Appl. No. 15/454,116. (5 pages).
Applicant-Initiated Interview Summary dated Oct. 2, 2017 From the US Patent and Trademark Office Re. U.S. Appl. No. 15/358,331. (3 pages).
Applicant-Initiated Interview Summary dated Oct. 6, 2017 From the US Patent and Trademark Office Re. U.S. Appl. No. 15/454,123. (2 pages).
Applicant-Initiated Interview Summary dated Mar. 7, 2018 From the US Patent and Trademark Office Re. U.S. Appl. No. 15/312,732. (3 pages).
Applicant-Initiated Interview Summary dated Jul. 19, 2017 From the US Patent and Trademark Office Re. U.S. Appl. No. 15/418,891. (3 pages).
Applicant-Initiated Interview Summary dated Jan. 26, 2018 From the US Patent and Trademark Office Re. U.S. Appl. No. 15/418,891. (3 pages).
Communication Pursuant to Article 94(3) EPC dated Mar. 4, 2019 From the European Patent Office Re. Application No. 15838758.9. (9 Pages).
Communication Pursuant to Article 94(3) EPC dated Mar. 11, 2019 From the European Patent Office Re. Application No. 17160061.2. (6 Pages).
European Search Report and the European Search Opinion dated Aug. 22, 2017 From the European Patent Office Re. Application No. 17160061.2. (9 Pages).
Ex Parte Quayle OA Dated Nov. 7, 2018 From the US Patent and Trademark Office Re. U.S. Appl. No. 15/501,862. (8 pages).
International Preliminary Report on Patentability dated Mar. 15, 2018 From the International Bureau of WIPO Re. Application No. PCT/IL2015/050892. (9 Pages).
International Preliminary Report on Patentability dated Mar. 16, 2017 From the International Bureau of WIPO Re. Application No. PCT/IL2015/050891. (16 Pages).
International Preliminary Report on Patentability dated Mar. 16, 2017 From the International Bureau of WIPO Re. Application No. PCT/IL2015/050892.
International Preliminary Report on Patentability dated Mar. 16, 2017 From the International Bureau of WIPO Re. Application No. PCT/IL2015/050893. (11 Pages).
International Search Report and the Written Opinion dated Dec. 6, 2016 From the International Searching Authority Re. Application No. PCT/IL2015/050892. (36 Pages).
International Search Report and the Written Opinion dated Mar. 10, 2016 From the International Searching Authority Re. Application No. PCT/IL2015/050893.
International Search Report and the Written Opinion dated Mar. 11, 2016 From the International Searching Authority Re. Application No. PCT/IL2015/050892.
International Search Report and the Written Opinion dated Feb. 26, 2016 From the International Searching Authority Re. Application No. PCT/IL2015/050891.
Invitation to Pay Additional Fees dated Dec. 3, 2015 From the International Searching Authority Re. Application No. PCT/IL2015/050891.
Invitation to Pay Additional Fees dated Jan. 12, 2016 From the International Searching Authority Re. Application No. PCT/IL2015/050893.
Notice of Allowance dated Jan. 28, 2019 From the US Patent and Trademark Office Re. U.S. Appl. No. 15/924,635. (15 pages).
Notification of Office Action dated Sep. 3, 2018 From the State Intellectual Property Office of the People's Republic of China Re. Application No. 201580052098.8. (4 Pages).
Notification of Office Action dated Jan. 19, 2018 From the State Intellectual Property Office of the People's Republic of China Re. Application No. 201580052098.8. (4 Pages).

(56) References Cited

OTHER PUBLICATIONS

Official Action dated Dec. 4, 2017 From the US Patent and Trademark Office Re. U.S. Appl. No. 15/358,325. (20 pages).
Official Action dated Jun. 5, 2017 From the US Patent and Trademark Office Re. U.S. Appl. No. 15/418,891. (28 pages).
Official Action dated Aug. 7, 2017 From the US Patent and Trademark Office Re. U.S. Appl. No. 15/358,325. (25 pages).
Official Action dated Jan. 9, 2019 From the US Patent and Trademark Office Re. U.S. Appl. No. 15/358,331. (40 pages).
Official Action dated Mar. 9, 2017 From the US Patent and Trademark Office Re. U.S. Appl. No. 15/401,045. (23 pages).
Official Action dated Jul. 10, 2017 From the US Patent and Trademark Office Re. U.S. Appl. No. 15/358,331. (32 pages).
Official Action dated Mar. 10, 2017 From the US Patent and Trademark Office Re. U.S. Appl. No. 15/402,342. (25 pages).
Official Action dated Dec. 13, 2017 From the US Patent and Trademark Office Re. U.S. Appl. No. 15/402,257. (44 pages).
Official Action dated Dec. 14, 2018 From the US Patent and Trademark Office Re. U.S. Appl. No. 15/454,116. (27 pages).
Official Action dated Nov. 14, 2018 From the US Patent and Trademark Office Re. U.S. Appl. No. 15/312,732. (25 pages).
Official Action dated Mar. 20, 2018 From the US Patent and Trademark Office Re. U.S. Appl. No. 15/454,123. (36 pages).
Official Action dated Mar. 22, 2019 From the US Patent and Trademark Office Re. U.S. Appl. No. 15/454,123. (32 pages).
Official Action dated Jul. 23, 2018 From the US Patent and Trademark Office Re. U.S. Appl. No. 15/924,635. (20 pages).
Official Action dated Jan. 26, 2018 From the US Patent and Trademark Office Re. U.S. Appl. No. 15/312,732. (50 pages).
Official Action dated Nov. 27, 2017 From the US Patent and Trademark Office Re. U.S. Appl. No. 15/418,891. (35 pages).
Official Action dated Aug. 28, 2017 From the US Patent and Trademark Office Re. U.S. Appl. No. 15/454,123. (32 pages).
Official Action dated Feb. 28, 2018 From the US Patent and Trademark Office Re. U.S. Appl. No. 15/358,331. (34 pages).
Official Action dated Jun. 28, 2018 From the US Patent and Trademark Office Re. U.S. Appl. No. 15/454,116. (67 pages).
Official Action dated Jun. 29, 2018 From the US Patent and Trademark Office Re. U.S. Appl. No. 15/312,732. (34 pages).
Official Action dated Jan. 30, 2019 From the US Patent and Trademark Office Re. U.S. Appl. No. 15/501,862. (6 pages).
Restriction Official Action dated May 2, 2018 From the US Patent and Trademark Office Re. U.S. Appl. No. 15/501,862. (6 pages).
Restriction Official Action dated Aug. 7, 2018 From the US Patent and Trademark Office Re. U.S. Appl. No. 15/501,862. (6 pages).
Restriction Official Action dated Feb. 7, 2018 From the US Patent and Trademark Office Re. U.S. Appl. No. 15/454,116. (6 pages).
Restriction Official Action dated Mar. 17, 2017 From the US Patent and Trademark Office Re. U.S. Appl. No. 15/418,891. (7 pages).
Supplementary European Search Report and the European Search Opinion dated Apr. 9, 2018 From the European Patent Office Re. Application No. 15838758.9. (12 Pages).
Supplementary European Search Report and the European Search Opinion dated Jun. 11, 2018 From the European Patent Office Re. Application No. 15838126.9. (11 Pages).
Supplementary European Search Report and the European Search Opinion dated Jun. 21, 2018 From the European Patent Office Re. Application No. 16840991.0 (7 Pages).
Translation Dated Sep. 13, 2018 of Notification of Office Action dated Sep. 3, 2018 From the State Intellectual Property Office of the People's Republic of China Re. Application No. 201580052098.8. (3 Pages).
Translation of Notification of Office Action dated Jan. 19, 2018 From the State Intellectual Property Office of the People's Republic of China Re. Application No. 201580052098.8. (2 Pages).
Box et al. "Rapid Communication: Robot-Assisted NOTES Nephrectomy: Initial Report", Journal of Endourology, 22(3): 503-506, Mar. 2008. Abstract.
Domingo et al. "Overview of Current Trends in Hysterectomy", Expert Reviews of Obstetrics & Gynaecology, 4(6): 673-685, 2009.
Hubens et al. "What Have We Learnt After Two Years Working With the Da Vinci Robot System in Digestive Surgery?", Acta Chirurgica Belgica, 104(6): 609-614, Nov.-Dec. 2004.
Irvine et al. "Anaesthesia for Robot-Assisted Laporoscopic Surgery", Continuing Education in Anaesthesia, Critical Care & Pain, 9(4): 125-129, Advance Access Published Jun. 25, 2009.
Kho et al. "Vaginal Versus Laparoscopic Hysterectomy. Vaginal Hysterectomy: The Best Minimally Invasive Approach", Contemporary OB/GYNObstetrics & Women's Health, 7 P., Oct. 1, 2013.
Komura et al. "An Inverse Kinematics Method for 3D Figures With Motion Data", Proceedings of the Computer Graphics International, CGI'03, Jul. 9-11, 2003, p. 266-271, Jul. 2003.
Lee "Anesthetic Considerations for Robotic Surgery", Korean Journal of Anesthesiology, 66(1): 3-11, Jan. 2014.
Piccigallo et al. "Design of a Novel Bimanual Robotic System for Single-Port Laparoscopy", IEEE/ASME Transactions on Mechatronics, 15(6): 871-878, Dec. 13, 2010.
Ramos et al. "Human Hybrid NOTES Transvaginal Sleeve Gastrectomy: Initial Experience", Surgery for Obesity and Related Diseases, 4: 660-663, 2008.
Teljeur et al. "Economic Evaluation of Robot-Assisted Hysterectomy: A Cost-Minimisation Analysis", BJOG: An International Journal of Obstetrics and Gynaecology, 121(12): 1546-1555, Published Online May 9, 2014.
Official Action dated Jul. 5, 2019 From the US Patent and Trademark Office Re. Application No. 15/501,862. (7 pages).
Advisory Action Before the Filing of an Appeal Brief dated May 21, 2019 From the US Patent and Trademark Office Re. U.S. Appl. No. 15/312,732. (23 pages).
Summons to Attend Oral Proceedings to Rule 115(1) EPC and Communication From the Examining Division dated May 14, 2019 From the European Patent Office Re. Application No. 16840991.0 (5 pages).
Notice of Reasons for Rejection dated Jul. 2, 2019 From the Japan Patent Office Re. Application No. 2017-532229 and Its Translation Into English. (11 Pages).

\* cited by examiner

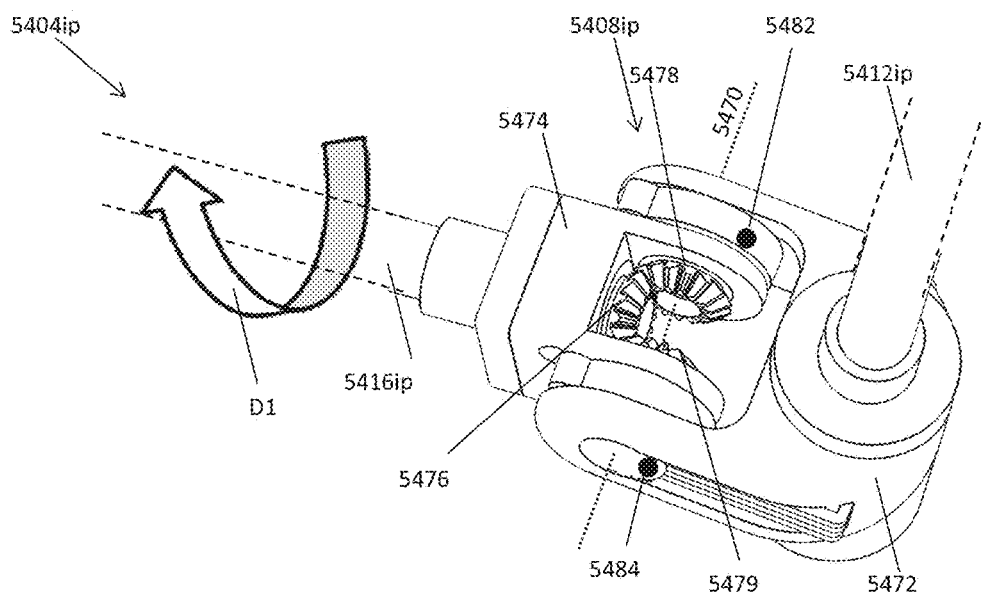
FIG. 54A
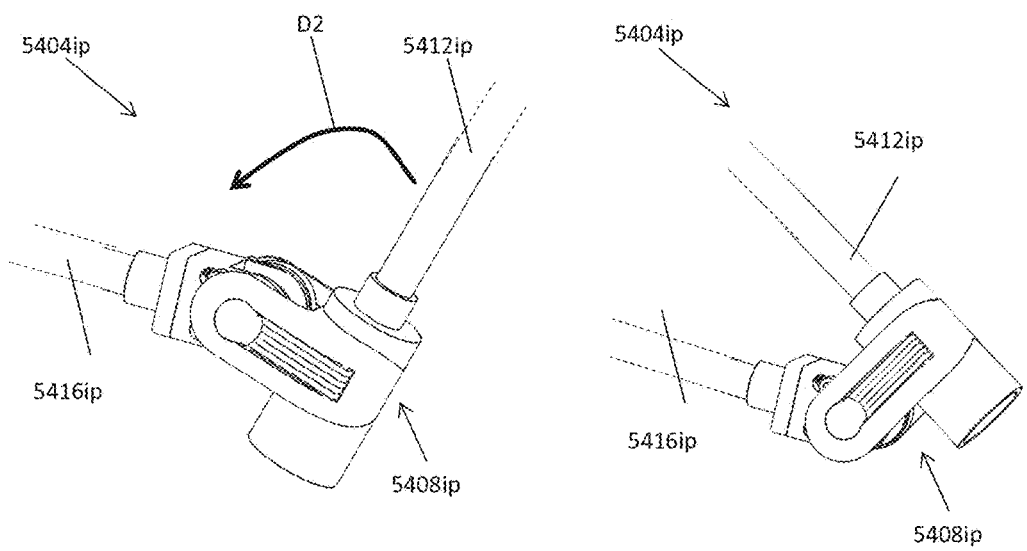
FIG. 54B
FIG. 54C

A1

B1

A2

B2

A3

B3

A4

B4

A1

B1

A2

B2

A3

B3

A4

B4

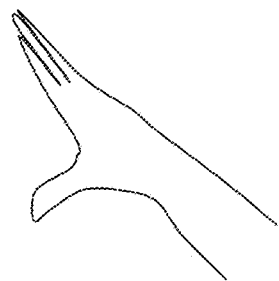
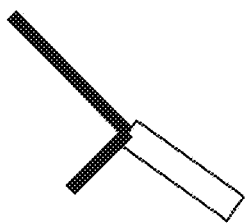
FIG. 64A                FIG. 64B
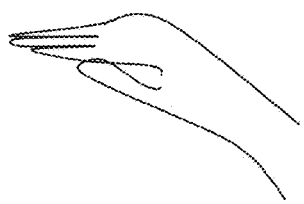
FIG. 64C                FIG. 64D
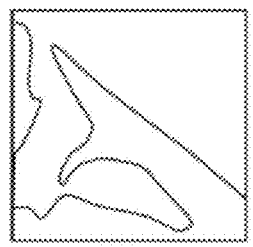
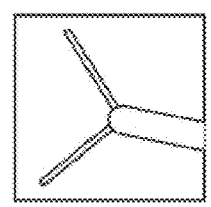
A                       B
FIG. 65

CONTROL OF DEVICE INCLUDING MECHANICAL ARMS

RELATED APPLICATIONS

This application is a continuation of U.S. patent application Ser. No. 16/121,704, filed on Sep. 5, 2018, which is a continuation of U.S. patent application Ser. No. 15/418,891, filed on Jan. 30, 2017, now U.S. Pat. No. 10,070,930, which is a continuation of PCT Patent Application No. PCT/IL2015/050891 having International Filing Date of Sep. 4, 2015, which claims the benefit of priority under 35 USC § 119(e) of U.S. Provisional Patent Application Nos. 62/045,756 and 62/045,802 both filed on Sep. 4, 2014.

U.S. patent application Ser. No. 15/418,891, filed on Jan. 30, 2017, is also a continuation of PCT Patent Application No. PCT/IL2015/050892 having International Filing Date of Sep. 4, 2015, which claims the benefit of priority under 35 USC § 119(e) of U.S. Provisional Patent Application Nos. 62/045,756 and 62/045,802 both filed on Sep. 4, 2014.

U.S. patent application Ser. No. 15/418,891, filed on Jan. 30, 2017, is also a continuation of PCT Patent Application No. PCT/IL2015/050893 having International Filing Date of Sep. 4, 2015, which claims the benefit of priority under 35 USC § 119(e) of U.S. Provisional Patent Application Nos. 62/045,756 and 62/045,802 both filed on Sep. 4, 2014.

The contents of the above applications are all incorporated by reference as if fully set forth herein in their entirety.

FIELD AND BACKGROUND OF THE INVENTION

The present invention, in some embodiments thereof, relates to of a device including mechanical arms, more particularly, but not exclusively, to methods and apparatus for control of a surgical device including mechanical arms.

Background art includes: "Design of a Compact Robotic Manipulator for Single-Port Laparoscopy" by Claudio Quaglia et al, Paper No: MD-13-1148 in J. Mech. Des. 136(9), 095001 (Jun. 13, 2014); "An inverse kinematics method for 3D figures with motion data" by Taku Komura et al, Proceedings of the Computer Graphics International (CGI'03);

Hubens et al., 2004, "What Have we Learnt after Two Years Working with the Da Vinci Robot System in Digestive Surgery?", Acta chir belg;

Michael Irvine, 2009, "Anaesthesia for Robot-Assisted Laparoscopic Surgery", Cont Edu Anaesth Crit Care and Pain;

Jeong Rim Lee, 2014, "Anesthetic considerations for robotic surgery", Korean Journal of Anesthesiology;

Teljeur et al., 2014, "Economic evaluation of robot-assisted hysterectomy: a cost-minimisation analysis", BJOG;

Box et al., 2008, "Rapid communication: robot-assisted NOTES nephrectomy: initial report", J Endourol;

DR. Domigo, 2009, "Overview of current hysterectomy trends", Expert Review of Obstetrics & Gynecology; and DR. Kho, "Vaginal versus laparoscopic hysterectomy", Contemporary OB/GYN Expert Advice, 2013.

Additional background art includes U.S. Pat. Nos. 8,224,485, 8,347,754, 7,833,156, 8,518,024, International Patent Application Publication No. WO 2010096580, and International Patent Application Publication No. WO 2013116869.

SUMMARY OF THE INVENTION

According to an aspect of some embodiments of the present invention there is provided a surgical system comprising:

a surgical device sized and shaped for insertion into a human body comprising at least one articulated limb, which limb comprises a plurality of sequentially coupled surgical device portions;

an input device, comprising at least one articulated limb, which limb comprises a plurality of sequentially coupled input device portions; and a controller which controls movement of one or more portion of the surgical device articulated limb;

wherein at least one portion of the input device limb corresponds to one or more portions of the surgical device limb;

wherein the controller controls movement of the one or more portions of the device limb based on movement of the at least one portion of the input device limb.

According to some embodiments of the invention, the system includes sequentially coupled independently bendable and rotatable flexible portions.

According to some embodiments of the invention, the input device limb includes sequentially coupled independently bendable and rotatable segments.

According to some embodiments of the invention, the flexible portions are coupled by segments.

According to some embodiments of the invention, the input device comprises segments coupled by joints; wherein each the input device joint corresponds to a surgical device flexible portion.

According to some embodiments of the invention, an angle at an input device joint controls an angle of a corresponding surgical device flexible portion.

According to some embodiments of the invention, the input device comprises segments coupled by joints;

wherein an angle between sequentially coupled segments controls an angle of flexion of a corresponding surgical device flexible portion.

According to some embodiments of the invention, the input device comprises:

an input device support segment;
a first segment;
a second segment;
a first joint coupling the first segment to the support segment; and
a second joint coupling the second segment to the first segment.

According to some embodiments of the invention, the surgical device limb comprises:

a surgical device support segment;
a first flexible section extending from the support segment and terminating in a coupling section; and
a second flexible section extending from the coupling section and terminating in a tool or a connector for a tool.

According to some embodiments of the invention, the input device support segment corresponds to the surgical device support segment;

wherein the first joint corresponds to the first flexible section;

wherein the second joint corresponds to the second flexible section.

According to some embodiments of the invention, at least one ratio between long axis lengths of input device segments is about a corresponding ratio of effective long axis lengths of surgical device segments.

According to some embodiments of the invention, at least one ratio between long axis lengths of surgical device effective segments is about that of a length ratio for corresponding human limb segments.

According to some embodiments of the invention, the system comprises two input device limbs corresponding to two surgical device limbs. According to some embodiments of the invention, the surgical device comprises a tool coupled to a distal end of the surgical device limb. According to some embodiments of the invention, actuation of the tool is controlled by one or more user interface on the input device.

According to some embodiments of the invention, the input device includes a handle coupled to a portion of the input device which extends away from the input device limb. According to some embodiments of the invention, the handle includes an extendable portion, extension thereof increasing a separation of at least one part of the handle from the input device.

According to some embodiments of the invention, the input device includes one or more locking mechanism; wherein the locking mechanism, when in a locked configuration, reduces movement of at least one of the input device portions with respect to one or more of the input device portions.

According to some embodiments of the invention, the coupling of the input device portions is low enough friction such that moving a portion of the input device causes movement of portions coupled proximally to the input device being moved.

According to some embodiments of the invention, the surgical device comprises more limbs controllable by the controller than the input device.

According to an aspect of some embodiments of the present invention there is provided an input device for control of a surgical device comprising:
at least one articulated limb which limb comprises a plurality of sequentially coupled portions;
at least one sensor configured to generate an indication of a relative position of at least a portion of the articulated limb with respect to another portion of the articulated limb;
a processor configured to generate, from the sensed positions, motor control signals, for control of a surgical device.

According to some embodiments of the invention, the limb comprises:
a support segment;
a first segment;
a second segment;
a first joint coupling the first segment to the support segment; and
a second joint coupling the second segment to the first segment.

According to some embodiments of the invention, one or more of the joints are rotational joints enabling rotation of segments coupled to the joints to rotate about segment long axes.

According to some embodiments of the invention, each first segment is bendable in a single bending plane about the first joint;
wherein each second segment is bendable in a single bending plane about the second joint.

According to some embodiments of the invention, the at least one sensor is a motion sensor attached to the articulated limb.

According to some embodiments of the invention, one or more sensor measures: rotation of one or more portion about a portion long axis; and
one or more angle between coupled portions.

According to some embodiments of the invention, the device comprises a gear coupled to a portion of the input device; and a sensor which senses rotation of the gear.

According to some embodiments of the invention, the input device includes a handle coupled to a portion of the input device which extends away from the input device limb. According to some embodiments of the invention, the handle includes an extendable portion, extension thereof increasing a separation of at least one part of the handle from the input device.

According to some embodiments of the invention, the sensor is a camera.

According to an aspect of some embodiments of the present invention there is provided a method of jointed device movement inside a body comprising:
measuring movement of at least one input object portion;
mapping the measured input object portion movement to a jointed device portion movement;
moving the device portion according to mapped measured movements.

According to some embodiments of the invention, the jointed device comprises a first device limb and a second device limb;
wherein the input object comprises a first input object limb and a second input object limb;
wherein measuring comprises measuring movement of one or more portion of the first input object limb and one or more portion of the second input object limb simultaneously;
wherein mapping comprises:
mapping the measured movements of the portion of the first input object limb to a corresponding portion of the first device limb; and
mapping the measured movements of the portion of the second input device limb to a corresponding portion of the second device limb;
wherein moving comprises moving simultaneously the device limbs according to the mapped movements.

According to some embodiments of the invention, the method comprises
initializing an input object limb by moving the input object limb into a configuration corresponding to a configuration of a device limb.

According to some embodiments of the invention, the input object is at least a portion of a user body.

According to some embodiments of the invention, mapping comprises: matching one or more input device portion to a corresponding surgical device portion; and scaling the measured movement.

According to some embodiments of the invention, the surgical device portion is an end effecter. According to some embodiments of the invention, the input object portion is a user body joint.

According to some embodiments of the invention, moving comprises moving simultaneously moving more than one device joint according to the mapped movements.

According to some embodiments of the invention, measuring comprises: repetitively capturing images of the user first limb and the user second limb; and processing the images to extract the movements of the user first limb and the user second limb. According to some embodiments of the invention, measuring comprises: filtering the measured movement of the user limb joints.

According to some embodiments of the invention, filtering comprises removing large movements. According to some embodiments of the invention, filtering comprises removing tremors. According to some embodiments of the invention, filtering comprises removing movements into a disallowed region.

According to some embodiments of the invention, the method comprises: selecting the input object portion; and selecting the device portion.

According to some embodiments of the invention, the input object portion is an input object limb; wherein the device portion is a device limb.

According to some embodiments of the invention, measuring comprises measuring movement of more than one portion of the input object limb; wherein the mapping comprises mapping measured movement of each the portion of the input object limb to movement of a portion of the jointed device limb. According to some embodiments of the invention, measuring comprises measuring finger movements of at least one user hand; wherein the mapping comprises mapping the measured finger movements to a device limb tool; wherein the moving comprises moving the device tool according to the mapped finger movements.

According to an aspect of some embodiments of the present invention there is provided an input device for control of a surgical device comprising:

at least one articulated limb which limb comprises a plurality of sequentially coupled portions;

a plurality of locking mechanisms each locking mechanism for preventing relative movement of between two sequentially coupled portions;

at least one sensor providing a signal relating to a level of contact of a user with the input device;

a processor configured to:

detect from the signal an insufficient level of contact;

send, upon detection of an insufficient level of contact, a single control signal instructing locking of the plurality of locking mechanisms.

According to an aspect of some embodiments of the present invention there is provided a surgical system, comprising:

circuitry which analyses images collected by an imager to provide measurement of movement of joints of a user limb;

a device sized and shaped for insertion into a body, which device comprising a first device limb;

at least one controller for moving joints of the device limb based on the measured movement.

According to some embodiments of the invention, the system comprises a display showing images of at least a portion of the device with at least a portion of a device surroundings. According to some embodiments of the invention, the system comprises at least one imaging device for collection of the displayed images. According to some embodiments of the invention, the at least one imaging device comprises an imaging device sized and shaped for insertion into a body. According to some embodiments of the invention, the at least one imaging device is coupled to the device.

According to some embodiments of the invention, device comprises a second device limb. According to some embodiments of the invention, the device comprises a third device limb. According to some embodiments of the invention, the third limb is larger than the first limb. According to some embodiments of the invention, the third limb includes a camera. According to some embodiments of the invention, the third limb includes fewer portions than the first and the second limb.

According to some embodiments of the invention, the device comprises one or more tool selected from an access tunnel, a suction element, an irrigation element.

According to an aspect of some embodiments of the present invention there is provided a method of jointed mechanism movement, comprising:

measuring user limb movements and a user finger movements simultaneously;

mapping the measured user limb movements to a device limb and the measured user finger movements to a device limb tool;

moving the device limb according to the mapped movements;

actuating the device limb tool according to the user finger movements;

wherein the moving and the actuating are simultaneous.

According to an aspect of some embodiments of the present invention there is provided a method of control of a surgical system including a surgical device comprising:

measuring movement of at least one user body portion;

detecting, from the measured movement, a system control gesture surgical device control movements;

controlling the surgical device based on detected surgical device control movements, or changing a state of the surgical system, based on a stored system state transition associated with the detected control gesture;

wherein the system includes a plurality of states, of measured movement of an input object for control of movement of the surgical.

According to some embodiments of the invention, the plurality of states uses a different mapping. According to some embodiments of the invention, plurality of states includes a motion control state where movements of an input device are mapped to control movement of the surgical device. According to some embodiments of the invention, the plurality of states includes a pause state where movements of an input device are not mapped to movement of the surgical device.

According to an aspect of some embodiments of the present invention there is provided a method of jointed device movement inside a body comprising: measuring movement of at least one user body portion; mapping the measured user body portion movement to a device portion movement; moving the device portion according to mapped measured movements.

According to an aspect of some embodiments of the present invention there is provided a method of jointed device movement inside a body, comprising: measuring movement of joints of a first user limb and joints of a second user limb simultaneously; mapping the measured movements of the first user limb joints to joints of a first device limb and the measured movements of the second user limb joints to joints of a second device limb; moving simultaneously the device limbs according to the mapped movements.

According to an aspect of some embodiments of the present invention there is provided a surgical system, comprising: a camera for measurement of movement of joints of a user limb; a device sized and shaped for insertion into a body comprising a first device limb; at least one controller for moving joints of the device limb based on the measured movement.

According to an aspect of some embodiments of the present invention there is provided a device sized and shaped for insertion into a body comprising:

at least one mechanical limb comprising:

a support segment;

a first flexible section extending from the support segment and terminating in a coupling section; and a second flexible section extending from the coupling section and terminating in a tool or a connector for a tool;

wherein one or more of the flexible sections is bendable by at least 120°;

wherein a long axis length of the first flexible section is at least double a maximum extent of the first flexible section perpendicular to a flexible section long axis;

wherein a long axis length of the second flexible section is at least double a maximum extent of the second flexible section perpendicular to a flexible section long axis.

According to an aspect of some embodiments of the present invention there is provided a device sized and shaped for insertion into a body comprising:

at least one mechanical limb comprising:

a support segment;

a first flexible section extending from the support segment and terminating in a coupling section; and a second flexible section extending from the coupling section and terminating in a tool or a connector for a tool;

wherein one or more of the flexible sections is in a single bending plane;

wherein one or more of the flexible sections is bendable by at least 120°.

According to some embodiments of the invention, each the flexible section has:

a flexible section long axis length; and a maximum flexible section extent perpendicular to the long axis;

wherein at least one of the flexible sections long axis length is at least double a maximum flexible section extent perpendicular to the long axis of the at least one of the flexible sections.

According to an aspect of some embodiments of the present invention there is provided a method of treatment comprising:

inserting a mechanical limb into a body, where the limb comprises at least two flexible portions;

bending the jointed mechanical limb within the body at two or more of the flexible sections to contact a target, such that a sum of angles between adjacent effective segment long axes, in at least one three dimensional plane, is at least 120'; and treating the target with the mechanical limb.

According to an aspect of some embodiments of the present invention there is provided a method of treatment comprising:

inserting a mechanical limb into a body through an entrance point in the body, where the limb comprises at least two flexible portions;

bending the jointed mechanical limb within the body at two or more of the flexible sections to contact a target, such that a length of the limb within the body measured as a sum of long axis lengths of portions of the limb is at least double a distance between the target and the entrance point;

treating the target with the mechanical limb.

According to an aspect of some embodiments of the present invention there is provided a method of hysterectomy comprising:

inserting a device comprising at least one mechanical limb into a body through an incision in a vaginal cavity;

bending the at least one mechanical limb within the body around 30% of a largest dimension of a uterus to access the uterus from outside the uterus;

separating the uterus from surrounding tissue using the mechanical limb; and removing the uterus through the incision.

According to an aspect of some embodiments of the present invention there is provided a device for incision comprising:

a device body sized and shaped to arrange patient tissue with a desired incision region of the tissue at a cutting edge disposed on the device body; and an outlet disposed on the device body coupled to a suction element for increasing a pressure between the user anatomy and the device body According to an aspect of some embodiments of the present invention there is provided a uterus manipulator comprising:

a portion sized and shaped for insertion into a uterus;

an elongated device body coupled to the portion for control of a portion position with respect to the elongated device body;

wherein the elongated device body is adapted to attach to a portion of a cervix.

According to an aspect of some embodiments of the present invention there is provided a surgical system comprising:

at least one mechanical arm; and a retractor tool;

wherein the retractor tool is extendable away from the one or more mechanic arm.

According to an aspect of some embodiments of the present invention there is provided a device sized and shaped for insertion into a body comprising:

at least one mechanical limb comprising:

a support segment;

a first flexible section extending from the support segment and terminating in a coupling section; and a second flexible section extending from the coupling section and terminating in a tool or a connector for a tool;

wherein a long axis of one or more of the flexible sections is bendable in a single bending plane;

wherein a long axis length of the first flexible section is at least double a maximum extent of the first flexible section perpendicular to a flexible section long axis;

wherein a long axis length of the second flexible section is at least double a maximum extent of the second flexible section perpendicular to a flexible section long axis.

According to an aspect of some embodiments of the present invention there is provided a device sized and shaped for insertion into a body comprising:

at least one mechanical limb comprising:

a support segment;

a first flexible section extending from the support segment; and terminating in a coupling section;

a second flexible section extending from the coupling section and terminating in a tool or an connector for a tool; and a control portion comprising at least one flexible torque transfer portion and coupled to the second flexible section, rotation of the control portion thereby rotating the second flexible section;

wherein the control portion passes through a hollow portion of the first flexible section, the flexible torque transfer portion is disposed within the first flexible portion, bending of the first flexible portion thereby bending the torque transfer portion.

According to an aspect of some embodiments of the present invention there is provided a device sized and shaped for insertion into a body comprising:

at least one mechanical limb comprising a portion comprising a support segment;

a first flexible section extending from the support segment and terminating in a coupling section; and a second flexible section extending from the coupling section;

wherein the first flexible section comprises bendable torque transfer section;

wherein a long axis of the second flexible section is bendable in a single bending plane.

According to an aspect of some embodiments of the present invention there is provided a grasper comprising:

at least two opposing portions coupled at a joint;

a torque element coupled to the opposing portions;

wherein application of torque in a first direction to the torque element screws the torque element towards the first and second opposing portions, increasing a separation between the portions;

wherein application of torque in a second direction to the torque element screws the torque element away from the first and second opposing portions, decreasing a separation between the portions.

According to an aspect of some embodiments of the present invention there is provided a surgical system comprising:

at least one mechanical limb sized and shaped for insertion into a body;

one or motor coupled to the limb for moving one or more part of the limb; and a processor configured to:

receive measurement of movement of input object;

generate a motor control signal based on the measured input object movement; and send the motor control signal to the one or more motor thereby controlling movement of the at least one mechanical limb.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 54A-54C are simplified schematic side views of a portion of an input device arm including a connection between input device segments in different configurations, according to some embodiments of the invention;

FIG. 64A is a simplified schematic of an open user hand, according to some embodiments of the invention;

FIG. 64B is a simplified schematic of a portion of a device arm including a hand tool where the hand tool is in an open position, according to some embodiments of the invention;

FIG. 64C is a simplified schematic of a closed user hand, according to some embodiments of the invention;

FIG. 64D is a simplified schematic of a portion of a device arm including a hand tool where the hand tool is in a closed position, according to some embodiments of the invention; and FIG. 65 is a series of photographic illustrations showing exemplary control of a device hand using measured user hand position, according to some embodiments of the invention.

DESCRIPTION OF SPECIFIC EMBODIMENTS OF THE INVENTION

Figure 1A:
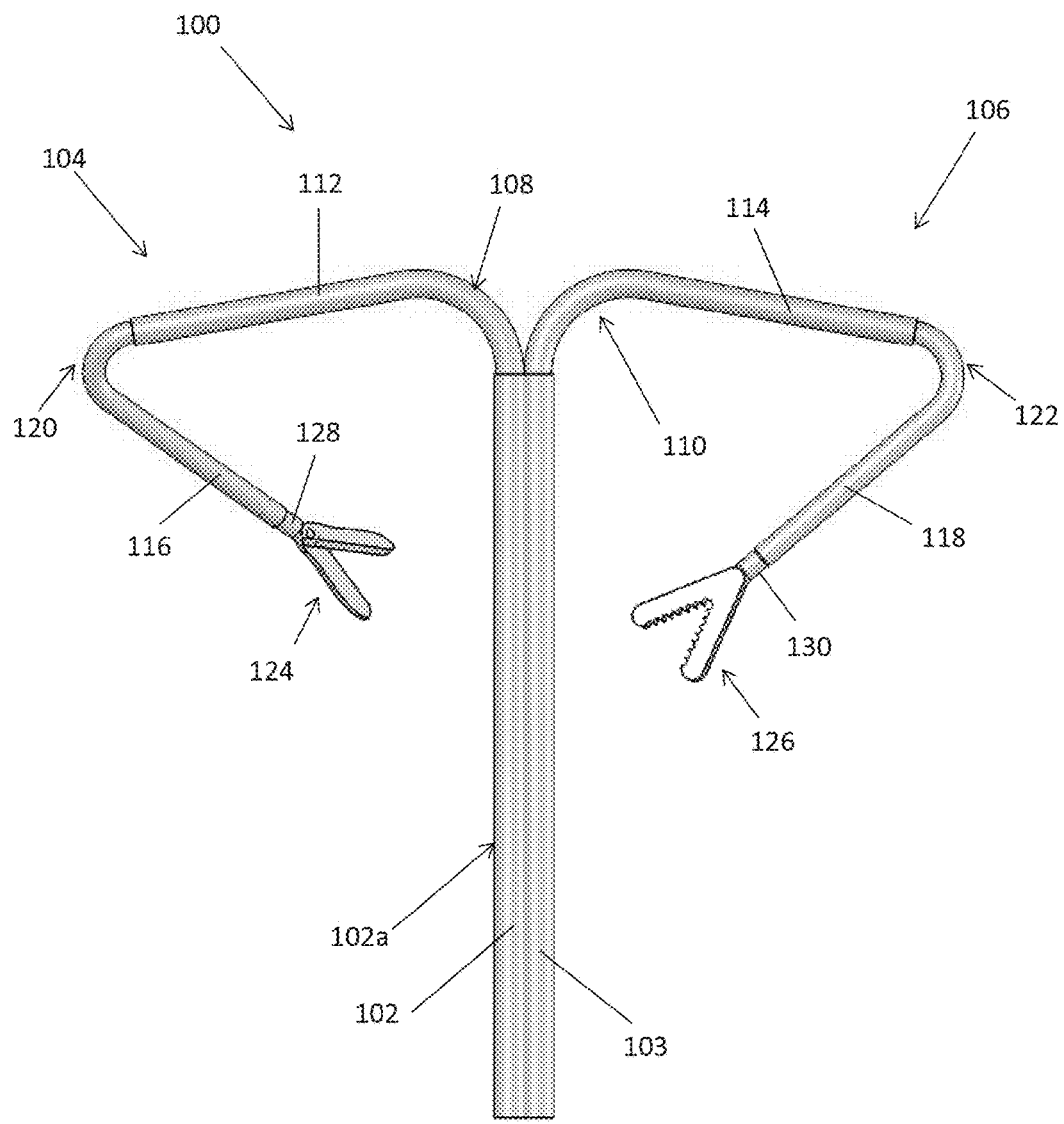
FIG. 1A is a simplified schematic side view of a surgical device including a plurality of arms, according to some embodiments of the invention.

The present invention, in some embodiments thereof, relates to of a device including mechanical arms, more particularly, but not exclusively, to methods and apparatus for control of a surgical device including mechanical arms.

Overview

A broad aspect of some embodiments of the invention relates to control of a surgical device using measured movement of one or more input object, where both the surgical device and one or more input object include a sequential structure of connected portions where movement of one or more portion of the input object controls movement of a sequentially corresponding portion of the surgical device.

For example, in some embodiments, input object joints correspond to flexible portions of a surgical device e.g. each input object joint corresponds to a single flexible portion of a surgical device.

In some embodiments, an input object includes user body portion/s, for example, where measured movement of a user limb controls movement of a surgical device limb. In some embodiments, an input object includes an input device which is moved (e.g. manually) by a user. In some embodiments, an input device includes an input device limb where movement of the input device limb controls movement of a corresponding surgical device limb. In some embodiments, a surgical device is controlled both by measured movement of a user's body and by movement of an input device controlled by a user.

A broad aspect of some embodiments of the invention relates to an intuitively controllable surgical system.

In some embodiments, the system includes an input object with a structure similar to that of a surgical device, where movement of the input object controls movement of the surgical device:

In some embodiments, a ratio between effective segment lengths of an input device segment pair (e.g. two adjacent input device segments) is substantially the same as an effective segment length ratio between a corresponding surgical device segment pair.

In some embodiments, each driven portion of the surgical device has a corresponding portion of the input device. In some embodiments, a surgical device arm and an input device arm include segments coupled by connecting portions. In some embodiments, an input device arm includes at least the number of joints and/or segments as a corresponding articulated surgical device arm. In some embodiments, the input device and the surgical device include the same number of segments and/or the same number of connecting portions.

In some embodiments, one or more portion of an input device has the same degrees of freedom as that of a corresponding portion of a surgical device. For example, in some embodiments, input device portion/s are bendable by about the same amount as corresponding surgical device portions. For example, surgical device portion/s which are rotatable around the surgical device portion long axis correspond to input device portions which are rotatable around the input device portion long axis.

Potentially, similar structure of the input object and surgical device provides intuitive control of the surgical device.

Overview—Exemplary Input Device Motion Control

A broad aspect of some embodiments of the invention relates to an input device for control of a surgical device, where both the input device and the surgical device have at least one part (e.g. limb) including a sequential structure of connected portions where movement of one or more portion of the input device controls movement of a sequentially corresponding portion of the surgical device. In some embodiments, a sequential structure of the input device and/or the surgical device includes segments (e.g. rigid portions) connected by connecting portions (e.g. pivot joints and/or flexible sections).

In some embodiments, sequential coupling of portions the surgical and/or input device is linear sequential coupling, where for example, central longitudinal axes of the portions are collinear where the portions are coupled.

In some embodiments, an input device limb includes segments sequentially coupled by joints. In some embodiments, a surgical device limb includes sequentially coupled flexible portions, optionally coupled by surgical device segments. In some embodiments, freedom of movement of input device segments about joints is about the same as freedom of movement of corresponding surgical device flexible portions. For example, in some embodiments, a flexible surgical device portion is bendable by the same angle as an angle between two input device segments coupled by a joint corresponding to the flexible surgical device portion.

In some embodiments, an angle between long axes of input device segments coupled by a joint controls an angle of a corresponding surgical device flexible portion. Where, for example, an angle of the surgical device flexible portion is defined between long axis tangents of the flexible portion at the flexible portion ends. Where, for example, an angle of the surgical device flexible portion is defined as an angle between effective segment long axis (e.g. where effective segment axes are described herein).

In an exemplary embodiment, an input device includes a more angular shape and/or a shape with a larger relative lateral extent than that of the surgical device. For example, in an exemplary embodiment, input device connecting portions are pivot connections between rigid segments, whereas surgical device connecting portions are long bendable sections (e.g. as described in the section of this document entitled "Exemplary long joints"). In some embodiments, pivot points connecting sections of the input device are not disposed at an intersection between effective input device limbs for example, potentially reducing a difference between input device and surgical device structures.

In some embodiments, an angle between an input device radius and an input device humerus controls an angle between a surgical device radius and a surgical device humerus where a ratio between effective lengths of the input device radius and humerus is substantially the same as a ratio between effective lengths of the surgical device radius and humerus.

In some embodiments, surgical device movements are scaled user hand movements.

For example, in some embodiments, a user selects scaling of user hand movement to input device (and surgical device) movement by selecting where to grasp an input device segment.

For example, in some embodiments, an input device includes a handle (optionally extendable) for scaling user hand movements.

In some embodiments, an input device includes one or more portion which is scaled up from that of the surgical device (e.g. a portion of the input device is a scaled up portion of a surgical device) meaning that large user hand movements transfer to small surgical device movements, potentially facilitating fine control of the surgical device with user (e.g. hand) movements.

In some embodiments, corresponding portions of the input device and the surgical device have differing numbers of segments and/or connecting portions. For example, in some embodiments, an input device segment controls movements of more than one portion of a surgical device (e.g. several segments). For example, in some embodiments, an input device includes two segments (e.g. rigid segments) connected by a connecting portion (e.g. a pivot) which control a portion of the surgical device which includes more than one two portion and/or more than one connecting portion. In some embodiments, an input device includes two segments (e.g. rigid segments) connected by a connecting portion (e.g. a pivot) which controls a portion of the surgical device including an extended flexible portion (e.g. surgical device includes an endoscope structure). In some embodiments, where a number of input device portions controls a different number of surgical device portions, mapping includes identifying effective segments, for example, where an effective input device segment includes a different number of input device portions than a corresponding surgical device segment.

In some embodiments, a surgical device includes one or more extending portion (e.g. one or more segment and/or joint which increases in long axis length). In some embodiments, an input device includes a corresponding extendable portion, the extent of extension of which controls an extent of extension of a corresponding surgical device portion.

In some embodiments, a user manually moves portion/s of the input device to control movement of the surgical device. In some embodiments, a user controls position of more than one part of the device simultaneously, for example, using one hand. In some embodiments, the input device includes two limbs (also herein termed "arms"), and a user controls each limb with one hand.

In some embodiments, the input device includes one or more arm constructed from rigid portions interconnected by joints. In some embodiments, the input device has a small number of freely moveable segments. For example, less than ten or less than 5, or less than 4 segments which are concurrently freely movable. Potentially, a small number of freely moveable segments facilitates user control of position and/or movement of each segment, for example, with a single user hand grasping a segment.

In some embodiments, input device arm/s have a similar structure and/or freedom of movement as human arms, potentially making manual control of movement and/or positioning of segments intuitive for a human user.

In some embodiments, an angle between long axes of two adjacent input device segments controls an angle between long axes of two corresponding adjacent surgical device segments. In some embodiments, a rotation of one or more input device segment controls rotation of a corresponding surgical device segment.

An aspect of some embodiments of the invention relates to an input device where joints coupling segments of the device are sufficiently low friction that the input device which is easily moveable by a user, when a user is controlling the surgical device by moving the input device. In some embodiments, the input device is resistive to movement which is not initiated by a user, the input device, for example including one or more locking mechanism. For example, potentially preventing accidental movement of a surgical device by undesired movement of the input device. In some exemplary embodiments of the invention, the input device has low resistance joints and includes one or more elements which can selectively lock a joint.

An aspect of some embodiments of the invention relates to an input device including one or more locking mechanism where the locking mechanism, when in a locked configuration, prevents movement of segments at a joint. In some embodiments, when the input device is not in use, the device is locked in position (e.g. automatically), for example, preventing movement of the surgical device.

In some embodiments, an input device locking mechanism includes one or more element (e.g. a toothed element) which interlocks with gear/s coupled to the joint to portion/s (e.g. at an input device joint) of the input device in position. In some embodiments, an input device locking mechanism includes an element which frictionally holds portion/s of the input device in position.

In this document, where the term "device" is used without a qualifier, the term refers to a surgical device including one or more articulated limb.

In some embodiments, one or more portion of a device is controlled by measured movement of an object (e.g. an avatar, also herein termed "input device") moved by a user. In some embodiments, an avatar manipulated by a user is a representation, optionally miniaturized, of at least a portion of a device (e.g. device arm). For example, one or more device portion (e.g. joint) is controlled by position and/or movement of a corresponding avatar portion (e.g. joint).

In some embodiments, movement of the avatar is measured using motion capture technology. In some embodiments, movement of the avatar is measured using one or more sensor e.g. mounted on and/or in the avatar.

In some embodiments, a user positions the device avatar with respect to a model of one or more portion of user anatomy, for example, a user moves an avatar to perform a treatment on an anatomic model and the device performs the treatment on the corresponding anatomy of a patient.

Overview—Exemplary Surgical Device Tool Control

A broad aspect of some embodiments of the invention relates to control of surgical device tools (e.g. end effecter/s coupled to distal end/s of surgical device limb/s). For example, control of opening and/or closing of a surgical device tool including two or more opposing sections (e.g. a gripper).

In some embodiments, an input device includes one or more user interface, for example, for controlling a surgical device end effecter. In some embodiments, surgical device end effecter/s are controlled by button/s located on the input device. In some embodiments, the input device includes representation/s of the surgical device end effecter/s, for example, so that a user can view a configuration of the surgical end effecter/s by looking at the input device.

In some embodiments, control of one or more device hand tool by mapped movement of a user hand and/or wrist movement and/or movement of a tool held by a user. In some embodiments, a device arm includes one or more hand tool coupled to the radius segment at a wrist joint. In an exemplary embodiment, each device arm includes a hand tool.

In some embodiments, a device hand tool includes more than one part and has an open and a closed configuration, where separating distal ends of the parts opens the tool and bringing distal ends of the parts together closes the tool (e.g. scissors, grasper with two or more opposing portions). In some embodiments, opening and closing of a device tool, "tool actuation", is controlled by opening and closing of a user hand, "user tool actuation".

In some embodiments, a device tool is controlled by measured movement of an object representing the tool, a "tool avatar" which held and/or moved by a user. For example, in some embodiments, a device including a scissors tool is controlled by a user holding a pair of scissors e.g. opening and closing of the device scissors (tool actuation) is controlled by opening and closing of the avatar scissors "avatar actuation". In some embodiments, a tool avatar is unattached to supporting element/s. In some embodiments, a tool avatar is coupled to an input device. In some embodiments, rotation of a tool avatar controls automatic (e.g. robotically controlled) movement of a mechanical arm.

In some embodiments, rotation of a device hand and/or hand tool is controlled by measuring user finger position (e.g. using motion capture technology and/or a one or more sensor mounted on a user hand). In some embodiments, rotation of the hand is controlled by measuring orientation of a tool avatar (e.g. using motion capture technology and/or using one or more sensor optionally mounted on the avatar).

In some embodiments, device arm movement and device tool actuation are synchronized (e.g. occur at the same time), according to synchronized user arm movement and user tool actuation and/or avatar tool actuation, optionally, for more than one arm and/or more than one device hand tool. In some embodiments, simultaneous measurement of user movements control device arm movement and tool actuation (e.g. opening and closing of the device).

Overview—Exemplary User Body Motion Control

A broad aspect of some embodiments of the invention relates to control of a jointed mechanical device where movement of one or more device portion is controlled by measured mapped movement of a corresponding user body portion (e.g. movement of a device elbow joint is controlled by measured mapped movement of a user elbow joint). In some embodiments, each device joint is controlled by measured movement of a corresponding user arm joint.

In some embodiments, one or more device arm portion is controlled by measured movement of a corresponding user arm portion and/or measured movement of a corresponding input device and remaining device portions are controlled using robotics, e.g. inverse kinematics. For example, in some embodiments, device arms are outstretched, and (e.g. to provide the user with a comfortable working arm position) user humerus segments are held downwards, at the user sides. User hand, radius and wrist position control movement of the device hand, radius and wrist position and elbow and shoulder position and movement are controlled by inverse kinematics.

In some embodiments, position and/or movement of one or more user body portion (e.g. segment joint and/or segment) is measured in 3D space e.g. with motion capture technology. For example, relative positions and/or movement of user segment (e.g. arm) joints are extracted from captured images (e.g. video images). Alternatively or additionally, measurements are collected by one or more motion sensor attached to the user. In some embodiments, a motion sensor is attached to each user segment and/or joint to be measured.

In some embodiments, one or more changing angle between two user arm segments is calculated from measured user joint movement. In some embodiments, corresponding device arm segment/s are moved according to the measured changing angle/s. In some embodiments, a user skeleton (e.g. including joint position and segment position) is modeled from measurements. In some embodiments, the modeled skeleton is used to control the surgical device limbs.

In some embodiments, control is relative for one or more portion of the device, the device changing an angle between two segments according to the corresponding user change in angle, for example if device and user starting angles are not the same, if the device has different anatomy (e.g. different segment ratios) than the user arm. In some embodiments, the device angle is changed by approximately the same number of degrees. In some embodiments, the device angle is changed by a scaled number of degrees.

Potentially, device control using measured user movement provides one or more of; user movements which are physically comfortable, and/or user control movements are intuitive and/or easily learnt, for example, resulting in a low amount of error movements.

In some embodiments, a user controls one or more device segment using user leg motion.

Overview—Exemplary System Modes

An aspect of some embodiments of the invention relates to transfer of the system between modes. In some embodiments, transfer is by detection of user gestures. For example, in some embodiments, a user transfers the system from a mode where measured user movement is mimicked by the surgical device to a pause mode, where mimicking ceases, by the user performing a gesture (e.g. lifting a user leg).

In some embodiments, the device is operated in more than one mode (e.g. during a single treatment). In some embodiments, a device is moved into position using a mode where each device portion is controlled by movement of a corresponding user body portion and then, for example, once the device hands are in position to e.g. operate on tissue, the user changes the control mode, e.g. to fewer device portions being controlled by user movement (e.g. as described above), e.g. to scaled down movements for fine work.

In some embodiments, some user body movements and/or gestures are used to control movement of a surgical device and other user body movements and/or gestures are used to change a mode of the system.

Overview—General

In some embodiments, one or more surgical device-user arm pair, or surgical device-input device arm pair is initialized (e.g. before treatment with the device) where surgical device arm position (e.g. angles between segments) is aligned with and user and/or input arm position (e.g. device arm and/or user arm are moved during initialization).

In some embodiments, movement of one or more portion of the surgical device (e.g. surgical device arm) is substantially at the same time as movement one or more portion of user and/or input device arms. Alternatively, in some embodiments, movement of the device (e.g. device arm) is delayed, for example, a user makes a movement (e.g. with the user's body and/or with an input device), then optionally authorizes the movement for control movement of the device. In some embodiments, one or more portion of the device moves at the same speed as the user controlled (e.g. movement of the user's body and/or user movement of an input device) movement. Alternatively, in some embodiments, the device moves at a different, optionally user defined, speed (e.g. slower). In some embodiments, a user selects one or more timing option. For example, during fine work, a user selects a mode where user movements are slowed and/or delayed to control device movements.

In some embodiments, the surgical device includes two or more arms. In some embodiments, movement of two surgical device arms is controlled by mapping movement of two user arms and/or of two input device arms. In some embodiments, movement of two surgical device arms is synchronized according to synchronized movement of two user arms and/or of two input device arms. A potential advantage of synchronized control of device arms being the ability of two or more device arms to work together, for example, to hold and/or stretch tissue and to cut the tissue concurrently, to grasp a portion of tissue together (e.g. to pass an object from one hand tool to another).

In some embodiments, a user selects a device limb to be controlled by mapped movement (e.g. control as described above using user movement and/or input device movement) of an input object limb. In some embodiments, the user selects a surgical device limb and selects a user and/or input device limb, and the selected surgical device limb is controlled by mapped movement of the selected user and/or input device limb. In some embodiments, a device includes more than two arms and a user selects two device arms, where a first device arm is controlled by mapped movement of a first user arm and/or first input device arm and a second device arm is controlled by mapped measured movement of a second user arm and/or a second input device arm. In some embodiments, non-selected arm/s remain stationary and/or are moved with a different method of control (e.g. using user leg motion, controlled by a second user, controlled automatically, e.g. by robotics).

In some embodiments, both input device movement and user body movement is used to control the surgical device, for example a first surgical device arm being controlled by user movement of an input device arm and a second surgical device arm being controlled by measured movement of portion/s of the user's body.

Optionally, the system (for example, as described herein) automatically assigns a user arm-surgical device arm pairs (and/or input device-surgical device arm pairs) for control of the surgical device where assignment is based on, for example, position of the surgical device arms (e.g. in some embodiments, the user does not specify which user and/or input arm is to control which surgical device arm).

In some embodiments, a user changes selected surgical arms by pausing control (e.g. control of movement of surgical device arm/s by mapped input object movement) of one or more selected surgical device arm and re-selecting one or more surgical device arm (selecting as described herein). In some embodiments, the user pauses and re-selects arms to switch control of a first device arm by a left user arm and control of a second device arm to control of the second device arm with the user right arm and control of the second device arm by a user left arm.

In some embodiments, a user pauses an initial surgical device arm in a desired position (e.g. to hold user anatomy in position) and selects another surgical device arm (e.g. a third arm) for continued two-arm movement.

In some embodiments, user control is assisted by visual feedback displayed to the user (e.g. on a screen), for example, data describing a configuration of at least part of the surgical device (e.g. images) is displayed, optionally in relation to real time imaged and/or previously imaged patient anatomy. In some embodiments, surgical device and/or anatomy images are video images and/or real-time ultrasound images and/or CT images and/or MRI images.

An aspect of some embodiments of the invention is related to a surgical system for key-hole surgery including a mechanical device with at least one limb for insertion into a body where a controller controls the movement of one or more portion of the limb according to measured movement of corresponding portion/s of a user limb (measured by a measurement device, e.g. a camera). In some embodiments, the device includes one or more imaging device for insertion into the body with the mechanical arm/s. Optionally, the system includes one or more external imaging device (e.g. MRI, CT, ultrasound). Optionally collected images from one or more device are displayed to a user on a display. Optionally additional data and/or processed collected data (e.g. from one or more system and/or device sensor, from a database) is displayed to the user on the display.

Optionally, in some embodiments, more than one user controls a surgical device, for example, at the same time. In some embodiments, different users control different portions of the surgical device, optionally using different types of control. For example, in some embodiments, a first user controls portion/s of a surgical device using an input device and a second user controls portion/s of the surgical device with measured user body movement. In some embodiments, multi-user control is sequential, where, for example, a first user's control movements are carried out by the surgical device and then a second user's movement. Alternatively, or additionally in some embodiments, multi-user control movements are carried out simultaneously by the surgical device In some embodiments, mapping between input object portions and surgical device portions uses segment lengths. In some embodiments, mapping uses effective lengths, e.g. as defined using method/s (e.g. as described in this document) for surgical device effective segments and/or effective segment lengths. In some embodiments, effective lengths change for different configurations (e.g. angles of bending) of the input objects. In some embodiments, effective input device segments are defined using one technique and these effective input device segments and/or relationships between these effective input device segments (e.g. angle/s between effective segments) are mapped to control corresponding surgical device segment/s and/or effective segment/s where surgical device effective segment/s are defined using the same or a different technique.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments, an angle between two effective input device segments (effective segments e.g. defined as described regarding FIGS. 5A-5D) is used to control bending of corresponding effective surgical device segments. For example, in some embodiments, a measured angle between two adjacent input device segments, also termed an angle of a joint connecting the segments is used to generate a control signal for actuation of a flexible portion corresponding to the input device segment e.g. bending and/or rotation (about a flexible portion long axis) of the flexible portion.

In some embodiments, an input device portion corresponds to a surgical device portion where the surgical device portion is actuated based on measured position and/or relative (e.g. with respect to other input device portion/s) position of the input device portion.

In some embodiments, control techniques and/or apparatuses for control as described in this document are performed by devices and/or systems and/or methods, for example as shown in and/or described regarding FIGS. 1A-41 and/or are used in treatments as described herein.

Other devices and/or systems and/or devices (e.g. surgical devices of the art) may be controlled using control techniques and/or apparatuses for control as described herein.

Overview—Exemplary Devices

A broad aspect of some embodiments of the invention relates to an intuitively controllable and flexible mechanical device (e.g. surgical device) for insertion into a patient, including one or more limbs, where intuitive control is related to the device including at least one limb with humanoid characteristics:

In some embodiments, a mechanical limb includes at least two coupled flexible portions, and, in some embodiments, movement (e.g. bending and/or rotation) of a first flexible portion and a second flexible portion is independently controllable. In some embodiments, one or more of the flexible portions is independently rotatable about a corresponding flexible portion long axis. In some embodiments, one of more the flexible portions is independently flexible and extendable (bendable). In some embodiments, flexion/extension and rotation about a flexible portion long axis of one or more flexible portion are controllable concurrently.

In some embodiments, one or more of the flexible portions is unidirectionally flexible and extendable (bendable). For example, in some embodiments, the flexible portion is bendable in one plane (herein "bending plane") e.g. where a central long axis of the portion bends in one plane. For example, in some embodiments, the flexible portion bends in one rotational direction around one or more bending plane. For example, in some embodiments, in some embodiments, the flexible portion is bendable in one rotational direction around a single bending plane. The term "unidirectionally bendable" herein refers to a portion being bendable in one rotational direction and/or bendable around a single bending plane.

In some embodiments, freedom of movement of the flexible sections relates to that of joints of a human arm, for example, the first flexible portion corresponding to a shoulder joint and the second flexible portion corresponding to an elbow joint.

In some embodiments, the flexible portions are coupled by a first segment (e.g. comprising a coupling section), which, in some embodiments, is rigid, the first segment, for example, corresponding to a humerus. In some embodiments, the first flexible portion is coupled (e.g. at a proximal end of the first flexible portion) to a support segment (e.g. corresponding to a torso).

In some embodiments, a limb support segment is long, for example, with respect to segments of a device limb, for example, 2 times, or 3 times, or 4 times, or 5 times or 10 times or 20 times a length of one or more segment.

In some embodiments, the first flexible section is multi-directionally bendable, for example, bendable in more than one bending plane (e.g. corresponding to human shoulder joint freedom of movement).

In some embodiments, flexion and rotation of flexible portions (e.g. corresponding, in some embodiments, to flexion and rotation of segments at joints) is sufficient such that the range of possible positions of flexible portions and/or segments is at least that of a human arm.

For example, in some embodiments, possible positions of joints include possible positions of corresponding human arm joints. For example, in some embodiments, a range of possible angles between device limb segments corresponds with a range of possible angles between corresponding human arm segments.

In some embodiments, each device arm segment is flexible and extendable around a joint. In some embodiments, each segment is rotatable around a segment long axis, which rotation rotates a portion of the arm distal to the rotating segment about the segment's long axis. In some embodiments, joint flexion/extension and segment rotation are adjustable concurrently.

In some embodiments, freedom of movement of a device mechanical arm is restricted, for example, to match an aspect of freedom of movement of a human arm. For example, in some embodiments, one or more flexible portion (e.g. each flexible portion) is uni-directionally bendable.

In embodiments where a mechanical arm includes rigid segments connected by flexible portions, analogy may be made between rigid segments and human arm segments (e.g. humerus and radius) and between flexible portions and human arm joints (e.g. shoulder, elbow, wrist). In some embodiments, a ratio of lengths (e.g. central long axis lengths) of segments is about a normal human ratio, for example, in some embodiments, a ratio between two segment long axis lengths is about a normal human ratio for the corresponding segments. For example, in some embodiments, a mechanical arm humerus length is about 5-40% or 10-30% or about 20% longer than the radius length, or lower or higher or intermediate ranges or percentages longer.

In some embodiments, an effective lengths and/or ratios between effective lengths of device limb segments corresponds to that of human limb segments (e.g. a ratio of humerus to radius length).

In some embodiments, device joint/s are long, such a portions of a device arm corresponding to a human body segment (e.g. humerus, radius) include portions of device joint/s. In some embodiments, ratio/s of human segment lengths correspond to ratio/s of effective surgical device segment lengths, where different definitions for effective segment lengths are described below.

In some embodiments, one or more ratio between dimensions of different portions of a mechanical limb is about a normal human ratio for the corresponding dimensions. For example, in some embodiments, a ratio between a length of a portion of the device acting as a humerus (effective humerus length) and a length of a portion of the device acting as a radius (effective radius length) is 1:1 to 2:1, or 1.1:1 to 1.5:1 or about 1.2:1, or lower or higher or intermediate ratios.

In some embodiments, a ratio of a length of a portion of the device acting as a humerus and a length of a portion of the device acting as a humerus remains fixed as the mechanical arm is moved. In some embodiments, a ratio of a length of a portion of the device acting as a humerus and a length of a portion of the device acting as a humerus changes fixed as the mechanical arm is moved.

In some embodiments, a ratio between effective segment lengths is about that of a normal human ratio for the corresponding segments.

In some embodiments, a ratio of effective segment lengths is maintained within a normal human ratio (and/or within a range around a normal human ration) when the mechanical arm is in different configurations (e.g. one or more flexible portion is bent).

In some embodiments, a mechanical arm lacks one or more of human arm segments (and/or includes one or more segment than the number of segments in a human arm) coupling flexible portions. For example, in some embodiments, a mechanical arm lacks a wrist joint. For example, in an exemplary embodiment, a first flexible portion and a second flexible portion are directly coupled (e.g. a distal end of the first flexible portion is directly coupled to a proximal end of the second flexible portion).

An aspect of some embodiments of the invention relates to a mechanical arm including humanoid structural characteristics where flexible portions of the mechanical arm are long and are associated with human arm joints as well as portion/s of rigid (e.g. bone) human arm segments (e.g. humerus, e.g. radius).

In some embodiments, one or more device arm includes a radius segment and a humerus segment sized, and an elbow joint and shoulder joint with flexion such that a hand and/or distal end of a device radius is movable to near to and/or axially past and/or into contact with the shoulder joint and/or the arm torso. A potential benefit being the ability to access a target (e.g. with hand tools) close to the torso.

An aspect of some embodiments of the invention relates to a flexible device where bending portions of the device are rounded for example, with a minimum a radius of curvature of one or more bending portion being at most 15 mm, or at most 10 mm, or at most 8 mm, or at most 5 mm. In some embodiments, an inner skeleton (e.g. including mechanical limbs as described herein) includes rounded bending portions. In some embodiments, a cover or sheath covering a mechanical limb includes rounded bending portions. In some embodiments, rounded bending portions of device mechanical arms are due to an inner structure, and are not only due to rounded bending portions of a cover or sheath (e.g. a protective cover). In some embodiments, a mechanical arm has minimal lateral extension associated with bending at device flexible portions.

An aspect of some embodiments of the invention relates to a device including one or more articulated mechanical limb, where one or more joint (flexible portion) is long. For example, in some embodiments, bending of one or more long joint is distributed along the joint in a direction of a joint long axis.

In some embodiments, a long axis length of a joint is long, e.g. with respect to a maximum extent of the joint perpendicular to the joint long axis. In some embodiments, one or more joint is long with respect to one or more segment length long axis length and/or is long in comparison with human joint to segment length ratios and/or is long with respect to rigid segment/s of a mechanical arm.

In some embodiments, a long flexible portion includes a central long axis length of the portion being at least double or 1.5-5 times, or 2-4 times, or at least four times, a maximum extent of the flexible section perpendicular to the section long axis.

An aspect of some embodiments, of the invention relates to a joint comprising a chain of coupled elements where bending of the joint is by pivoting of individual elements. In some embodiments, each element pivots about an element bending plane. In some embodiments, a bending axis of one or more of the elements (e.g. all of the elements) is coplanar. In some embodiments, elements pivot in one direction around the bending axis.

A broad aspect of some embodiments of the invention relates to rotation of a portion of a mechanical arm about a portion long axis, where rotation is rotation of component/s coupled to the portion and extending away from the portion.

In some embodiments, an elongate portion (e.g. segment, flexible portion) of the arm has a main central axis (where the main axis is a central (e.g. symmetrical) axis of the device with the largest extent), where the main axis is herein termed "long axis" or "central long axis" or "longitudinal axis" or "central longitudinal axis".

An aspect of some embodiments of the invention relates to actuation of thin mechanical limbs. In some embodiments, one or more portion of a mechanical limb is rotated by rotating a portion coupled to the limb and extending away from the limb. For example, in some embodiments, portion/s of a mechanical limb inserted into a patient are rotated by rotation of a portion extending outside of a patient (e.g. using motor/s outside the patient). In some embodiments, sequentially connected portions are rotated by portions which extend through hollows within other portions. In some embodiments, lack of motors located within a mechanical limb facilitate thin mechanical limbs.

In some embodiments, a surgical device system includes a motor unit including a plurality of motors for driving multiple parts of a surgical device including at least one mechanical limb (e.g. more than one motor is used to drive different portions of a mechanical limb). In some embodiments, the mechanical limb is inserted into a patient body while the motor unit remains outside the patient body.

In some embodiments, each segment of a mechanical arm is rotated around a segment long axis by component/s located externally to the segment.

In some embodiments, one or more portion of a mechanical arm is rotated by rotation of an extension (also herein termed "control portion") coupled to the portion, where the extension extends outside the portion and/or arm.

In some embodiments, an extension includes one or more flexible torque transfer portion able to transfer torque along a torque transfer portion long axis while the portion is bent, a potential benefit being the ability to rotate a portion remotely (e.g. from outside the arm) when one or more arm joint is flexed and/or extended.

In some embodiments, one or more extension is nested, where the extension passes through (e.g. through a hollow portion of) one or more arm element, for example, through one or more other extension and/or one or more segment and/or one or more connecting portion. A potential benefit of nested extensions is compactness of the mechanical arm and/or segments forming the external shape of the arm.

In some embodiments, a flexible torque transfer section of an extension (control portion) passes through a hollow portion of, and is aligned with a flexible portion of the device. In some embodiments, the flexible portion is unidirectionally bendable. In some embodiments, bending of the outer flexible portion causes the torque transfer portion to bend. In some embodiments, a long axis of the torque transfer portion unrestrained in possible planes of bending.

An aspect of some embodiments of the invention relates to control of flexion/extension of a portion of a mechanical limb by varying tension on elongated element/s coupled to the portion where in some embodiments, one or more elongated element is coupled to an external surface of the device limb. In some embodiments, elongated element/s extend outside the device (e.g. extend outside a patient body when the device is within a patient body e.g. extend to where they are actuated by a motor unit outside the patient). In some embodiments, elongated element/s are coupled to an inside surface of one or more hollow device portion.

An aspect of some embodiments of the invention relates to a bendable torque transfer portion including a first end and a second end, where the portion transfers torque applied to the first end to the second end when the portion is bent.

In some embodiments, a torque transfer portion includes a plurality of elements interconnected by a plurality of connectors. In some embodiments, the connectors are sufficiently strong to transfer torque between the elements.

In some embodiments, one or more element (or, in an exemplary embodiment, each element) includes two or more portions, where the portions are independently elastically compressible and expandable in a direction parallel to a torque transfer portion long axis.

An aspect of some embodiments of the invention is related to a surgical system for key-hole surgery including a mechanical device with at least one limb for insertion into a body where the device includes humanoid structural characteristics (e.g. as described herein). In some embodiments, the device is actuated by a motor unit which is not inserted into the body. In some embodiments, the device includes one or more imaging device for insertion into the body with the mechanical limb/s. Optionally, the system includes one or more external imaging device (e.g. MRI, CT, ultrasound). Optionally collected images from one or more device are displayed to a user on a display. Optionally additional data and/or processed collected data (e.g. from one or more system and/or device sensor, from a database) is displayed to the user on the display.

In some embodiments, data displayed to a user includes image and/or measurements, optionally processed before display, for example, internal device measurements (e.g. from one or more device sensor, for example inserted with the device and/or mounted on a device arm).

In some embodiments, optionally displayed images (e.g. video images) are collected by a camera mounted on the device or inserted with the device, optionally at a position with relation to the arms which mimics human eye to arm positioning. Optionally, a position of the camera is changed during use of the device, for example, movement of the camera close to device hands to provide a close-up view, (e.g. of surgery).

In some embodiments, images are re-orientated before display to a user, for example, images are orientated to an intuitive direction for the user. For example, in some embodiments, images collected from a first point of view (e.g. by an internal camera) are orientated to a user point of view above the body. For example, in some embodiments, two or more sets of images are orientated to be in the same orientation (e.g. images are overlaid) for example, previously collected images (e.g. CT, MRI) and real time images, for example from internal camera/s and/or internal and/or external ultrasound.

An aspect of some embodiments of the invention relates to actuation of a mechanical device limb. In some embodiments, two gears are driven at the same speed and direction to provide rotation without bending of a device limb flexible portion. In some embodiments, two gears are driven at different speeds and/or direction to provide bending of a device limb flexible portion.

For example, in some embodiments, a first gear and a screw mechanism are coupled to a central shaft. One or more elongated element is coupled between the flexible portion and the screw mechanism, such rotation of screw mechanism without rotation of the elongated element/s causes the elongated elements to move laterally along a long axis of the shaft, generating flexion or extension of the flexible portion. In some embodiments, elongated elements are coupled to a second gear. In some embodiments, when both the first and second gears are rotated in the same direction and speed, the flexible portion rotates and the flexible portion does not change flexion/extension. In some embodiments, rotation of the second gear while the first gear remains stationary generates flexion/extension but not rotation of the flexible portion. In some embodiments, when first and second gears are differentially rotated (e.g. in different directions and/or in the same direction at different speeds and/or the first gear is rotated while the second gear remains stationary) the flexible portion both rotates and bends (flexion/extension). In some embodiments, each gear is driven by a motor. In some embodiments, each flexible portion is driven by the above described mechanism including two gears.

In an exemplary embodiment, the device is inserted into a body through a single incision. In some embodiments, the device is inserted into a natural orifice (e.g. vagina, rectum, mouth and/or nostril). Optionally, the device is inserted through one or more incision in a natural orifice.

In some embodiments, the mechanical arms have a small transverse dimension, such that, in some embodiments, one or more arm is inserted into a body through a small incision and/or is inserted into a narrow natural orifice (e.g. vagina) and/or is inserted into a narrow channel (e.g. channel inside natural orifice, e.g. esophagus).

Optionally, in some embodiments, one or more part of a device includes an electrosurgery tip e.g. monopolar electrosurgery tip, bipolar electrosurgery tip.

In some embodiments, one or more additional component or tool (e.g. service tunnel, suction tool, irrigation tool, inflation tool) are inserted, optionally through a single incision, with the mechanical arm/s.

An aspect of some embodiments of the invention relates to a mechanical limb including more than one bendable portion, where bending of at least one portion is controlled by changing tension of an elongated element coupled to the portion and where bending of at least one other portion is controlled by applying torque to (e.g. screw mechanism) an elongated element coupled to the portion.

An aspect of some embodiments of the invention is related to a grasper where movement of an element (e.g. by a motor) to control actuation of the grasper is separated from the grasper by at least a segment (e.g. control of grasper at least at the radius). In some embodiments, grasper actuation is by rotation of a grasper extension coupled to the grasper.

In an exemplary embodiment, grasper actuation is controlled outside the arm, e.g. in the torso of the mechanical arm to which the grasper is coupled, e.g. outside the device.

In some embodiments, the grasper extension includes one or more grasper torque transfer portion (e.g. as described elsewhere in this document).

In some embodiments, the grasper extension extends away from the grasper through one or more hollow portion in one or more segment and/or connecting section and/or torque transfer portion.

In some embodiments, actuation of the grasper is by a screw mechanism where grasper actuation is by turning a grasper extension (e.g. an elongated element) coupled to the grasper and extending away from the grasper. In some embodiments, continuous rotating of the elongated element cyclically opens and closes the grasper. In some embodiments, rotating the elongated element in a first direction (e.g. clockwise) closes the grasper and rotating the elongated element in a second direction (e.g. anticlockwise) opens the grasper. A potential benefit of grasper actuation by a screw mechanism is, in comparison to grasper actuation being controlled by pulling/releasing an elongated element which extends through at least one segment is that grasper hold on an object between grasper opposing portions is unaffected by bending and/or movement of the device arm through which the elongated element travels.

In some embodiments, one or more mechanical limb flexible portion is bendable and/or segment is sized such that a distal end of the limb (optionally including a length of an end effecter) is positionable at a limb support segment. In some embodiments, the support segment is tubular.

In some embodiments, a mechanical limb is bendable such that the limb is bendable by 180° or more with respect to a limb support segment.

In some embodiments, a flexible portion includes a plurality of elements (e.g. links, e.g. as described herein). In some embodiments, the term flexible portion refers to a portion which is bent using a single control and/or as a single unit.

Overview—Exemplary Treatments

A broad aspect of some embodiments of the invention relates to a surgical device for insertion into a body including at least one mechanical limb where the limb is sufficiently flexible such that the device is able to bend to access a target from a different direction to a direction of insertion of the mechanical limb.

In some embodiments, a surgical device limb includes at least two flexible portions where, in some embodiments, at least one of the portions is bendable (flexion/extension) by at least 120°, or by at least 90, or by at least 100°, or by at least 140°, or by at least 160°, or by at least 180°, or by at least 190°, or by at least 200°, or by at least 210° or lower or higher or intermediate angles. In some embodiments, bending of two flexible limb sections is of a combined angle of at least 180°. In some embodiments, one or more flexible portion is maximally bendable by 400°, 350°, 300°, or 270°. In some embodiments, a limb is maximally bendable by 400°, 350°, 300°, or 270°.

In some embodiments, device limb flexible portion/s are long where, a long axis length of at least one flexible section is at least double, or at least 1.5 times, or at least 3 times, or at least 4 times, or at least 5 times, or at least 8 times or at least 10 times, a maximum extent of the flexible section perpendicular to the flexible section long axis.

An aspect of some embodiments of the invention relates to a surgical device including at least one limb for insertion into a body, where the limb includes flexible portions which are unidirectionally bendable and is highly bendable (e.g. large possible angle of flexion and/or extension).

In some embodiments, a surgical device limb includes at least two independently unidirectionally bendable flexible portions where, in some embodiments, at least one of the portions is bendable (flexion/extension) by at least 120°, or by at least 90-180°, or by at least 100-120°, or lower or higher or intermediate angles. In some embodiments, bending of two flexible limb sections is of a combined angle of at least 180°. Where, for example, a sum of a first angle between long axis tangents at ends of a first flexible section and a second angle between long axis tangents at ends of a first flexible section are at least 180°. Where, for example, a sum of a first angle between long axes of an adjacent segment pair and a second angle between long axes of a different segment pair is at least 180°. Where adjacent segment pairs are defined as segments directly coupled by a flexible section.

In some embodiments, each flexible portion is independently rotatable about a flexible portion long axis.

A broad aspect of some embodiments of the invention relates to a method of treatment (e.g. endoscopic surgery), where a device including at least one jointed mechanical limb is inserted into a body (e.g. a patient), optionally through an incision, where the limb bends within the body to access and treat a target (e.g. a body organ). In some embodiments, the ability of the limb to bend within the body is used to compensate for insertion direction sub-optimality.

In some embodiments, bending of the flexible limb portions, is such that a direction in which the device contacts and/or accesses the target is different (e.g. at least 90° larger or smaller than, in at least one 3D plane) from a direction of device entry into the body.

In some embodiments, bending of the flexible limb portions, is when at least two joint angles are each larger than 0°, where joint angles are measured as the angle between coupled device segment (and/or effective segment) long axes. In some embodiments, bending of the limb is such that a sum of all limb joint angles is more than 0°, 10° or more, 45° or more, or 90° or more, or 180° or more or 360° or more.

In some embodiments, bending of the limb is such that a direction of device entry into the body is different (e.g. at least 10° larger or smaller, at least 45° larger or smaller, at least 90° larger or smaller) from a direction of a straight line connecting the target to the incision.

In some embodiments, a device including one or more limb accesses a target by bending around an obstacle. For example, one or more limb bends in a path which curves away from a straight line between the insertion point and the target (e.g. the path not passing through the target, e.g. where the obstacle is between a point of insertion of the device and the target). In some embodiments, a device includes more than one limb. In some embodiments, device limbs approach a target from the same direction, in some embodiments, device limbs approach a target from different directions, e.g. with an access direction difference of up to 20°, 20° or more, or 45° or more, or 90° or more, or 180° or more or 270° or more.

In some embodiments, the target is a portion of an organ and the obstacle is a different portion of the organ. For example, in some embodiments, a target region is at the back of an organ and the device is inserted through an incision in front of the organ. As the device is introduced, one or more part of the device bends around the organ, to access the target at the back of the organ, "hugging" the organ, for example, the device contacting and/or encircling 10-100%, or 20-90%, or 50-90%, or lower or higher or intermediate ranges or percentages of a circumference of the organ.

In some embodiments, bending of the device including one or more limb within the body is to access a target underneath (e.g. deeper within the body) an obstacle, where a shortest straight line drawn between the target and the body surface (e.g. skin surface) passes through the obstacle. For example, in some embodiments, the ribcage is an obstacle (e.g. an obstacle to organs under the ribcage), and thoracic surgery is performed by inserting a device through an abdominal incision. In an exemplary embodiment, the device inserted into the abdominal incision follows a path under the ribs, bending from a position under the ribs to access a target inside the ribcage.

In some embodiments, a mechanical device is inserted into a patient from a direction which is not substantially from above, for example, where an angle of insertion of the device with respect to the vertical is more than 75°, or more than 90°, 75-175° (where angles of over 90° correspond to an angle of insertion from a direction underneath the patient when the patient is in a supine or prone position). In some embodiments, the mechanical device is inserted into the patient laterally, for example between the patient legs e.g. into a patient through a pelvic outlet.

In some embodiments, images guide a user performing the treatment. For example, images acquired by a camera inserted with the mechanical device. In some embodiments, the camera is mounted on (e.g. at a distal end of) a bendable mechanical limb, where, for example, the camera structure and/or flexibility is as described above for mechanical device limb/s. In some embodiments, images collected by other imaging methods e.g. MRI, CT, ultrasound etc. (e.g. previously acquired images) are used to guide treatment.

An aspect of some embodiments of the invention relates to a method of treatment where one or more mechanical device limb within a patient body follows a long path, where a length of the limb within the body (e.g. measured a sum of long axis lengths of portions of the limb within the body) is long in comparison to a distance between the target and point of insertion of the device into the body, herein termed "entrance point". In some embodiments, a length of a device limb within the body is at least 1.2 times, or at least 1.5 times, or at least double, or at least triple, or at least quadruple times, or at least 5 times a straight line distance between the target and the entrance point. A potential benefit of a long path is access to a wide range of desired targets for a given entrance point (e.g. incision). A potential benefit of a long path is the ability to insert the device at a wide range of entrance points, for a given target.

In some embodiments, the device includes more than one limb, where the limbs together access and treat a target. In an exemplary embodiment, the device includes two limbs, where, optionally, both limbs bend to access and treat a target.

A potential benefit of device bending within the body is the ability to insert the device at a desirable entry point and/or at a desirable insertion angle while treating a target from a desirable direction. In some embodiments, a wide range of treatment angles (angle at which a device limb approaches a target) are available for a given angle of insertion and/or for a given entrance point.

In some embodiments, treatment (e.g. surgery) is by accessing target from a direction superior to the target, (e.g.

as is usually the case in laparoscopic surgery) while inserting of the device is through a natural orifice located inferior of the target.

For example, in an exemplary embodiment, a device is inserted into a body through a vagina (incision is inferior of a uterus) and bends within the body to accesses a target region at the top (superior portion) of a uterus, from an inferior direction (e.g. standard laparoscopic direction e.g. a direction more directly impinging on a target region than that a standard laparoscopic direction e.g. in a substantially posterior-inferior direction). A potential benefit of accessing the uterus from an inferior direction through an incision in the vagina is the ability to operate using of established laparoscopic surgical techniques, but through an incision in the vagina, which is potentially less invasive than an abdominal incision In some embodiments, bending of the device occurs by bending of flexible device portions as the device is inserted into the body, e.g. a segment bending as it is inserted and/or previously inserted segments bending as successive segments are inserted. In some embodiments, a straight device is inserted into the body and once the device is inserted it bends e.g. by actuation of the device portions and/or under friction between the device and patient tissue within the body. In some embodiments, a device with one or more folded portion is inserted into the body and bends to unfold.

An aspect of some embodiments of the invention relates to a method of hysterectomy through the vagina. In some embodiments, a device is inserted through an incision made in the vagina. In an exemplary embodiment, a device is inserted through an incision in the vagina posterior fornix into the Pouch of Douglas. In some embodiments, one or more portion of the device bends around the uterus to perform surgery on the uterine area (e.g. uterus, vagina, cervix, tissue surrounding the uterus, fallopian tube/s, ovary/s). In some embodiments, one or more portion of the device bends to access the uterus from the outside of the uterus, e.g. as device entrance through the posterior fornix is in a direction away from the uterus. In some embodiments, the device enters the abdominal cavity at the base of the uterus, closer to the cervix than the fundus and bends, to approach the uterus from an at least partially inferior direction and/or from a direction of a straight line from a point on an outer abdominal skin surface (e.g. umbilicus) to the uterus (e.g. a laparoscopic direction). In some embodiments, one or more device shoulder is positioned closer to the cervix than to the fundus. In some embodiments, one or more device shoulder is positioned closer to the fundus than to the cervix.

In some embodiments, the incision in the posterior fornix is made using a veress needle through which the abdominal cavity is then optionally inflated. In some embodiments, the incision is enlarged and/or dilated before insertion of the device. In some embodiments, the incision in the posterior fornix is made using a trocar.

In some embodiments, a port inserted into the vagina seals the abdominal cavity and/or provides support to the surgical device (e.g. inserted through the port) and/or to a uterus manipulator (e.g. inserted through the port).

Alternatively or additionally, in some embodiments, a port is placed into the incision sealing the incision and/or providing support to the device. Optionally, the port is coupled to the cervix e.g. to provide support to the port. Optionally, the port is coupled to a uterus manipulator.

Optionally, a uterus manipulator is used in gynecological surgery (e.g. hysterectomy surgery). In some embodiments, a uterus manipulator is secured while allowing access to the vagina posterior fornix. Optionally, in some embodiments, the device supported by coupling to a port, the port, for example, coupled to the cervix. Optionally, a port is coupled to the uterus manipulator. A potential benefit of supporting the device by a port coupled to the cervix is the ability to access the abdominal cavity through an incision in a thin tissue layer, where the layer is, for example, unable to provide sufficient support to a port, (e.g. incision in the vagina posterior fornix).

In some embodiments, the abdominal cavity is inflated before incision is made from the vaginal cavity in the Vagina posterior fornix. A potential benefit being, that, generally, inflation increases separation between organs, potentially reducing the risk of incising causing damage to other tissue (e.g. rectum). In some embodiments, an incision is initially made in the abdomen (e.g. umbilical incision), through which the abdomen is inflated (e.g. with carbon dioxide).

In some embodiments, inflation of the abdomen is made through an internal incision in a fallopian tube. In some embodiments, a device including an inner cavity and a cutting edge is inserted from the uterus into a fallopian tube. In some embodiments, the cutting edge punctures through the fallopian tube to the abdominal cavity. The abdominal cavity is then inflated by gas inserted through the device inner cavity. In some embodiments, the device including an inner cavity uses suction and pressure feedback, for example, as described above, when making the incision in the fallopian tube.

An aspect of some embodiments of the invention relates to a port which is coupled to a portion of a patient body through which a device including a mechanical arm is inserted. In some embodiments, the port is inserted into and/or coupled to a natural orifice (e.g. the vagina). In some embodiments, a uterus manipulator and/or other optional tools are inserted into the patient through the port. Potentially, the port prevents and/or reduces movement with respect to the patient of (e.g. supporting portions) of the tools inserted through it. Optionally, in some embodiments, the port is coupled to a portion of the system, for example, a patient support surface.

In some embodiments, a treatment (e.g. hysterectomy) includes inserting a port into a natural orifice and/or coupling a port to a natural orifice and then inserting one or more mechanical device limb into a patient through the port.

An aspect of some embodiments of the invention relates to making an incision where tissue is brought towards a cutting edge (e.g. tissue is brought to an element comprising a cutting edge) for example, by increasing pressure between tissue to be cut and a cutting edge (e.g. using suction). In some embodiments, once an incision is made, pressure between the cutting edge and tissue reduces preventing further cutting. In some embodiments, pressure is further reduced (e.g. by cessation of applied suction) once a measured reduction in pressure indicates that an incision has been made.

In some embodiments, a device for incision is sized and shaped such that increasing pressure between the a device end including a cutting edge and body tissue to be cut brings the tissue into contact with the device.

For example, in some embodiments, an incision is made in the vagina posterior fornix using a device including a cutting edge with a concave portion (e.g. inlet and/or hollow and/or depression and/or cup-shape) sized such that the cervix fits into the concave portion and that an increase in pressure in the depression brings the posterior fornix into contact with an edge of the concave portion. In some embodiments, an edge of the concave portion includes an optionally sharp cutting edge. In some embodiments, the concave portion is placed over the cervix with the sharp edged portion located at the vagina posterior fornix. The cup and/or tissue are brought together until the cutting edge makes an incision in the vagina posterior fornix. A potential benefit is control over the position and/or extent of the incision (e.g. using a different depth concave portion and/or a different length cutting edge). In some embodiments, the tissue and concave portion are brought together by suction. Optionally, reduction in suction pressure is used to ascertain that an incision has successfully been made. A potential benefit of using suction is cutting with minimal force and/or control over the speed and/or force of cutting, for example, reducing risk of damaging the rectum.

In some embodiments, an incision is made in a fallopian tube by a device including a cutting edge inserted into the fallopian tube. In some embodiments, pressure between the cutting edge and fallopian tube is reduced, collapsing the tube bringing a portion of the tube into contact with the cutting edge.

An aspect of some embodiments of the invention relates to protecting user tissue, for example, by pushing and/or holding patient anatomy away and/or shielding from a surgical zone. In some embodiments, a system including mechanical arms (e.g. as described herein) includes a retractor tool (e.g. as described herein).

In some embodiments, the tool is mounted on a support and a device including mechanical arms is mounted on the support.

In some embodiment, the tool is extendable away from one or more mechanical arm (e.g. in one or more direction), where the tool extends by expansion and/or is pushed (e.g. by a motor).

In some embodiments, mechanical device arm/s and the tool are actuated by the same motor unit.

In some embodiments, the retractor tool is coupled to a mechanical arm and/or a mechanical arm includes a retractor tool end effecter.

In some embodiments, a tool inserted into a patient includes an expandable portion. In some embodiments, the tool is inserted, expanded, and used to push and/or hold user tissue away from portion/s of a patient body being operated on. For example, in some embodiments, the bowels are pushed away from the uterus by the tool e.g. during a hysterectomy. In some embodiments, the tool is inserted the same direction of insertion and/or through the same incision as a device including mechanical arms.

In some embodiments, one or more mechanical limb is inserted at a different angle and/or inserted to a different depth and/or is inserted through a different incision. For example, assisting access to a target by more than one mechanical limb, optionally from different directions.

In some embodiments, at least a portion of a surgical device mechanical limb is covered with a cover, for example, a sterile cover e.g. providing a sterile separation between a device arm and the patient. For example, an electrically insulating cover.

In some embodiments, devices and/or systems and/or methods described in this document are used in thoracic treatments (e.g. thyroidectomy).

In some embodiments, devices and/or systems and/or methods described in this document are used in splenectomy.

In some embodiments, devices and/or systems and/or methods described in this document are used in reproductive surgery (e.g. infertility treatment, sterilization).

In some embodiments, devices and/or systems and/or methods described in this document are used in reconstructive pelvic surgery.

In some embodiments, treatment is performed on an abdominal target is performed by inserting device arm/s into the abdomen e.g. through a surface abdominal incision and/or through the pelvic outlet (e.g. through a natural reproductive and/or excretory orifice) and bending the arms to approach a target.

In some embodiments, treatment is performed on a thoracic target by inserting one or more device arm under the rib cage from an incision superior or inferior to the rib cage, where device arm/s are bent to access the target. In some embodiments, e.g. as described herein, one or more device arm is inserted between adjacent ribs.

In some embodiments, one or more device limb includes a chain of at least two rigid segments coupled by flexible connecting sections also herein termed "joints". In some embodiments, at least two rigid segments are long where, for example, a long axis length of one or more long rigid segment is at least 1.5 times, or at least double, or at least triple, or at least 5 times, or at least 10 times, or intermediate values, a maximum extent of the segment perpendicular to said long axis. A potential benefit of long rigid portions, for example, in comparison to a larger number of shorter portions, is that movement and/or control errors are reduced e.g. as movement and/or control errors are a sum of error movement for each joint.

In some embodiments, a proportion of a device and/or device limb long axis length which is rigid (and/or formed by rigid segments) is high, for example 20% or more, 40% or more, than 60% or more, or 80% or more. In some embodiments, a proportion of a sum of rigid segment long axis lengths is large in comparison to a total device and/or limb long axis length, for example 20% or more, 40% or more, than 60% or more, or 80% or more.

In some embodiments, a method of treatment includes inserting a device including one or more mechanical limb (e.g. as described herein) and one or more laparoscopic tool. In some embodiments, a target is simultaneously and/or sequentially treated by one or more mechanical limb and a laparoscopic tool.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Device with Arms

Referring now to the drawings, FIG. 1A is a simplified schematic side view of a device 100 (e.g. surgical device) including a plurality of arms, according to some embodiments of the invention. In some embodiments, the device includes a first arm 104 and a second arm 102.

In some embodiments each arm 104, 106 includes a support segment 102, 103, coupled to a first segment 112, 114 by a first connecting section 108, 110, where first segment 112, 114 is coupled to a second segment 116, 118 by a second connecting section 120, 122, and a third segment 124, 126 coupled to second segment 116, 118 by a third connecting section 128, 130.

Figure 1B:
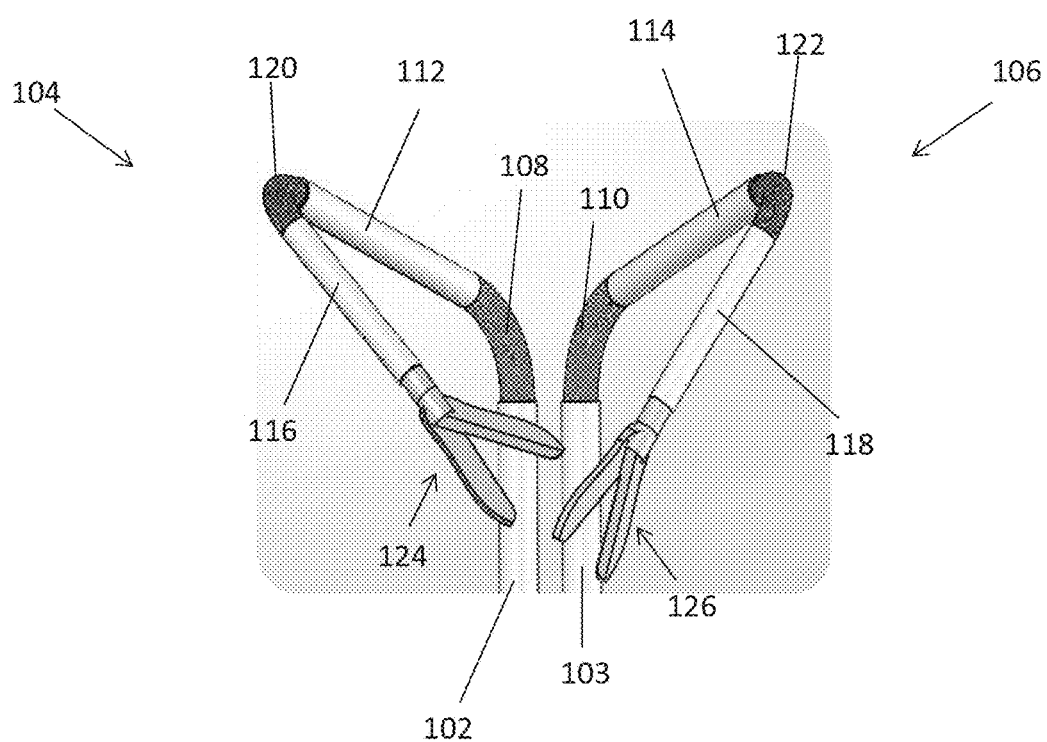
FIG. 1B is a simplified schematic of a device including a plurality of arms, according to some embodiments of the invention.

In some embodiments, one or more support segments 102, 103 are rigid. In some embodiments one or more of support segments 102, 103 are flexible or include a flexible portion In some embodiments, support segments 102, 103 are coupled, e.g. by a cover 102a. In some embodiments, support segments are coupled at only a portion of the torso length or are not coupled: FIG. 1B is a simplified schematic of a device 100 including a plurality of arms 104, 106, according to some embodiments of the invention.

In some embodiments, one or more arm includes a humanoid like structure. For clarity, in some portions of this document, device segments and connecting sections are referred to by anatomical names: Support segments 102, 103 are also termed first torso 102 and second torso, first connecting sections 108, 110 are also termed first shoulder joint 108, second shoulder joint 110, first segments, 112, 114 are also termed first humerus 112 and second humerus 114, second connecting sections 120, 122 are also termed first elbow joint 120, and second elbow joint 122, second segments 116, 118 are also termed first radius 116 and second radius 118 and third segments 124 and 126 are also termed first hand tool 124 and second hand tool 126.

In some embodiments, one or more connecting section includes a hinge. In some embodiments, one or more connecting section is flexible and/or includes a flexible portion. In an exemplary embodiment, for example, as described in more detail below, a device arm includes an elbow joint and a shoulder joint where bending of the joint is distributed along the joint in a direction of a joint long axis.

In some embodiments, torsos 102, 103 are close together, for example, a long axis of first torso 102 and a long axis of second torso 103 are within 5 mm, or 3 mm, or 1 mm of each other.

In some embodiments, one or more device segment has a substantially cylindrical external shape (e.g. radius, humerus). In some embodiments, joints have circular long axis cross-section. Alternatively, in some embodiments, one or more device segment and/or joint has non-circular cross section external shape, for example, oval, square, rectangular, irregular shapes.

In some embodiments, a mechanical arm includes one or more short and/or adjustable segment. In some embodiments, flexible portions are directly connected.

Figure 1C:
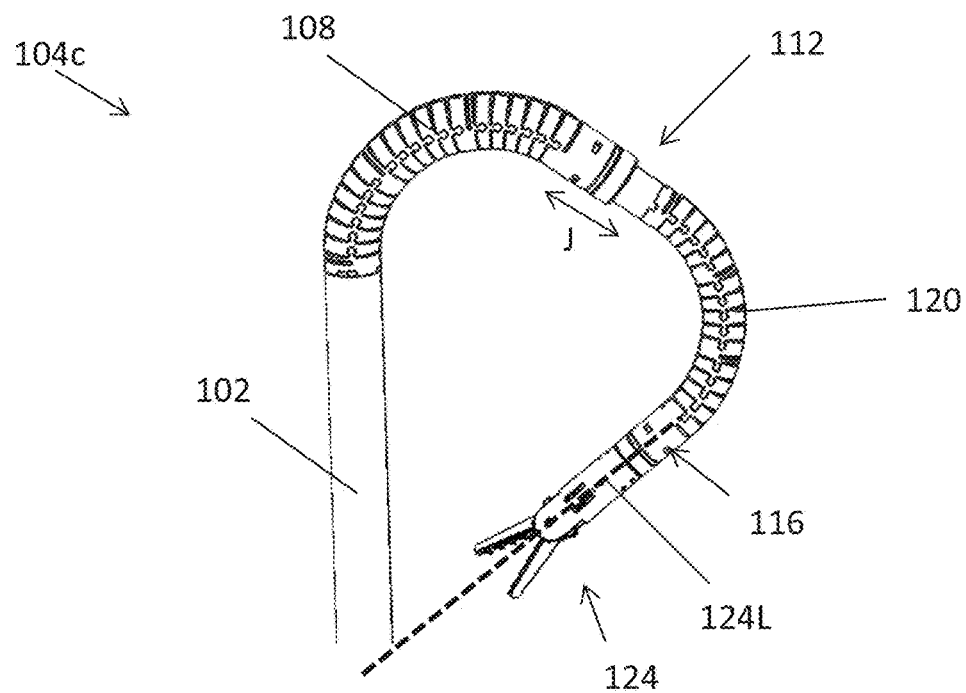
FIGS. 1C-1D are simplified schematic side views of mechanical arms, according to some embodiments of the invention.
Figure 1D:
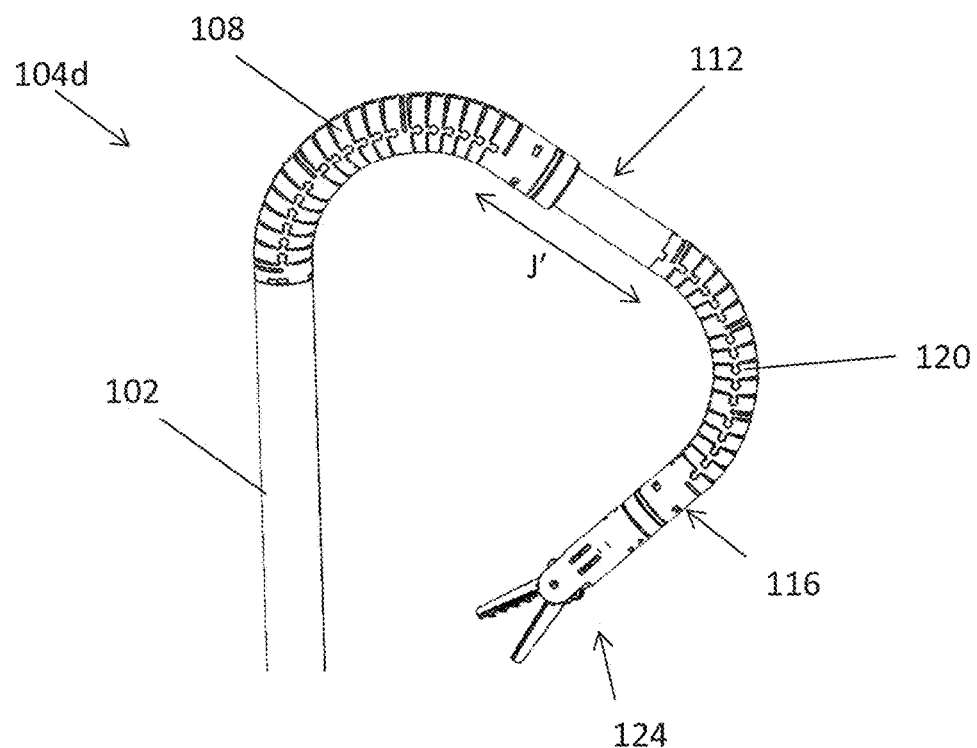

FIGS. 1C-1D are simplified schematic side views of mechanical arms, according to some embodiments of the invention. FIG. 1C illustrates an exemplary embodiment where a humerus segment 212 is short, for example, the segment including a long axis length, J of 1-50 mm, or 1-35 mm, or 10-20 mm, or approximately 10 mm or lower or higher or intermediate ranges or lengths.

In some embodiments, a user selects arm/s including desired segment lengths, where for example, selection is based on patient anatomy and/or a procedure to be performed. For example, when treating a child a user, in some embodiments, selects one or more arm with one or more short segment (e.g. as illustrated by FIG. 1C). For example, when treating an obese patient, a user, in some embodiments, selects an arm with one or more a long segment for example, a standard arm with a long humerus segment (e.g. as illustrated by FIG. 1D) (e.g. humerus segment length, J' is 10-100 mm, or 20-35 mm, or 10-20 mm, or lower or higher or intermediate ranges or lengths).

In some embodiments, a device includes a kit with different structured arms (e.g. different segment lengths, e.g. different arm sizes).

Alternatively or additionally, in some embodiments, one or more segment length is adjustable, e.g. during a treatment and/or during set-up of the device. For example, in some embodiments, the arm illustrated in FIG. 1C is adjustable (e.g. by telescoping of humerus segment 212) is adjustable to the configuration illustrated in FIG. 1D.

In some embodiments, extension and/or retraction of one or more segment is effected by a portion connected to the segment (e.g. a segment extension) being moved with respect to other portions of a mechanical arm. For example, in some embodiments, a segment extension (e.g. extension 3316E FIG. 33B) is moved (e.g. by a motor located in a motor unit e.g. motor unit 4000 FIG. 40) to increase a length of a segment (e.g. segment 3316 FIG. 33B). In some embodiments, a motor uses a screw mechanism to move the segment extension (for example, a screw mechanism similar to a screw mechanism for actuating a gripper e.g. as described regarding FIG. 36A-36B).

Exemplary Freedom of Movement, Exemplary Human Freedom of Movement

In some embodiments, a device limb has at least the freedom of movement of human arms. Generally, segments of human limbs (e.g. arms, legs) move by flexion and extension from a proximal segment joint, and rotation around the proximal segment joint. For example, a human radius flexes and extends at the elbow and rotates around the elbow.

The term proximal joint herein refers to the joint which is least removed from the torso to which a segment is coupled, e.g. a hand proximal joint is the wrist, a radius proximal joint is the elbow joint, a humerus proximal joint is the shoulder joint.

The term proximal segment herein refers to the segment which is least removed from the torso to which a segment is coupled (e.g. by a proximal segment joint). For example, a hand proximal segment is the radius, a radius proximal segment is the humerus, a humerus proximal segment is the torso.

In some embodiments, one or more joint is uni-directionally bendable and extendable. In some embodiments, segment rotation around a segment proximal joint is achieved by rotation of a proximal segment around a proximal segment long axis. For example, rotation of the hand around the wrist joint is by rotation of the radius around a radius long axis.

Generally, human freedom of movement for arms includes limits to the angles of rotation and flexion. Optionally, in some embodiments, the device is restricted to human freedom of movements e.g. during one or more control mode.

Figure 2A:
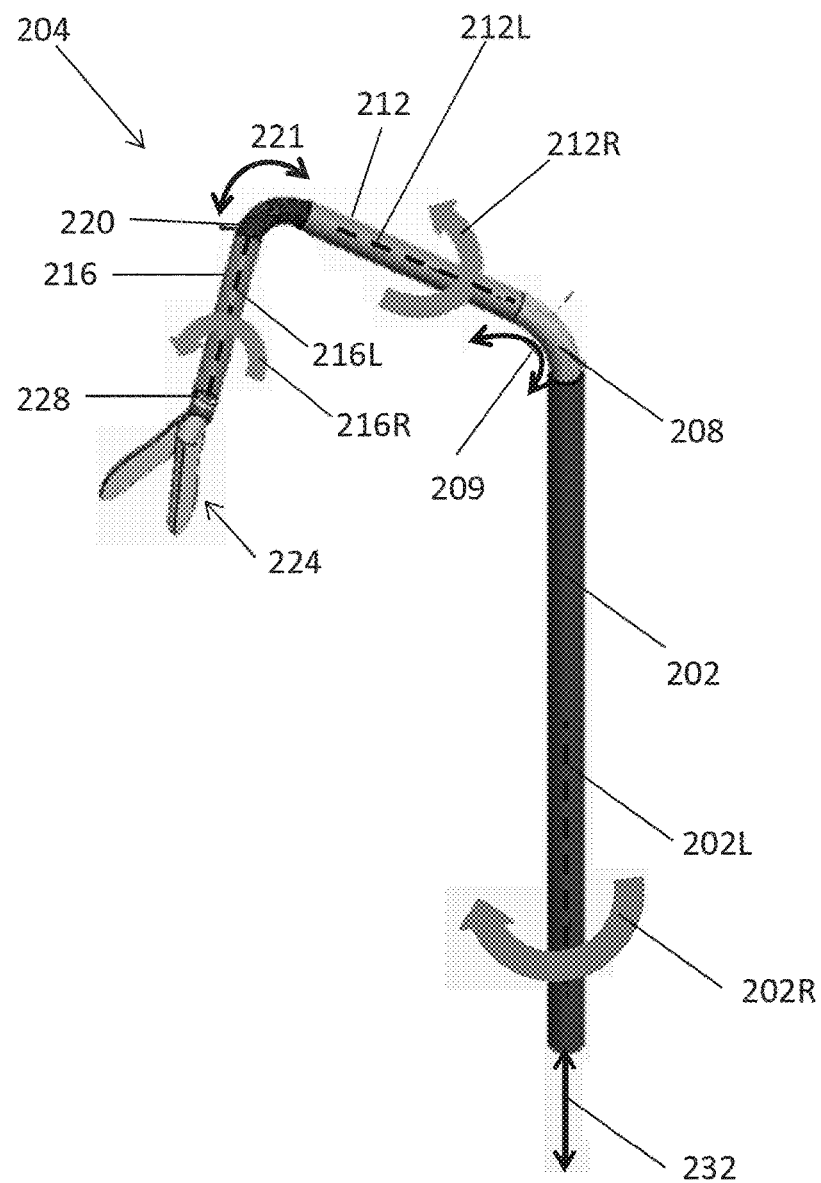
FIG. 2A is a simplified schematic side view of a mechanical arm, according to some embodiments of the invention.

FIG. 2A is a simplified schematic side view of a mechanical arm 204, according to some embodiments of the invention.

In some embodiments, each segment of arm 204 is rotatable around a segment long axis. For example, in some embodiments, torso 202 is rotatable 202R around a torso long axis 202L. For example, in some embodiments, humerus 212 is rotatable 212R around a humerus long axis 212L. For example, in some embodiments, radius 216 is rotatable 216R around radius long axis 216L.

Figure 3:
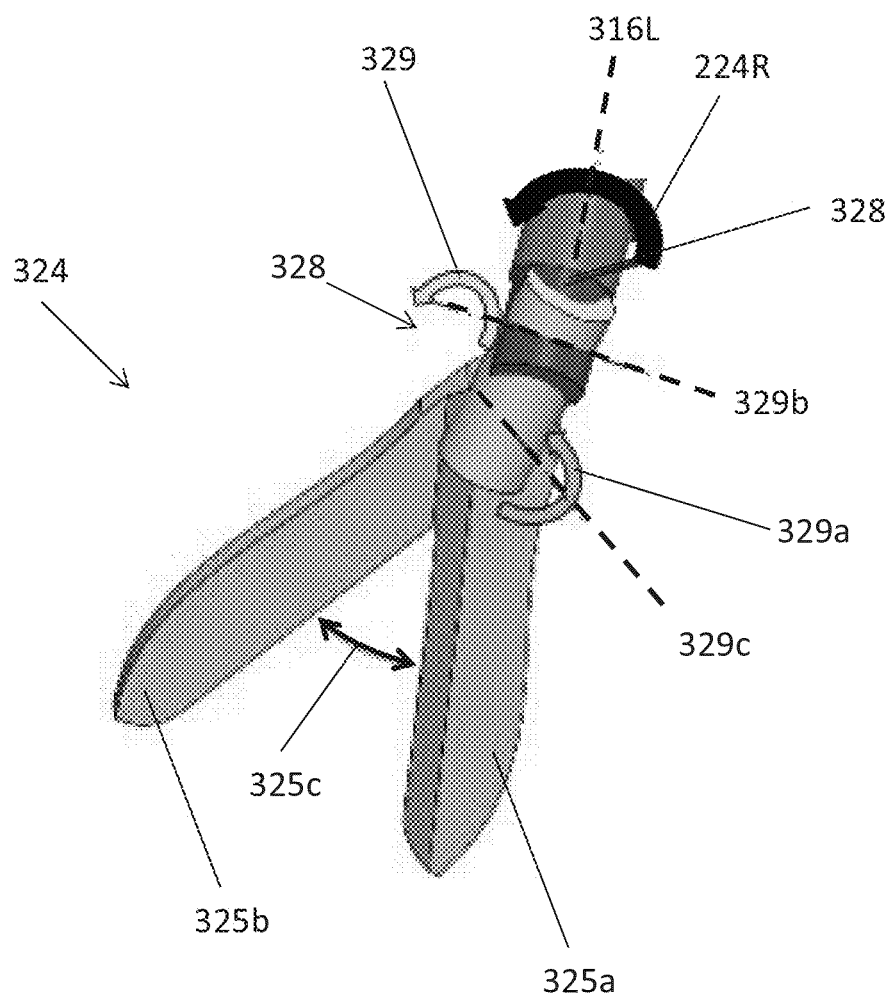
FIG. 3 is a simplified schematic side view of a hand segment, according to some embodiments of the invention.

FIG. 3 is a simplified schematic side view of a hand segment 324, according to some embodiments of the invention. In some embodiments, hand segment 324 is rotatable around a hand long axis.

In some embodiments, one or more segment is rotatable in both directions (e.g. clockwise and anticlockwise around the segment long axis). Alternatively, in some embodiments one or more segment is rotatable about a segment long axis in one direction only.

Referring back to FIG. 2A, in some embodiments, for example, analogous to human ability to stand and/or crouch and/or jump, the device is movable 232 in a direction parallel to torso long axis 202L.

In some embodiments, each segment flexes and extends at a segment proximal joint. For example, in some embodiments, radius 216 flexes and extends at elbow joint 220. For example, in some embodiments, humerus 212 flexes and extends at shoulder joint 208. Referring to FIG. 3, for example, in some embodiments, hand tool 324 is flexes and extends at wrist 328.

In some embodiments, flexion and extension of a segment at a joint is measured as an angle through which the joint bends. In some embodiments, flexion and extension of a segment is measured as an angle between a long axis of the flexed segment and a long axis of a proximal segment to the flexed segment. For example, the angle between a flexed radius long axis and a humerus long axis.

In an exemplary embodiment, flexible portions (e.g. elbow joint 220, humerus 212) bend uniformly, for example, where bending a radius of curvature is constant along the flexible portion when the portion is bent. In some embodiments, one or more flexible portion includes sub-portion/s with different radiuses of curvature (e.g. where a stack of a plurality of links forming a flexible portion is composed of links with different dimension/s (e.g. different lengths) and/or gaps (e.g. gaps 2799 FIG. 27) between links have different dimensions.

Figure 2B:
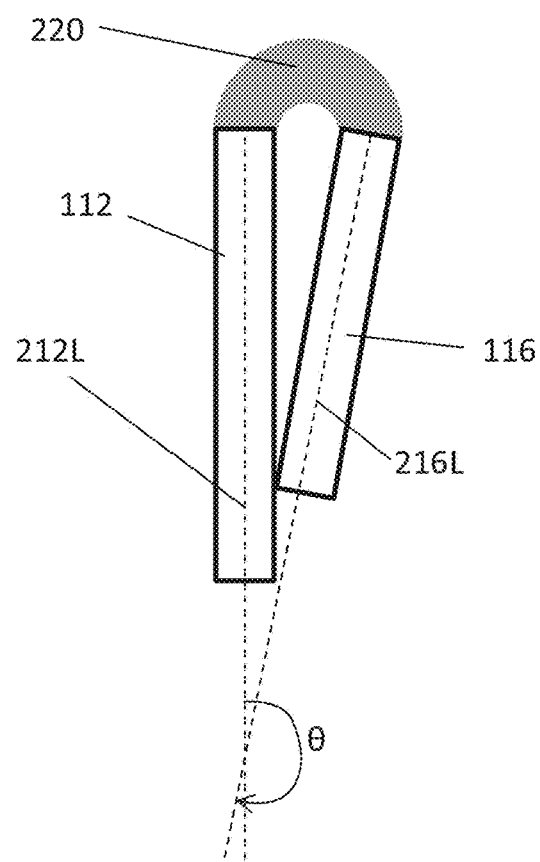
FIG. 2B is a simplified schematic of two segments connected by a joint, according to some embodiments of the invention.

FIG. 2B is a simplified schematic of two segments 212, 216 connected by a joint 220, according to some embodiments of the invention. FIG. 2B illustrates measurement of flexion of segment 216 as an angle, θ, between a first segment long axis 216L and a second segment long axis 212L.

In some embodiments, θ is more than 180°, due to, for example, sufficient joint length (e.g. length of a long axis of the joint is longer than double combined diameter/cross sectional maximum extent of both segments) and ability of the joint to flex and/or extend.

Figure 2C:
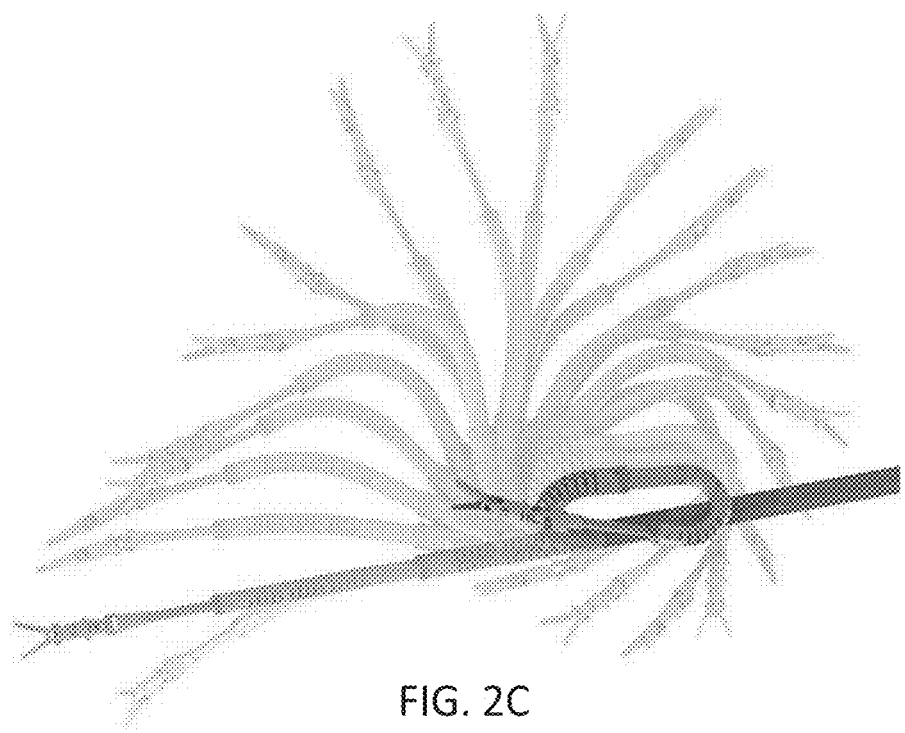
FIG. 2C shows illustrations of possible limb positions, and/or movement of a device with time, according to some embodiments of the invention.

FIG. 2C shows illustrations of possible limb positions, and/or movement of a device with time, according to some embodiments of the invention. FIG. 2C shows potential flexibility of an exemplary device limb including exemplary angles of bending of joints of 180° and more.

Referring back to FIG. 2A, in some embodiments, humerus 212 flexes and extends 209 at shoulder joint 208 (also herein termed shoulder flexion), by up to at least 45°, or by up to at least 90°, or by up to at least 180°. In some embodiments, shoulder flexion is more than 180°. In some embodiments, shoulder flexion is up to 250°, or up to 300°. In an exemplary embodiment, shoulder flexion is about 200°.

In some embodiments, radius 216 flexes and extends from elbow joint 220 (also herein termed elbow flexion), by up to at least 45°, or by up to at least 90°, or by up to at least 180°. In some embodiments, elbow flexion is more than 180°. In some embodiments, elbow flexion is up to 250°, or up to 300°. In an exemplary embodiment, elbow flexion is approximately 200°.

Referring now to FIG. 3, in some embodiments, a hand segment 324 (e.g. hand tool) flexes and extends 329b at wrist joint 328. In some embodiments hand segment 324 is rotatable around the wrist joint in a plane perpendicular to radius long axis 329a (e.g. in a plane including scissor blades 325a, 325b), for example, in movement corresponding to human radial and/or ulnar deviation. In some embodiments, flexing and extending of hand segment 324 is about an axis 329b perpendicular to a long axis of the radius 316L. In some embodiments, radial and ulnar deviation is about an axis 329c.

In some embodiments, hand segment 224, 324 flexes and extends from wrist joint 228, 328 (also herein termed wrist flexion), by up to at least 45°, or by up to at least 60°, or by up to at least 90°, or by up to at least 180°. In an exemplary embodiment wrist flexion is 90° (e.g. ±45°).

In some embodiments, a mechanical arm includes less structural complexity (e.g. less portions) and/or less freedom of movement than that of human arms.

For example, in some embodiments, a mechanical arm does not include a wrist joint. For example, in some embodiments, flexion and extension of an end effecter is controlled by a flexible section corresponding to an elbow joint. For example, in some embodiments, an end effecter is coupled to a rigid portion (e.g. corresponding to a radius) and the flexion of both the end effecter and the rigid portion is controlled by a flexible section connected to the rigid portion.

Referring now back to FIG. 1C, in some embodiments, a mechanical arm 104c includes an end effecter 124 coupled to a second segment 116 where the coupling is a rigid coupling (e.g. without a third connecting section, e.g. without a wrist joint). In some embodiments, mechanical arm 104c includes a support segment 102 coupled to a flexible first portion 108, where flexible first portion 108 is coupled to a flexible second portion 116.

In some embodiments, end effecter 124 and second segment 116 are one piece and/or are rigidly connected.

In some embodiments, end effecter 124 is rotatable independently of second segment 116, e.g. end effecter 124 is rotatable around an end effecter long axis 124L.

In some embodiments, hand segment (e.g. 124, 126, FIG. 1A and FIG. 1B, 224 FIG. 2A, 324 FIG. 3) includes a hand tool. In some embodiments, a hand tool includes a scissors (e.g. 124 FIG. 1A, 224 FIG. 2A, 324 FIG. 3). Hand tools are described in more detail below.

In some embodiments, a device includes at least two flexible portions, where each flexible portion is bendable by at least 120°. In some embodiments, two flexible portions are bendable together by up to 180°. In some embodiments, two flexible portions are bendable together by more than 180°. In some embodiments, each of one or two or more device flexible portion is bendable by 180° or more. In an exemplary embodiment, combined flexions provide a total bending of the device of 360° or more. For example, device joints are bent such that the device forms a circle and/or coil in space, e.g. as illustrated by FIG. 2C.

In some embodiments, one or more arm segment is able to move with more than human freedom of movement: For example, in an exemplary embodiment, humerus rotation about a humerus long axis and/or radius rotation about a radius long axis and/or hand rotation about a humerus long axis.

Exemplary Device Flexibility

In some embodiments, the device, e.g. within a patient, is highly flexible. A potential benefit being, for example, flexibility of path and/or movement of the device within a patient (e.g. reducing tissue damage) and/or the ability to perform surgical procedures in a desired way (e.g. position of incisions, angle from which incisions are made).

As described previously, in some embodiments, the angle of each segment (and/or effective segment) with respect to adjacent segments is adjustable e.g. by flexion/extension of segments around coupling joints. Optionally, each segment is flexible/extendable and rotatable around a segment proximal joint.

In some embodiments, for one or more segment, segment flexion is up to 180° or more, and the segment is rotatable by up to 180° or more about a proximal segment joint: In some embodiments, possible positions of a segment distal end form a cylinder around the segment proximal joint. A potential benefit being a wide range of possible positions of the device in space.

Exemplary Distance of Hands to Torso, Angle Between Arm Radiuses

In some embodiments, the device is flexible such that, positions of one or more hand of a device and/or one or more distal end of a radius of a device are locatable substantially at the torso and/or shoulder joint. In some embodiments, more than one hand and/or distal end of radiuses are locatable substantially at the torso and/or shoulder joint when torsos are close together (e.g. within 10 mm, within 5 mm, or 3 mm, or 1 mm of each other) and optionally. A potential benefit being the ability to access a target (e.g. with one or more hand tool) close to the torso.

In some embodiments, separation between a distal end of the radius and the shoulder joint is reducible to 40%, or 20%, or 10%, or 5%, or 1%, of a length of the humerus or radius. In some embodiments separation between a distal end of the radius and the torso is reducible to 40%, or 20%, or 10%, or 5%, or 1%, of a length of the humerus or radius.

In some embodiments, an angle (herein "radius angle") between a first arm radius long axis and a second arm radius long axis is adjustable between substantially zero (arms are held out parallel, forwards of the torso), through intermediate angles, for example where hands are forward of the torso and together, and up to 180°, for example, where elbows are outward and hands are together.

A potential benefit of parallel radiuses (and other low radius angles e.g. less than 20°) is the ability of the device to interact (e.g. operate) on an area with restricted access e.g. in some embodiments, the device accesses a target through a narrow passage. A potential benefit of larger angles between arm radiuses (e.g. over 45°), is the ability for the arms (e.g. arm hands) to access a target close to the torso.

Exemplary Long Device

In some embodiments, a potential length of a device (e.g. a length including a hand axial length, a radius axial length, a humerus axial length and a torso axial length) within a body is long.

In some embodiments, a potential length of a device within a human body with respect to a deepest extent of the device within a human body is long. In some embodiments, a length of the humerus segment is 20-100 mm, or 40-80 mm, or 50-70 mm, or about 60 mm. In some embodiments, a length of the radius segment is 10-90 mm, or 20-70 mm, or 30-60 mm, or about 50 mm.

For example, in some embodiments, an ability of the device to bend and/or fold means that the device travels a long path within a patient's body, optionally, in comparison to a maximum depth of insertion into a body (maximum depth e.g. measured as the longest straight path from a skin surface and/or an incision site to a portion of the device).

Exemplary Long Joints

In some embodiments, one or more joint is long in an axial direction. For example, in some embodiments, a joint is long with respect to one or more segment length. For example, in some embodiments, a joint is long with respect to one or more segment maximum cross sectional dimension (e.g. segment diameter).

In some embodiments, device joints are long with respect to human anatomy joint lengths (e.g. with respect to segment lengths and/or diameters).

In some embodiments, a joint long axis length is at least 1.5 times, or 2 times, or 3 times, or 5 times a maximum cross sectional extent of the joint (e.g. diameter of the joint).

A potential benefit of a long joint is increased possible flexion and/or extension, for example, in some embodiments, a long joint means that, flexion and/or extension is not prevented by segments coming into contact with each other.

A potential benefit of a device including one or more long joints (e.g. as opposed to a device with pivot joints and/or hinges) is the ability to bend the device with a smaller lateral extent of the device. A further potential benefit is a rounder and/or less sharp curve of the joint, for example, potentially less invasive and/or damaging to tissue. For example, referring to FIG. 5A, long joints and/or joints with a large radius of curvature (e.g. in some embodiments, a minimum radius of curvature of a joint is 2-15 mm, or 4-12 mm, or 6-10 mm or intermediate values) have a small lateral extent. For example, a small lateral extent is associated with a length, L, between a midpoint of a long joint and an intersection of effective segment long axes being 5-50%, or 10-40%, or lower or higher or intermediated ranges or percentages, of an effective length of a limb distal to the joint (e.g. of limb length B'), for example, when the joint is bent by 45° or more.

Exemplary Structure, Dimensions

In some embodiments, a torso thickness (e.g. diameter) and/or a shoulder joint thickness (e.g. diameter) is 1 mm-20 mm, or 3 mm-15 mm, or 5 mm-10 mm or intermediate values. In an exemplary embodiment, a torso diameter and/or a shoulder joint diameter is about 8 mm.

In some embodiments, a humerus thickness (e.g. diameter) and/or an elbow joint thickness (e.g. diameter) is 1 mm-15 mm, or 2 mm-10 mm, or 4 mm-8 mm or intermediate values. In an exemplary embodiment, a humerus thickness (e.g. diameter) and/or an elbow joint thickness (e.g. diameter) is about 6 mm.

In some embodiments, a radius thickness (e.g. diameter) and/or a shoulder joint thickness (e.g. diameter) is 0.5 mm-10 mm, or 1 mm-6 mm, or 3 mm-4 mm or intermediate values. In an exemplary embodiment, a radius thickness (e.g. diameter) and/or a wrist joint thickness (e.g. diameter) is about 3-4 mm.

In some embodiments, a central long axis length of the humerus segment is 20-100 mm, or 40-80 mm, or 50-70 mm, or about 60 mm or intermediate values. In some embodiments, a central long axis length of the radius segment is 10-90 mm, or 20-70 mm, or 30-60 mm, or intermediate values or about 50 mm.

In some embodiments, a minimum radius of curvature of a joint is 2-15 mm, or 4-12 mm, or 6-10 mm or intermediate values.

In an exemplary embodiment, a minimum radius of curvature of a joint is about 10 mm. In an additional exemplary embodiment, a minimum radius of curvature of a joint is 6 mm.

In some embodiments, one or more segment is thin. In some embodiments, a thin segment has a maximum extent perpendicular to a segment long axis of about 20% of a long axis length or less, or 10% of the long axis length or less, or 8% of the long axis length or less or 6% of the long axis length or less or intermediate values. A potential benefit of a thin device is reduced invasiveness of the device within a body, for example, the device displaces and/or damages less tissue than a wider device of the same length.

Figure 4A:
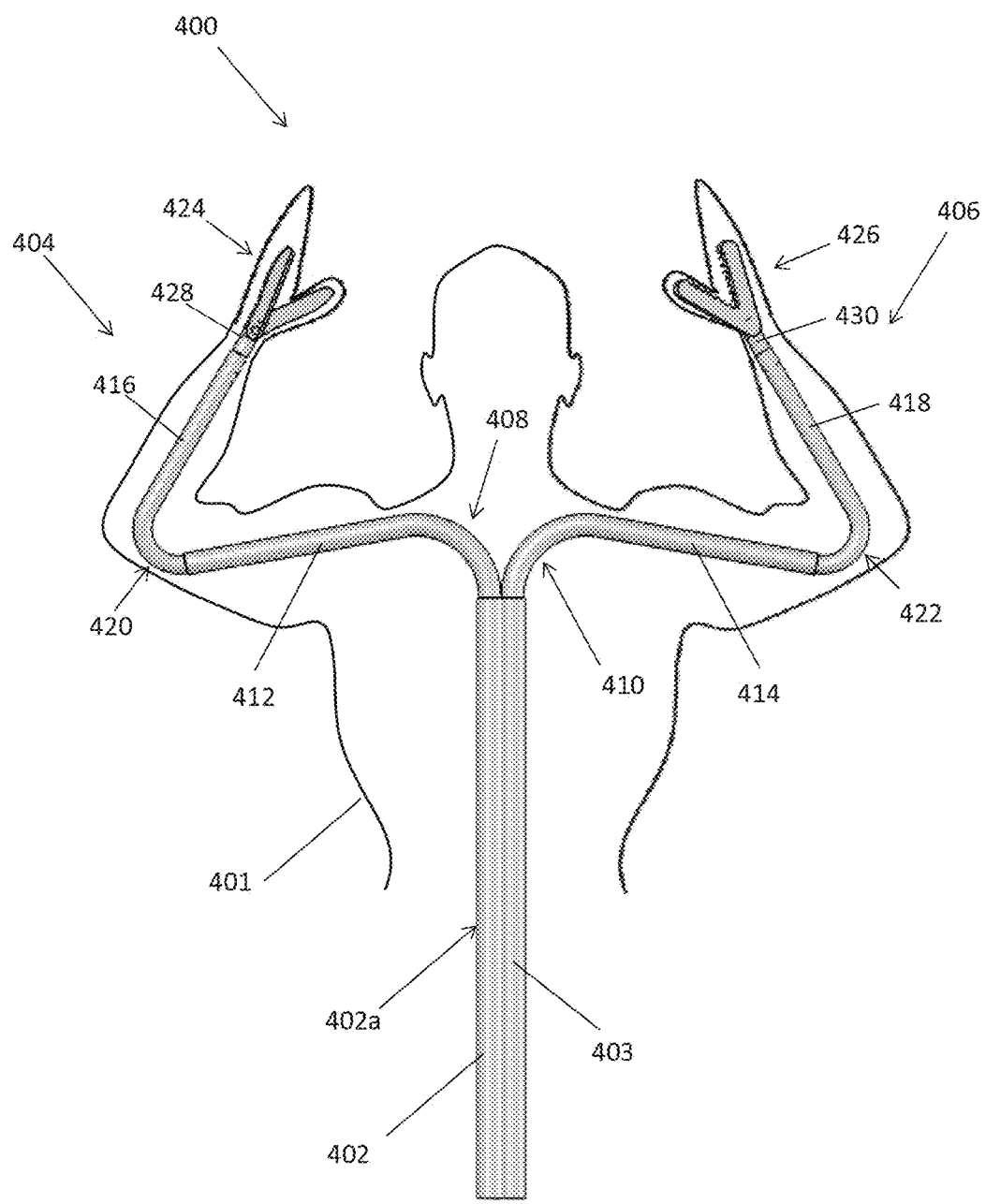
FIG. 4A is a simplified schematic side view of a device where device humanoid proportions are illustrated by comparison to a simplified schematic of a human upper body, according to some embodiments of the invention.
Figure 4B:
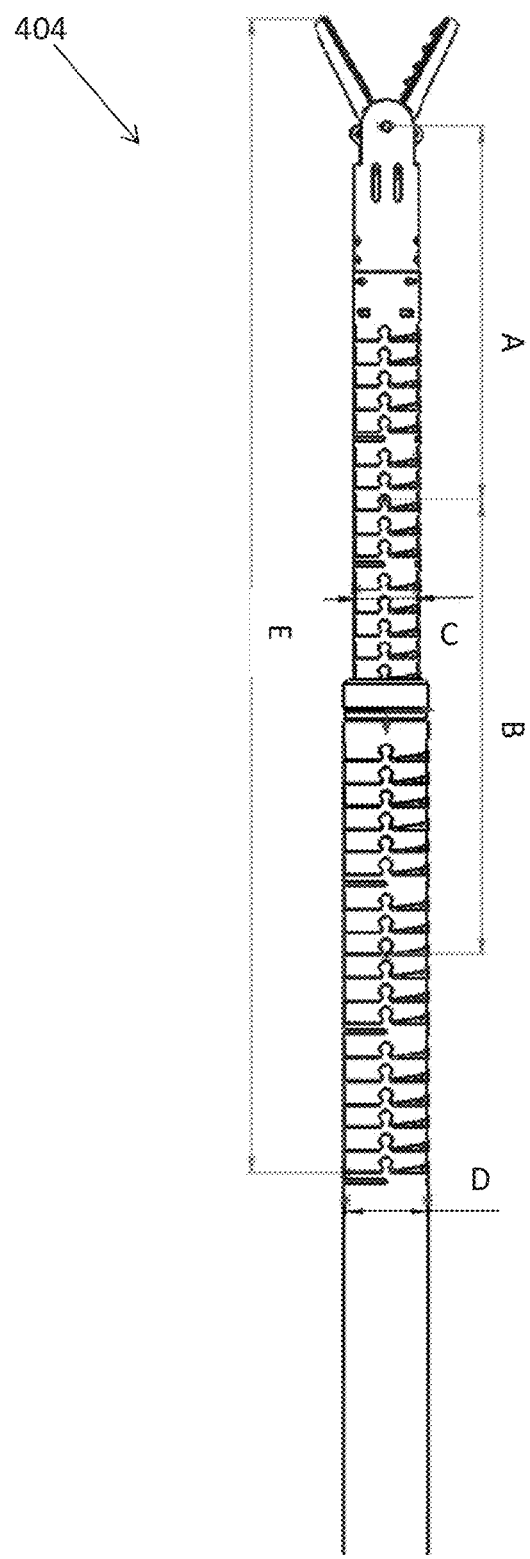
FIG. 4B is a simplified schematic side view of a mechanical arm, according to some embodiments of the invention.

FIG. 4B is a simplified schematic side view of a mechanical arm 404, according to some embodiments of the invention. In an exemplary embodiment, In some embodiments, a support segment and a shoulder joint have about the same thickness and/or cross sectional shape and/or dimension/s. In some embodiments, a shoulder joint and humerus segment have about the same thickness and/or cross sectional shape and/or dimension/s. In some embodiments, an elbow joint and a radius segment have about the same thickness and/or cross sectional shape and/or dimension/s.

In some embodiments, a thickness of an elbow joint and/or a radius segment, (e.g. dimension C FIG. 4B) is 1-20 mm, or 3-15 mm, or 7-11 mm, or about 9 mm, or lower or higher or intermediate ranges or thicknesses. In an exemplary embodiment, dimension C is 9 mm.

In an exemplary embodiment, a support segment thickness (e.g. diameter), dimension D, is 8 mm.

In some embodiments, a central long axis length E of a portion of the mechanical arm including a shoulder joint, a humerus segment, a elbow joint, and a radius segment including a length of an end effecter is 50-200 mm, or 80-150 mm, or 90-120 mm, or about 110 mm, or lower or higher or intermediate ranges or lengths. In an exemplary embodiment length E is 111.7 mm.

In some embodiments, two support segments (torso segments) of a device including two or more mechanical limbs are configured (e.g. attached to a base) such that a long axes of the limb support segments are substantially parallel (e.g. within 5° or 10°, or 20° of parallel). In some embodiments, long axes of the limb support segments are configured at different directions.

Exemplary Structural Differences and Similarities to Human Arms

In some embodiments, two or more segments have length ratios similar to human segment length ratios. FIG. 4A is a simplified schematic side view of a device 400 where device humanoid proportions are illustrated by comparison to a simplified schematic of a human upper body 401, according to some embodiments of the invention. In some embodiments a ratio between two dimensions of a device and/or an arm is substantially similar to an equivalent average human ratio. For example, in some embodiments, a humerus segment central long axis length is about 20% longer than a radius segment central long axis length. In some embodiments, a humerus segment long axis length is about 15% longer or about 25% longer than a radius length.

In some embodiments, an effective segment length is measured along a central long axis between mid-points of flexible sections, or, if the segment is the most distal segment, along a central long axis between a distal end of the segment and a midpoint of the flexible section attaching a proximal end of the segment to the arm.

In some embodiments, the device lacks one or more segment (e.g. is composed entirely of flexible portions). In some embodiments, effective segment length, in some embodiments, is measured along a central long axis (or, in some embodiments as the length of a straight line) between flexible portion midpoints. In some embodiments, for the most distal flexible portion, an effective segment length is measured along a central long axis (or, in some embodiments as the length of a straight line) between a distal end of the most distal flexible portion to a midpoint of the flexible portion coupled to a proximal end of the most distal flexible portion.

In some embodiments, effective segment length is measured as a length of a straight line between intersections of extensions of axes tangential to long axes at centre points of adjacent segments (or, where there is no segment, extensions of axes tangential to long axes of flexible portions where flexible portions connect). Where an effective segment length of the most distal effective segment, in some embodiments, is measured as a length of a straight line between intersections of a long axis extension of an axis tangential to a long axis at a center point of an adjacent segment (or, where there is no segment, a extension of an axis tangential to a long axis of the flexible portions where flexible portions connect) to a distal end of the most distal segment (or, where there is no most distal segment, the device distally terminating in a flexible portion and/or end effecter, to a distal end of the most distal flexible portion).

In some embodiments, one or more segment effective length ratio is about the same as an average humanoid segment length ratio. For example, referring back to FIG. 4B, in some embodiments, an effective radius length is A and an effective humerus length is B where the ratio of long axis lengths A to B is about that of a human radius to humerus lengths (e.g. about 1:1.2).

In some embodiments, when a device arm is in different configurations, for example, different extents of bending of the different flexible portions, one or more effective segment length ratio remains within a range which is similar to that of the corresponding human segment ratio.

Figure 5A:
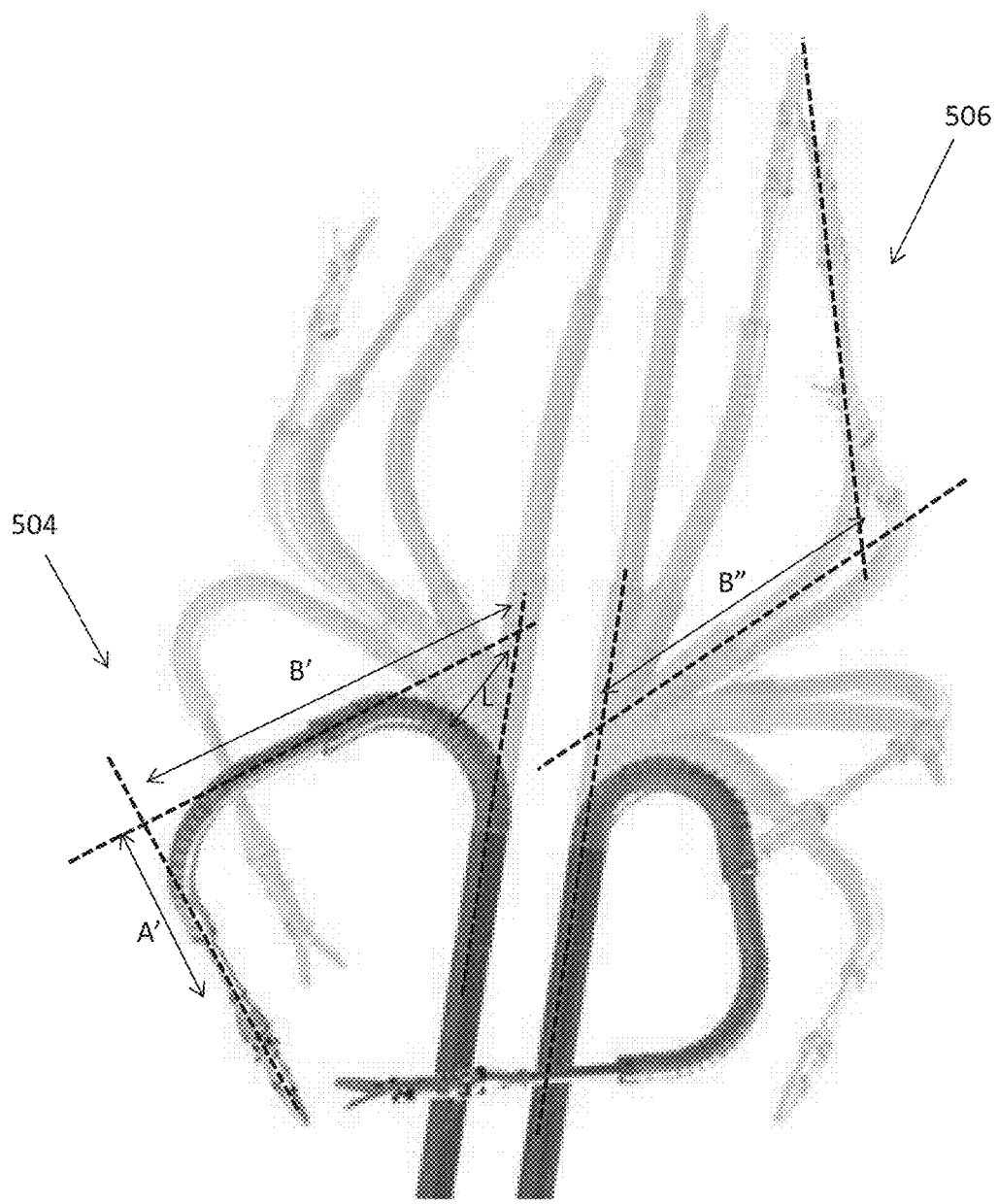
FIG. 5A shows illustrations of possible device positions, and/or movement of a device with time, according to some embodiments of the invention.

FIG. 5A shows illustrations of possible device positions, and/or movement of a device with time, according to some embodiments of the invention. For example, arm configuration 504 shows a configuration where effective segment lengths, A', B' are both increased from their lengths when the device arm is straight. Effective segment lengths are measured from intersections between extended central long axis of a central portion of the segment and, in the case of the most distal segment (e.g. effective length A'), from the distal end of the segment to an intersection.

In some embodiments, increasing bending at the joints, increases individual effective segment lengths. For example, effective length B" is less than that of effective length B'. However, ratios between effective lengths, for example between effective humerus and radius length is changed most from the ratio when the arm is in a straight position where one joint is bent and another joint is straight. For example, when a device arm is bent at the shoulder joint and straight at the elbow joint, the humerus effective length is increased from the humerus length when the arm is in a straight position, whereas the radius effective length is unchanged from when the arm is in a straight position.

Figure 5B:
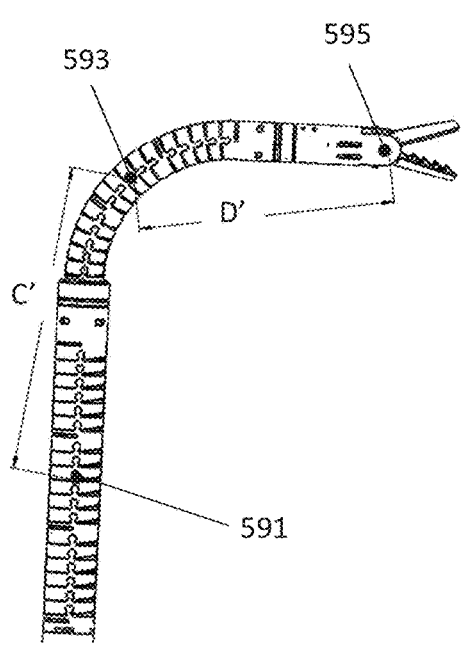
FIGS. 5B-5D are simplified schematic side views of a mechanical arm, according to some embodiments of the invention.
Figure 5C:
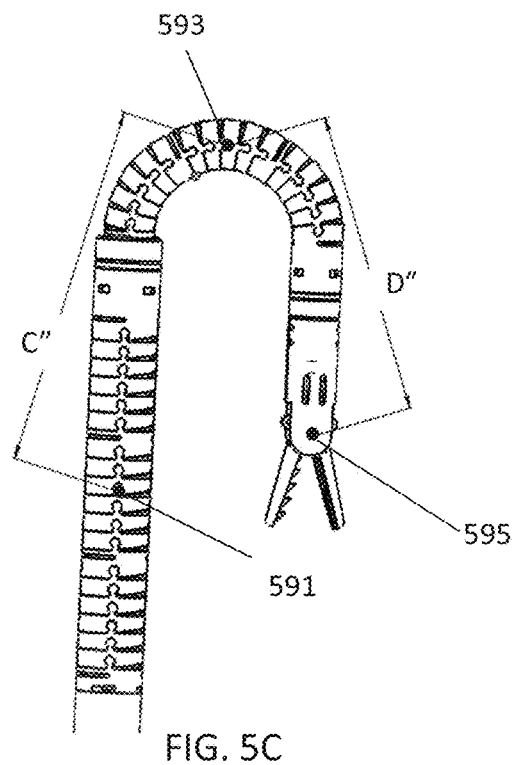
Figure 5D:
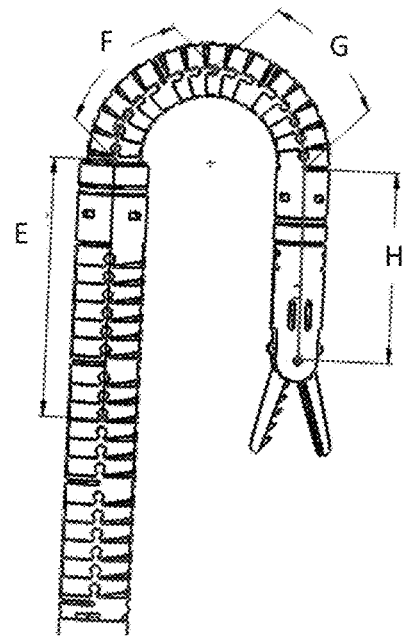

FIGS. 5B-5D are simplified schematic side views of a mechanical arm, according to some embodiments of the invention.

Alternatively, effective limbs are considered to be the straight lines connecting the center points (longitudinal and/or radial) of flexible sections. FIG. 5B and FIG. 5C show effective limbs, where an effective first segment, with length C' is the straight line connecting shoulder midpoint 591 and elbow midpoint 593 and an effective second segment with length D' is the straight line connecting wrist midpoint 595 and elbow midpoint 593.

In an exemplary embodiment, length A (FIG. 4B) is 36.2 mm and length B is 44 mm (FIG. 4B). In an exemplary embodiment, length C' (FIG. 5B) is 48 mm, length D' (FIG. 5B) is 40 mm, length C" (FIG. 5B) is 44 mm and length D" (FIG. 5B) is 36.6 mm and a ratio of effective first segment length to effective second segment length remains about the same, at about 1.2 (e.g. for different angles of bending of the elbow joint when the shoulder joint remains stationary).

Alternatively, effective limbs are considered to be measured along the central longitudinal long axes of portions of the arm, where the first segment effective length is measured along a longitudinal long axis measured from a wrist midpoint to an elbow midpoint (e.g. length E+F illustrated in FIG. 5D) and the second segment effective length is measured along a longitudinal long axis measured from a wrist midpoint to an elbow midpoint (e.g. length G+H illustrated in FIG. 5D). Where in an exemplary embodiment, length E is 31.3 mm, length F is 18.3 mm, length G is 18.3 mm, and length H is 23 mm.

Referring back now to FIG. 4A, in some embodiments, the device is thinner than human anatomy. For example, in some embodiments, a ratio of a device segment axial length with respect to a maximum device segment cross sectional area is larger than an average human anatomy ratio e.g. more than 1.5 times, or more than 2 times, or more than 4 times, or more than 10 times.

A potential benefit of a thin device is the ability to approach an internal body target by displacing tissue minimally and/or with minimum damage to tissue. For example, in some embodiments, an incision size required for insertion of the device is small. In some embodiments, a device includes one arm and an incision size is or less than 17 mm, or less than 15 mm, or less than 10 mm, or about 8 mm. In some embodiments, a device includes more than one arm and an incision size is or less than 30 mm, or less than 20 mm, or about 16 mm.

In some embodiments, the device has narrower shoulder with respect to device segment lengths, than an average human shoulder e.g. a maximum device shoulder as measured between first arm end of the humerus proximal to the first torso and a second arm end of the humerus proximal to the second torso is less than with respect to a humerus length is less than 75% of an average human ratio, or less than 50%, or less than 25%.

In some embodiments a torso length, for example, with respect to one or more arm segment length, is longer than that of a human torso length. A potential benefit of a long torso is the ability to insert the device into a patient to a wide range of required depths.

Exemplary Arm Configurations

In some embodiments, arms have different geometries and/or features. For example, in some embodiments, different arms have different hand tools: Referring back to FIG. 1A, first arm 104 has a scissors hand tool 124 and second arm 106 has a gripper hand tool 126. Hand tools will be described in more detail below.

Figure 6:
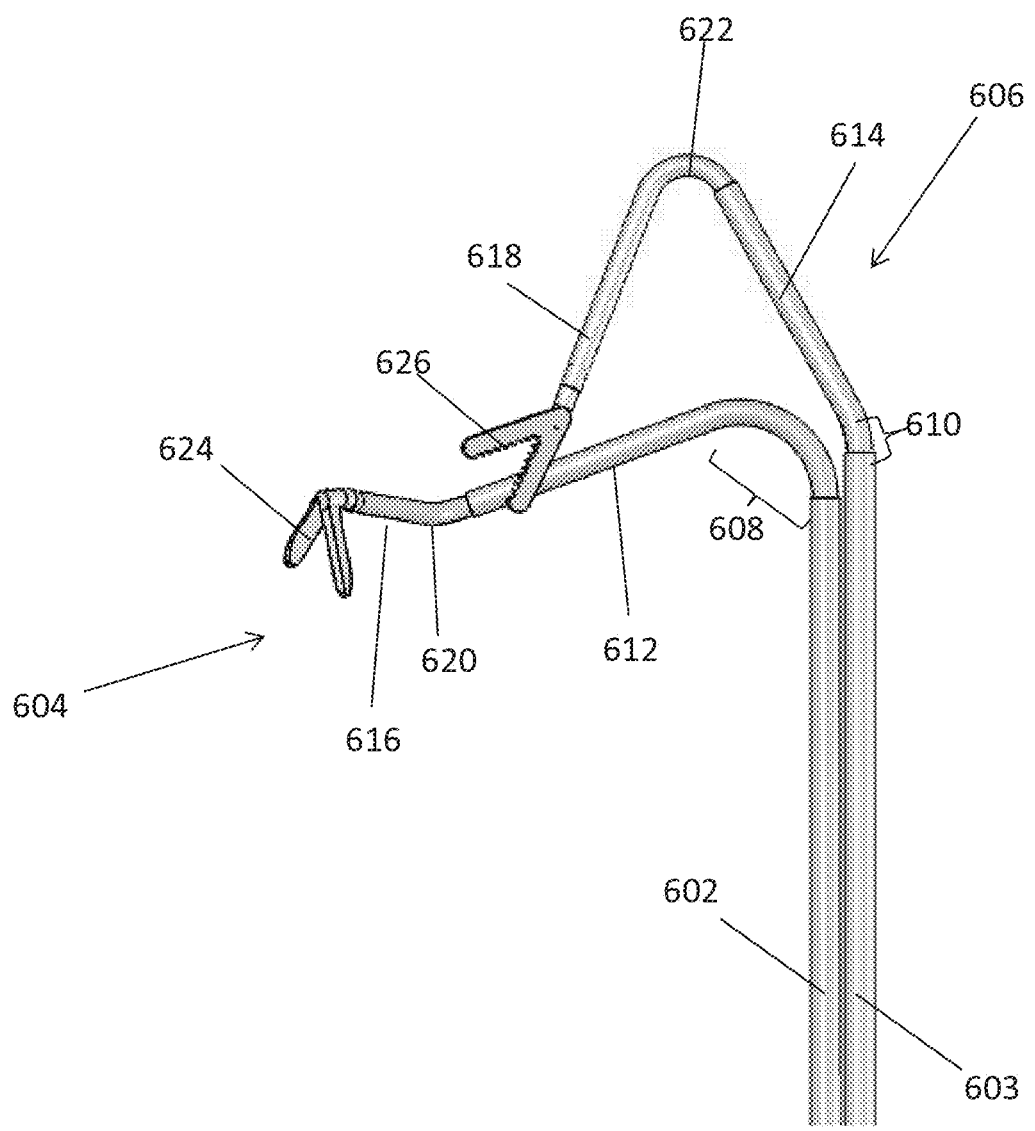
FIG. 6 is a simplified schematic side view of a device including a plurality of arms, according to some embodiments of the invention.

In some embodiments, different arms have different segment and/or joint geometry. FIG. 6 is a simplified schematic side view of a device including a plurality of arms, according to some embodiments of the invention. In some embodiments, a first arm 604 has a longer shoulder joint 608 than a second arm shoulder joint 610. Optionally, in some embodiments, segment dimensions and/or hinge dimensions, and/or freedom of movement are different for different arms.

Exemplary Number of Arms

Figure 7:
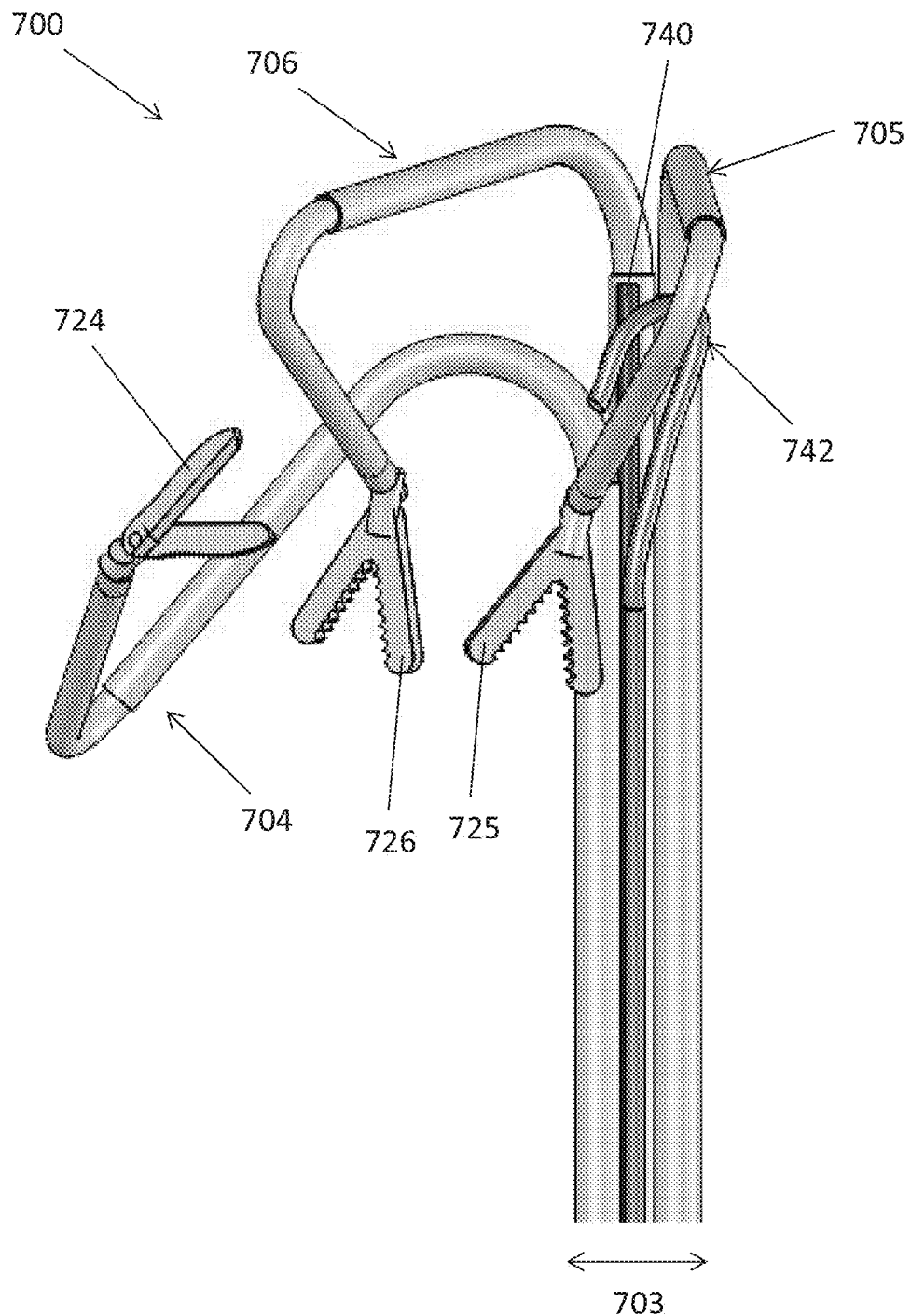
FIG. 7 is a simplified schematic side view of a device including more than two arms, according to some embodiments of the invention.

In some embodiments, the device includes two arms. In some embodiments, the device includes one arm. In some embodiments, the device includes more than two arms. FIG. 7 is a simplified schematic side view of a device 700 including more than two arms, according to some embodiments of the invention. In some embodiments, device 700 includes a first arm 704, a second 706 arm and a third arm 705.

Optionally, one or more arm has a different hand tool. In some embodiments, first arm 704 has a scissors hand tool 724 and second arm 706 and third arm 705 have gripper hand tools 726, 725. Hand tools are described below in more detail.

Optionally, two or more torsos are coupled to each other.

In some embodiments, one or more device mechanical limb is larger than one or more other limb. In some embodiments, a device includes three mechanical arms and with a first and second arm with about the same dimensions e.g. segment long axis lengths and/or joint long axis lengths and/or maximum segment extent perpendicular to a segment long axis and/or maximum joint extent perpendicular to a joint long axis. In an exemplary embodiment, a third arm is larger than a first and second arm.

In some embodiments a larger arm has one or more portion dimension (where dimensions include segment long axis, joint long axis, segment maximum extent perpendicular to the segment long axis and joint maximum extent perpendicular to the joint long axis) 1.5 times larger, or 2 times larger, or 5 times larger, or 10 time larger, than a corresponding first and/or second arm segment dimension. A potential benefit of a larger arm being, for example, the ability of the arm to apply more force (e.g. to tissue) and/or the ability of the arm to contact a larger surface area of tissue.

In some embodiments, a larger arm (e.g. a larger third arm) includes additional elongated elements for control of movement of the arm (e.g. as described below). For example, in some embodiments, a larger arm includes two elongated elements, or more than two elongated elements, or four elongated elements. In some embodiments, a third arm includes fewer joints than a first and second arm. In some embodiments, a third arm is used to hold and/or push and/or reposition patient anatomy, for example, to provide access to and/or increase tension on a target area.

In some embodiments, a third arm is controlled by mimicking of leg movement. In some embodiments, a third arm is controlled by mimicking of movement of a first user leg and a fourth arm is controlled by mimicking of movement of a second user leg.

Exemplary Additional Tools

Optionally, in some embodiments, device 700 includes one or more additional component, where the component is, for example, coupled to a mechanical limb. In some embodiments, the component is inserted into the body, optionally into the same incision as one or more mechanical device limb e.g. the component is an additional tool.

In some embodiments, device 700 includes a service tunnel 740. In some embodiments, service tunnel is formed by an opening and a hollow portion within a device arm. In some embodiments, service tunnel is a separate component. In some embodiments, service tunnel 740 provides access to the site of the arms for example, for transfer of suturing wires.

In some embodiments, device 700 includes a tube 742 for suction and/or irrigation. Optionally, tube 742 is inserted through service tunnel 740. In some embodiments, suction tube is used to extract fluid during surgery, e.g. blood, as is known in the art of surgery.

In some embodiments, the device includes one or more imaging device (e.g. camera, ultrasound device), for example, for providing images from within the patient. Internal cameras are described in more detail below.

In some embodiments, the device includes one or more sensor, for example, to provide information as to conditions within the device and/or inside the patient e.g. a temperature sensor, a motion sensor, a pressure sensor. In some embodiments, one or more pressure sensor is used to provide force feedback to a user.

In some embodiments, torsos and optionally additional tools and are positioned and/or coupled close together e.g. within 20 mm, or 10 mm, or 5 mm of each other, a potential benefit being insertion of the device into a small incision and/or small natural orifice.

In some embodiments, an additional tool is used to hold and/or push user tissue e.g. to hold tissue away for cutting, to provide tension to tissue to be cut. Optionally, a hand tool for holding tissue includes an expanding portion the surface of which can be expanded by one or more portion unfolding and/or inflating and/or sliding past other portions (e.g. fan-like construction).

Exemplary System

Figure 8:
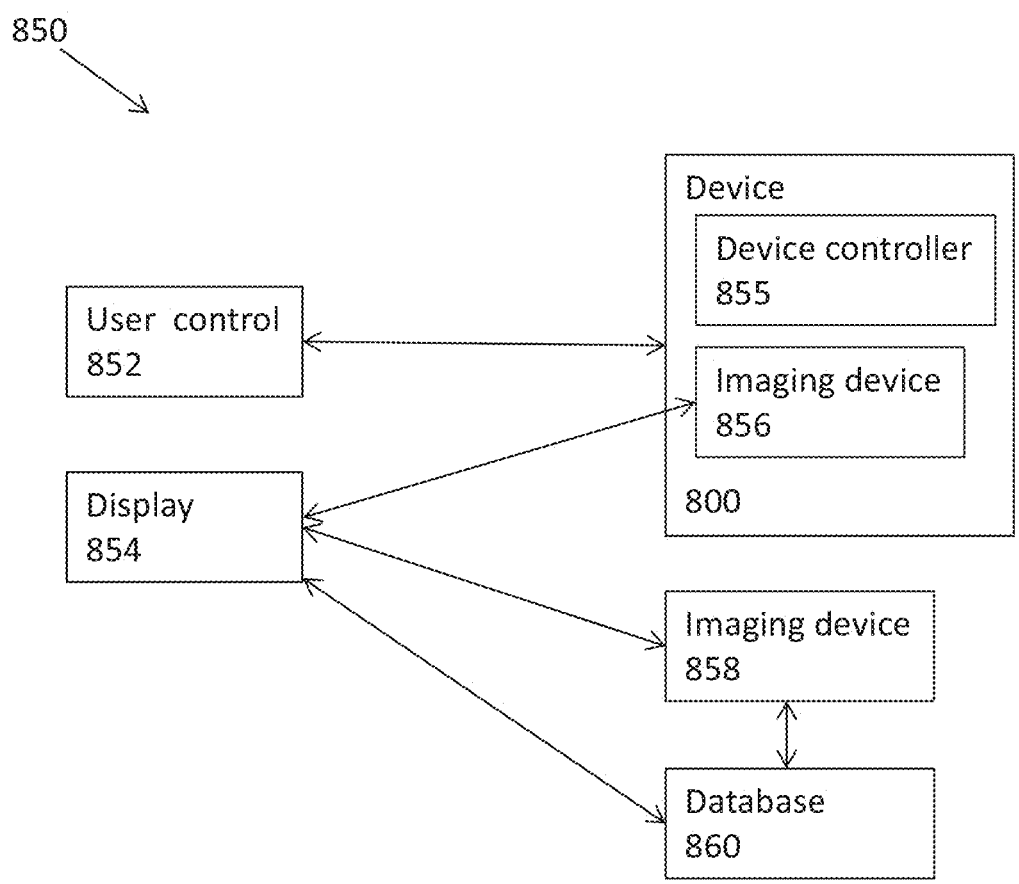
FIG. 8 is a simplified schematic block diagram of a surgical system, according to some embodiments of the invention.

In some embodiments, a device including a plurality of arms is part of a surgical and/or treatment system. FIG. 8 is a simplified schematic block diagram of a system, 850 according to some embodiments of the invention.

In some embodiments, the system includes a user control 852 through which a user directs a device 800 including a plurality of arms.

In some embodiments, device 800 includes one or more imaging device 856.

In some embodiments, device 800 includes a device controller 855, for example motors (e.g. for controlling movement of arm segments).

Optionally, one or more part of device control is external to the device. Optionally, one or more part of device control is manual, for example, where a user directly controls movement (e.g. by inserting and/or extracting the device into a body, e.g. by pulling one or more elongated element, e.g. by rotating one or more segment extension).

In some embodiments, system 850 includes one or more imaging device 858, for example an external imaging device e.g. ultrasound.

In some embodiments, the system includes a display 854, for example to show information and/or images to the user.

In some embodiments, system 850 includes a database 860, for example for storing of images collected by imaging devices 856, 858.

Optionally, system 850 includes one or more processing application. In some embodiments, device control is automatic, where a processing application, for example, controls motor and/or actuator movement.

In some embodiments, one or more of imaging device 856 and/or imaging device 858 and/or database 860 and/or display 854 include a processing application. In some embodiments, a single processing application controls more than one system element. For example, in some embodiments, user control 852 and display 854 are part of a single unit (e.g. computer and/or touch-screen).

In some embodiments, one or more part of system 850 are in different locations. For example, in some embodiments, device 800 is in a first location and user control 852 and display 854 are in a second location. For example, facilitating a patient being operated by a surgeon in a different location e.g. in a different room and/or a number of km away.

Exemplary Imaging and Display

Exemplary Device Including Imaging Device

Optionally, in some embodiments, device includes one or more imaging device (e.g. camera, endoscope, ultrasound etc.), which is optionally inserted with the device including one or more mechanical limb into the patient. In an exemplary embodiment, the imaging device is a camera.

In some embodiments, positioning of the camera with respect to device limbs is about that of average positioning of a human head to corresponding human arms.

For example, in some embodiments, a ratio between a distance of the camera to one or more portion of a mechanical arm is about the same as a ratio of one or more portion of the device to an equivalent human body portion.

In some embodiments, the camera is positioned at the same position relative to the device arms and/or hands as human eyes are from human arms and/or hands, e.g. the camera is at located the corresponding (e.g. scaled) length of the humerus above the shoulder joint.

In some embodiments, the camera is positioned such that images have a field of view (FOV) and/or angle of the device portion/s as human eyes have of corresponding user body portion/s. A potential benefit being that the camera provides an intuitive view of the device assisting user control using user body movement.

Figures 9A, 9B:
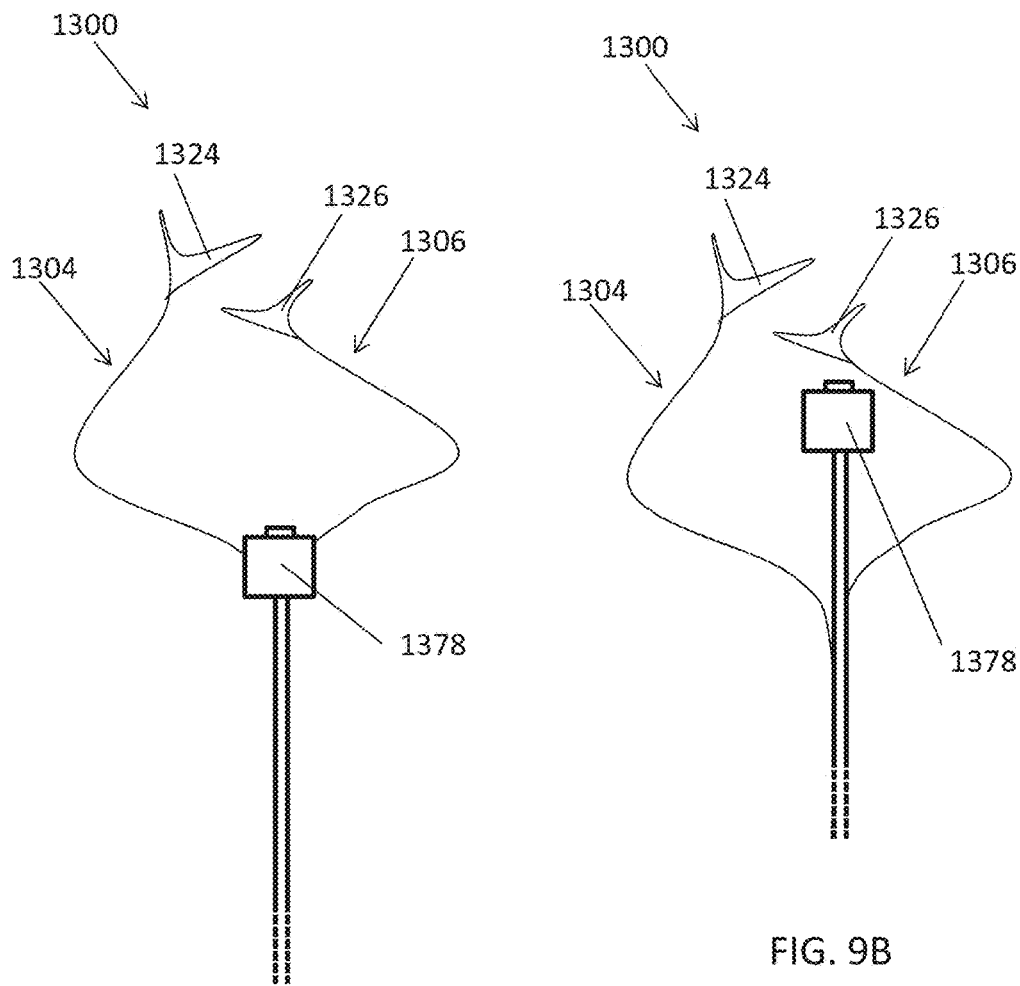
FIG. 9A is a simplified schematic of a device including a plurality of arms and a camera, according to some embodiments of the invention.
FIG. 9B is a simplified schematic of a device including a plurality of arms and a camera, according to some embodiments of the invention.

FIG. 9A is a simplified schematic of a device 900 including a plurality of arms 904, 906 and a camera 978, according to some embodiments of the invention. FIG. 9B is a simplified schematic of a device 900 including a plurality of arms 904, 906 and a camera 978, according to some embodiments of the invention.

In some embodiments, a position of camera 978 with relation to arms is adjustable. For example, as illustrated in FIG. 9B in some embodiments, camera 978 moves, for example, closer to hand tools 924, 926, e.g. to provide detailed images for close work. Such movement is analogous to natural human positioning for close work, where often, the hands and head are brought close together for fine work.

Optionally, the user controls the position of the camera. In some embodiments, user head and/or neck position and/or movement is measured and used to control the camera.

Figure 9C:
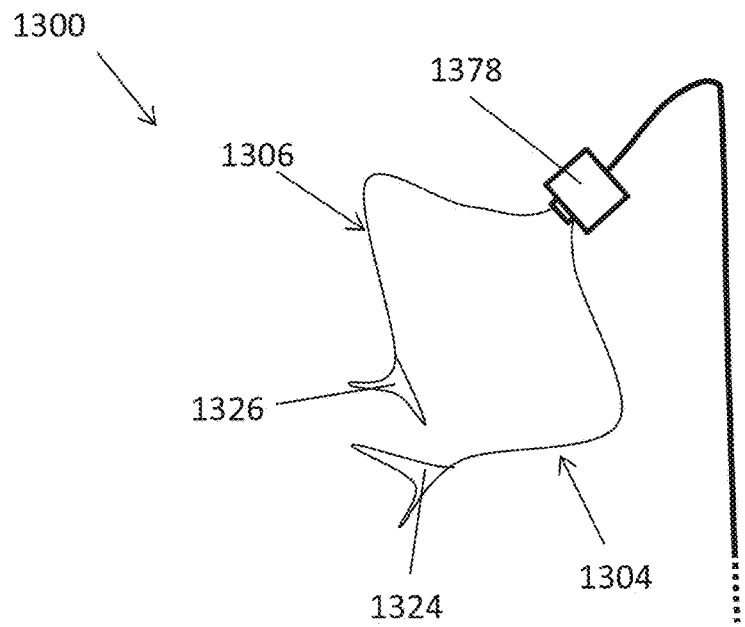
FIG. 9C is a simplified schematic of a device including a plurality of arms and a camera bent at a device shoulder joint, according to some embodiments of the invention.

In some embodiments, an imaging device (e.g. camera) bends, for example, with one or more device joint. FIG. 9C is a simplified schematic of a device 900 including a plurality of arms 904, 906, and a camera 978 bent at a device shoulder joint, according to some embodiments of the invention.

Figure 9D:
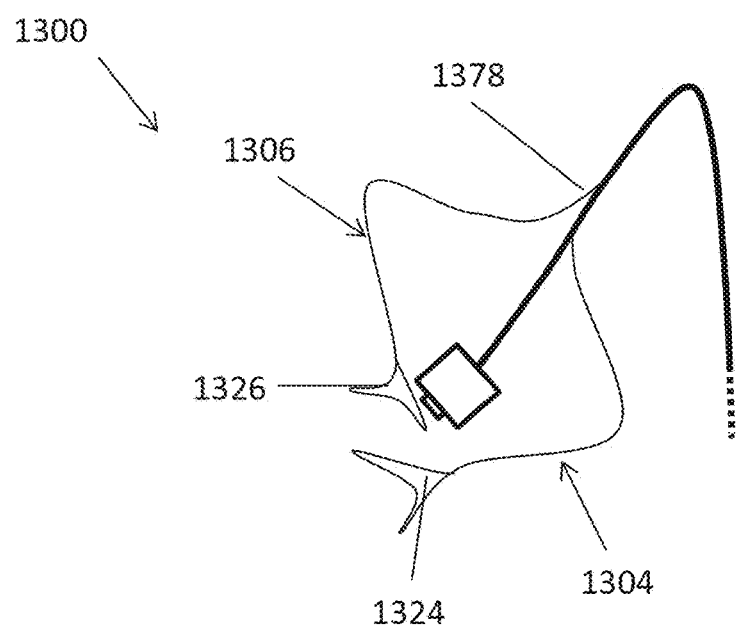
FIG. 9D is a simplified schematic of a device including a plurality of arms and a camera bent at a device shoulder joint, according to some embodiments of the invention.

FIG. 9D is a simplified schematic of a device 900 including a plurality of arms 904, 906, and a camera 978 bent at a device shoulder joint, according to some embodiments of the invention. As illustrated in FIG. 9D, in some embodiments, the bent imaging device is movable, for example, with respect to the device arms.

In some embodiments, a mechanical arm (e.g. with structure as described elsewhere in this document) includes a camera. For example, in some embodiments, a mechanical arm end effecter and/or third segment includes one or more camera. For example, in some embodiments, a mechanical arm includes a structure with more than one flexible section connected by more than one rigid section, where a camera is disposed on the arm (e.g. at a distal end of the arm).

As mentioned elsewhere in this document (e.g. regarding FIG. 7) in some embodiments, one or more arm includes fewer joints than a first and second arm.

Figure 10A:
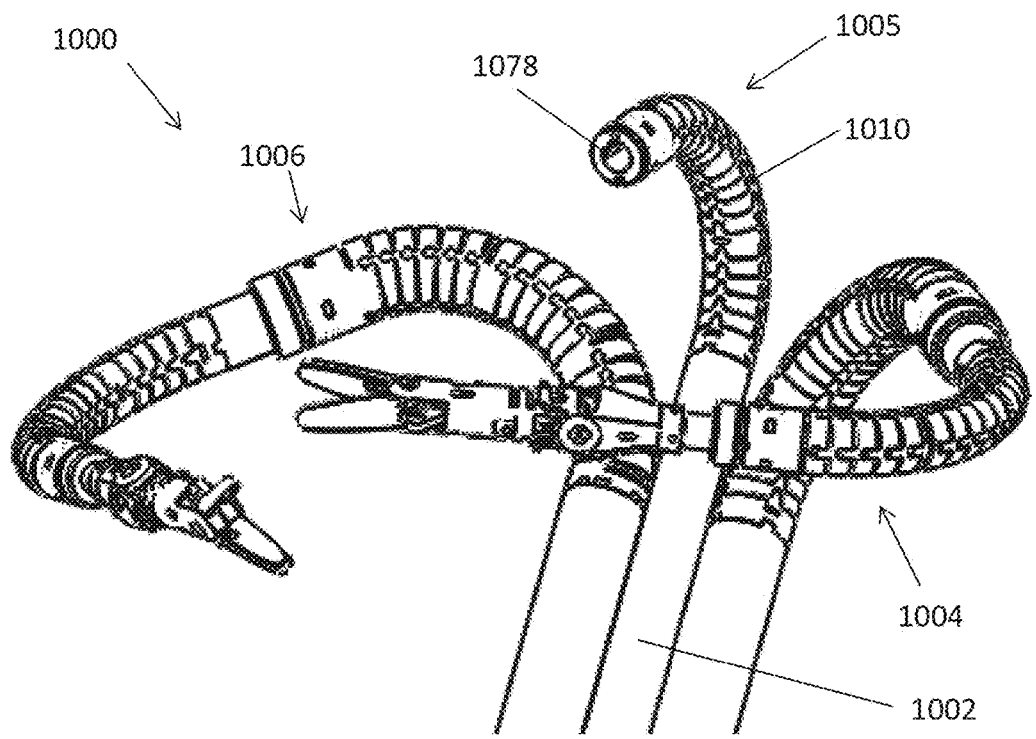
FIG. 10A is a simplified schematic of a device including a plurality of arms and a camera, according to some embodiments of the invention.

FIG. 10A is a simplified schematic side view of a device 1000 including a mechanical arm 1005 which includes a camera 1078, according to some embodiments of the invention. In some embodiments, mechanical arm 1005 includes a support section 1002 connected by a first flexible section 1010 to camera 1078. In some embodiments, camera 1078 is disposed at a distal end of arm 1005.

In some embodiments, movement of a mechanical arm including a camera is controlled by measured movement of a user's head. For example, by movement of a user's head in space and/or by movement of a user's head with respect to one or other body part (e.g. torso and/or neck).

In some embodiments, movement of a mechanical arm including a camera is controlled by measured movement of a user's limb (e.g. arm). For example, the arm includes at least a first and a second flexible portion (e.g. as described elsewhere in this document), the movement of which is controlled by a user shoulder and elbow joint respectively).

Additionally or alternatively, in some embodiments, movement of a mechanical arm including a camera is controlled by movement of portion/s of an input device (e.g. as described elsewhere in this document).

Additionally or alternatively, in some embodiments, a position of one or more tool inserted into a patient body (e.g. a camera, e.g. a mechanical arm, e.g. tube 742 FIG. 7) is controlled by one or more device arm. For example, in some embodiments, a tool is grasped by one or more device arm and moved into a desired position. For example, in some embodiments, a tool (e.g. a camera e.g. camera 1378 FIG. 13) includes an elastically deformable portion such that, upon positioning of the tool the tool remains in position until the tool is repositioned. For example, in some embodiments, a suction tube (e.g. tube 742 FIG. 7) is positioned by a surgical arm moving the tube. In some embodiments, a tool (e.g. a tube e.g. tube 742 FIG. 7) includes one or more elastically deformable portion, such that, for example, the tool is moved into a desired position by a movement of a mechanical device arm, returning towards an original position once the tool is released.

Exemplary External Imaging Device

Referring back now to FIG. 8, optionally, in some embodiments, the system includes an imaging device 858 separate to device 800. In some embodiments, imaging device 858 provides real time imaging when device 800 is moving within the patient (e.g. conducting surgery). For example, in some embodiments, an external ultrasound is used for example, to provide images of device 800 inside the body.

In some embodiments, imaging device 858 (e.g. MRI, CT, nuclear imaging, ultrasound etc.) collects images before insertion of device 800, for example, to provide an anatomic map to aid surgery. In some embodiments, imaging device 858 provides images during use of device 800 within the body and/or after the device is removed.

Exemplary Display

In some embodiments, images are displayed, (e.g. to a user). For example, in some embodiments, images from an internal imaging device are displayed to provide feedback as to a position of the device within the patient. Referring back to FIG. 8, in some embodiments, one or more image is displayed on display 854 to a user.

In some embodiments, display 854 is a screen (e.g. computer monitor) visible to the user. In some embodiments, display 864 is part of a virtual reality (VR) environment, e.g. display 864 is one or more screen inside a VR visor.

Exemplary Displayed Images

In some embodiments, display 854 shows images of device 800 within a patient. In some embodiments, images are provided by one or more internal camera where the camera is, for example, inserted with device 800 (e.g. camera 978, FIG. 9A) are displayed. In some embodiments, images are provided by a separate imager, e.g. an external ultrasound imager. In some embodiments, real time images are displayed, for example, real time images from the camera within the patient, external real time imaging (e.g. external ultrasound). In some embodiments, displayed images are previously acquired e.g. CT, MRI, nuclear imaging images. In some embodiments, images are calculated images, e.g. an anatomic model.

Exemplary Image Processing

In some embodiments, collected images are displayed. For example, in some embodiments, images captured by an internal camera are directly displayed. For example, in FIG. 45, upper image 4554*a* displayed by display 4554 is an image provided by camera 4501.

Alternatively or additionally, in some embodiments, images are processed before display.

In some embodiments, images are combined and/or superimposed for display. For example, in some embodiments, real time imaging (e.g. from a camera within the patient) is superimposed or displayed concurrently with previously acquired images or other data (e.g. CT and/or MRI and/or an anatomic model and/or device sensor data etc.).

Figure 45:
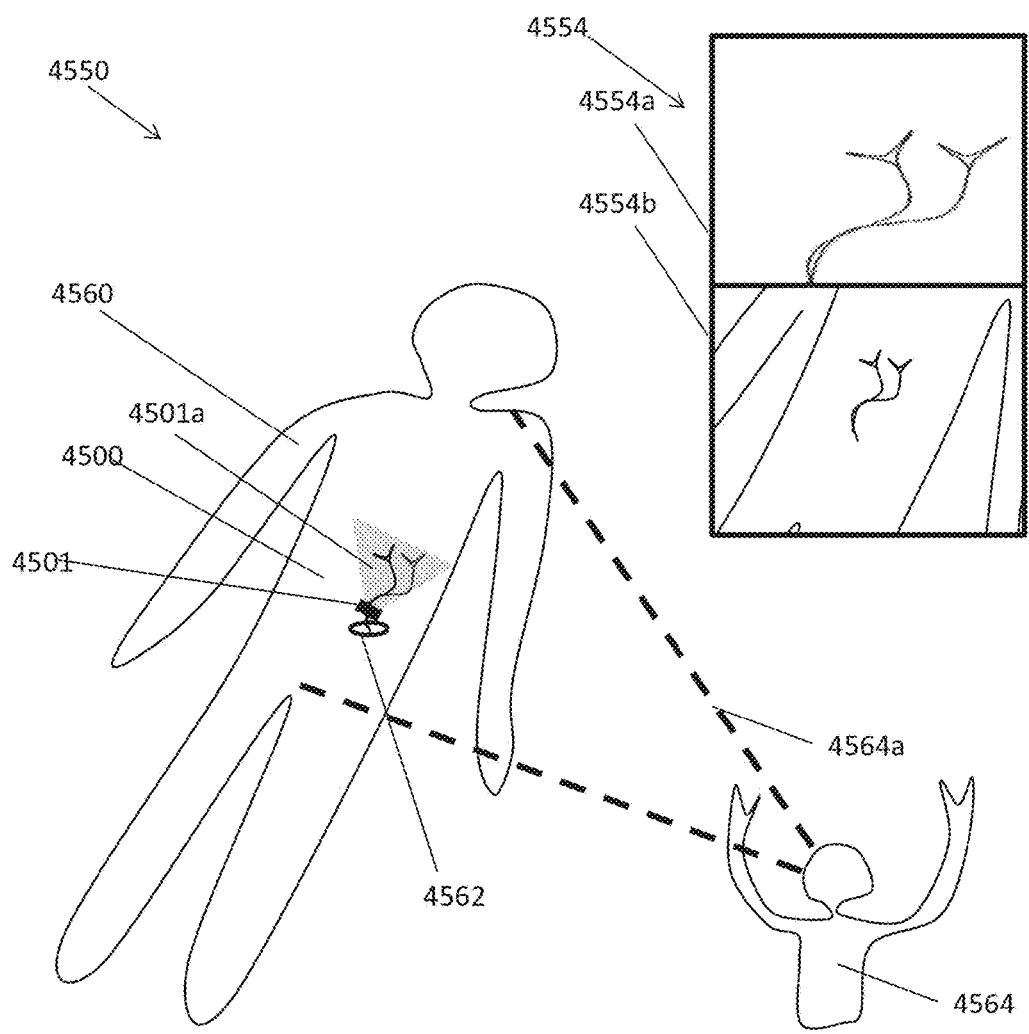
FIG. 45 is a simplified schematic illustrating use of a surgical system, according to some embodiments of the invention.

In some embodiments, images are re-orientated before display. Referring now to FIG. 45, for example, in some embodiments, internal camera 4501 has a field of view (FOV) 4501*a* and views a body part from one direction and a user view 4564*a* of this organ is from another direction: In some embodiments, the captured images from the camera are re-orientated to the user view, for example lower image 4554*b* displayed on display 4554 which shows an image collected by camera 4501 which has been orientated to the user view of the patient 4564*a*. For example, in some embodiments, a device including a camera is inserted through the vagina providing a proximal view of the device arms and uterus but the patient is in a supine position on a surgery bed and, for example, a user view of the uterus is in the posterior direction. In some embodiments, captured images from the camera are processed (e.g. by a processing application) and re-orientated to the user view.

In some embodiments, a user controls (e.g. through a user interface) the displayed view, for example, the user rotates and/or zooms in or out on the image. In some embodiments, a measured user view (e.g. distance and orientation of the user's head with respect to the patient and/or device) with respect to the patient is used to re-orientate captured images.

Exemplary Device Support, Optionally Device does not Require Support from a User In some embodiments, the device is stand-alone and, for example, does not require support of a user. In some embodiments, one or more portion of the device is at least partially supported by a support. In some embodiments, the user does not directly interact with the device. In some embodiments, movement of the device is substantially automated.

Figure 11A:
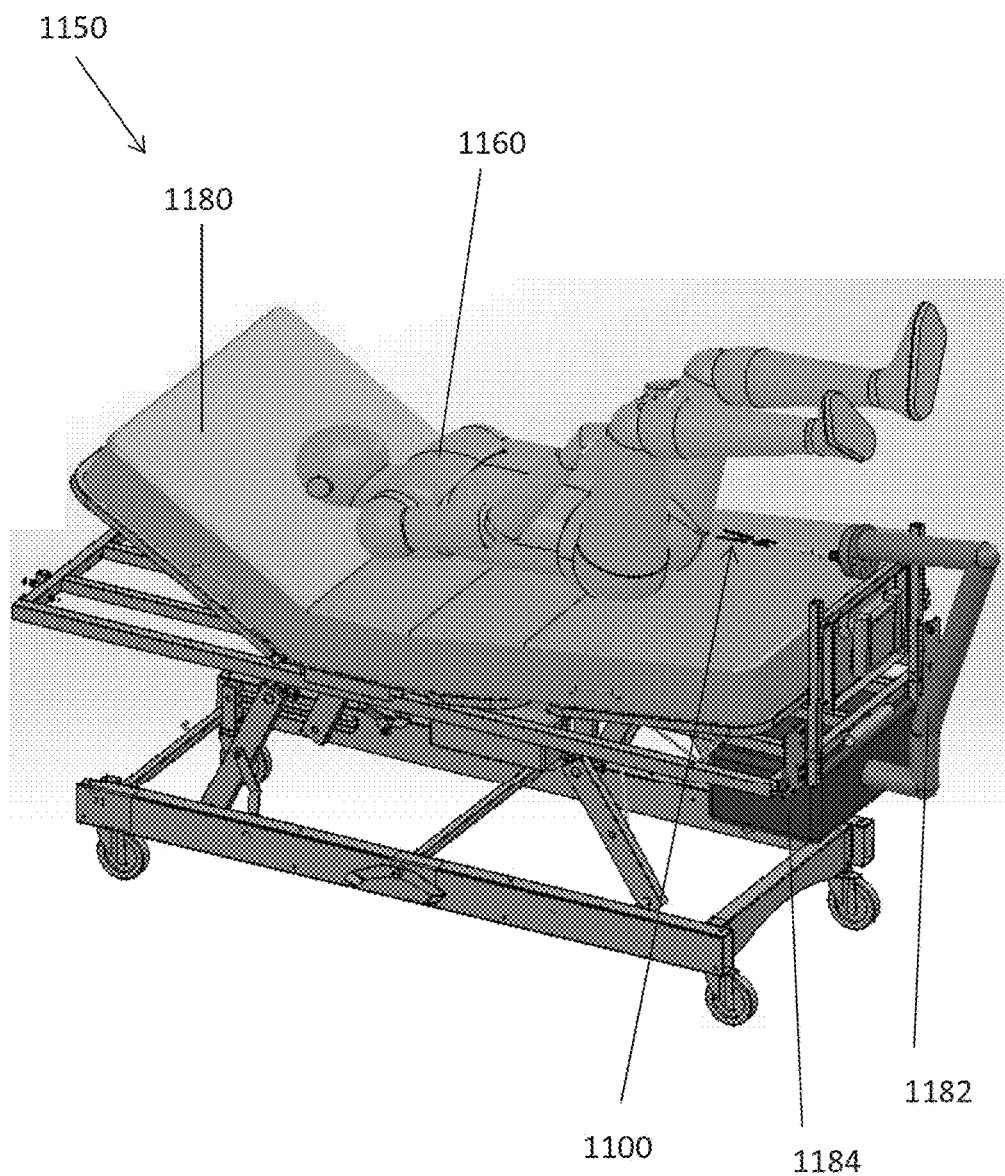
FIG. 11A is a simplified schematic view of a system where a device is held by a support, according to some embodiments of the invention.

FIG. 11A is a simplified schematic view of a system 1150 where a device 1100 is held by a support 1182, according to some embodiments of the invention.

In some embodiments, a device 1100 is coupled to a bed 1180. In some embodiments, a patient 1160 lies on bed 1180 for surgical procedures using device 1100. In some embodiments, one or more component of the device, for example one or more part of device control (e.g. motors) is located underneath bed, e.g. in a housing 1184. In some embodiments, support 1182 connects device 1100 to housing 1184. Optionally, other components, for example transformers, connectivity to other components e.g. the display, are located in housing 1184.

In an exemplary embodiment, a main motor unit for control of movement of the device is located in housing 1184, where for example, in some embodiments, torque transfer element/s transfer torque from motor/s within housing 1184 to device 1100 and/or elongated elements for effecting flexion of device joints are coupled to motors within housing 1184.

In some embodiments, control of movement of the device above the bed, using a motor unit underneath the bed is via an orientation controller, for example using a parallelogram linkage, e.g. as described in International Patent Application Publication No. WO2011/036626 which is herein incorporated by reference into the specification in it's' entirety.

A potential benefit of one or more component being located underneath a bed (e.g. inside housing 1184), is reduced footprint of the system in an operating room. A further potential benefit of components being located underneath a bed as opposed to above and/or around the bed is potentially improved access to a patient (e.g. in an emergency situation).

A potential benefit of the device being coupled to a bed is the ability to move and/or change an angle of the bed, for example, during surgery, while the device remains in the same position relative to the bed and/or patient. Alternatively, or additionally, in some embodiments, a device position with respect to the patient and/or the bed is adjustable, for example, before treatment with the device and/or during surgery.

Optionally, in some embodiments, support 1182 moves device into position for surgery. In some embodiments, support 1182 moves device into a desired position for insertion into patient 1160. In some embodiments, support 1182 moves device vertically, and/or horizontally, and/or laterally, and/or inserts device 1100 into a patient 1160 and/or withdraws device 1100 from the patient.

In the embodiment illustrated by FIG. 11A, support arm 1182 and housing 1184 are located at the foot end of 1584. A potential benefit of this location is ease of surgery through a patient's undercarriage, for example, through the vagina. In FIG. 11A, patient 1160 is illustrated in a suitable position for insertion of the device into the vagina, the patient's legs are elevated and apart (e.g. held by stirrups which are not shown).

Figure 11B:
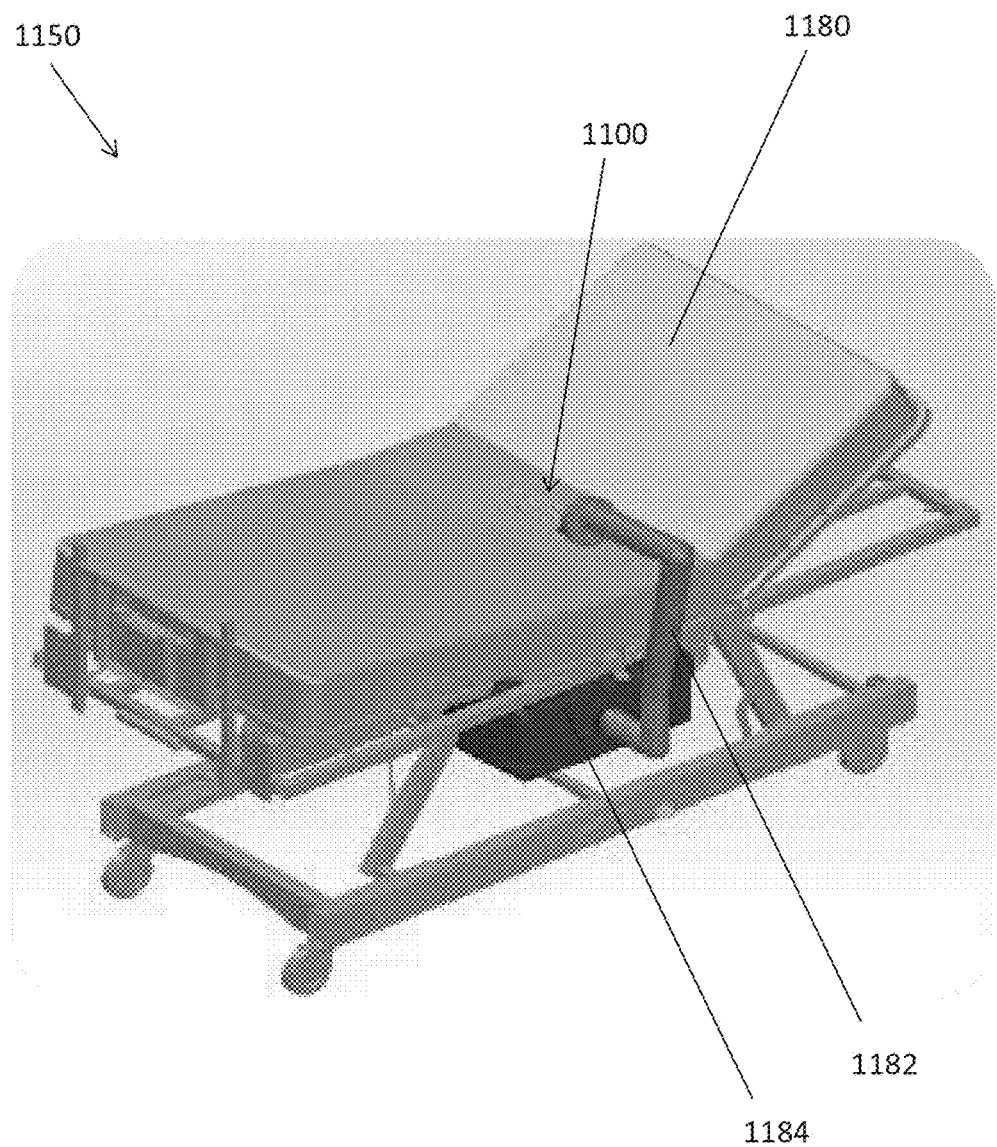
FIG. 11B is a simplified schematic view of a system where a device is held by a support, according to some embodiments of the invention.

FIG. 11B is a simplified schematic view of a system 1150 where a device 1500 is held by a support 1582, according to some embodiments of the invention. In the embodiment illustrated by FIG. 11B, support arm 1182 and housing 1184 are located at a long axis center of the bed 1180. A potential benefit of this location is ease of abdominal and/or thoracic surgery using the device.

In some embodiments, a housing position underneath the bed and/or a position around the bed from where the arm meets the housing are adjustable. For example, the arm and/or housing are moved for different surgeries.

Figure 12:
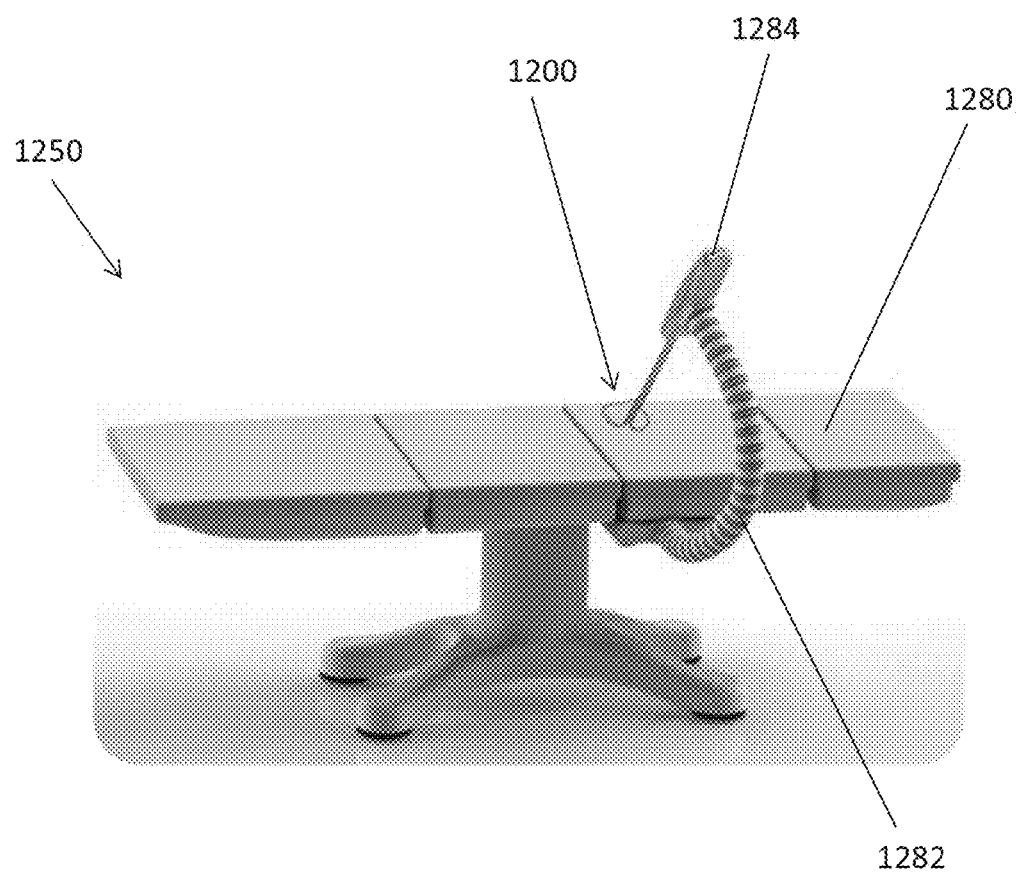
FIG. 12 is a simplified schematic side view of a system including a device with two arms held by a support, and coupled to an operating surface, according to some embodiments of the invention.

FIG. 12 is a simplified schematic side view of a system 1250 including a device with two arms 1200 held by a support 1282, and coupled to an operating surface 1280, according to some embodiments of the invention.

Optionally, in some embodiments, device support 1282 couples device 1200 to operating surface 1280 (e.g. a table/bed e.g. by which a patient is supported). In some embodiments device support 1282 is flexible e.g. along the entire device support length. In some embodiments, device support 1282 includes a chain of coupled segments. In some embodiments, motor/s 1284 for actuation of device 1200 are located within a support head.

A potential benefit of a flexible and/or adjustable device support is the ability to position the device with relation to the operating surface in wide variety of positions and/or angles. Further potential benefits include; a small system footprint, shorter time for preparation, for example patient preparation (e.g. anesthesia), an easy docking process. Further potential benefits include, an ability to change the position of the patient's lower body with respect to the patient's upper body, optionally during treatment and/or surgery with the device, e.g. ability to adjust the Trendelburg position optionally during treatment and/or surgery. Further potential benefits include small cost and/or size of capital equipment and/or no need for a dedicated operating room e.g. as device and/or system is easily moveable (e.g. small size and/or weight and/or lack of requirement of special operating room infrastructure).

In some embodiments, a device is inserted into a patient from a direction which is not above the patient (e.g. laterally, e.g. between patient legs). In some embodiments, attachment of the device to a patient bed enables insertion directions which are not from above.

In some embodiments, a surgical system includes a port, for example, through which a device is inserted into a patient. In some embodiments, the port is coupled to the patient, for example, inserted into a natural orifice and/or an incision.

Figure 13:
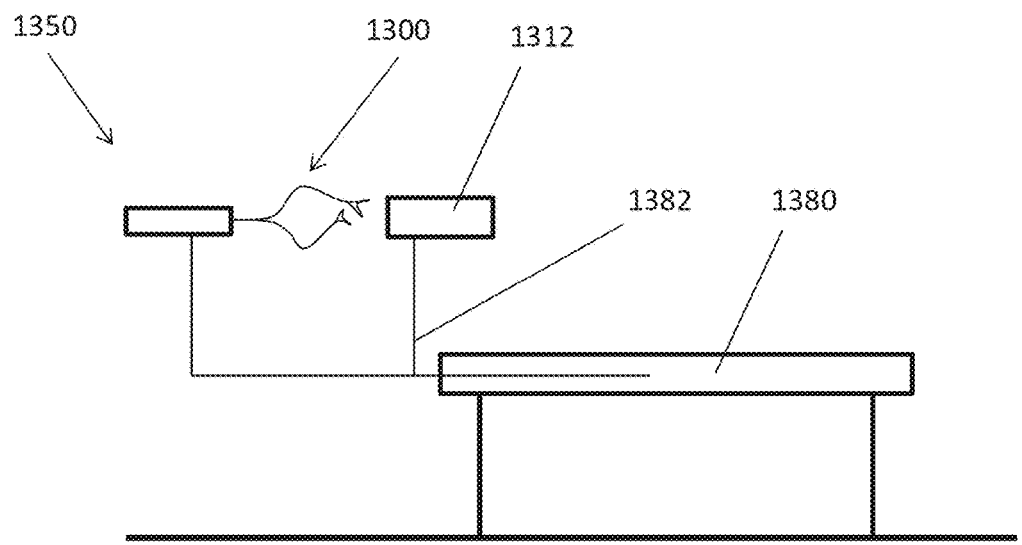
FIG. 13 is a simplified schematic side view of a system including a port coupled to an operating surface by a support, according to some embodiments of the invention.

In some embodiments, a port is coupled to a support. FIG. 13 is a simplified schematic side view of a system 1350 including a port 1312 coupled to an operating surface 1380 by a support 1382, according to some embodiments of the invention. In some embodiments, a device 1300 and a port 1312 are coupled by the same support 1382.

Figure 14:
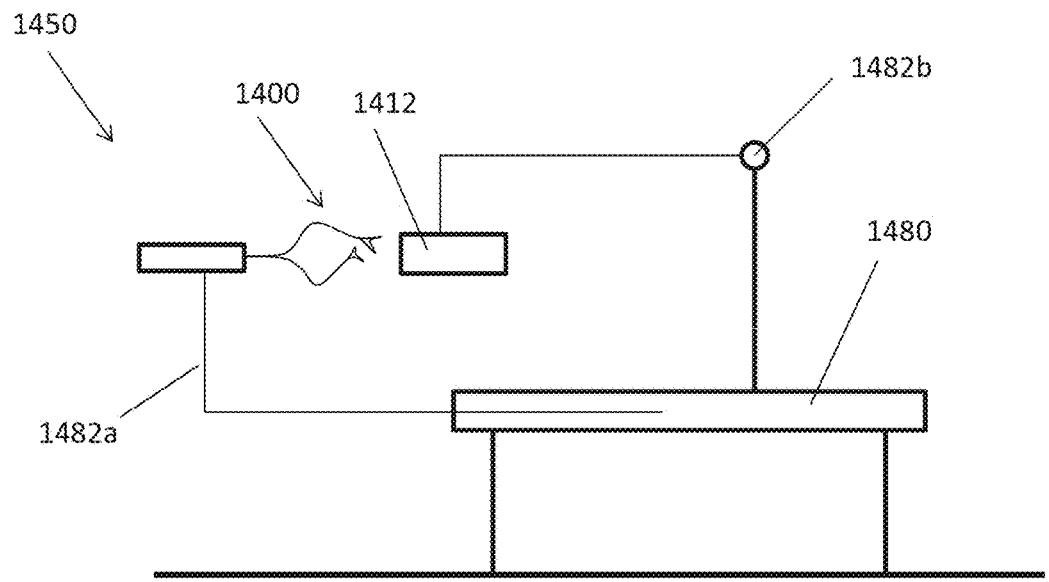
FIG. 14 is a simplified schematic side view of a system including a port support and a device support, according to some embodiments of the invention.

In some embodiments, a device and a port are held by different support elements. FIG. 14 is a simplified schematic side view of a system 1450 including a port support 1482*b* and a device support 1482*a*, according to some embodiments of the invention. In some embodiments, both a device 1400 and a port 1412 are coupled to an operating surface 1480. Alternatively or additionally, in some embodiments, device 1400 and/or port 1412 are held by a support coupled to one or more other object, e.g. the floor, the ceiling.

A potential benefit of supports (e.g. device and/or port supports) is reduction of unwanted movement of the device and/or port.

In some embodiments, a support is a laparoscopic positioner, for example including an attachment to a support surface rail. In some embodiments, commercially available surgical positioning arms are suitable for use with the device of the invention, for example, surgical arms sold by Fisso® of Switzerland.

Figure 15:
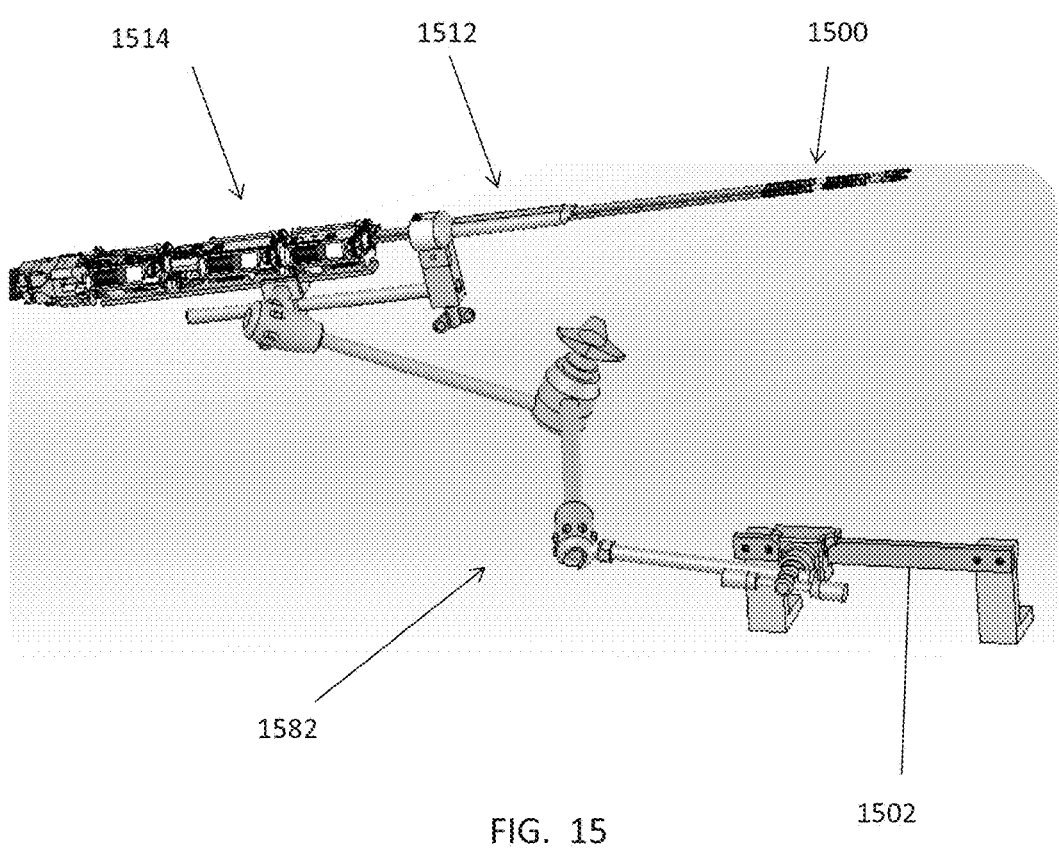
FIG. 15 is a simplified schematic of a device, held by a support, according to some embodiments of the invention.

FIG. 15 is a simplified schematic of a device 1500, held by a support 1582, according to some embodiments of the invention.

In some embodiments, support 1582 attaches to a portion of a patient operating surface, e.g. rail 1502. In some embodiments, position of attachment of support 1582 on rail 1502 is adjustable, for example enabling linear adjustment of position of attachment of the support to the patient operating surface.

Figure 40:
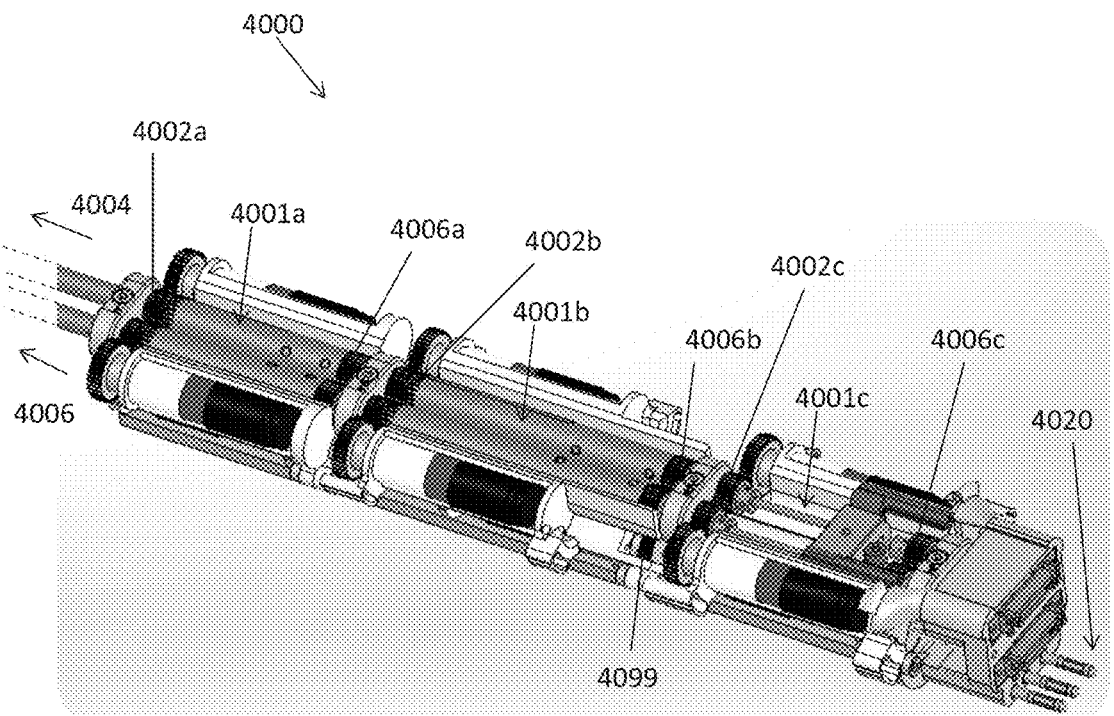
FIG. 40 is a simplified schematic side view of a motor unit for actuation of a device including mechanical arms, according to some embodiments of the invention.

In some embodiments, support 1582 is attached to port 1512 and a motor unit 1514 (operation of motor unit 1514 is, in some embodiments, for example, as described regarding motor unit 4000, FIG. 40), device 1500 being supported by attachment to motor unit 1514.

In some embodiments, support 1582 includes a plurality of articulations where angles between segments and/or segment lengths are adjustable, for example, enabling adjustment of position and/or angle of a device 1500 including mechanical limbs and/or a port 1512 and/or motor unit 1514 (e.g. which actuate device 1500 limb/s).

In some embodiments, one or more motor is used to move device 1500, with respect to one or more portion of the system (e.g. with respect to port 1512 and/or motor unit 1514), for example, into and/or out of a patient. In some embodiments, motor unit 1514 includes one or more motor for movement of one or more device arm with respect to the motor unit, where, for example, one or more support segment position is changed with respect to the motor unit. In some embodiments, movement of device 1500 is controlled by a user using input object control and/or a user interface.

Exemplary User Held Device

In some embodiments, the device is held by a user.

For example, in some embodiments, a user holds positions and/or inserts the device while controlling the device, e.g. holding device with one arm, controlling device arm movement with the other arm, e.g. manually inserting the device, once the device is inserted, controlling device arm movements with user arms.

For example, in some embodiments, a first user supports and/or inserts the device into a patient and a second user controls movement of device arms within the patient.

In some embodiments, a device is partially supported by a support and a user provided additional manual support and/or guiding of the device.

Exemplary Method of Use

Figure 16:
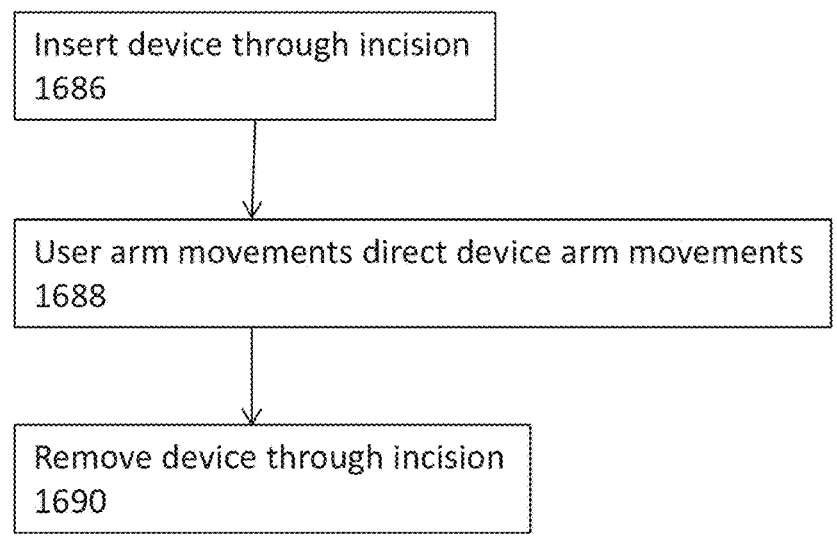
FIG. 16 is a flowchart of a method of use of a device, according to some embodiments of the invention.

FIG. 16 is a flowchart of a method of use of a device, according to some embodiments of the invention.

At 1686, a device including a plurality of arms is inserted through an incision in a patient. At 1688, an object controls device arm movement, for example, measured user arm movements and/or measured movement of an input device (e.g. moved by a user) direct device arm movement within the patient. At 1690, the device is removed through the incision.

Exemplary Incisions and Types of Surgery

Figures 17A, 17B:
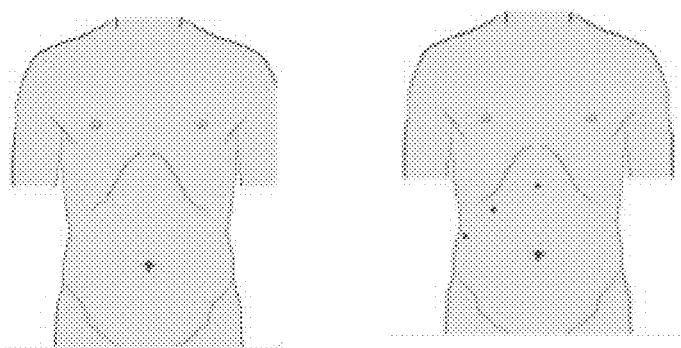
FIG. 17A is a simplified schematic of a single incision in a patient, according to some embodiments of the invention.
FIG. 17B is a simplified schematic of multiple incisions in a patient, according to some embodiments of the invention.

In some embodiments, the device is used in surgeries using a single incision. In some embodiments, the device is used in laparoscopic surgery, including, for example, SILS (Single Incision Laparoscopic Surgery). FIG. 17A is a simplified schematic of a single incision in a patient, according to some embodiments of the invention. In some embodiments, the device is inserted through a single incision, e.g. as illustrated in FIG. 17A which illustrates a single umbilical incision.

In some embodiments, different parts of the device are inserted into more than one incision. FIG. 17B is a simplified schematic of multiple incisions in a patient, according to some embodiments of the invention. For example, in some embodiments, a first device arm is inserted through a first incision and a second device arm is inserted in a second incision. In some embodiments, the device is inserted through a single incision and additional tools, for example a tool for inflation of the abdominal cavity are inserted through one or more separate incision.

Figure 17C:
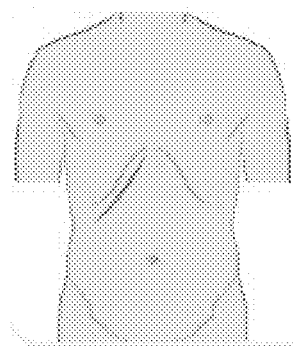
FIG. 17C is a simplified schematic of an incision in a patient, according to some embodiments of the invention.

FIG. 17C is a simplified schematic of an incision in a patient, according to some embodiments of the invention. The incision illustrated in FIG. 17C is larger than necessary for insertion of the device into the body and/or larger than laparoscopic surgery incision. For example, the largest extent of the incision on the skin surface is larger than 1 cm or more, or 2 cm or more, or 10 cm or more, or 20 cm or more. In some embodiments, the device is used where at least a portion of the inserted device and/or portion of the device under a skin level is visible to a user. Optionally, e.g. when the device is at least partially visible, the system lacks an imager inserted into the body and/or images are not displayed to the user.

Exemplary Insertion into a Natural Orifice

In some embodiments, the device is used in NOTES (Natural Orifice Translumenal Endoscopic Surgery). In some embodiments, a device including at least one mechanical limb (e.g. as described elsewhere in this document) is inserted into a natural orifice, for example, the vagina, rectum, mouth. In some embodiments, once the device is inserted into a natural orifice, the device is inserted further into the body through an incision in the natural orifice. In some embodiments, once the device is inserted into the natural orifice, the device is inserted further into the body through a natural channel (e.g. esophagus, colon) and then, optionally, through an incision in the natural channel.

A potential benefit of treatments and/or operating using the device when performing NOTES is the ability of the device to bend within the body, potentially providing a wide range of angles of approach to a target (e.g. surgery and/or treatment of target).

In some embodiments, a device including one or more jointed mechanical arms provides a large range of access directions and/or treatment movements when inserted into a narrow orifice and/or lumen e.g. larger than less flexible laparoscopic tools.

Figure 18:
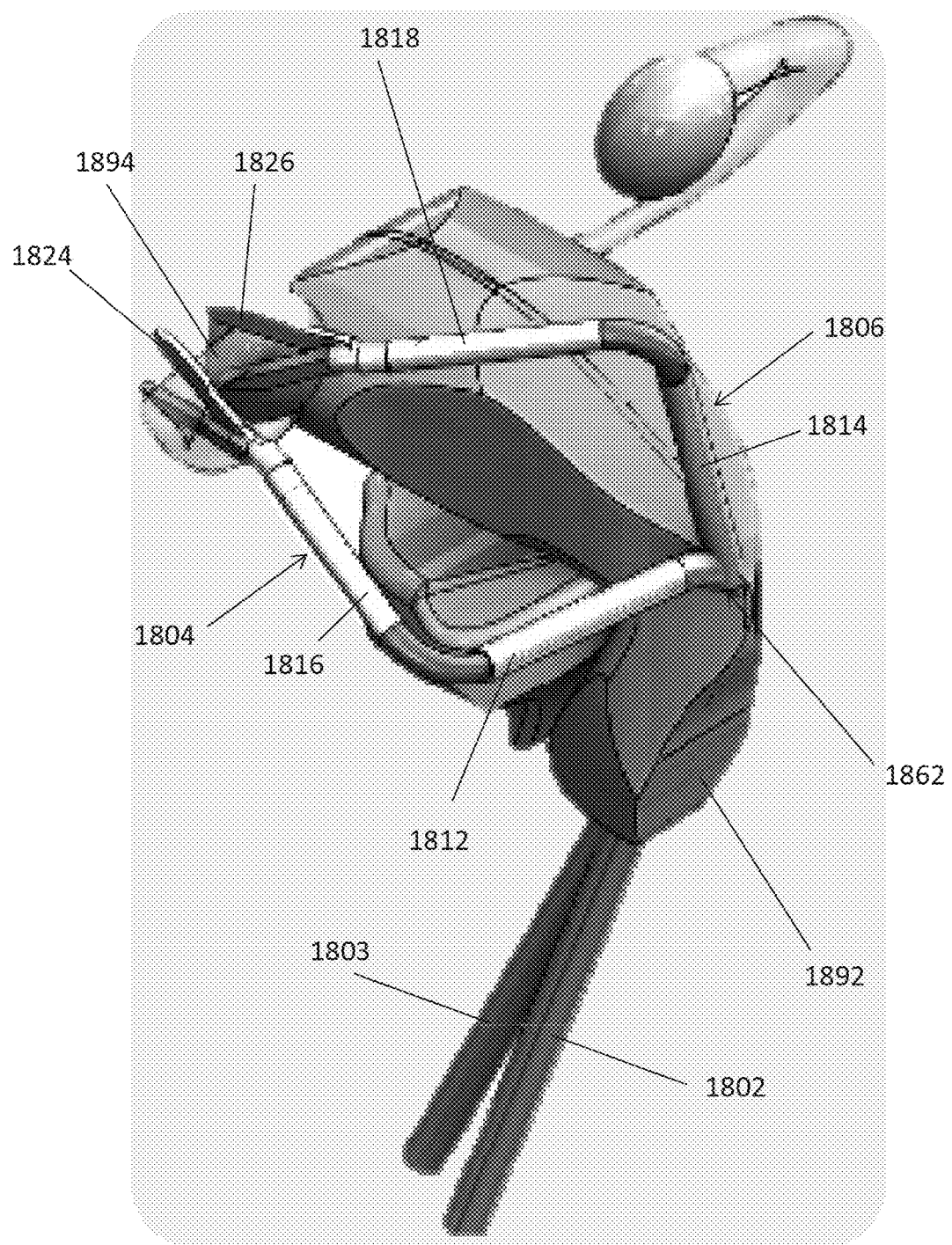
FIG. 18 is a simplified schematic of a device inserted through a natural orifice performing surgery, according to some embodiments of the invention.

FIG. 18 is a simplified schematic of a device including at least one mechanical limb (e.g. as described elsewhere in this document) is inserted through a natural orifice performing surgery, according to some embodiments of the invention. In some embodiments, the device is inserted into a patient vagina, and further into a patient body through an incision e.g. in the vagina. FIG. 18 illustrates a device including a plurality of arms 1804, 1806 which has been inserted from the vagina through the cervix into the uterus 1892. Device hand tools 1824, 1826 are operating on a fallopian 1894 tube where access is provided through an incision 1862 in the uterus.

In an exemplary embodiment, a device including at least one mechanical limb (e.g. as described elsewhere in this document) is inserted through the vagina and an incision in the posterior fornix into the Pouch of Douglas to, for example, operate on the uterus (e.g. perform hysterectomy). In an alternative embodiment, a device including at least one mechanical limb (e.g. as described elsewhere in this document) is inserted through the nostril and/or mouth to a sinus to operate on the sinus. In an alternative embodiment, a device including at least one mechanical limb (e.g. as described elsewhere in this document) is inserted through the esophagus to operate on the stomach.

Exemplary Mechanical Arm Controller Located Remotely

In some embodiments, a controller including elements (e.g. motors) for rotation of device arm segments and/or bending of device arm segments are located remotely, for example, in some embodiments, control elements (e.g. motors) are located in a device torso and/or in a device support (e.g. as described previously).

Exemplary Remote Control of Flexion and Extension

In some embodiments, flexion and/or extension of segments about joints and/or bending (e.g. flexion and/or extension of effective segments with respect to each other) is controlled remotely by means of elongated elements (e.g. wire, ribbon, tape, cable) coupled to each segment; by changing tension of one or more of the elongated elements (e.g. pulling, releasing), the segment coupled to the element flexes or extends. In some embodiments, a segment is bent in one direction by pulling on a first elongated element, for example, coupled to a first side of the segment) and straightened by pulling on a second elongated element, for example, coupled to a second side of the segment (e.g. opposing the first side of the segment).

In some embodiments, one or more elongated element for control of bending of segment/s and/or effective segment/s is coupled to the device inside one or more hollow portion of the device. For example, as described regarding elongated element 3480 FIG. 34B and/or elongated elements 3580 and 3581 FIG. 35B where, for example, the elongated elements are coupled to an inner surface of one or more hollow device portion, for example, by guiding elements, e.g. 3486*a* 3486*b* 3486*c* FIG. 34B, 3586*a* 3586*b* FIG. 35B.

In some embodiments, one or more elongated element is coupled to an outer surface of one or more device portion (e.g. a hollow device portion). For example, referring to FIG. 31C, in some embodiments, elongated elements (not illustrated) are coupled to outer surfaces of portion/s of a device arm by fins 3181, 3183. In some embodiments, a surgical device limb is covered (e.g. in a sheath) for example, potentially protecting externally coupled elongated element/s.

In an exemplary embodiment, one or more elongated element is a ribbon shape, for example, including a flattened cross sectional shape (e.g. elongated element cross section is perpendicular to an elongated element long axis), where, for example, a largest extent of the cross section is 1.25 times, or 1.5 times, or 2 times, or 3 times, or 4 times, or 10 times a smallest extent of the cross section. A potential benefit of a ribbon-shaped elongated element, for example, in comparison to a wire elongated element is increased strength for a given smallest cross sectional extent. In some embodiments, a ribbon shaped elongated element is advantageous in a nested structure, where multiple elements are located in a limited cross-sectional space.

In some embodiments, flexion and/or extension of one or more segment is by pulling an elastic elongated component (e.g. made of nitinol, NiTi), where, upon release of the elongated component, the elongated component elastically returns the segment, e.g. as described in International Patent Application Publication No. WO2011/036626.

Exemplary Remote Control of Rotation

In some embodiments, rotation of segments is controlled by rotation of an extension of the segment coupled to the segment (e.g. by a connector), which extension extends to a location, for example, at a distance from the segment (e.g. extending outside the device). In some embodiments, rotation of a segment is by rotation of a bent segment extension.

In some embodiments, segment extensions are nested (disposed) inside one or more proximal segment, for example, a hand extension is nested inside radius and/or humerus and/or torso, a radius extension is nested inside a humerus and/or torso.

Figure 19:
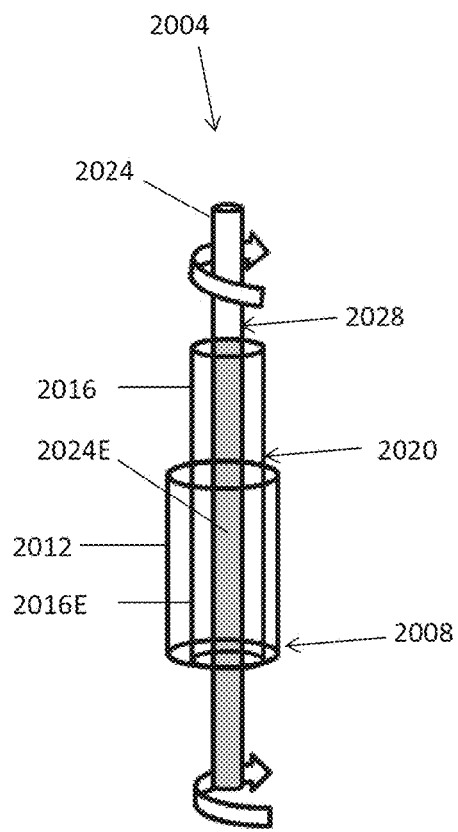
FIG. 19 is a simplified schematic of an arm with nested segment extensions, according to some embodiments of the invention.

FIG. 19 is a simplified schematic of an arm 2004 with nested segment extensions, according to some embodiments of the invention. In some embodiments, a hand 2024 coupled to a hand extension 2024E (shaded grey) is rotatable by rotation of hand extension 2024E, as illustrated by the white arrows on FIG. 19. In some embodiments, hand extension is nested inside a humerus 2012, and a radius extension 2016E. In some embodiments, radius extension 2016E is nested inside humerus 2012.

Figure 20:
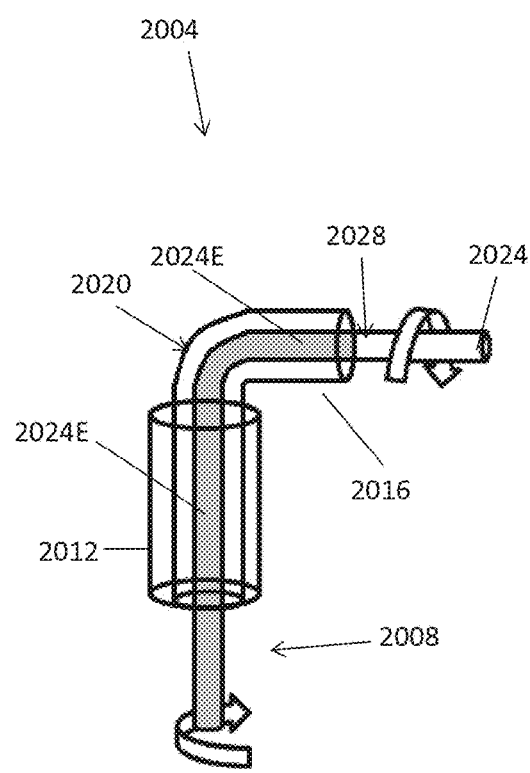
FIG. 20 is a simplified schematic of an arm, including a segment extension 2024E with a bendable torque transfer portion, according to some embodiments of the invention.

In some embodiments, a segment extension includes a torque transfer portion, such that a segment is rotatable using a segment extension when the segment extension is bent. FIG. 20 is a simplified schematic of an arm 2004, including a segment extension 2024E with a bendable torque transfer portion, according to some embodiments of the invention.

Exemplary Torque Transfer Portion

In some embodiments, a bendable torque transfer portion includes a plurality of coupled torque transfer elements.

Figure 21:
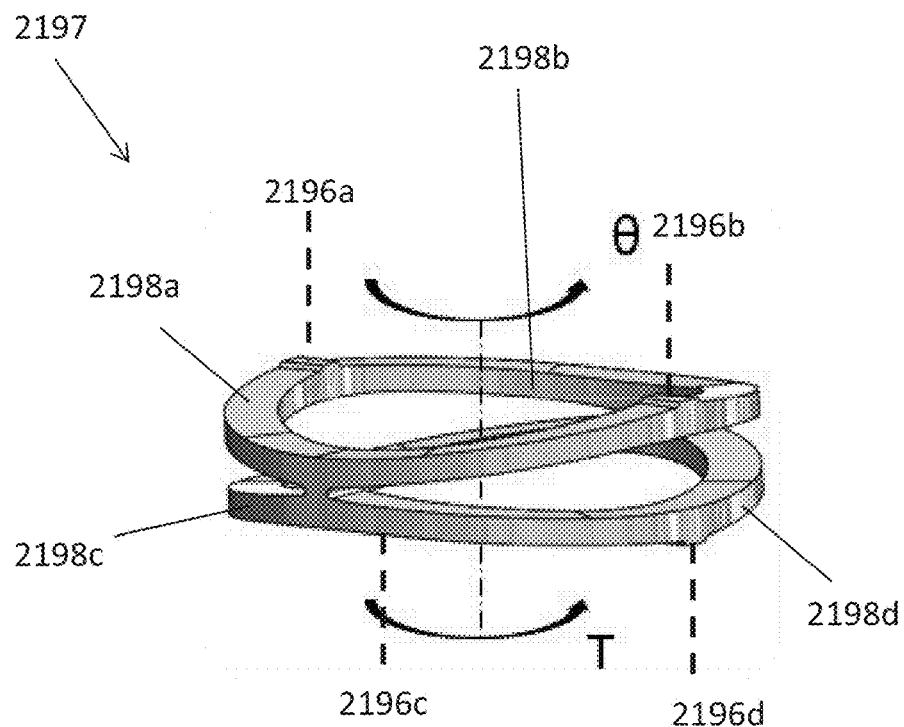
FIG. 21 is a simplified schematic of a torque transfer element according to some embodiments of the invention.

FIG. 21 is a simplified schematic of a torque transfer element according to some embodiments of the invention. In some embodiments, the torque transfer portion includes a stack of elements coupled by torque transfer portion connectors.

In some embodiments, torque transfer elements are shaped and stacked such that rotation of a single torque transfer element creates a torque (e.g. transferred by connector/s between elements) in the same direction on adjacent torque transfer elements, causing the adjacent torque transfer elements to rotate.

In an exemplary embodiment, a torque transfer element is coupled to an upper torque transfer element with two connectors 2196*a*, 2196*b*, and a lower element with two connectors 2196*c*, 2196*d*. In some embodiments, each element includes four beams, two upper beams 2198*a*, 2198*b*, connected to an upper adjacent element (not illustrated) and two lower beams 2198*c*, 2198*d* connected to a lower adjacent element (not illustrated). In some embodiments, connectors between elements transfer torque between elements. In some embodiments, one or more beam is rigid along a beam long axis, for example, resisting collapse of the beam and/or twisting of the torque transfer portion.

In some embodiments, a torque transfer portion with two or more elements, e.g. as illustrated in, FIG. 21 has open spaces at 90° intervals around the torque transfer portion, meaning that the torque transfer portion is bendable and/or deflectable from a straight position in any direction perpendicular to a torque transfer portion long axis by compression and expansion of open spaces.

In some embodiments, links include more than four beams and/or more than four connectors, and, for example, torque transfer portion has open spaces at less than 90° around the torque transfer portion.

Figure 22:
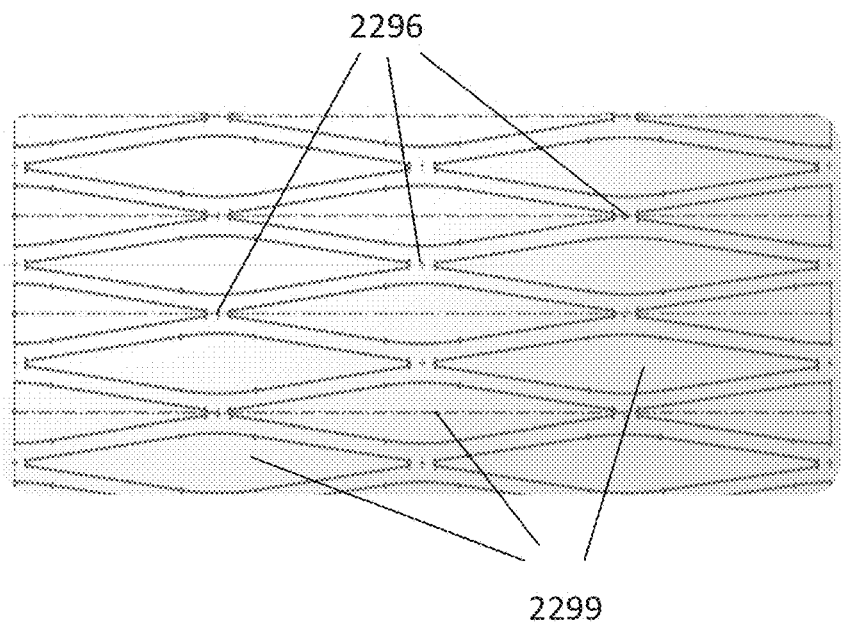
FIG. 22 is a torque transfer portion spreading pattern, according to some embodiments, of the invention.

In some embodiments, a maximum bending and/or deflection of the torque transfer portion corresponds to where open spaces on the inner bend are closed. In some embodiments, a minimum bending radius of a torque transfer portion is 15 mm, or 10 mm, or 8 mm, or 6 mm, or 4 mm. In an exemplary embodiment, a minimum bending radius of a torque transfer portion is 10 mm. In an alternative exemplary embodiment, a minimum bending radius of a torque transfer portion is 6 mm. FIG. 22 is a torque transfer portion spreading pattern, according to some embodiments, of the invention. Visible in FIG. 22 are connections 2296 between elements and open spaces 2299 between the beams.

Figure 23:
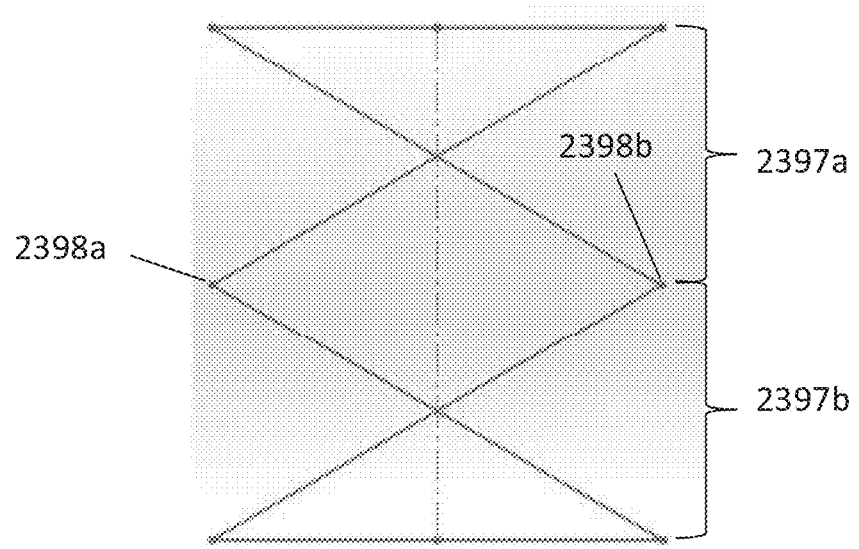
FIG. 23 is a simplified schematic side view of a straight torque transfer portion with a first and a second link, according to some embodiments of the invention.
Figure 24:
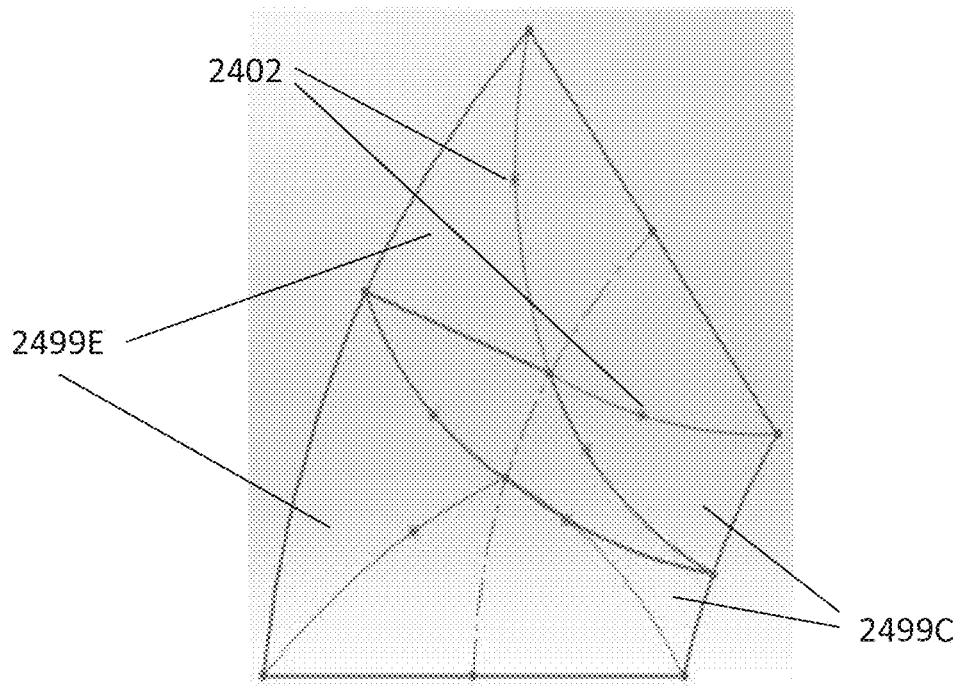
FIG. 24 is a simplified schematic side view of a bent torque transfer portion with two links, according to some embodiments of the invention.

FIG. 23 is a simplified schematic side view of a straight torque transfer portion with a first and a second element 2397*a*, 2397*b*, according to some embodiments of the invention. FIG. 24 is a simplified schematic side view of a bent torque transfer portion with two elements, according to some embodiments of the invention. In FIG. 23, midpoints 2402 illustrate exemplary elastic bending of the beams.

In some embodiments, as illustrated by FIG. 24, when the torque transfer portion bends, open spaces between elements on the outer side of the bend expand 2499E and/or open spaces on the inner side of the bend contract 2499C.

In some embodiments, during bending, a torque transfer portion length (e.g. as illustrated by a dotted line in FIG. 23 and FIG. 24) does not change in length (maintains an original length).

In some embodiments, elements are constructed by laser cutting a hollow tube.

In some embodiments, a torque transfer portion is able to transfer 100 g over 100 mm, 0.1 Nm. In some embodiments, a torque transfer portion is able to transfer 0.01-1 Nm or 0.01-0.5 Nm or lower or higher or intermediate ranges or torques. In some embodiments, torque transfer ability of the torque transfer portion is associated with strength of connections e.g. connections 2292 FIG. 22 and/or a resistance to collapse of the torque transfer portions.

Figure 25:
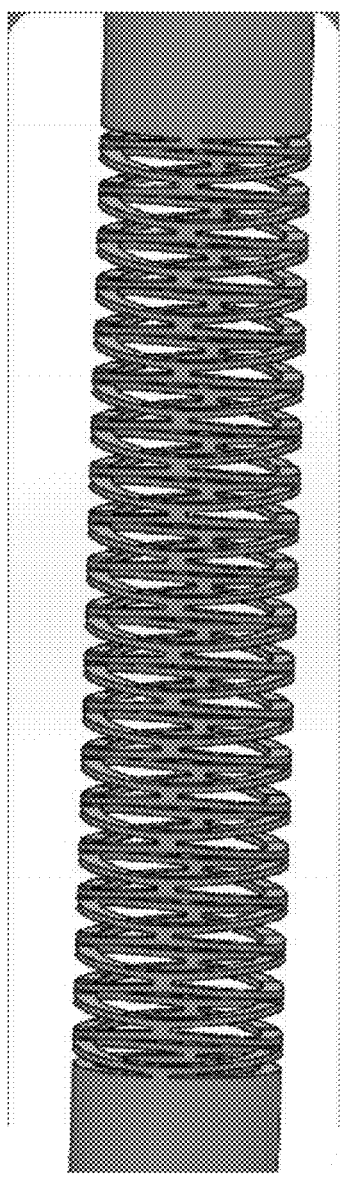
FIG. 25 is a simplified schematic side view of a straight torque transfer portion with plurality links, according to some embodiments of the invention.
Figure 26:
FIG. 26 is a simplified schematic side view of a bent torque transfer portion with a plurality of links, according to some embodiments of the invention.

FIG. 25 is a simplified schematic side view of a straight torque transfer portion with plurality elements, according to some embodiments of the invention. FIG. 26 is a simplified schematic side view of a bent torque transfer portion with a plurality of elements, according to some embodiments of the invention.

Exemplary Joints

Figure 27:
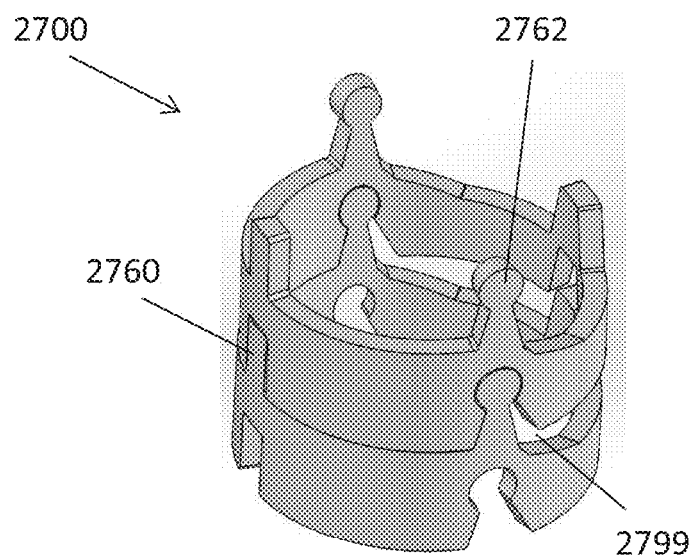
FIG. 27 is a simplified schematic of a straight joint including two links, according to some embodiments of the invention.

In some embodiments, joints are formed by one or more link. In some embodiments, joints are formed by a stack of a plurality of links. FIG. 27 is a simplified schematic of a straight joint 2700 including two links 2702, according to some embodiments of the invention.

Figure 28:
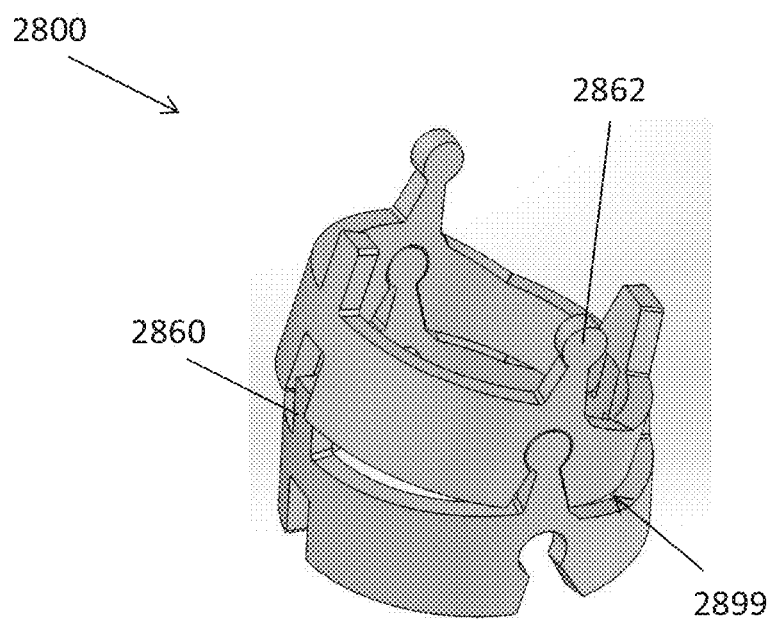
FIG. 28 is a simplified schematic of a joint including two links, where the links are rotated about a joint long axis, according to some embodiments of the invention.

FIG. 28 is a simplified schematic of a joint 2800 including two links, where the links are rotated about a joint long axis, according to some embodiments of the invention.

In some embodiments, links include one or more air gap 2799, 2899 for example, allowing deflection in one direction (e.g. so that, flexion and/or extension is uni-directional). In some embodiments air gaps 2799, 2899 are located on the same side of sequential links. In some embodiments, air gaps 2799, 2899, do not extend around the links, restricting a direction of bending of the joint.

In some embodiments, one or more link includes a wedge 2760, 2860, which, for example, prevents the links from disassembling, e.g. when the joint bends. In some embodiments, links include connectors 2762, 2862 (e.g. link pins), which couple a link to adjacent links.

In an exemplary embodiment, each link is rotatable by up to 16° from the joint long axis. In some embodiments, for 90° of flexion 6 links are used, in some embodiments, for 180° of flexion 12 links are used.

Figure 29:
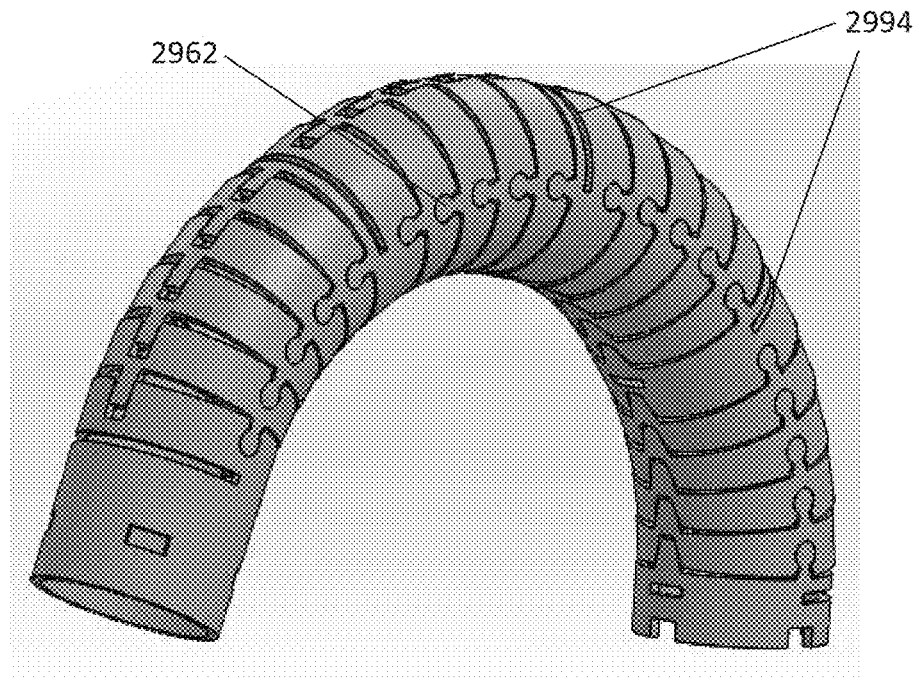
FIG. 29 is a side view of a joint including a plurality of links, where the links are rotated about a joint long axis, according to some embodiments of the invention.

FIG. 29 is a side view of a joint including a plurality of links, where the links are rotated about a joint long axis, according to some embodiments of the invention.

Figure 30:
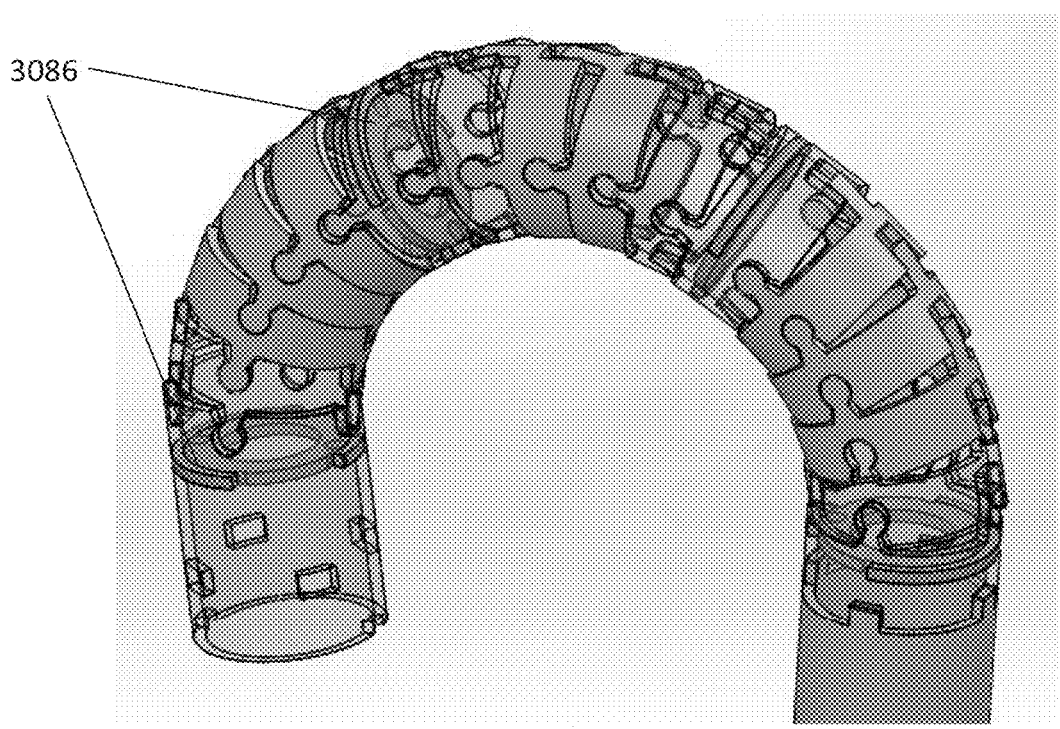
FIG. 30 is a simplified schematic side view of a joint including a plurality of links, where a plurality of links include guiding rings, according to some embodiments of the invention.

In some embodiments, guiding element, (e.g. fin or ring as described in more detail below), is coupled to a link. In some embodiments, guiding elements are coupled to more than one link. FIG. 30 is a simplified schematic side view of a joint including a plurality of links, where a plurality of links include guiding elements 3086, according to some embodiments of the invention. In the embodiment illustrated by FIG. 30 guiding elements are rings.

In some embodiments, guiding elements are coupled to links by a portion of the ring that protrudes through a hole or slot. Referring back to FIG. 29, slots 2994 are visible in some links.

In an exemplary embodiment, guiding fins and/or rings are fitted to joints by inserting the rings inside the joints.

Exemplary Arm Embodiments

Figures 31A, 31B:
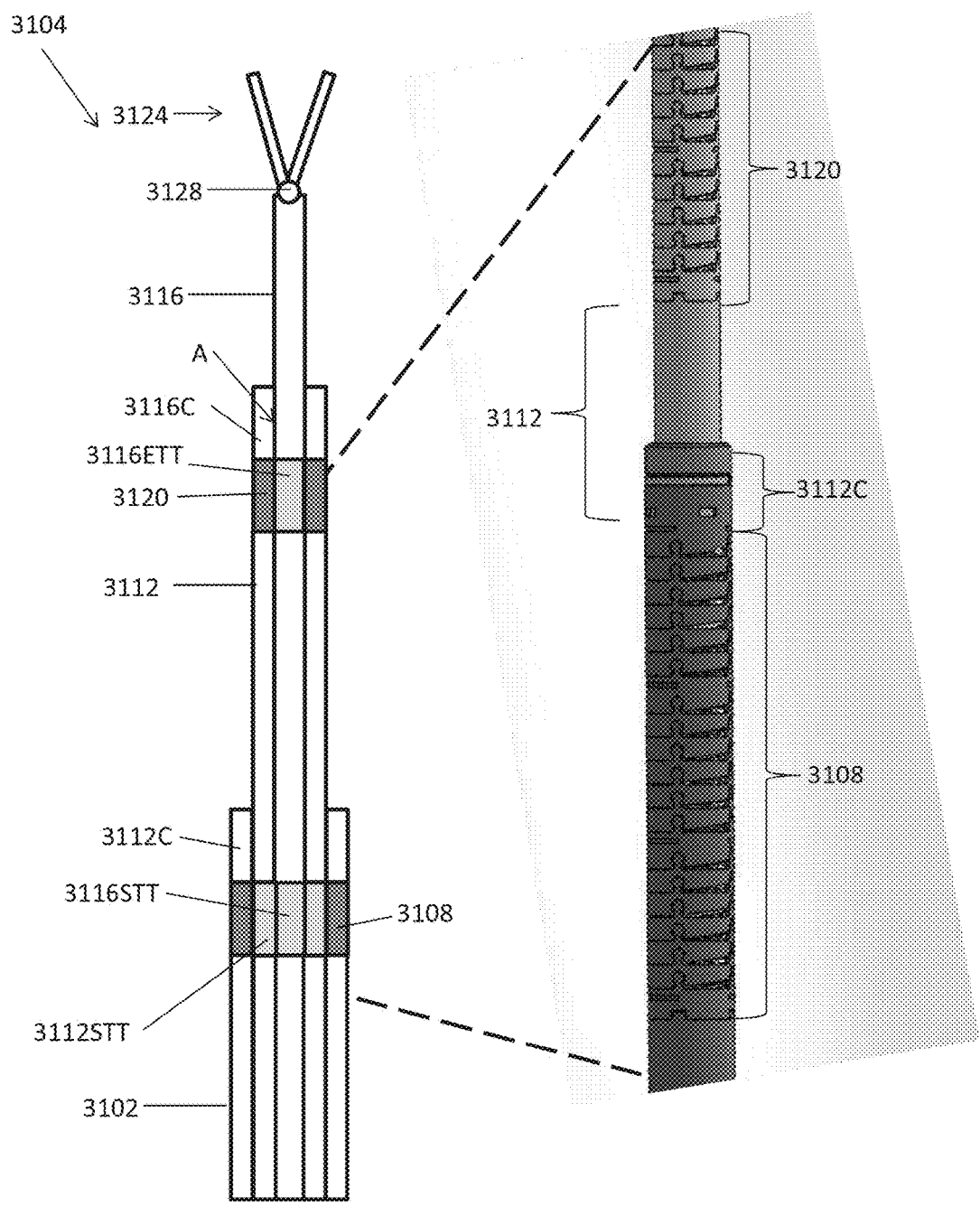
FIG. 31A is a simplified schematic cross sectional view of an arm with nested segment extensions, according to some embodiments of the invention.
FIG. 31B is a simplified schematic of a side view of a portion of an arm, according to some embodiments of the invention.

FIG. 31A is a simplified schematic cross sectional view of an arm 3104 with nested segment extensions, according to some embodiments of the invention. FIG. 31B is a simplified schematic of a side view of a portion of an arm, according to some embodiments of the invention. Dashed lines illustrate the portion of the arm illustrated in FIG. 31A illustrated by FIG. 31B.

In some embodiments, arm 3104 includes a hand tool 3124 coupled to a radius 3116 at a wrist joint 3128.

In some embodiments, radius 3116 is coupled to a radius extension including two torque transfer portions; an elbow torque transfer portion 3116ETT disposed inside an elbow joint 3120 and a shoulder torque transfer portion 3116STT disposed inside a shoulder joint 3108. In some embodiments, radius 3116 is coupled to a humerus 3112 by a connector 3116C. In some embodiments, portion 3116C connects radius 3116 to humerus 3112 whilst allowing free rotation of humerus 3122. In some embodiments, at region A of FIG. 31A, protrusion/s on radius portion 3116 fit into indentation/s on portion 3116C. In an exemplary embodiment, a ring shaped protrusion on radius portion 3116 (e.g. a ring of material connected (e.g. welded) to radius portion 3116) fits into an indentation on portion 3116C. Similarly, in some embodiments, portions 3112C and 3112 are connected by matching protrusion/s and indentation/s (e.g. a ring protrusion on portion 3112 fitting into a matching indention in portion 3112C).

In some embodiments, a "connecting section" includes a connector and a joint, for example shoulder joint 3108 and connector 3112C, for example elbow joint 3120 and connector 3116C.

Figure 31C:
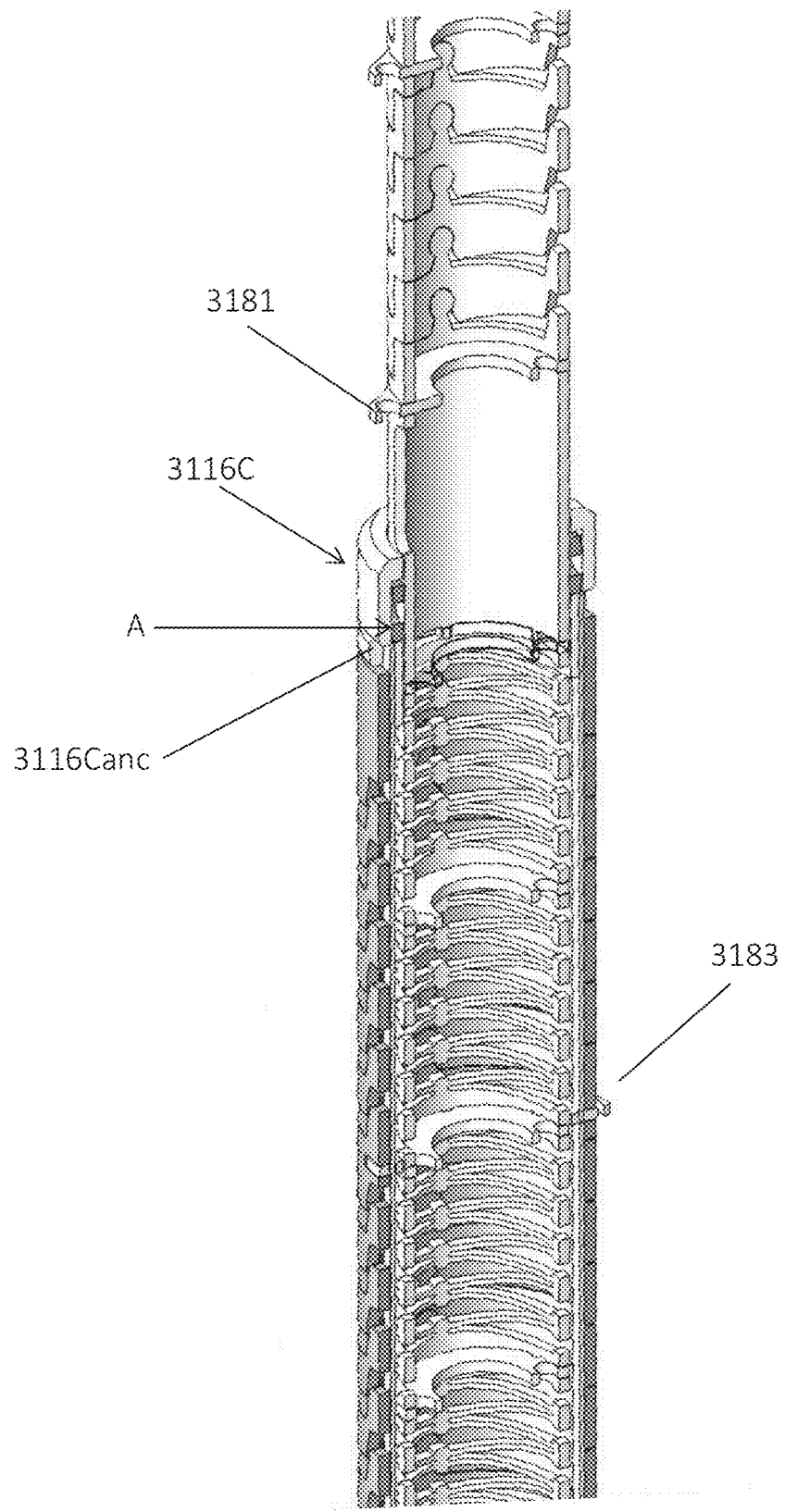
FIG. 31C is a simplified schematic cross sectional view of an arm with nested segment extensions, according to some embodiments of the invention.

FIG. 31C is a simplified schematic cross sectional view of a portion of an arm, according to some embodiments of the invention. In some embodiments, for example, at A portion includes a ring protrusion which fits into an indentation on portion 3116C.

In some embodiments, portion 3116C provides anchoring to one or more elongated element: for example, where elongated element/s are connected/coupled to portion 3116Canc.

In some embodiments, one or more connector couples portions whilst allowing one portion to rotate within the connector about the portion's long axis. For example connecting portion 3116C allows radius 3116 to rotate within connecting portion 3116C about a radius long axis.

In some embodiments, humerus 3112 is coupled to a humerus extension including one torque transfer portion, a shoulder torque transfer portion 3112STT disposed inside shoulder joint 3108. In some embodiments, the humerus is coupled to a torso 3102 by a connector 3112C.

In some embodiments, a mechanical arm includes a first and a section flexible portion (e.g. elbow joint and shoulder joint) which are coupled together with a short connecting segment (e.g. a humerus section coupling a shoulder and elbow joint is short). In some embodiments, coupling between the flexible portions is a point connection (e.g. a shoulder and elbow joint are directly connected).

In some embodiments, a rigid anchoring portion (e.g. portion 3116C) connects two flexible portions, where the anchoring portion provides anchoring of elongated elements which control flexion and extension of the joint which is, for example, proximal to the elongated portion. In some embodiments, anchoring is provided by a portion of one of the joints, e.g. a distal portion of the proximal joint.

Figures 32, 33A:
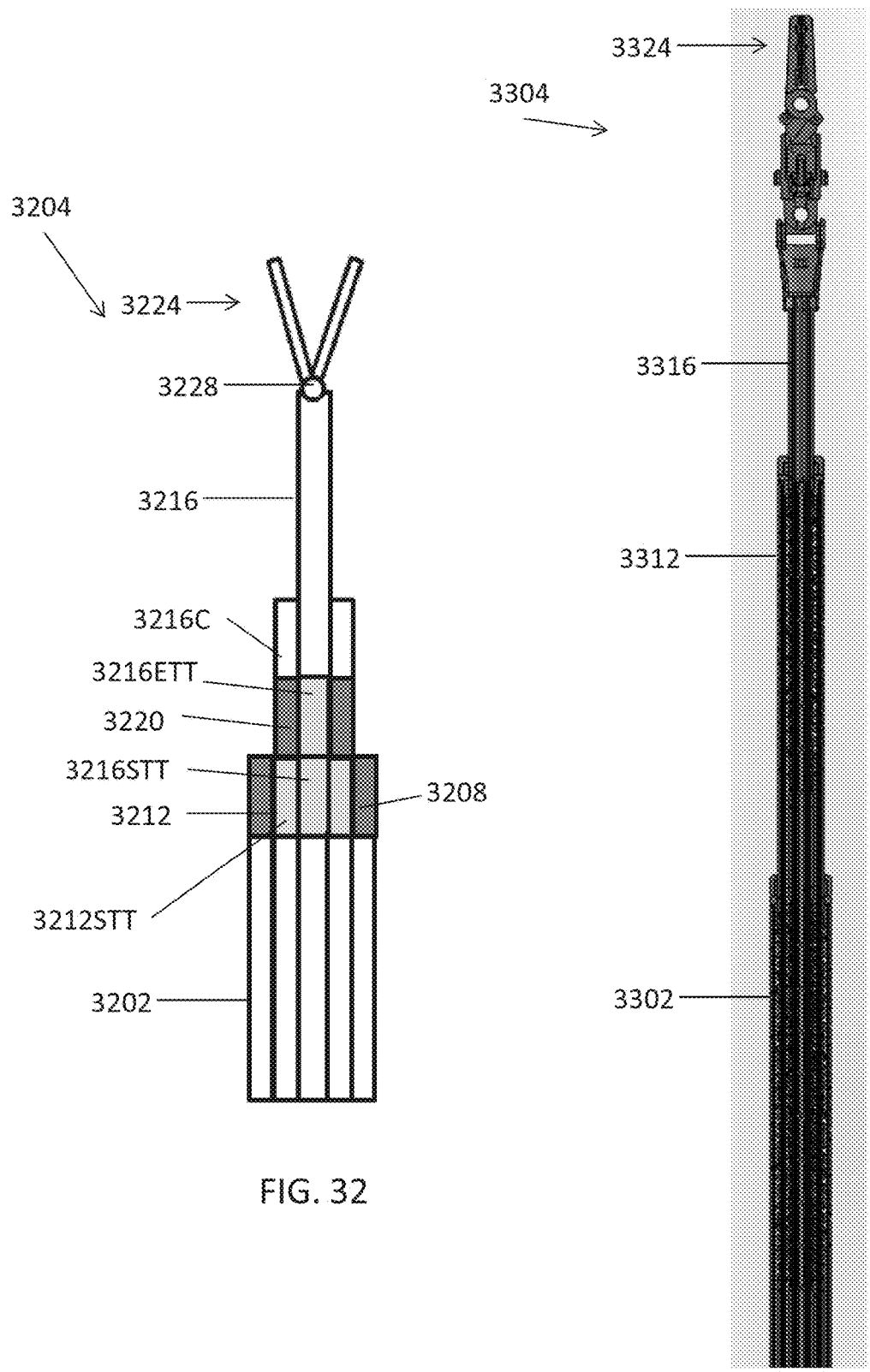
FIG. 32 is a simplified schematic cross sectional view of an exemplary arm with nested segment extensions, according to some embodiments of the invention.
FIG. 33A is a simplified schematic of a hand tool coupled to a radius, coupled to a radius segment extension, according to some embodiments of the invention.

In some embodiments, one or more rigid segment is absent: FIG. 32 is a simplified schematic cross sectional view of an arm 3204 with nested segment extensions, according to some embodiments of the invention. In some embodiments, elbow joint 3220 and shoulder joint 3208 are directly coupled (e.g. arm 3204 lacks a humerus portion).

FIG. 33A is a simplified schematic cross sectional view of an exemplary arm 3204 with nested segment extensions, according to some embodiments of the invention.

Figures 33B, 33C:
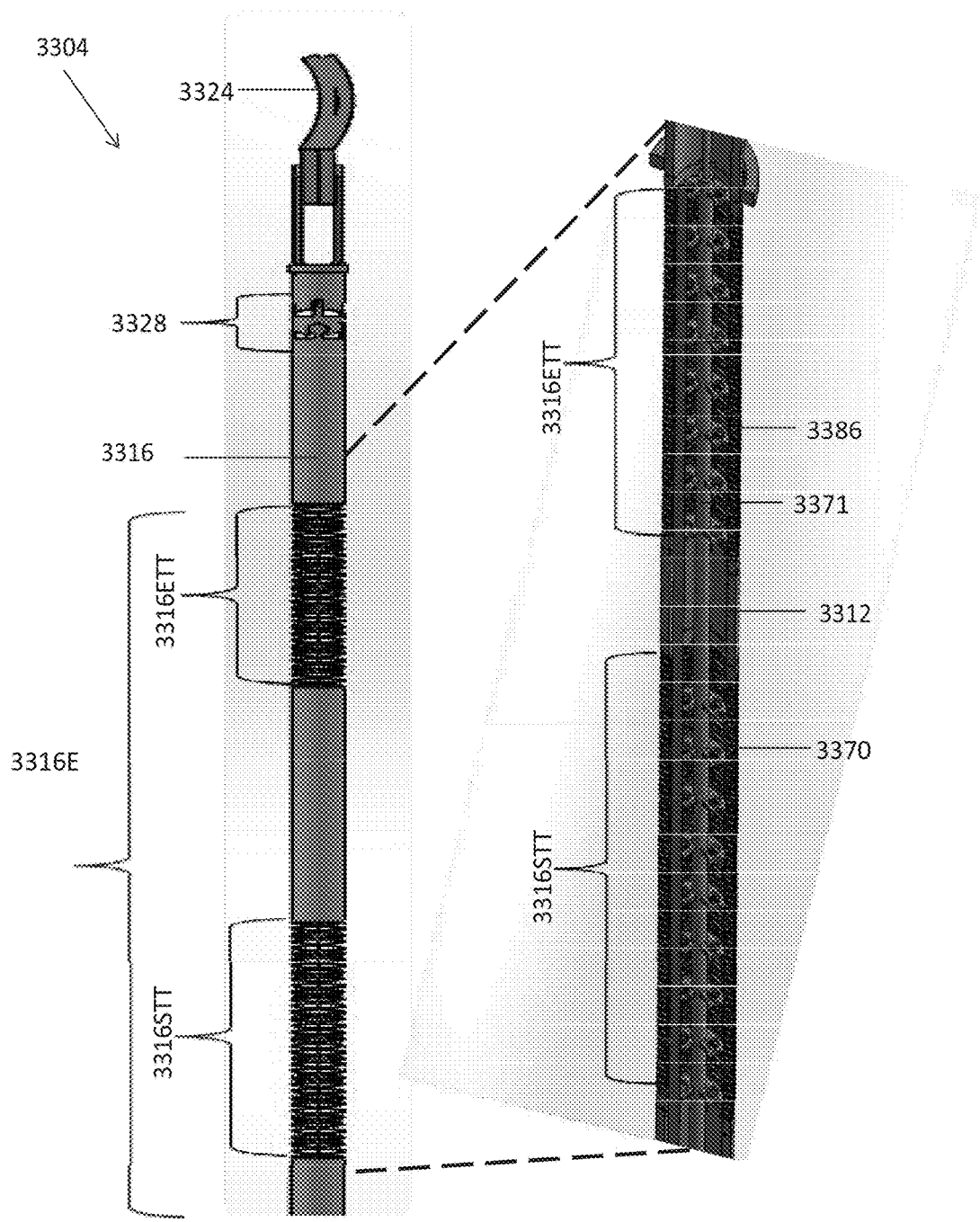
FIG. 33B is a simplified schematic cross sectional view of a portion of a radius extension, according to some embodiments of the invention.
FIG. 33C is a simplified schematic cross sectional view of a portion of a radius extension, according to some embodiments of the invention.

FIG. 33B is a simplified schematic of a hand tool 3324 coupled to a radius, coupled to a radius segment extension 3316E, according to some embodiments of the invention. In some embodiments, radius segment extension 3316E includes an elbow torque transfer portion 3316ETT and a shoulder torque transfer portion 3316STT.

As was described previously, in some embodiments, elongated elements are used to control flexion and extension of the arm segments at arm joints. In some embodiments, elongated elements pass through an axial void in a segment and/or joint and/or segment extension and/or torque transfer portion.

FIG. 33C is a simplified schematic cross sectional view of a portion of a radius extension, according to some embodiments of the invention. In some embodiments, one or more elongated element 3370 is coupled to torque transfer portion links 3324STT, 3324ETT, by guiding elements. In some embodiments, guiding elements are fins 3386. Alternatively or additionally, in some embodiments, guiding elements are rings.

In some embodiments, during rotation of a segment extension (and segment), elongated elements remain in position within the element, for example rotate with the element, e.g. as they are coupled in position by guiding elements (e.g. fins 3386).

In some embodiments, an electricity supply cable 3371 passes through the radius segment extension, for example, to supply electricity to a hand tool (e.g. for electro surgery).

Figure 34A:
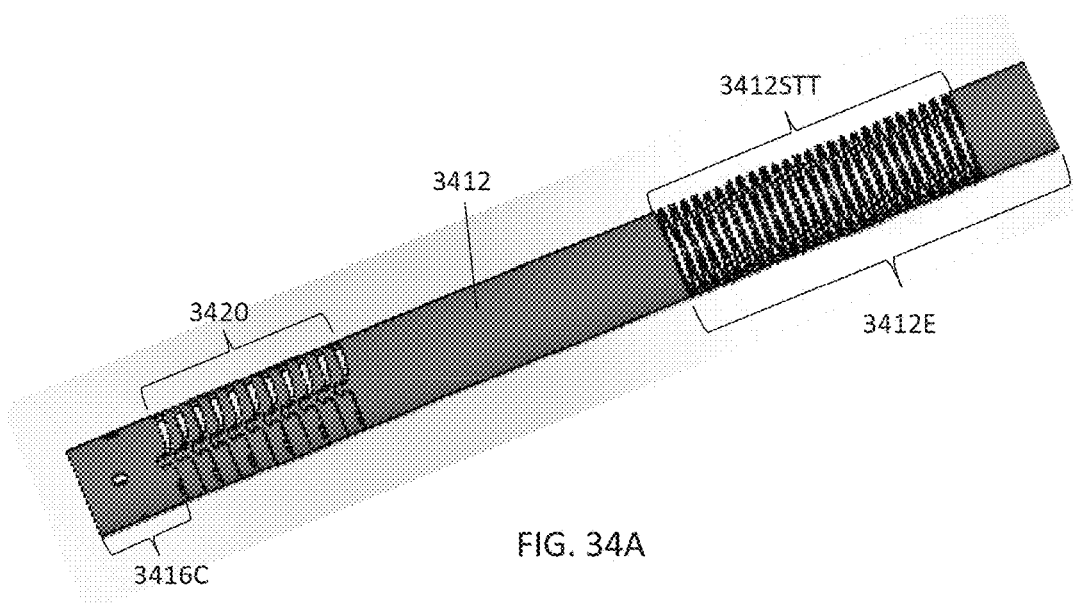
FIG. 34A is a simplified schematic side view of a device arm portion including a humerus coupled to a humerus extension, according to some embodiments of the invention.
Figure 34B:
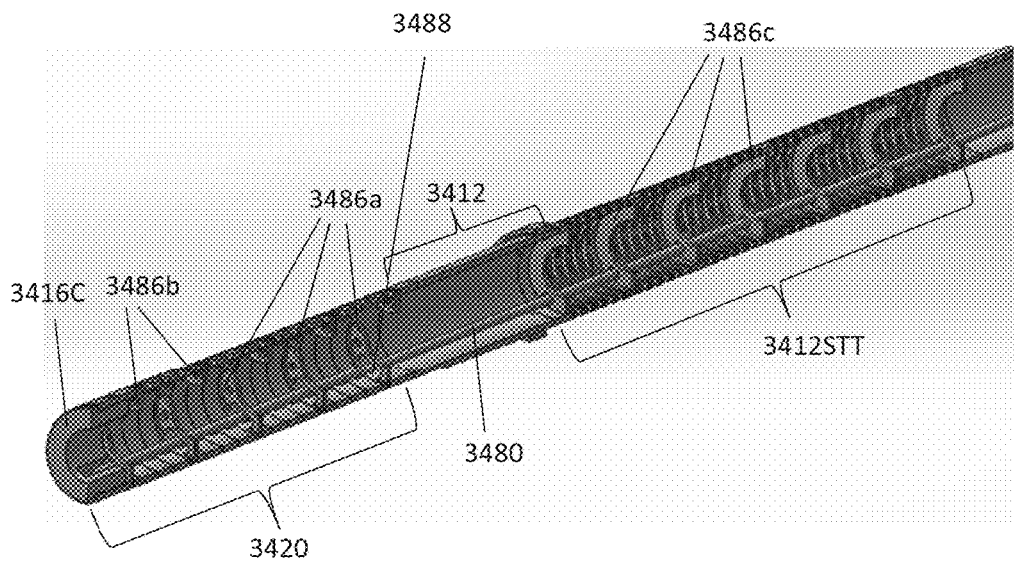
FIG. 34B is a simplified schematic cross sectional view of a humerus coupled to a humerus extension, according to some embodiments of the invention.

FIG. 34A is a simplified schematic side view of a device arm portion including a humerus coupled to a humerus extension 3412E, according to some embodiments of the invention. FIG. 34B is a simplified schematic cross sectional view of a humerus 3412 coupled to a humerus extension 3412E, according to some embodiments of the invention.

In some embodiments, elbow joint 3420 is coupled to two or more elongated elements, a first elongated element 3480 is pulled to bend (flex or extend) radius 3416 in one direction, and a second elongated element (not illustrated) is pulled to bend the radius in the opposite direction. In some embodiments, elbow joint 3420 is coupled to more than two elongated elements, potentially increasing a maximum load (e.g. radius, tissue held by a hand tool) that the elements move.

In an exemplary embodiment, elongated element 3480 is coupled to elbow joint 3420 links by guiding elements (e.g. fins 3486a) and to shoulder torque transfer portion links by guiding elements (e.g. fins 3486c). In some embodiments, fins 3486 each hold the elongated element, in a gap 3488, whilst allowing elongated element 3480 to slide (e.g. be pulled, be released) within gap 3488. In some embodiments, one or more guiding element is a ring. In some embodiments fins and/or rings hold an elongated element at an inner edge of a hollow region (e.g. of a segment and/or joint, and/or torque transfer portion).

Similarly, in some embodiments, a second elongated element (not illustrated) is coupled to a different part of the inner edge of the hollow region. For example, the second elongated element is coupled to a diametrically opposing side of elbow joint 3420 by second elongated element fins 3486b coupled to links on the opposite side of elbow joint 3420. In some embodiments, first elongated element fins 3486a and second elongated element fins 3486b are coupled to different links, for example, alternating links. In an exemplary embodiment, the first elongated element fins and the second elongated element fins are coupled to alternative links, with two links without fins between every first elongated element fin second elongated element fin pair.

In some embodiments, one or more elongated element 3420 is fixed to a portion 3416C. For example, in some embodiments, a distal end of elongated element 3420 is fixed to portion 3416C. Alternatively, in some embodiments, elongate element is only slidably coupled, for example, looping through a gap in portion 3416C.

Figure 35A:
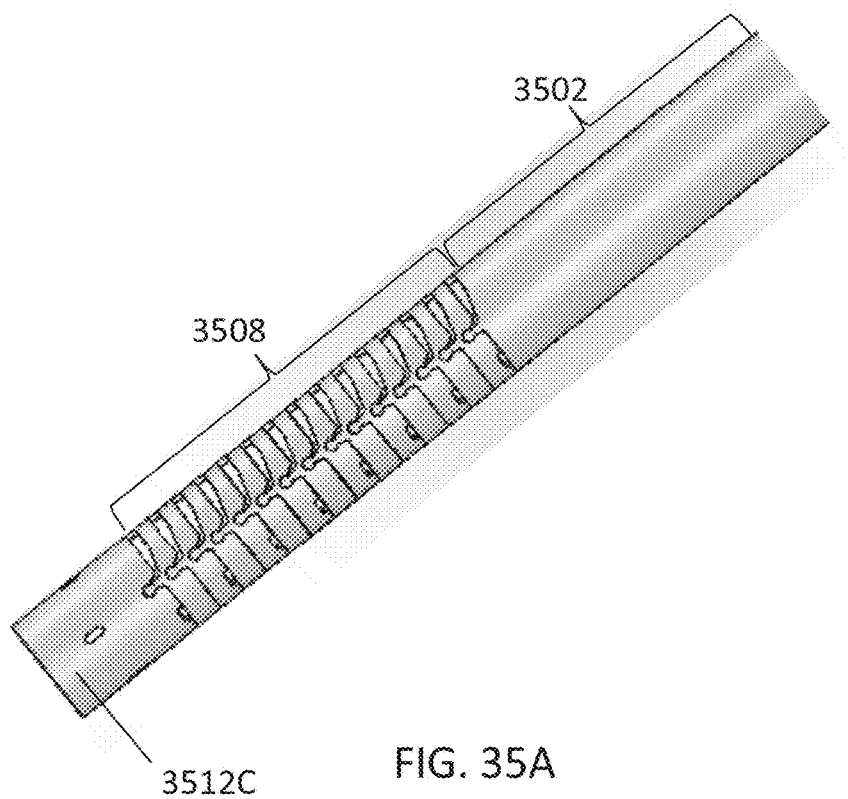
FIG. 35A is a simplified schematic side view of a shoulder joint coupled to a torso, according to some embodiments of the invention.
Figure 35B:
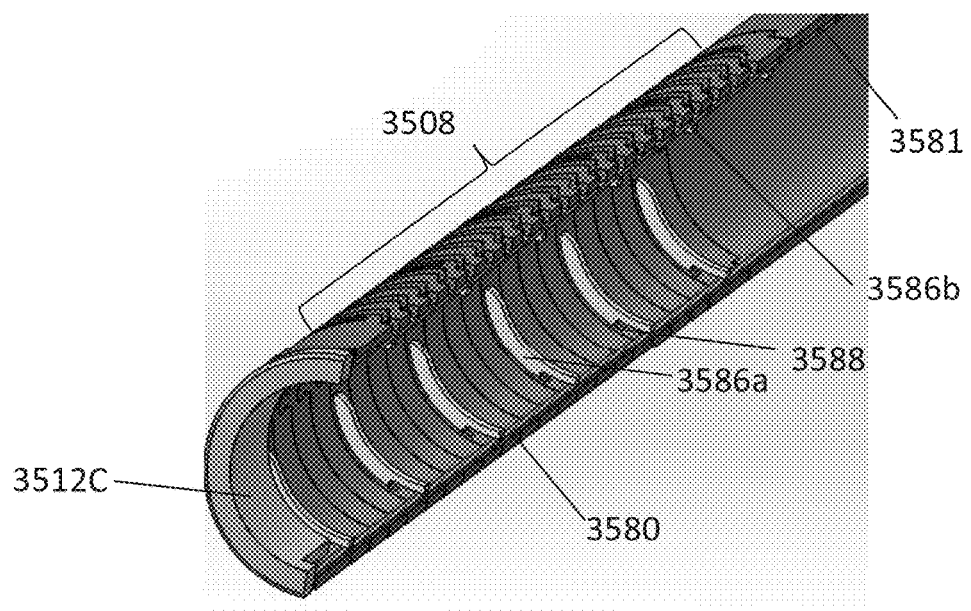
FIG. 35B is a simplified schematic cross sectional view of a shoulder joint coupled to a torso, according to some embodiments of the invention.

FIG. 35A is a simplified schematic side view of a shoulder joint 3508 coupled to a torso 3502, according to some embodiments of the invention. FIG. 35B is a simplified schematic cross sectional view of a shoulder joint 3508 coupled to a torso 3502, according to some embodiments of the invention. In some embodiments, a first elongated element (e.g. cable, ribbon, wire, tape) 3580 is coupled to links in shoulder joint by fins 3586a. In some embodiments, a second 3581 elongated element cable is coupled to links in shoulder joint by fins 3586b. In some embodiments, one or more additional elongated element is coupled to a first elongated element, potentially providing increased strength. In some embodiments, cables and fins have functionality as described above, regarding the radius and radius extension.

Exemplary Motor Actuation

In some embodiments, a device including one or more mechanical limb (e.g. as described elsewhere in this document) is actuated by a motor unit coupled to a proximal end of the arm/s.

Figure 39:
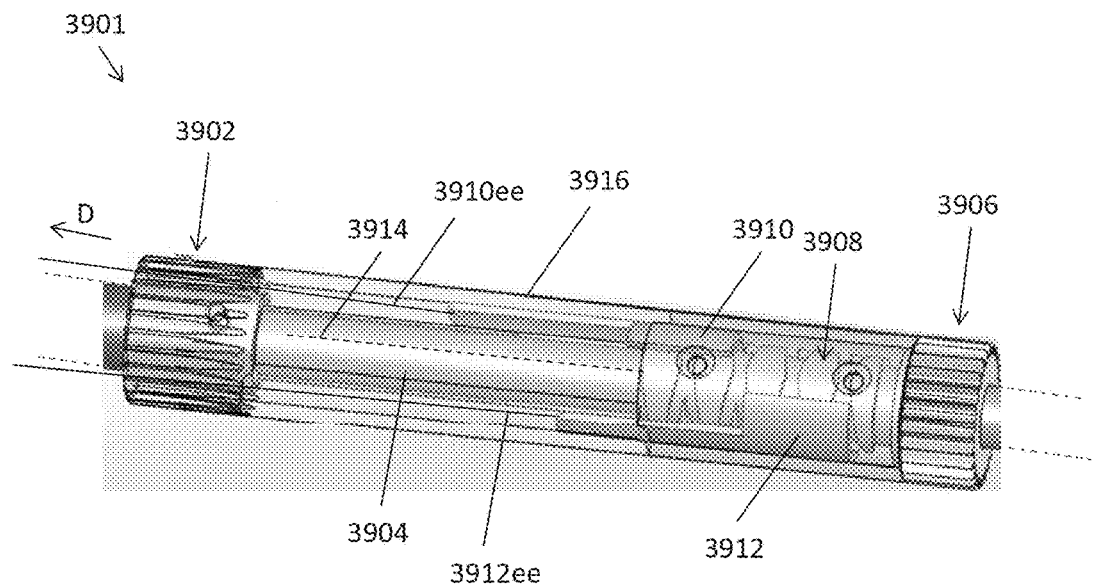
FIG. 39 is a simplified schematic side view of an actuation mechanism for control of a mechanical limb joint, according to some embodiments of the invention.

In an exemplary embodiment, bending (flexion and extension) and rotation of a single joint is controlled by movement of two gears. FIG. 39 is a simplified schematic side view of an actuation mechanism 3901 for control of a mechanical limb joint, according to some embodiments of the invention.

In some embodiments, a rotation gear 3902 is coupled to a central shaft 3904, where central shaft 3904 is coupled to an extension (e.g. 3316E, FIG. 33A). In some embodiments, a distal portion of central shaft 3904 (in direction D of rotation gear 3902) is coupled to the extension. In some embodiments, rotation of rotation gear 3902 causes rotation of central shaft 3904 which in turn rotates the extension coupled to the central shaft.

In some embodiments, a bending gear 3906 is coupled to a portion including screw threading 3908. Rotation of the bending gear 3906 causes rotation of screw threading 3908. In some embodiments, a first nut 3910 and a second nut 3912 are coupled to screw threading 3908 such that rotation of the screw threading generates linear movement of nuts parallel to a long axis 3914 of central shaft 3904 where first nut 3910 and second nut 3912 move in different directions. In some embodiments, first nut 3910 and second nut 3912 are connected to elongated elements 3910ee and 3912ee respectively, where linear movement of the nuts pulls one elongated element whilst releasing and/or pushing on the other, generating flexion/extension of the joint.

In some embodiments, rotation of the joint is effected by rotation of both rotation gear 3902 and bending gear 3904. In some embodiments, bending of the joint is effected by rotation of the bending gear only. In some embodiments, concurrent bending and rotation of the joint is effected by rotation of the rotation gear and bending gear by different extents and/or in different directions. For example, in some embodiments, concurrent bending and rotation of the joint is effected by holding the bending gear stationary whilst rotating the rotation gear.

In some embodiments, a cover 3916 covers the central shaft, screw threading and nuts, for example, potentially preventing debris or other material from entering the mechanism.

In some embodiments, each mechanical device joint is coupled to an actuation mechanism as described above (e.g. by an extension coupled to the joint). For example, in some embodiments, each extension portion (e.g. as describe above) is coupled to a central shaft, and elongated portions for control of flexion and extension (e.g. as described above) are coupled to nuts of the actuation mechanism. In some embodiments, actuation mechanisms for a single mechanical limb are arranged linearly, with central shafts disposed in a nested configuration, the inner central shafts protruding for control by the gears.

FIG. 40 is a simplified schematic side view of a motor unit 4000 for actuation of a device including mechanical arms, according to some embodiments of the invention. In some embodiments, a device including a first mechanical arm 4002 and a second mechanical arm 4006 are controlled by motor unit 4000.

In some embodiments, a first actuation mechanism 4001a, including first rotation gear 4002a and first bending gear 4006a, drives flexion/extension and rotation of a shoulder joint. Referring now to FIGS. 35A-35B, for example, in some embodiments, first actuation mechanism 4001a rotates the shoulder joint by rotating portion 3502 and effects flexion and extension of joint 3508 by movement of elongated elements (e.g. 3581 in FIG. 35B) attached to portion 3512C.

In some embodiments, a second actuation mechanism 4001b, including second rotation gear 4002b and second bending gear 4006b, drives flexion/extension and rotation of an elbow joint. In some embodiments, one or more driving gear coupled to a motor is disposed underneath motor unit 4000. For example, in some embodiments, a gear which drives second bending gear 4006b, which gear is coupled to a motor is disposed on an underside of motor unit 4000. For example, gear 4099 drives a second actuation mechanism corresponding to second mechanical arm 4006. Referring now to FIGS. 34A-34B, for example, in some embodiments, second actuation mechanism 4001b rotates the elbow joint by rotating portion 3412E and effects flexion and extension of joint 3508 by movement of elongated elements (e.g. 3480 in FIG. 34B) attached to portion 3416C.

In some embodiments, a third actuation mechanism 4001c, including third rotation gear 4002c and third bending gear 4006c, actuates an end effecter (e.g. opens and closes a gripper) and drives rotation of a wrist joint. Referring to FIG. 1C, in some embodiments, third actuation mechanism 4001b rotates and actuates end effecter 124; For example, in some embodiments, rotation of third rotation gear 4006c opens and closes an end effecter (e.g. end effecter 124, FIG. 1A). For example, in some embodiments, a gripper includes a rotation/screwing open-close mechanism e.g. as described regarding FIG. 36B, and rotation of third rotation gear 4006c opens and closes an end effecter. In some embodiments, rotation of rotation gear 4006c rotates nut 3602.

In embodiments where a device arm also includes a wrist joint (e.g. as illustrated by FIGS. 33B-33C) which can bend, the motor unit includes an additional mechanism for actuating flexion/extension of the wrist joint.

In some embodiments, similarly, second mechanical limb 4006 is actuated by three actuation mechanisms, including, for example, 6 motors. In an exemplary embodiment, a device for insertion into the body includes two mechanical limbs, actuated by 12 motors.

In some embodiments, one or more additional motor (e.g. a 13$^{th}$ motor) moves the device arms towards and/or away from the motor unit. For example, in some embodiments, a position of attachment of the motor unit (e.g. to a support and/or to a patient support surface) is changed e.g. by a motor.

For example, referring to FIG. 15, in some embodiments, a position of attachment of support 1582 with respect to rail 1502 is changed (e.g. by a motor located on support 1582). For example, in some embodiments, a position of attachment of motor unit 1514 with respect to support 1482 is changed (e.g. by a motor located on support 1582).

For example, moving the device into and/or out of a patient body e.g. when the motor unit is supported in a fixed configuration and/or to automate movement of the device into the patient. In some embodiments, a motor located within motor unit 4000 moves the device arms into and/or out of a patient.

In some embodiments, for example, so that rotation of a joint also causes rotation of joints distal of the rotated joint, more than one actuation mechanism is driven in rotation of the joint. For example, in some embodiments, for rotation of the shoulder joint, gears 4002a, 4006a, 4002b, 4006b, 4002b, 4006b are rotated in the same direction. For example, in some embodiments, for rotation of the elbow joint, gears 4002b, 4006b, 4002b, 4006b are rotated in the same direction. For example, in some embodiments, for rotation of the end effecter, gears 4002b, 4006b are rotated in the same direction. In some embodiments, concurrent rotation of nested portions with outer portions prevents stress on and/or tangling of internal elongated elements (e.g. elongated element/s which are used to effect flexion/extension, e.g. elongated element/s providing power supply).

In some embodiments, one or more actuation mechanism is used to flex/extend a joint. For example, in some embodiments, to bend a shoulder joint, elongated elements for bending of both the shoulder joint and elbow joint are moved. In some embodiments, if elongated elements for the elbow are not moved and/or released, tension in the elongated elements associated with the elbow joint resist movement of the shoulder joint. For example, bending of the shoulder joint is effected by rotation of gears in first actuation mechanism 4001a and second actuation mechanism 4001b are rotated.

In some embodiments, the motor unit includes one or more position sensor, and/or is controlled by a processor including a memory which stores commands. In some embodiments, data from position sensor/s and/or from control memory is used to infer a position of device portion/s.

In some embodiments, a motor unit is small, for example, with 100-600 mm, or 200-400 mm, or about 300 mm long axis length and about 20-100 mm, or 30-80 mm, or 60 mm maximum extent perpendicular to the motor unit long axis.

Figure 41:
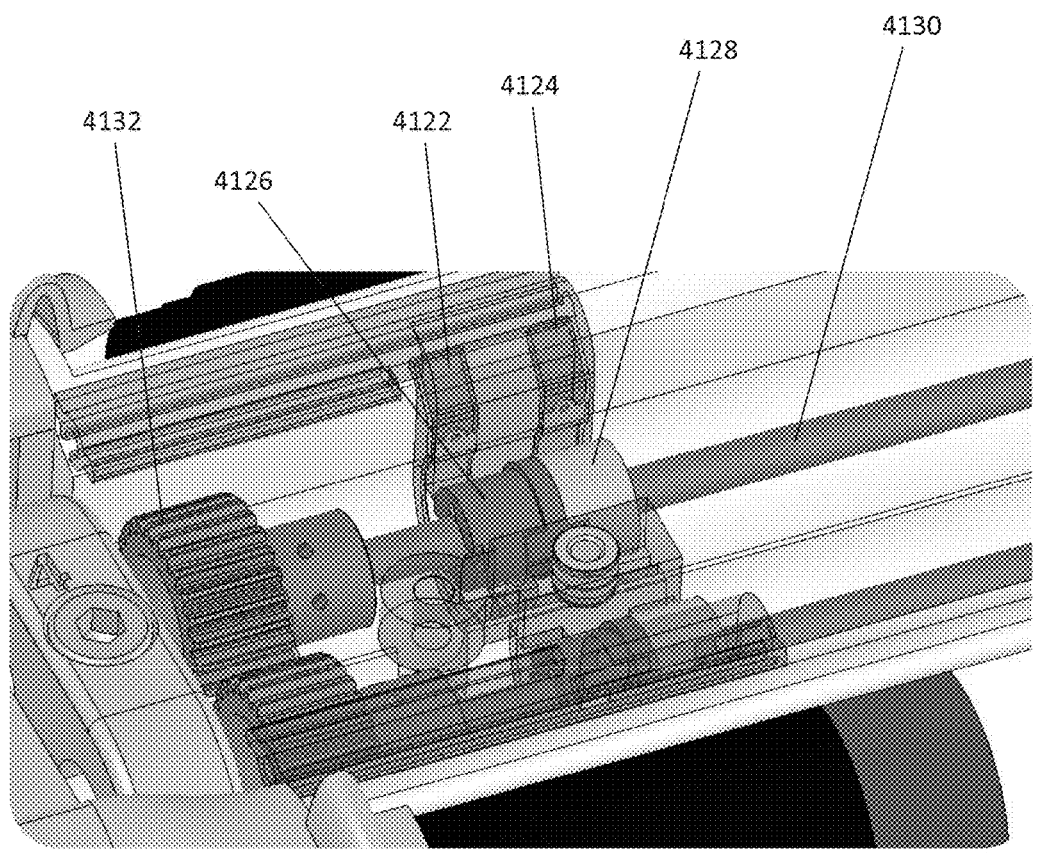
FIG. 41 is a simplified side view of a portion of a motor unit including elements for electrical supply to an end effecter, according to some embodiments of the invention.

In some embodiments, motor unit 4002 includes structure (e.g. including electrical contact/s), for example, for delivery of monopolar and/or bipolar energy to the device (e.g. to a device end effecter). FIG. 41 is a simplified side view of a portion of a motor unit including elements for electrical supply to an end effecter, according to some embodiments of the invention.

In some embodiments, portion 4130 is coupled to an end effecter such that, when 4130 is rotated, it rotates an end effecter, for example, portion 4120 is coupled to portion 3316C of FIG. 33B. In some embodiments, gear 4132 actuates the end effecter, for example, rotation of gear 4132 opening and/or closing jaws of a grasper end effecter. In some embodiments, contacts 4122 and 4124 provide electricity supply to ring portions 4126 and 4128 respectively. In some embodiments, one of contacts 4122, 4124 provides positive voltage and the other negative, providing bipolar power supply. In some embodiments, each of ring portions 4126 and 4128 are electrically connected (e.g. through wires running through 4130) to an end effecter, where one of the ring portions is coupled to one side of a grasper and the other to the other side of a grasper. For example, referring to FIG. 36B, in some embodiments, 3624a and 3624b are electrically coupled to ring portions 4126 and 4128.

In some embodiments, electrical power supply is supplied through wires to the motor unit, for example, referring to FIG. 40, in some embodiments, contacts 4020 are connected to an electrical power supply.

Figure 10B:
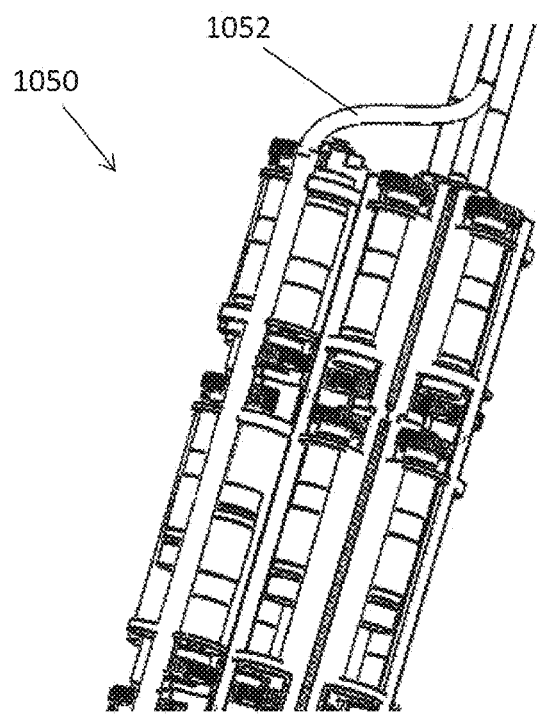
FIG. 10B is a simplified schematic side view of part of a motor unit for actuation of a device including more than two arms, according to some embodiments of the invention.

In some embodiments, a motor unit drives more than two mechanical limbs and/or drives additional device elements. For example, in some embodiments, a motor unit drives two device limbs and a camera. FIG. 10B is a simplified schematic side view of part of a motor unit 1050 for actuation of a device including more than two arms, according to some embodiments of the invention. In some embodiments, motor unit 1050 includes actuation device/s for joint/s of a third limb. For example, in the embodiment illustrated by FIG. 10A, a motor unit has a single actuation unit for actuation of joint 1010. In some embodiments, motor unit includes one or more curved portion 1052, for example, through which central shaft/s pass. In some embodiments, central shaft/s passing through curved portion 1052 include torque transfer portion/s (e.g. as described elsewhere in this document).

Exemplary Hand Tools

In some embodiments, one or more device limb most distal segment (e.g. hand segment) includes a hand tool.

In some embodiments, tools directly treat the patient (e.g. cutting, moving tissue), e.g. other portion of the device limbs locating the tool/s in the correct position and/or moving the tool/s.

In some embodiments, additionally and/or alternatively, a hand tool collects information. For example, in some embodiments, a hand tool is a camera. For example, in some embodiments, a hand tool includes one or more sensor.

In an exemplary embodiment, a hand tool is attached by a wrist joint to the distal end of the radius segment. In some embodiments, a device limb includes one or more tool coupled to the limb at a point other than the distal end of the limb e.g. a joint. For example, in some embodiments, a limb includes a tool coupled to the elbow joint or near to the elbow joint on the radius and/or humerus, the tool e.g. for holding tissue away from the hand tools.

In some embodiments, a limb does not include a hand tool and, for example, the radius (e.g. distal end) pushes or moves tissue. In some embodiments, a tool e.g. scissors, grasper, is used as a blunt instrument e.g. for pushing tissue.

Exemplary Scissors

In some embodiments, a device arm includes a scissors hand tool. Referring back to FIG. 3, scissor hand tool 324 includes a first portion 325a coupled to a second portion 325b. In some embodiments, scissors hand tool 324 cut by a flat surface of first portion 325a sliding into close proximity and/or contact with a flat surface of second portion 325b. Optionally one or more portions 325a, 325b include a sharpened edge. In some embodiments, scissor hand tool 324 cuts tissue. Alternatively, or additionally, in some embodiments scissor hand tool 324 is used to push and/or hold patient tissue, e.g. when scissors are closed. In some embodiments, one or more part of scissor hand tool 324 is charged for electrosurgery, as described in more detail below.

Exemplary Grasper

Figure 36A:
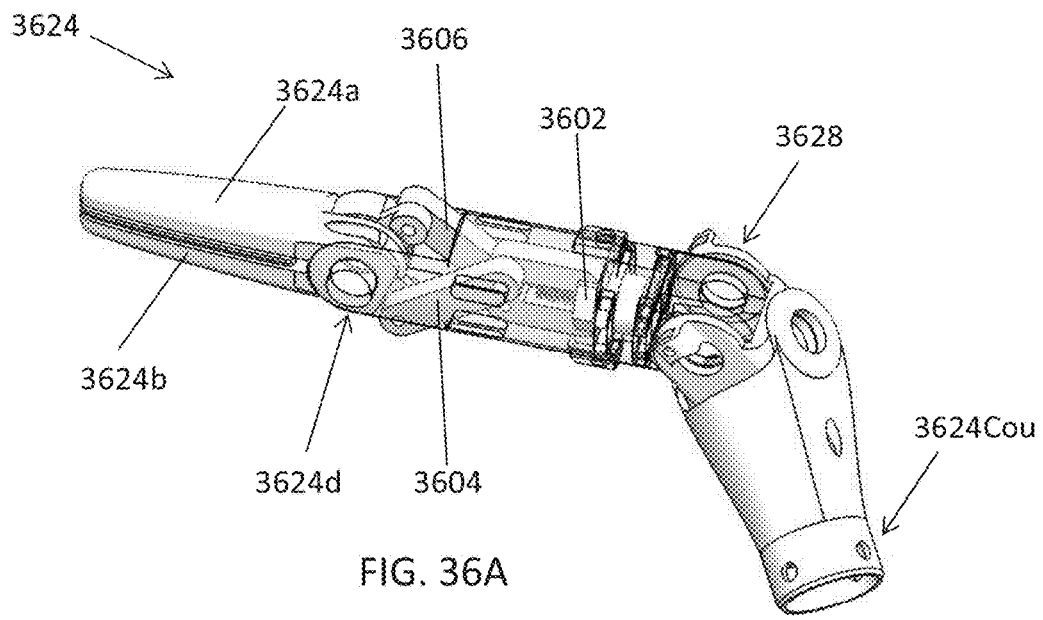
FIG. 36A is a simplified schematic of a closed grasper hand tool, according to some embodiments of the invention.
Figure 36B:
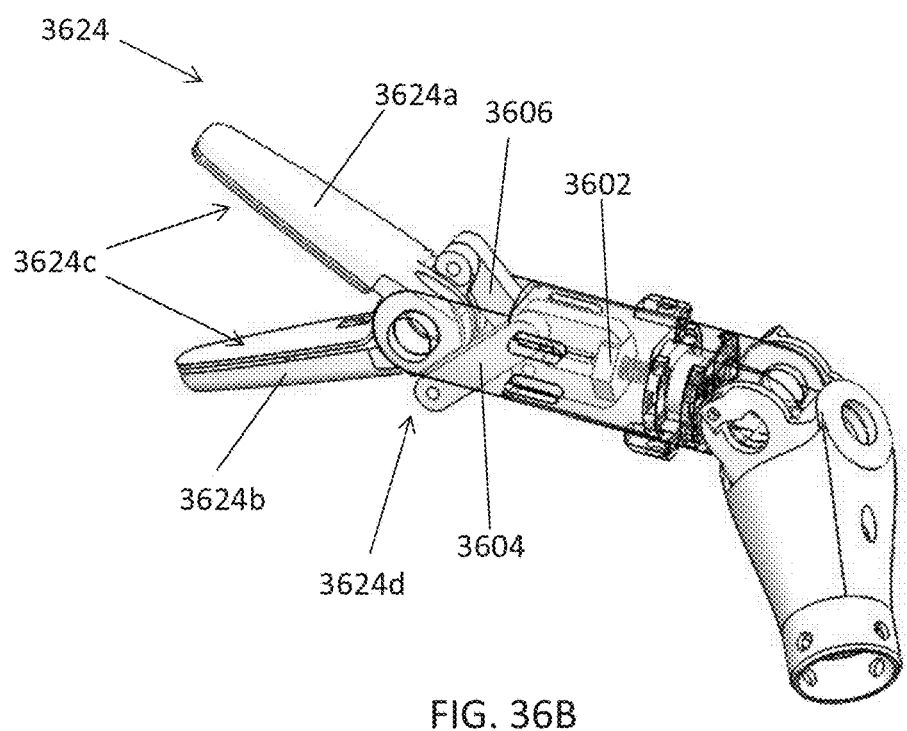
FIG. 36B is a simplified schematic of an open grasper hand tool, according to some embodiments of the invention.

In some embodiments, a device arm includes a grasper hand tool. In some embodiments, a grasper includes two or more opposing portions and the grasper is closed by bringing two or more opposing portions together, for example, to grasp an object (e.g. patient tissue). In some embodiments, opposing portions move apart to open the grasper. FIG. 36A is a simplified schematic of a closed grasper hand tool 3624, according to some embodiments of the invention. FIG. 36B is a simplified schematic of an open grasper hand tool 3624, according to some embodiments of the invention.

In some embodiments, a first grasper side 3624a is pivotally coupled to a second grasper side 3624b. In some embodiments, in moving from an open grasper configuration to a closed grasper configuration, opposing surfaces of first grasper side and second grasper side move towards each other. In some embodiments, as illustrated in FIG. 36A, if there is no object in between grasper sides 3624a, 3624b, the closing the grasper brings the opposing surfaces 3624c of the sides into in contact.

Optionally, in some embodiments, one or more side of a grasper includes protrusions, for example, one or more serrated edge and/or one or more protruding tooth. Potentially protrusions provide improved grip (e.g. increased gripping force) on tissue that the gripper is holding.

In some embodiments, gripper opposing surfaces are smooth and/or flat (e.g. as illustrated in FIG. 36A and FIG. 36B). In some embodiments, gripper opposing surfaces are serrated and/or interlocking and/or include teeth, potentially increasing pressure and/or grip, e.g. as is known in the art of surgical grippers.

In some embodiments, user tissue is held in between opposing surfaces 3624c. In some embodiments, grasper hand tool holds tissue between the opposing surfaces 3624c, a potential benefit being the ability to pull and/or tear patient tissue.

In some embodiments, a turning and/or screwing mechanism opens and closes the grasper sides: In some embodiments, a nut 3602 is coupled to a first beam 3604 and a second beam 3606. First beam 3604 is coupled to grasper first side 3624a and second beam 3606 is coupled to grasper second side 3624b. In some embodiments, turning nut 3602, for example, in one direction (e.g. clockwise) pushes the nut towards the grasper sides, increasing an angle between first and second beams and opening the grasper sides, as is illustrated in the transition between FIG. 36A and FIG. 36B. In some embodiments, nut 3602 is turned by turning an elongated element coupled to the nut, where the elongated element optionally extends out of the hand tool and/or device arm. In an exemplary embodiment, the elongated element is a single nitinol element (e.g. cable, tape, wire). Other methods of actuating (opening and closing) pincer sides using torque are envisioned and included in this application.

A potential benefit of using torque and/or a self locking mechanism such as a nut and/or screw is that movement of the arm interacting with the elongated elements does not loosen the grip of the grasper.

Figure 37:
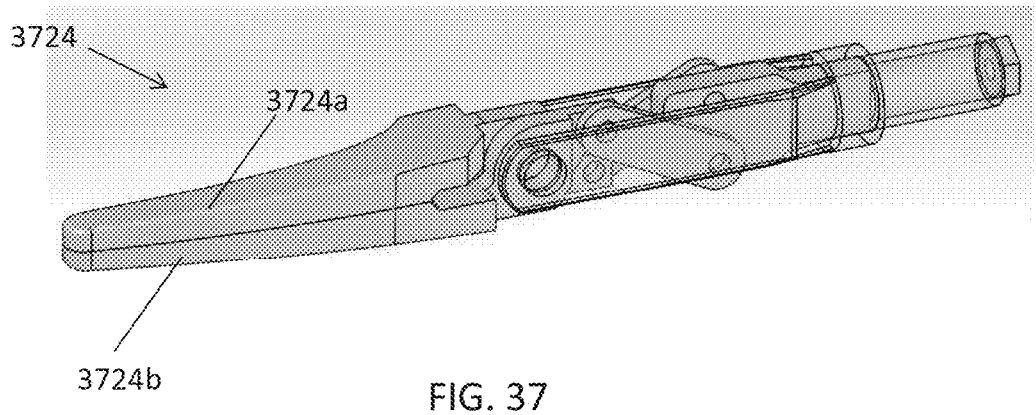
FIG. 37 is a simplified schematic of a closed grasper hand tool, according to some embodiments of the invention.

Alternatively or additionally, in some embodiments, opening and closing of a grasper hand tool is controlled by pulling and releasing of one or more elongated element, as is known in the art of grasper control. FIG. 37 is a simplified schematic of a closed grasper hand tool 3724, according to some embodiments of the invention.

In some embodiments, a hand tool is coupled (e.g. by a wrist joint 3628) to a connecting portion 3624Cou which couples the hand tool to the radius. In some embodiments, the wrist joint is a pivot. Alternatively, in some embodiments a device arm does not include a bendable wrist joint, for example, hand tool 3624 is directly coupled to a radius segment.

Exemplary Grasper with Humanoid Structure

Figure 38:
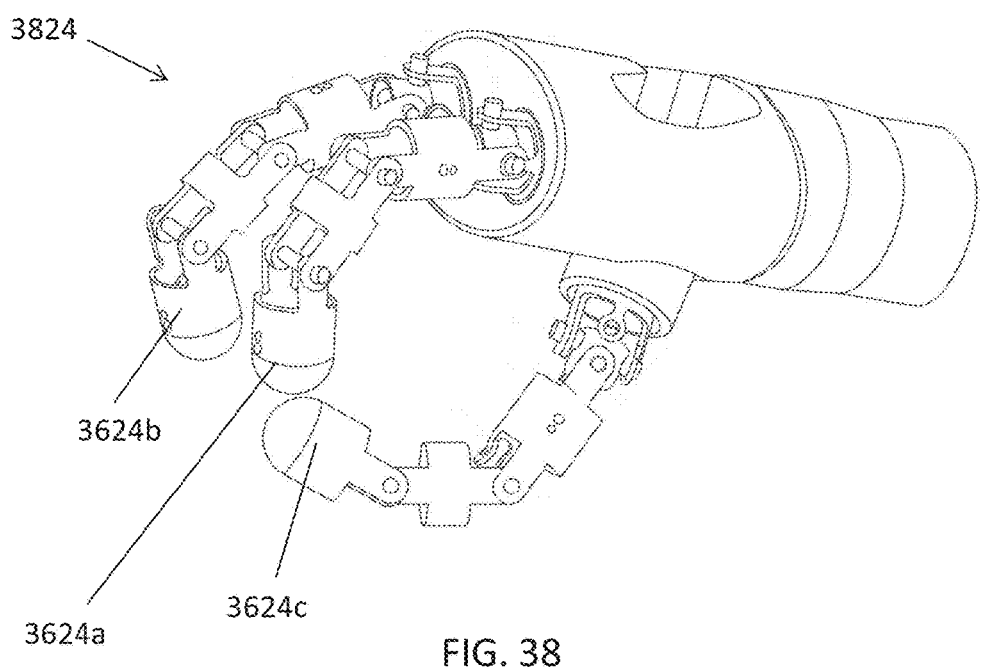
FIG. 38 is a simplified schematic of a gripper hand tool, according to some embodiments of the invention.

In some embodiments, a device arm includes a grasper with a humanoid structure (a gripper hand tool). In some embodiments, one or more opposing portion of a grasper hand tool is articulated. In some embodiments, one or more opposing portion includes the same number of segments and connecting joints as a human finger. FIG. 38 is a simplified schematic of a gripper hand tool 3824, according to some embodiments of the invention. Potential benefits of a hand tool with humanoid structure include is intuitive movement of the tool, the ability to perform surgical movements (e.g. suturing) in the same way as manual surgery.

Other Exemplary Hand Tools

In some embodiments, a hand tool is used to hold and/or push user tissue e.g. to hold tissue away for cutting, to provide tension to tissue to be cut. Optionally, a hand tool for holding tissue includes an expanding portion the surface of which can be expanded by one or more portion unfolding and/or inflating and/or sliding past other portions (e.g. fan-like construction).

In some embodiments, one or more hand tool is, for example, a drill, a screwdriver, a needle, a scalpel, a suction device, a harmonic scalpel, other devices (e.g. surgical devices) as known in the art of endoscopic procedures.

Exemplary Electrosurgery

Optionally, in some embodiments, one or more device hand tool includes one or more charged portion for electrosurgery. In some embodiments, a device hand tool includes monopolarly charged part for monopolar electrosurgery. In some embodiments, one part of a hand tool is negatively charged and another part of the hand tool is positively charged, for bipolar electro surgery.

In an exemplary embodiment, referring to FIG. 36A and FIG. 36B, first grasper side 3624a is oppositely charged to second grasper side 3624b (e.g. first grasper side 3624a is positively charged, second grasper side 3624b is negatively charged or vice versa), for bipolar electrosurgery.

In an exemplary embodiment, referring to FIG. 3, first portion 325a is oppositely charged to second portion 325b (e.g. first portion 325a is positively charged, second portion 325b is negatively charged or vice versa), for bipolar electrosurgery.

In some embodiments, for example, a user controlling movement of a device with user arm movements activates charge for electrosurgery using an additional user interface (e.g. a foot pedal).

Exemplary Disposability, Replaceablity, Sterility

In some embodiments, one or more portion of the device including mechanical arms (e.g. as described herein) is sterile and/or sterilizable (e.g. device limbs are sterile). In some embodiments, one or more part of the device is replaceable, for example, in some embodiments, one or more device limb is replaced and/or one or more tool is replaced, e.g. between treatments.

In some embodiments, an end effecter is screw attached to the mechanical arm, and, for example, is unscrewed to remove it from the arm.

In some embodiments, one or more mechanical arm is friction coupled to the motor unit, for example, potentially enabling removal and/or exchange of the mechanical arms.

In some embodiments, mechanical arms include a sterile sheath and/or a sterile sheath is placed over a mechanical arm e.g. before treatment with the device commences.

Exemplary Surgical Device Control Systems

In some embodiments, a surgical device is controlled (e.g. movement of the surgical system) using an input device. Alternatively or additionally, in some embodiments, a surgical system is controlled by measured user body movement.

Figure 42:
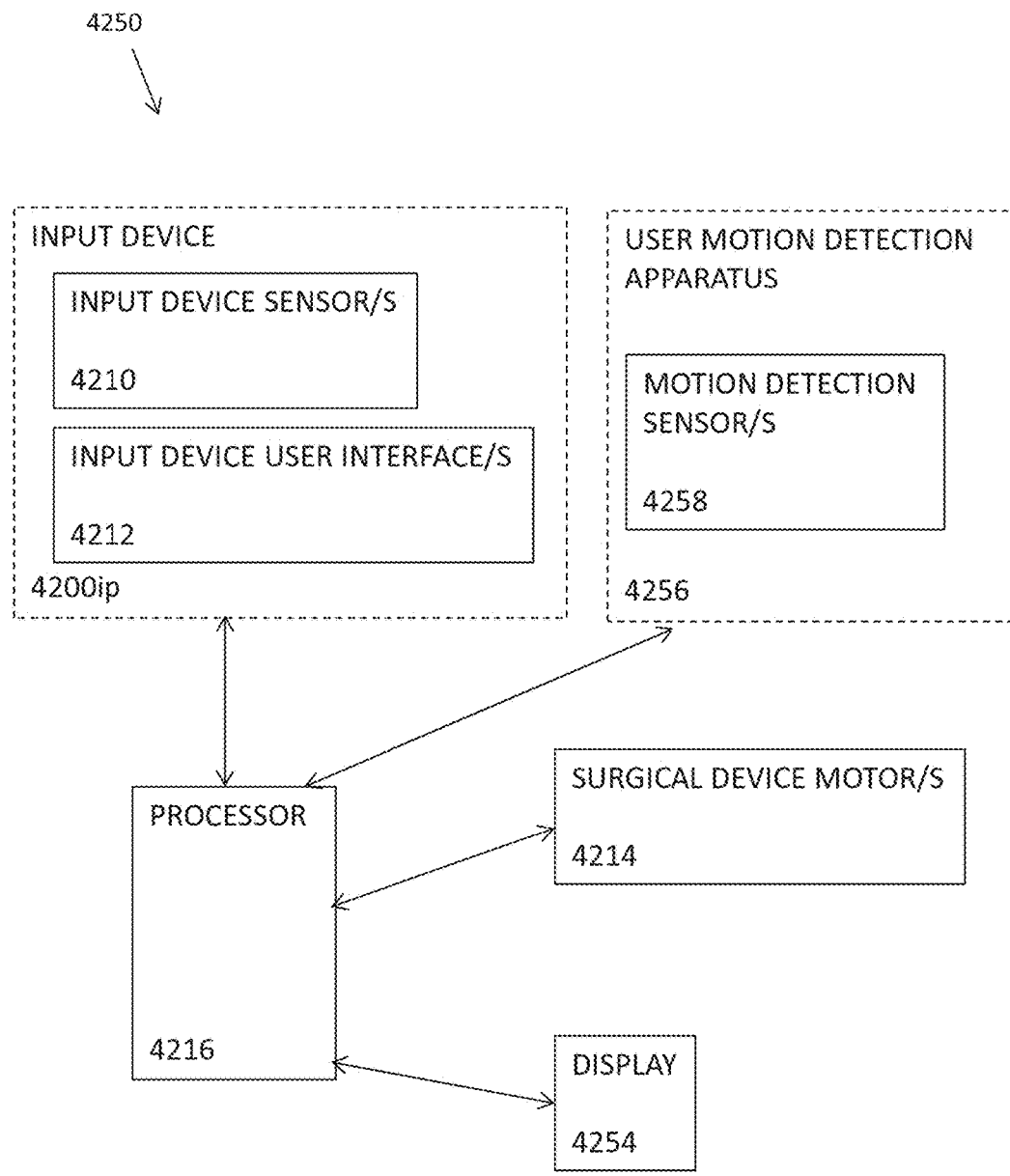
FIG. 42 is a simplified schematic block diagram of a control system, according to some embodiments of the invention.

FIG. 42 is a simplified schematic block diagram of a control system, 4250 according to some embodiments of the invention.

In some embodiments, system 4250 includes an input device 4200ip, where input device 4200ip includes one or more sensor 4210. In some embodiments, one or more sensor 4210 produces an output based on a position of the input device (e.g. sensors are described in more detail elsewhere in this document).

Optionally, in some embodiments, input device 4200ip includes one or more user interface 4212, for example, one or more button and/or a touch screen (e.g. mounted to an input device arm).

Alternatively or additionally, in some embodiments, user interface/s are mounted to another portion of an input device, e.g. on a surgical device support and/or on another location, e.g. a patient bed.

Optionally, in some embodiments, input device 4200ip includes an internal processor and/or memory (not illustrated), for example, for processing and/or storing signals produced by sensor/s 4210 and/or user interfaces/s.

Alternatively or additionally to input device 4200ip, in some embodiments, system 4250 includes a user motion detection apparatus 4256. In some embodiments, apparatus 4256 includes one or more motion detection sensor 4758. In an exemplary embodiment, motion detection sensor/s 4758 are one or more camera. In some embodiments, one or more motion detection sensor 4758 includes an internal processor, for detection of user body portion position and/or movement from collected images, and the internal processors send detected body portion positions to processor 4716. In some embodiments, sensor/s 4758 send raw image data to processor 4216.

In some embodiments, system 4250 includes a processor 4216 which receives signals from input device 4200ip (and/or from user motion detection apparatus 4256) and, based on received signals generates control signal/s which control one or more surgical device motor 4214.

In some embodiments, (e.g. as described in the section below "Exemplary Filtering") signals received by the processor from the input device are filtered, for example, in generation of the control signals.

Optionally, in some embodiments, processor 4216 communicates with a display 4254. For example, in an exemplary embodiment, a display displays a graphical representation of the input device and/or surgical device, for example, based on signals received from input device 4200ip and/or surgical device motors 4214.

Exemplary Method of Control

In some embodiments, movement and orientation of the device hands is controlled by movement of the user hands and/or movement of an input device and movement of other portions of the device, is controlled by robotics, for example, controlled by inverse kinematics, as known in the art, where inverse kinematics is concerned with calculating joint angles of body segments given motion of some body segments in 3D space.

In some embodiments, movement and/or position of one or more joint of the device is controlled using robotics e.g. inverse kinematics optionally with movement constraints.

In some embodiments, movement of one or more joint (and/or segment) is controlled by measured mapped movement of the corresponding user joint and/or measured movement of a corresponding input device joint, where one or more other joint is controlled automatically, e.g. by robotics. A potential benefit of a user controlling one or more joint is that the user controls a path of the device, for example, avoiding obstacles (e.g. avoiding damage to an obstacle e.g. organ).

In some embodiments, movement of a device arm end effecter (e.g. hand tool) is controlled by measured mapped movement of a corresponding user body portion and/or measured mapped movement of a corresponding input device portion (e.g. the user wrist joint and/or hand position and/or radius distal end) and movement of one or more other joint is controlled automatically, e.g. by robotics.

In some embodiments, a user navigates (e.g. assisted by displayed images) the device on a desired path (e.g. within a body), for example around obstacles. As the path and/or movement of the joints is specified by the user, in some embodiments, motion of the device is less efficient (e.g. less fast, longer length of path) than that of a device controlled using robotics where, for example, movement to position of an end effecter in a desired position is calculated and/or optimized automatically.

In some embodiments, control of one or more device arm is semi-robotic where measured movement of user body portion/s and/or measured movement of an input device is used as a starting point for robotics calculations where position and/or movement of the device is calculated (e.g. using inverse kinematics). In some embodiments, in mapping measured user body movement position of one or more device portion is within 30% or within 20% or within 10% of a user body position.

Figure 43:
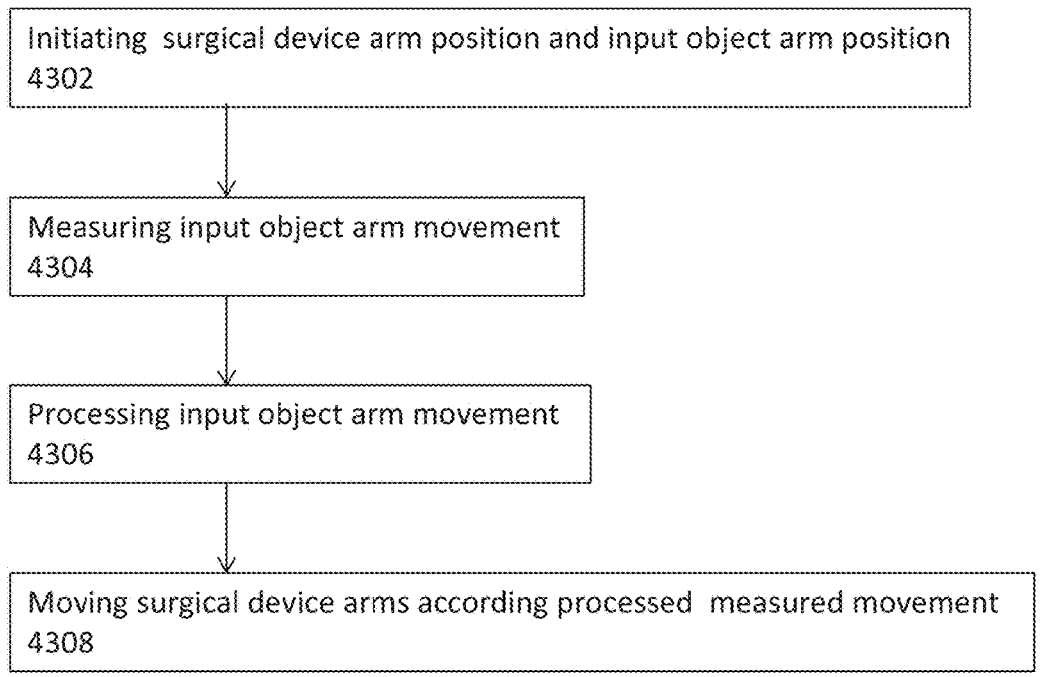
FIG. 43 is a flow chart of a method of control of a device arm, according to some embodiments of the invention.

FIG. 43 is a flow chart of a method of control of a device arm, according to some embodiments of the invention.

At 4302, optionally, a position of a surgical device and/or user arms and/or input device arms is initialized (e.g. matched). In some embodiments, at 4302, a surgical device arm position (e.g. angles between segment long axes) and a user arm position are initialized.

At 4304, user joint movement and/or input device movement is measured.

In some embodiments, once a device arm and a user arm (and/or input device arm) are approximately (e.g. in some embodiments, matching is only required once a discrepancy between user device arm positions is above a tolerance) in the same positions, at 4304, position of at least one user arm is measured.

At 4306, measured movement is processed. In some embodiments, processing includes mapped of measured input object movement to surgical device joint movement, e.g. where user body movement is used to control the device, for example using a mapping of user anatomy to joint anatomy.

In some embodiments, mapping of input device movement to surgical device movement includes mapping of angles between of effective input device segments to angles between of effective surgical device segments. Described previously are different descriptions of effective surgical device segments, in different embodiments, each method described in this document of determining and/or measuring effective surgical device segments is used in mapping of input device movement to surgical device movement.

In some embodiments, mapped midpoints of input object device portions (e.g. midpoint/s of joint/s) are used to control a surgical device (e.g. by mapping movement of the input object device joint midpoints to surgical device joint midpoints).

In some embodiments, mapping includes correction for discrepancy between input object structure and surgical device structure.

Optionally, in some embodiments, processing includes filtering of measured movement (e.g. to remove disallowed movements). In some embodiments, processing includes processing according to a control mode, for example control modes as described regarding FIG. 63A (e.g. introduction of a time delay in a timing mode).

At 4308, one or more surgical device arm is moved according to the processed desired device movement.

Exemplary Surgical System Including an Input Device

In some embodiments, a surgical system includes a surgical device which is controllable by movement of an input device. In some embodiments, the surgical device is inserted into a patient (e.g. during laparoscopic surgery).

Figure 44A:
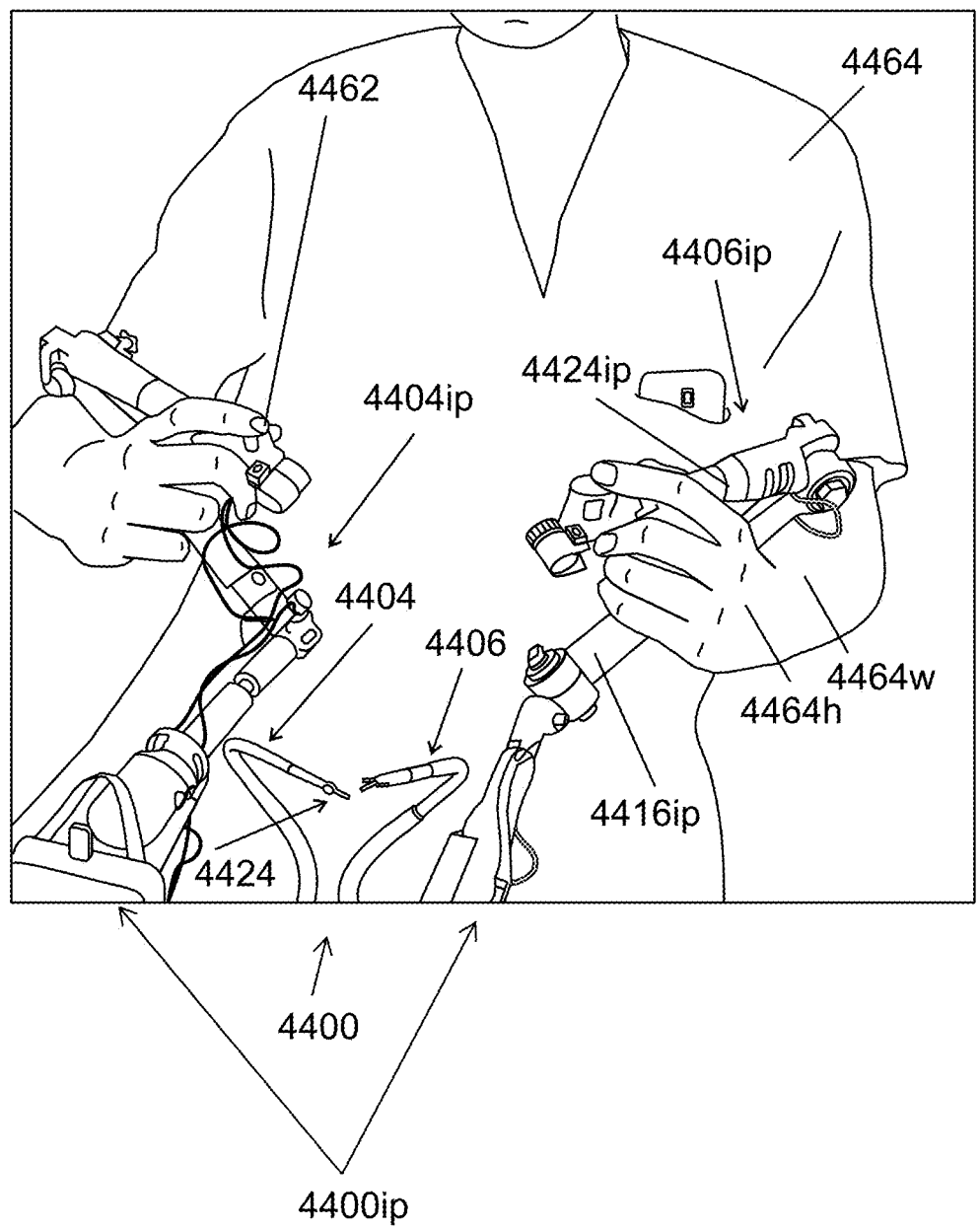
FIG. 44A is a photograph of a user controlling a surgical device using an input device, according to some embodiments of the invention.

FIG. 44A is a photograph of a user 4464 controlling a surgical device 4400 using an input device 4400ip, according to some embodiments of the invention.

In some embodiments, an input device includes an input device first arm 4404ip and an input device second arm 4406ip. In some embodiments, an input device includes less or more than two arms, for example, one arm, three arms, 2-6 arms.

In some embodiments, each input device arm controls movement of a corresponding surgical device arm, for example, input device first arm 4404ip controlling surgical device first arm 4404ip, and input device second arm 4406ip controlling surgical device second arm 4406.

In some embodiments, an input device arm is used to control another portion of a surgical device, for example, an imager inserted with the surgical device. In some embodiments, more than one arm is used to control a single portion (e.g. arm) of a surgical device.

In some embodiments, the surgical device includes a first surgical arm 4404 and a second surgical arm 4406. In some embodiments, the input device includes a first input device arm and a second input device arm, where, for example, movement of first input device arm 4404ip controls movement of first surgical arm and/or movement of second input device arm controls movement of second surgical arm 4406ip.

In some embodiments, a user moves an input device manually, for example, by grasping and/or guiding a portion of the input device with a user hand. In some embodiments, a user guides more than one portion of an input device arm with the user's hand and/or arm. For example, as illustrated in FIG. 44A, user 4464 controls an input device arm radius by grasping and/or guiding the input device radius 4424ip with the user's hand 4464h while guiding the input device humerus 4416ip with the user's wrist and/or arm 4464w.

In an exemplary embodiment, a user grasps a portion of one input device arm in each hand. For example, as illustrated in FIG. 44A, a user moves each input device arm 4404ip, 4406ip, by grasping and/or guiding input device radiuses.

Figure 44B:
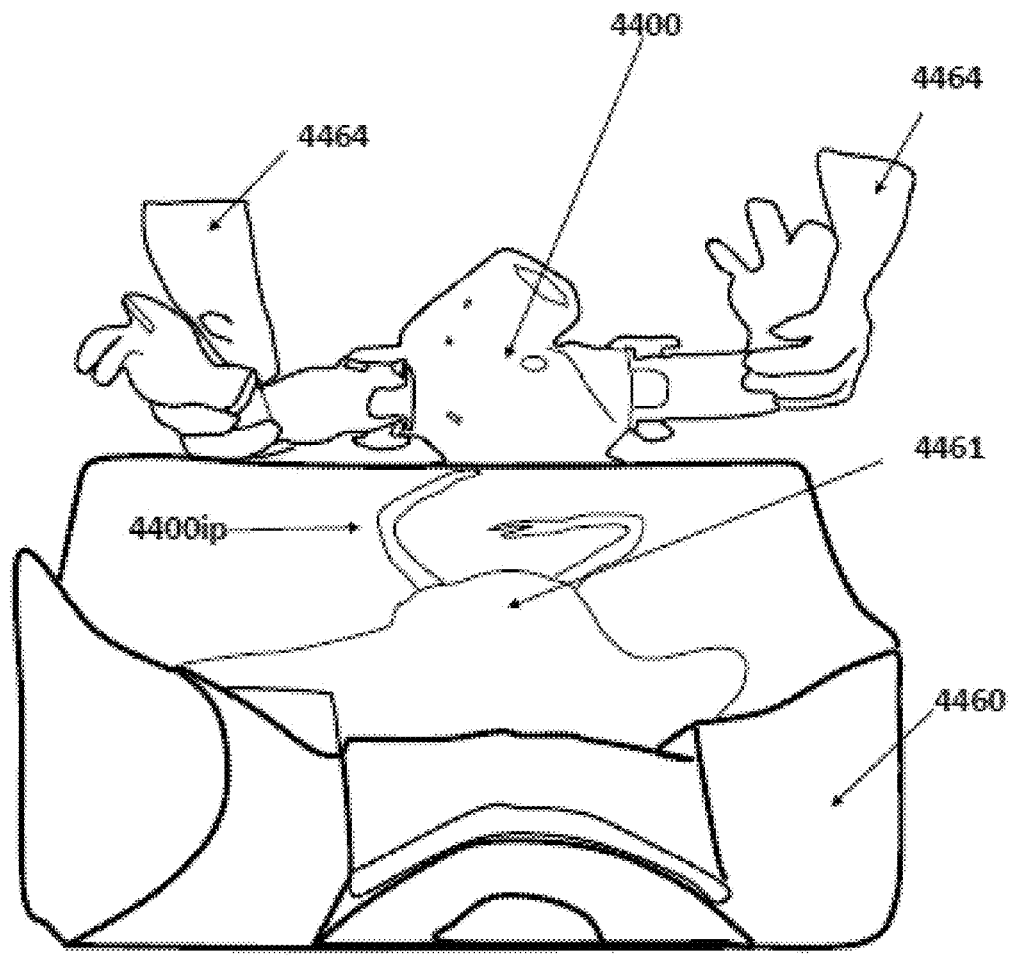
FIG. 44B is a photograph of a user controlling a surgical device using an input device, according to some embodiments of the invention.

FIG. 44B is a photograph of a user 4464 controlling a surgical device 4400 using an input device 4400ip, according to some embodiments of the invention.

FIG. 44B illustrates an example where swine anatomy 4461 was placed inside an anatomical model 4460, a user then performed a hysterectomy using a trans-vaginal approach, with surgical device 4400 by moving portions of input device 4400ip. FIG. 44B illustrates use of a humanoid input device and surgery where the surgical device is inserted in a non-laparoscopic direction while the surgeon 4464 is in a laparoscopic position.

In some embodiments, as described previously, a surgical system uses measured user body movement to control a surgical device.

FIG. 45 is a simplified schematic illustrating use of a surgical system, according to some embodiments of the invention. In some embodiments, movement of a device 4500 which has been inserted into a patient 4560 (e.g. through an incision 4562) is controlled by mimicking user 4564 movement.

For example, as described previously regarding FIG. 42, in some embodiments, a system includes a motion detection apparatus. In an exemplary embodiment, one or more sensor is mounted on a display (where exemplary functionality of displays is, for example, described elsewhere in this document).

Figure 46:
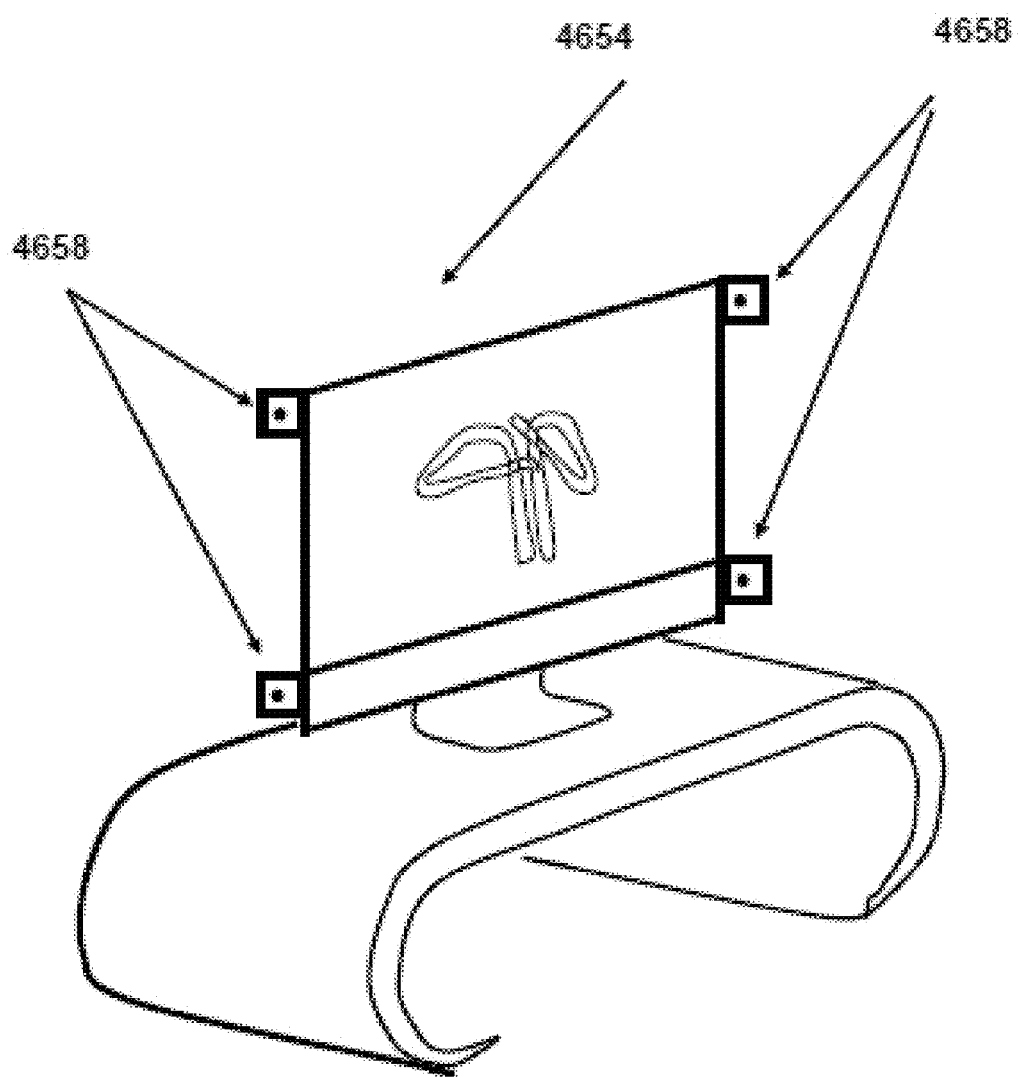
FIG. 46 is a simplified schematic side view of a display including motion detection sensors, according to some embodiments of the invention.

FIG. 46 is a simplified schematic side view of a display 4654 including motion detection sensors 4658, according to some embodiments of the invention. In some embodiments, sensors 4658 include cameras. FIG. 46 illustrates an exemplary embodiment, where display 4654 displays a representation of the surgical device and/or images of the surgical device.

Exemplary Positioning of Parts of a Surgical System

Figure 47A:
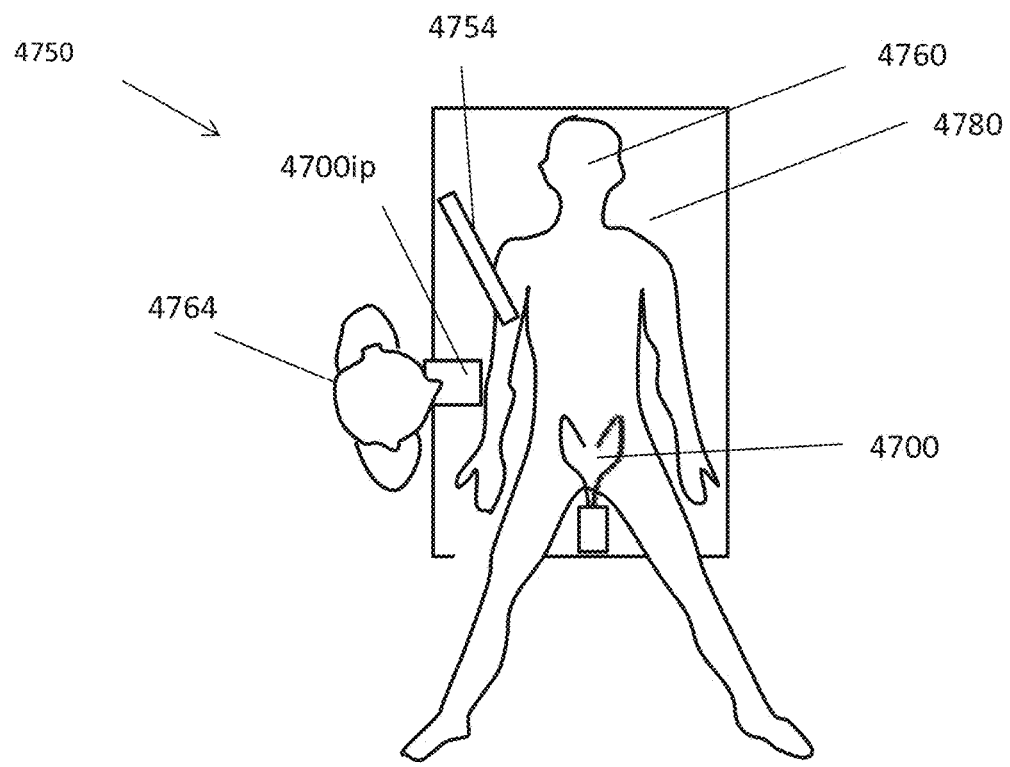
FIG. 47A and FIG. 47B are simplified schematics of a surgical system, according to some embodiments of the invention.
Figure 47B:
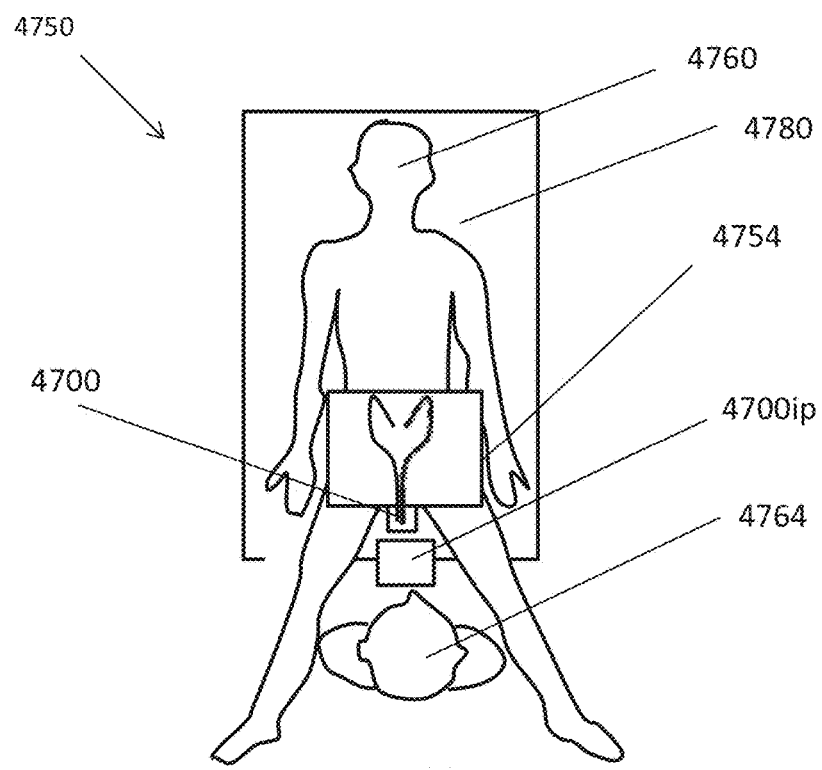

FIG. 47A and FIG. 47B are simplified schematics of a surgical system, according to some embodiments of the invention. In some embodiments, patient 4760 being treated (e.g. having surgery) is supported, at least partially, by a patient support surface 4780 (e.g. a surgical table and/or a patient bed, the term patient support surface is also herein interchangeably termed "bed"). In some embodiments, a surgical device 4700, which is optionally mounted to bed 4780, is used to treat (e.g. perform surgery on) patient 4760. In some embodiments, at least a portion of surgical device 4700 is inserted into patient 4760, for example through a natural orifice (e.g. the vagina) and/or through an incision.

In some embodiments, an input device 4700ip is positioned in close proximity to the patient, for example, mounted on a patient bed and/or within 1 m or 50 cm, or 20 cm of the patent. In some embodiments, the ability to place a user (e.g. surgeon) in close proximity to the patient enables the user to be within the sterile field, and/or potentially reduces response time of the user in an emergency situation, for example, potentially enabling communication of the surgeon with the patient and/or other members of a medical team.

Figure 51:
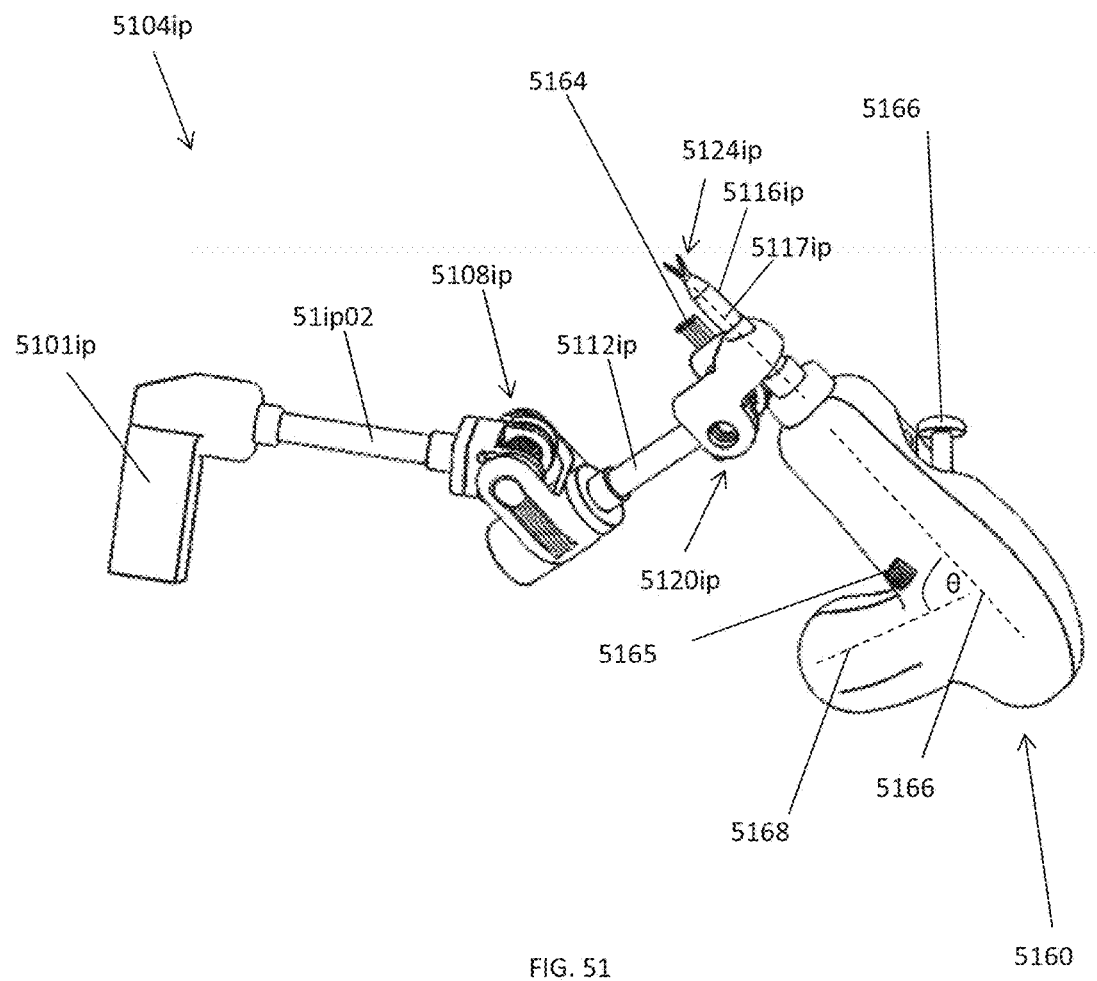
FIG. 51 is a simplified schematic side view of an input device arm including a handle, according to some embodiments of the invention.

In some embodiments, input device 4700ip is attached to a patient bed and/or to the floor (e.g. support 5101ip, FIG. 51 is coupled to a patient bed and/or floor).

In some embodiments, for example, as illustrated by FIG. 47A, input device 4700ip is positioned such that the surgeon is positioned in a traditional laparoscopic surgical position e.g. in proximity to a patient torso.

In some embodiments, for example, as illustrated by FIG. 47B, input device 4700ip is positioned between a patient's legs (e.g. input device 4700ip is sized and/or shaped such that it fits between (e.g. at least partially splayed) patient legs. For example, in some embodiments, an input device surgical footprint (e.g. the floor space taken by an input device) is 1 $cm^2$–1 $m^2$, or 10 $cm^2$–50 $cm^2$, or 20 $cm^2$–50 $cm^2$, or lower, or higher, or intermediate ranges or areas.

For example, in an exemplary embodiment, (e.g. as illustrated by FIG. 47B) patient 4760 legs are splayed, for example, where legs are held by stirrups (not illustrated) attached to bed 4780. Surgical device 4700 is, for example, is inserted into patent 4760 vaginally and input device 4700ip and/or surgeon 4764 are located between patient legs.

In some embodiments, a surgical system includes a display 4764 (e.g. as described in reference to display 854, FIG. 8). In some embodiments, display 4764 is positioned and/or angled to replicate a position of a display in a laparoscopic procedure, e.g. as illustrated in FIG. 47A. In some embodiments, a patient body forms a display where, for example, projected onto the patient's body are image/s (e.g. from camera/s inserted into the patient and/or collected by an imager e.g. MRI, CT, ultrasound etc.).

In some embodiments, display 4764 is positioned and/or angled to replicate an open surgery surgeon's view of the treatment, even though the treatment is a laparoscopic procedure, e.g. as illustrated in FIG. 47B.

Referring now to FIG. 45, in some embodiments, a device is controlled, additionally or alternatively, by measured body movement of a user. In some embodiments, for a user to control device movement with measured body movement, the user is in an allowable area, for example, a designated field of vision of camera/s detecting user body movement. In some embodiments, a system includes indication as to the allowable area (e.g. markings on the floor, a marked and/or designated chair). In some embodiments, an allowable area is adjustable by the user (e.g. the user, in some embodiments, moves motion detection equipment to a desired location).

Exemplary Control Using an Input Device

In some embodiments, a user controls the device by moving an object (herein termed "input object" or "avatar").

In some embodiments, the position and/or movement of one or more portion of the device within the patient is controlled by the user moving an avatar of one or more portion of the device. In some embodiments, the avatar is a model, optionally miniature or enlarged, of one or more portion of the device. Optionally, the avatar includes one or more sensor which, in some embodiments, measure the position and/or movement of the avatar. In some embodiments, movement of the avatar is measured using motion capture technology. In some embodiments, the avatar includes markers and/or is coated, at least partially, in reflective material, e.g. to aid motion capture. In some embodiments, the avatar is part of a fixed control consol.

In some embodiments, the avatar is hand held and/or fixable to a table and/or desk.

Exemplary Mapping of Input Device Movement to Surgical Device Movement

Figure 48A:
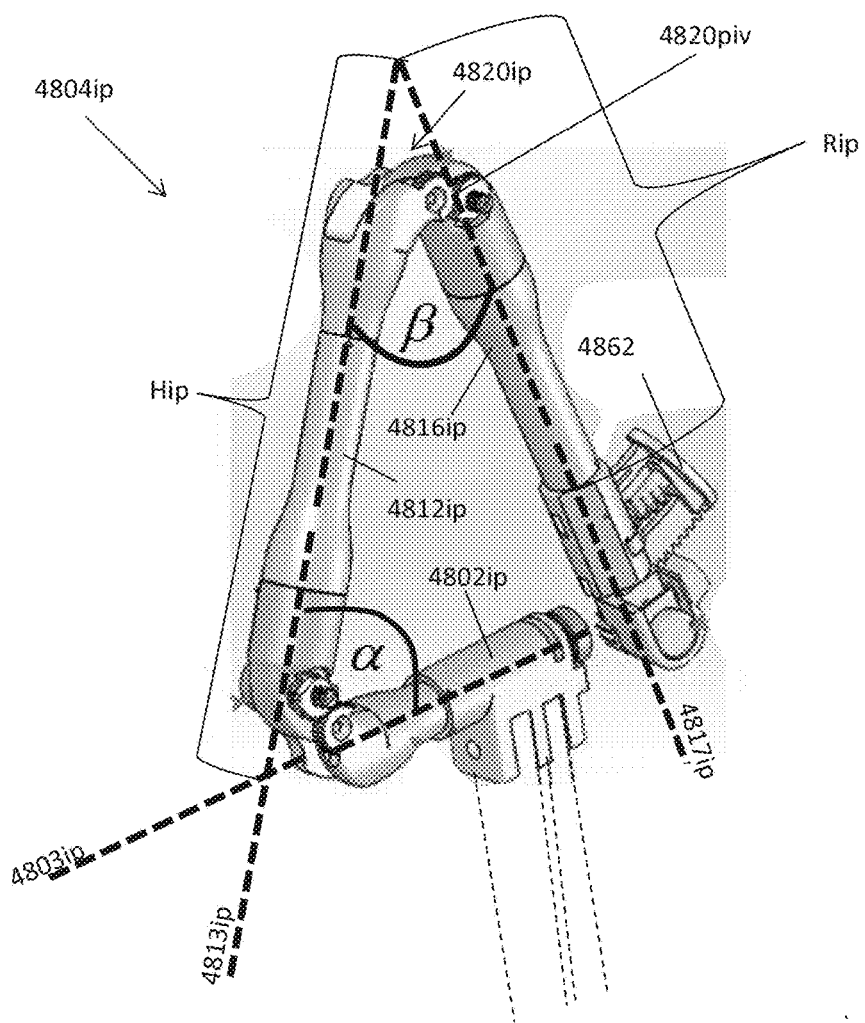
FIG. 48A is a simplified schematic side view of an input device arm, according to some embodiments of the invention.
Figure 48B:
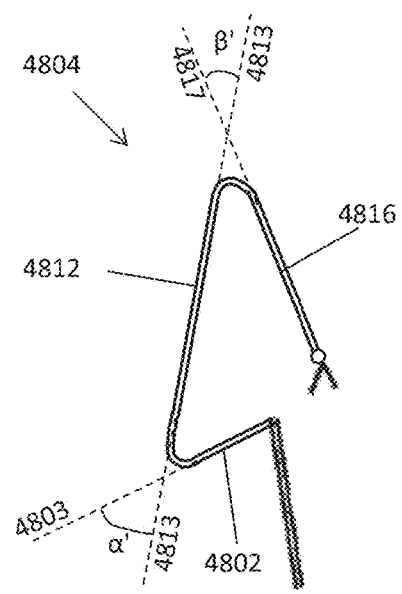
FIG. 48B is a simplified schematic side view of a surgical device arm, according to some embodiments of the invention.

FIG. 48A is a simplified schematic side view of an input device arm 4804ip, according to some embodiments of the invention. FIG. 48B is a simplified schematic side view of a surgical device arm 4804, according to some embodiments of the invention. In some embodiments, input device arm 4804ip controls surgical device arm 4804.

In some embodiments, an input device structure has one or more ratio and/or dimension which is substantially the same as (also herein termed "matching") a ratio and/or dimension (optionally scaled) of a surgical device and, optionally, one or more other dimension and/or ratio which does not match those of a surgical device.

For example, in an exemplary embodiment, a length ratio between two effective segment lengths of an input device and a surgical device are substantially the same, for example, with 0-5%, or 0-1%, or 0-0.5%, or lower or higher or intermediate ranges or values of a difference between the ratios. Where an effective segment length is the length of a central long axis of the segment between intersections of long axes of other segments and/or between an axis intersection and a termination of the segment.

For example, referring to FIG. 48A: An effective length of an input device arm 4800ip humerus 4812ip is length Hip, measured between intersections of humerus long axis 4813ip with the support (e.g. support long axis 4803ip) and radius long axis 4817ip. An effective length of an input device arm 4800ip radius 4816ip is length Rip, measured between intersection of radius long axis 4817ip and termination of input device radius 4816ip.

Potentially, an effective input device radius length corresponding to an effective surgical device radius length which does not include a length of an end effecter means that accuracy of control is maintained for surgical devices with different end effecters (e.g. different sized end effecters).

In some embodiments, one or more matching segment length ratio between an input device and a surgical device enables intuitive control of the surgical device with the input device, for example, despite structural differences between the devices. For example in some embodiments, a surgical device (e.g. as described elsewhere in this document) includes long connecting portions, whereas, in some embodiments, (e.g. as illustrated in FIG. 44A and/or FIG. 48A and/or FIG. 49A) input device arm joints include pivots.

In some embodiments, effective segment length ratios between the input device and surgical device match, but actual segment length ratios do not match. For example, in some embodiments, a surgical device includes long connecting portions (e.g. as described in the section of this document entitled "Exemplary long joints"), and an input device capable of controlling the surgical device includes short connecting portions for example, pivot connections (e.g. as illustrated in FIG. 48A). Potentially, an advantage being ease of control of the input device (e.g. input device segments rotate freely about pivots, e.g. input device segments do not move with unwanted degrees of freedom from long joints) and/or a surgical device which has an non-angular shape (e.g. less likely to damage patient tissue).

In an exemplary embodiment, a thickness of one or more input device segment (e.g. diameter of cylindrical segments and/or largest segment cross sectional dimension) is different (e.g. larger) than to those of a surgical device. Increased input device segment thickness potentially provides space for sensors and/or locking devices (e.g. as described regarding FIG. 54A, FIGS. 55A-55B, FIG. 56, elsewhere in this document) and/or provides an input device with dimensions which are comfortable and/or easy for a user to maneuver.

In an exemplary embodiment, input device segment thickness is 20-26 cm, or 13-18 cm, or 13-26 cm, or lower, or higher or intermediate ranges or thicknesses.

In an exemplary embodiment, surgical device segment thickness is 6-8 cm, or 4-8 cm, or 4-6 cm or lower, or higher or intermediate ranges or thicknesses.

In an exemplary embodiment, a ratio between surgical device segment thickness and input device segment thickness is 1:0.5, to 1:3, or lower, or higher or intermediate ranges or ratios.

In an exemplary embodiment, a ratio between surgical device segment length and input device segment length is 1:0.5, to 1:3, or lower, or higher or intermediate ranges or ratios.

Exemplary Control of Angles Between Surgical Device Segments

In some embodiments, a measured angle and/or change in angle between long axes of two input device segments, is used to control and/or change an angle between corresponding long axes of two surgical device segments.

In some embodiments, measurement is of a physical angle (e.g. angle α) between long axes of two device segments. In some embodiments, measurement is of a change in angle between long axes of two device segments.

For example, in some embodiments, an angle α' between a long axis 4813 of a surgical device humerus 4812 and a long axis 4803 of a surgical device support 4802 is controlled by an angle α between a long axis 4813ip of an input device humerus 4812ip and a long axis 4803ip of an input device support 4802ip.

For example, in some embodiments, an angle (3' between a long axis 4817 of a surgical device radius 4816 and a long axis 4813 of a surgical device humerus 4812 is controlled by an angle θ between a long axis 4817ip of an input device radius 4816ip and a long axis 4813ip of an input device humerus 4812ip.

In an exemplary embodiment, a surgical device is controlled using a one-to-one mapping of an angle between adjacent input device segments and corresponding adjacent surgical device segments.

Exemplary Control of Rotation of Surgical Device Segments

Figure 48C:
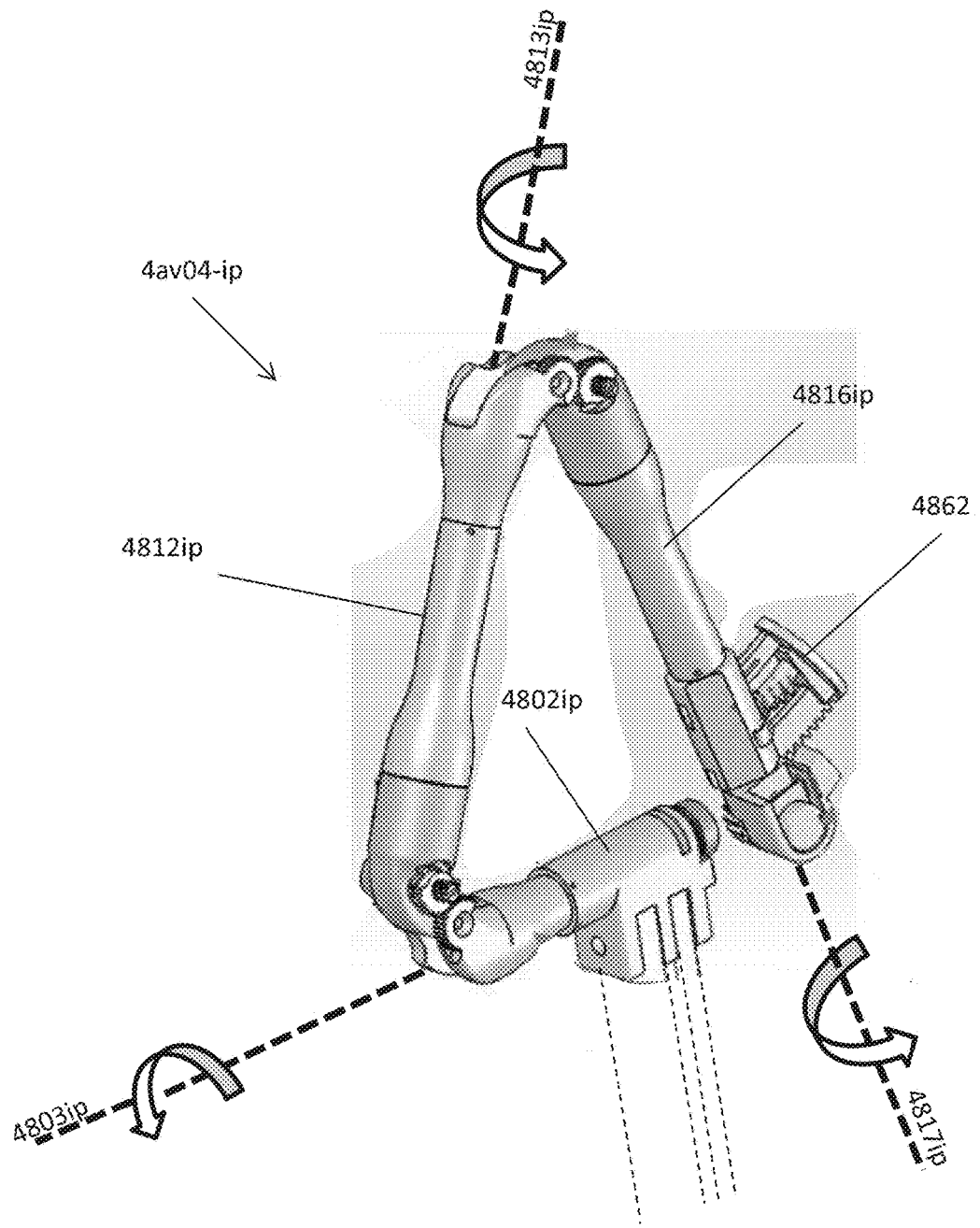
FIG. 48C is a simplified schematic side view of an input device arm, according to some embodiments of the invention.

FIG. 48C is a simplified schematic side view of an input device arm 4804ip, according to some embodiments of the invention.

In some embodiments, rotation of an input device segment about a long axis of the segment is used to control rotation of a corresponding surgical device segment.

In some embodiments, measurement is of a physical angle of rotation. In some embodiments, measurement is of a change in angle of rotation.

Exemplary Input Device Structure

Figure 49A:
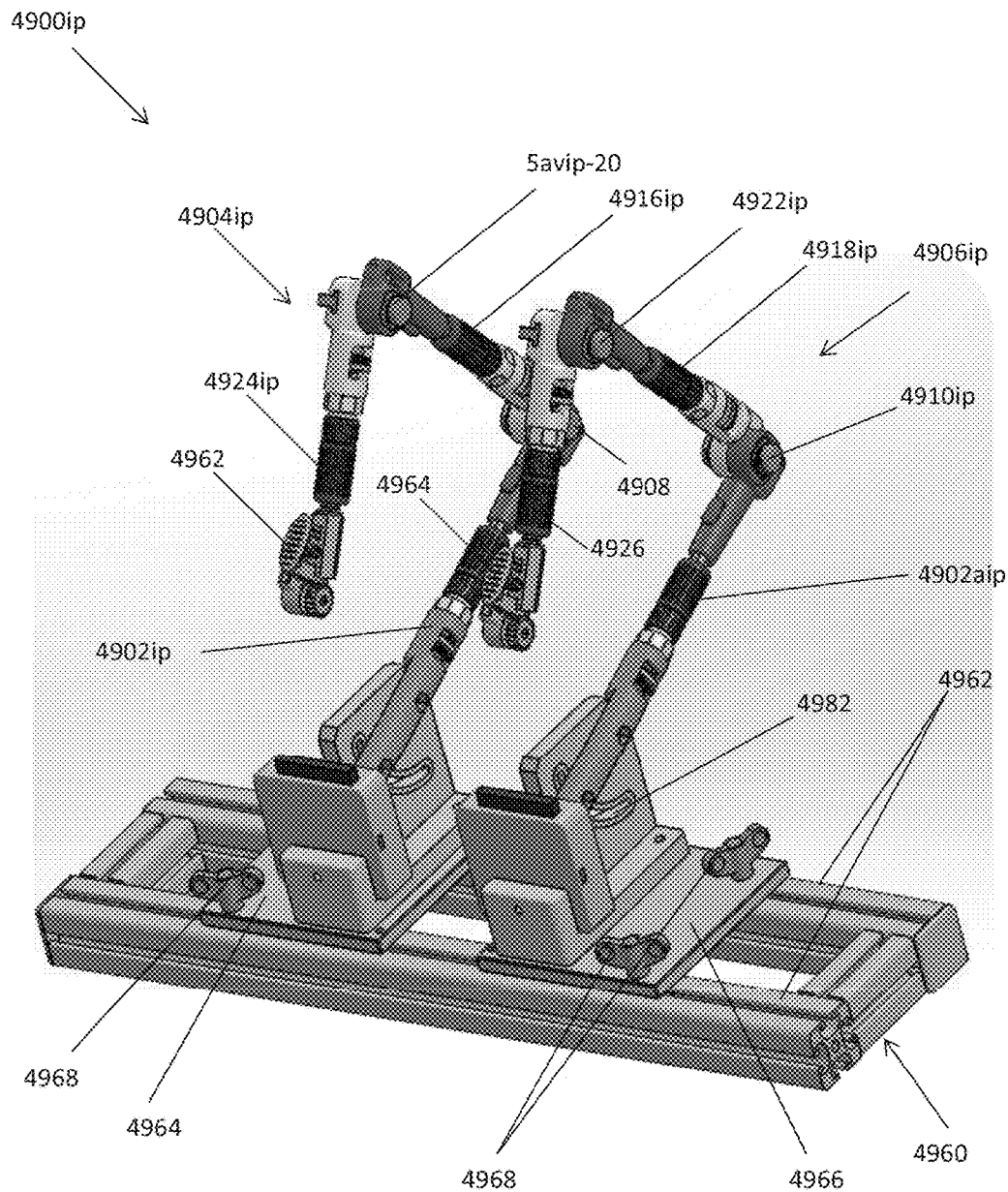
FIG. 49A is a simplified schematic side view of an input device, according to some embodiments of the invention.

FIG. 49A is a simplified schematic side view of an input device, according to some embodiments of the invention.

In some embodiments, one or more input device arm segments (e.g. segments) where adjacent segments are connected by connecting sections (e.g. joints). In some embodiments, for example, unlike some embodiments of the surgical device, one or more arm connecting section is a pivot joint.

In some embodiments, one or more input device arm (e.g. arm 4904ip and/or arm 4906ip) includes a support segment (e.g. 4902ip, 4902aip) coupled to a first segment (e.g. 4912ip, 4914ip) by a first connecting section (e.g. 4908, 4910) where first segment (e.g. 4912ip, 4914ip) is coupled to a second segment (e.g. 4916ip, 4918ip) by a second connecting section (e.g. 4920ip, 4922ip) and a third segment (e.g. 4924ip, 4926ip) is coupled to second segment (e.g. 4916ip, 4918ip) by a third connecting section (e.g. 4928ip, 4930ip).

In some embodiments, one or more (e.g. all) input device segment is rotatable around a segment long axis.

In some embodiments, an angle between adjacent segment long axes (flexion) is adjustable.

In some embodiments, one or more support segment 4902ip, 4904ip is connected to an input device platform 4960.

In some embodiments, an angle of support segment/s with respect to platform 4960 is adjustable, where adjustment is, for example, during set up of the device (e.g. arms are adjusted by a user) and/or during use of the input device. In some embodiments one or more input arm support section (e.g. support section 4920ip) is connected to platform 4960 at an adjustable point on hole 4982. In some embodiments, an angle of one or more an input arm support section is initialized e.g. to be parallel or perpendicular to the floor. In some embodiments, adjustable angle of input arm support section/s enables initializing arm position where, for example, the platform is angled with respect to the floor.

In some embodiments, adjustment of an angle of an input device support section is used to change an angle of a surgical device support segment, for example an angle of entry of the surgical device into a patient (e.g. through a port). In some embodiments, a different control method is used to change an angle of entry of one or more portion of a surgical device entering a patient (e.g. through a port and/or a natural orifice). In some embodiments, different portions of a surgical device (e.g. different limbs) are inserted into the patient at different angles. In some embodiments, a support segment is an elongated element, for example, where connecting portions and segments connected to the limb support segment have a maximum length of less than 50% of a length of the support structure, or less than 20% (e.g. where a surgical device limb includes a similar structure to a traditional laparoscopic tool).

In some embodiments, a separation between input device arms 4904*ip*, 4906*ip* is adjustable, for example, by adjustable attachment of one or more input device arm to input device platform 4960. In some embodiments, position of one or more input device arm on a device platform is adjustable in one, or two, or three dimensions.

In an exemplary embodiment, platform 4960 includes slider rails 4962, and each arm is attached to a slider 4964, 4966 which is tightened into position on the slider rails using wing nuts 4968.

Figure 49B:
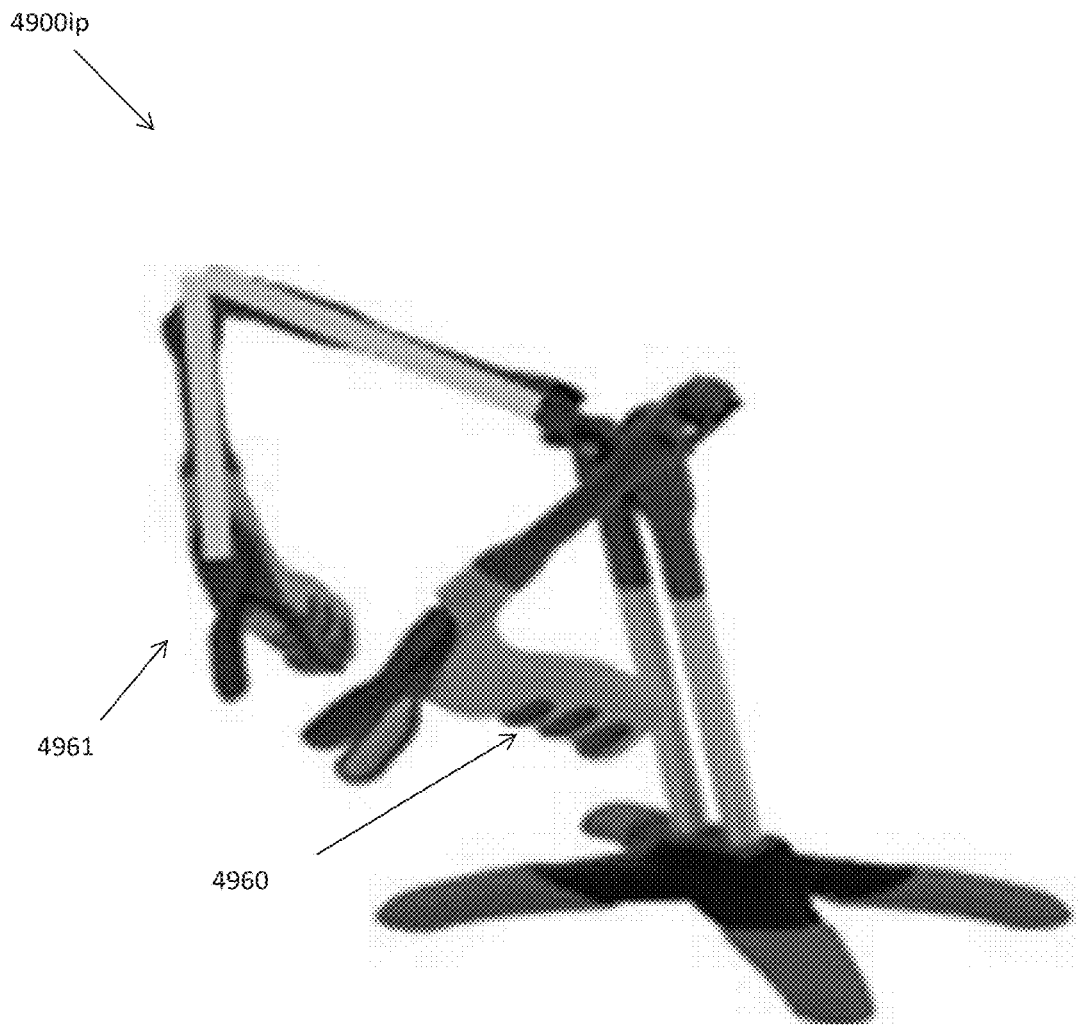
FIG. 49B is a simplified schematic side view of an input device including handles according to some embodiments of the invention.

FIG. 49B is a simplified schematic side view of an input device including handles 4960, 4961, according to some embodiments of the invention. In some embodiments, one or more input device limb includes a handle. In some embodiments, each input device limb includes a handle.

In some embodiments, an input device is small, for example potentially reducing cost and/or facilitating desired positioning (close to a patient, e.g. as described regarding FIGS. 47A-47B). For example, in some embodiments a small input device limb has a maximum dimension (e.g. when straightened) of 5-100 cm, or 10-50 cm, or 10-30 cm, or lower or higher or intermediate ranges or dimension.

In some embodiments, an input device is structured such that a connecting section pivot point is not at an intersection between effective segments. For example, referring to FIG. 48A, a connecting section 4820*ip* pivot point 4820*piv* is not at an intersection between axes 4813*ip* and 4817*ip*. In some embodiments, a pivot point (e.g. pivot point) 4820*piv* is disposed closer to a longitudinal center point the segments pivoting around the pivot point (e.g. segments 4av12*ip*, 4816*ip*) than the intersection of the axes of the segments (e.g. intersection between axes 4813*ip* and 4817*ip*). Potentially, an input device structure where the pivot points between segments are disposed closer to a longitudinal center point of the segments rotating around the pivot point matches surgical device structure where joints between segments are long. In some embodiments, pivot points enable bending of 180° and/or more than 180°.

In some embodiments, an input device includes one arm. In some embodiments, an input device includes two arms, or more than two arms. In some embodiments, an input device includes an arm for each inserted surgical device arm. For example, in some embodiments, an input device includes an arm for each mechanical surgical device arm and an additional input device arm for control of a camera (e.g. camera 1078 FIG. 10A).

Exemplary Input Device

Figure 50A:
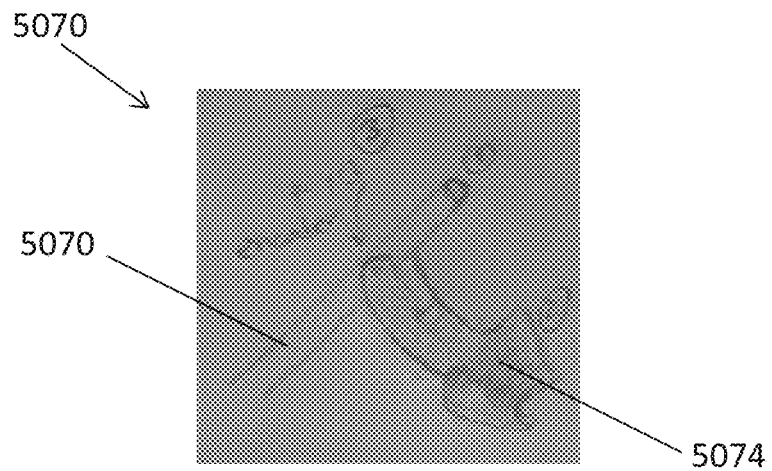
FIG. 50A is a simplified schematic of a controller, according to some embodiments of the invention.
Figure 50B:
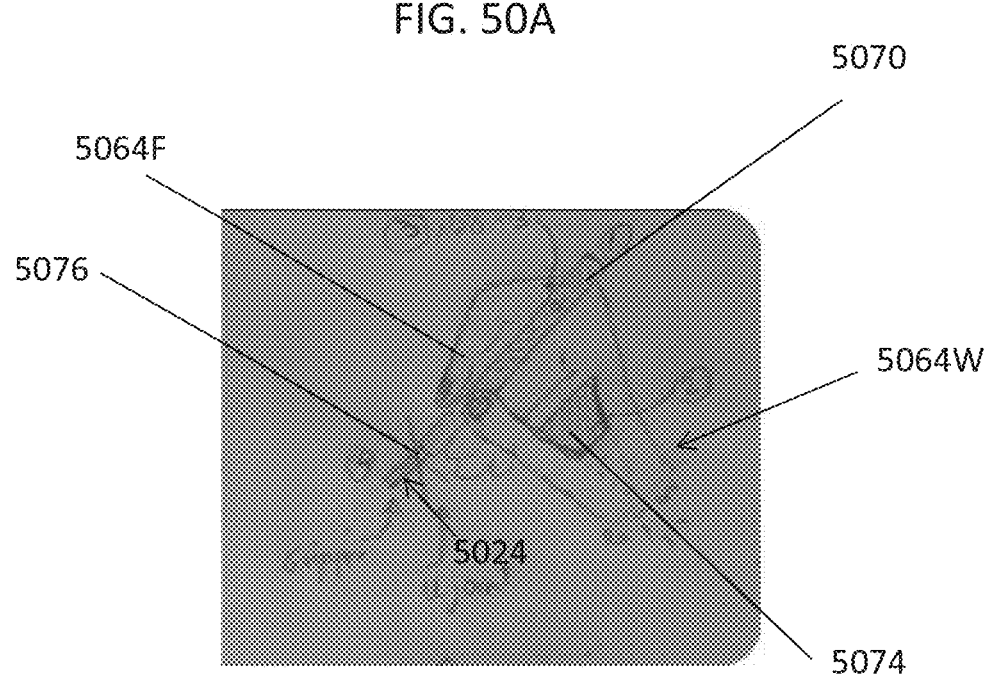
FIG. 50B is a simplified schematic of a controller held by a user, according to embodiments of the invention.

In some embodiments, the user controls the device using a handheld controller. FIG. 50A is a simplified schematic of a controller 5007, according to some embodiments of the invention. FIG. 50B is a simplified schematic of a controller 5070 held by a user, according to embodiments of the invention.

In some embodiments controller 5070 includes a stylus 5072 coupled to a wrist attachment 5074. Referring to FIG. 50B, in some embodiments, stylus 5062 is held between user fingers 5064F (e.g. like a pen). In some embodiments, a portion of wrist attachment 5074 sits in a user palm and a portion of the wrist attachment is fixed to a user wrist 5064W. In some embodiments, movement of the stylus is mimicked by a device arm. In some embodiments, the angle between the stylus and wrist attachment 5074 controls device arm elbow flexion. In some embodiments changing the wrist angle will control the device shoulder flexion.

In some embodiments, controller includes a hand tool 5024 (e.g. a gripper). In some embodiments, hand tool 5024 is coupled to stylus 5072 by a joint 5076, for example, a universal joint. In some embodiments, a user controls the hand tool by moving the hand tool at the joint. Alternatively or additionally, in some embodiments, a user controls the hand tool using one or more user control (e.g. button) on the stylus.

In some embodiments, a user controls device movement using, for example, voice activated control/s, user motion which is not mimicked (e.g. legs, fingers) a joystick, a mouse, a keyboard, one or more foot control (e.g. a foot pedal).

Exemplary Input Device Including a Handle

In some embodiments, an input device arm includes one or more handle. In some embodiments, a user moving the input device arm (e.g. in order to control movement of a corresponding portion of the surgical device) grasps a handle.

FIG. 51 is a simplified schematic side view of an input device arm including a handle 5160, according to some embodiments of the invention.

In some embodiments, a user grasps handle 5160 with one hand, for example, in some embodiments, the user controlling two input device arms, one with each hand.

In an exemplary embodiment handle 5160 includes a gun shape with a barrel portion 5162 and a grip portion 5164 (e.g. handle 5160 is a laparoscopic tool handle, in some embodiments, other laparoscopic tool handles of the art are used for handle 5160). Where, for example, barrel portion 5162 has a barrel long axis 5166 which is parallel (e.g. collinear) to a long axis 5117*ip* of an input device radius 5116*ip*.

In some embodiments, a long axis 5168 of grip portion 5164 includes a component which is perpendicular to barrel portion long axis 5166, for example, grip portion long axis 5168 being at an angle θ 45-135°, or 70-110° or about 90°, or lower or higher or intermediate ranges or to barrel portion long axis. In some embodiments, barrel portion long axis and grip portion long axis are co-planar.

In some embodiments, grip portion 5164 is sized and shaped to be griped comfortably by a user hand, for example, with a rounded cross section where a maximal cross sectional dimension of grip is 2-8 cm.

A potential benefit of handle 5160 is a comfortable user control, whist maintaining an intuitive relationship between geometry of the input device and the surgical device (e.g. one or more limb length ratios of the input device is substantially the same as an input ratio of the surgical device). A further potential benefit of handle 5160 is the ability to make the input device small while maintaining user ability to move the input device in a desired way (e.g. smaller than is comfortable and/or easy for a user to control movement of).

Figure 52A:
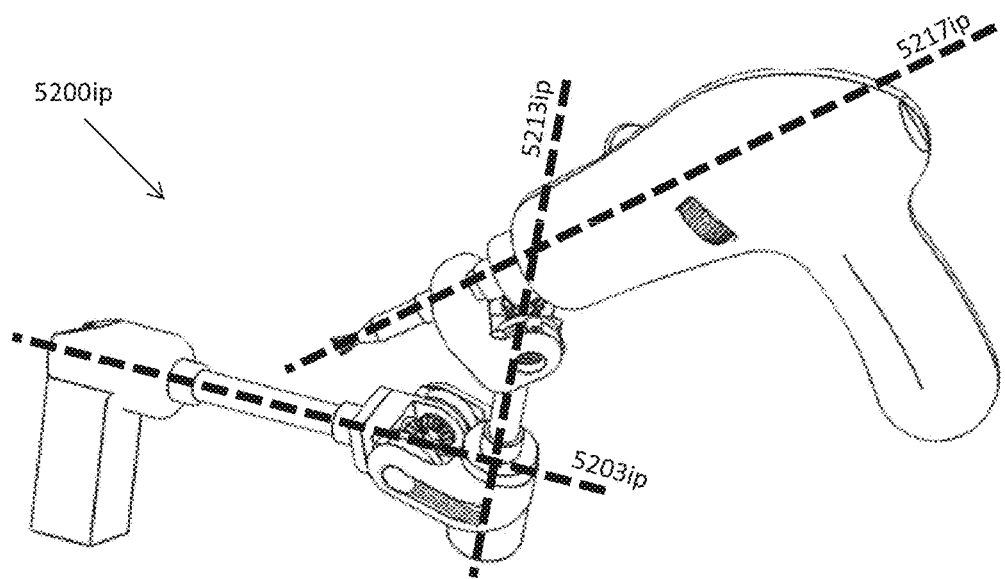
FIG. 52A is a simplified schematic side view of an input device arm including a handle, according to some embodiments of the invention.
Figure 52B:
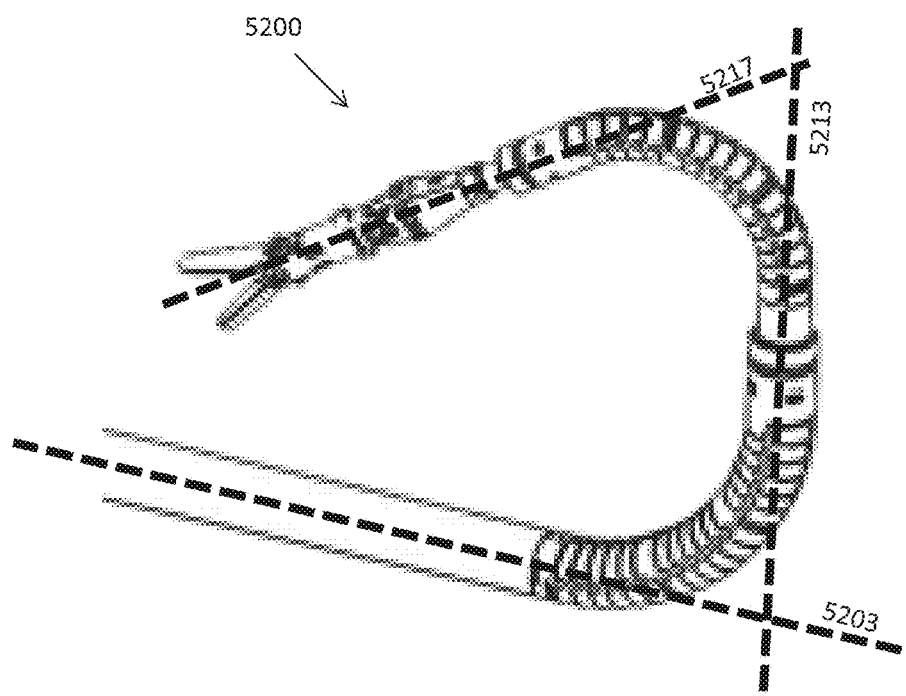
FIG. 52B is a simplified schematic side view of a surgical device arm, according to some embodiments of the invention.

FIG. 52A is a simplified schematic side view of an input device arm including a handle, according to some embodiments of the invention. FIG. 52B is a simplified schematic side view of a surgical device arm, according to some embodiments of the invention. FIG. 52A and FIG. 52B illustrate control of surgical am by input device, where angles of input device long axes substantially match segment long axes of surgical device.

Exemplary User Interface/s

In some embodiments, a system includes one or more user interface, for example, in some embodiments, an input device includes one or more user interface.

In some embodiments, one or more input device user interface is mounted on an input device arm, for example, such that, a user gripping the arm, uses the user interface whilst maintaining a user hand position. For example, referring back to FIG. 44A input arm 4404ip includes a button 4462 which, in FIG. 44A user 4464 is using (the user's finger is in position to press button 4462) whilst holding input device arm 4404ip. In an exemplary embodiment, button 4462 is coupled to a spring loaded lever where depression of button 4462 causes a coupled portion to rotate. In some embodiments, a rotation sensor senses the extent of rotation.

Exemplary user interfaces include push button/s, slide button/s, scroll wheel/s, touch sensitive buttons and/or LCD displays.

In some embodiments, a user interface mounted on an input device a controls an end effecter, for example, opening and/or closing of an end effecter (e.g. opening and/or closing of an end effecter with opposing portions e.g. scissors, gripper). For example, in an exemplary embodiment, a signal from the rotation sensor associated with button 4462 is used to control a corresponding end effecter.

For example, referring back to FIG. 44A, in some embodiments, button 4462 controls opening and closing of a surgical device end effecter 4424.

In some embodiments, a user depresses button 4462 to change an end effecter 4424 configuration (from open to closed, or from closed to open). In some embodiments, an extent of depression of button 4462 controls an extent of opening of end effecter 4424. Where, for example, full depression of button 4462 relating to end effecter 4424 being fully open and/or lack of depression of button 4462 relating to end effecter 4424 being closed, and/or an extent of depression of button 4462 relating to an extent of opening of end effecter 4424. In some embodiments, button Additional exemplary user interface buttons are illustrated in FIGS. 48A-48B button 4862, FIG. 49A buttons 4962, 4964 and FIG. 51 buttons 5166, 5164.

In some embodiments, a user interface button returns to an original state when a user ceases to apply pressure to the button (e.g. a spring loaded button). Optionally, a button returning to an original state returns a surgical device end effecter to an original state. Alternatively, in some embodiments, a button remains in position (e.g. a depressed and/or semi-depressed position) until a user releases the button.

In an exemplary embodiment, relative movement of a button 5166 is used to control actuation of an end effecter. In some embodiments, a user presses on button 5166, to open and close a corresponding surgical device arm end effecter.

In an exemplary embodiment, scroll button 5165 is a coupled to a rod where a rotation sensor measures the rotation of button 5165. In some embodiments, scroll button 5165 is used to control opening and/or closing of an end effecter. In some embodiments, one or more button (e.g. scroll button 5165) controls a camera inserted with the mechanical arm/s and/or a display of collected images.

In some embodiments, rotation of a corresponding surgical device end effecter about an end effecter long axis and/or around a long axis of a segment to which the end effecter is coupled is controlled by rotation of handle 5160 about axis 5166. Alternatively or additionally, in some embodiments, rotation of a corresponding surgical device end effecter is controlled by rotation of button 5165. In some embodiments, a both rotation of handle 5160 about axis 5166 and button 5165 control rotation of a corresponding surgical device end effecter, for example, enabling a user to avoid and/or move out of uncomfortable and/or un-ergonomic handle positions.

I don't know if it is described well—rotation of the gripper can be controlled both by rotation of the handle (5160) around axis 5166, or by rotation of knob 5165.

Therefore the surgeon operates the handle as a laparoscopic handle, and if he reaches an un-ergonomic posture he can use knob 5165 to change the rotation of the handle to a more comfortable position.

In some embodiments, a user manually moves one or more portion of an input device to operate an end effecter. For example, in some embodiments, an input device includes a scissors, and a user manually opens and closes the scissors, for example, controlling opening and controlling of a surgical device scissors. In some embodiments, an input device includes a plurality of portions coupled to a distal end of an input device limb and, for example, movement (e.g. manual movement) of one or more of the portions controls movement of corresponding portion/s of a surgical device end effecter.

Exemplary Scaling Using an Input Device

In some embodiments, an input device arm/s include portion/s which are the same size or larger than surgical device arms. In an exemplary embodiment, a ratio of a segment effective length of an input device to a segment effective length of a surgical device is between 5:1 and 1:1, or between 3:1 and 1:1, or lower or higher or intermediate ranges or ratios. Potentially, a system including larger input device arms than surgical arms, assist a user in fine movement control of the surgical device.

In some embodiments, a surgical system includes different sized input device arms and/or different sized surgical device arms. For example, in some embodiments, depending on the surgery (e.g. dimension of surgical movements in a surgery) and/or user preference, a user selects an input device arm size. For example, in some embodiments, an input device includes different sized arms, for example, the arms controlling surgical device arms of the same size. For example, in some embodiments, a user selects surgical device arm/s and then selects an input device size (e.g. from a kit of different sized input device arms). In some embodiments, a user changes input device during a treatment (e.g. surgery), for example, changing an input device to a larger device when fine surgical movements are required.

In some embodiments, a user manually controls scaling of user hand movements on the surgical device. In some embodiments, a user can generate larger or smaller movements of a distal end of an input device arm radius (e.g. relating to a position of a surgical device end effecter) for the same hand movement, by selecting a portion of the radius to grasp: For example, movement of a user's hand grasping an input device arm at and/or close to the distal end of the input device radius (e.g. as illustrated in FIG. 44A), generates a smaller movement of the distal portion of the radius than the same than the same hand movement when a user grasps the input device radius more proximally (closer to the connection between the radius and humerus).

In some embodiments, a handle attached to a segment which the user uses to move at least a portion of the input device (e.g. a handle, for example, as described in the previous section "Exemplary input device including a handle") provides scaling of user movements. For example, in some embodiments, the handle extends distally of an input device segment, meaning that large user hand movements are translated to smaller movements of the proximal end of the segment to which the handle is attached.

Exemplary Input Device with Adjustable Scaling

Figure 53A:
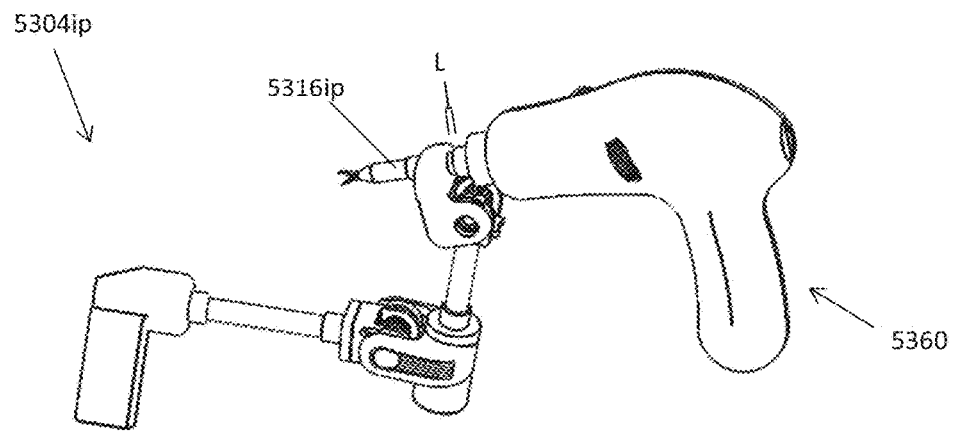
FIG. 53A is a simplified schematic side view of an input device arm including a handle, according to some embodiments of the invention.
Figure 53B:
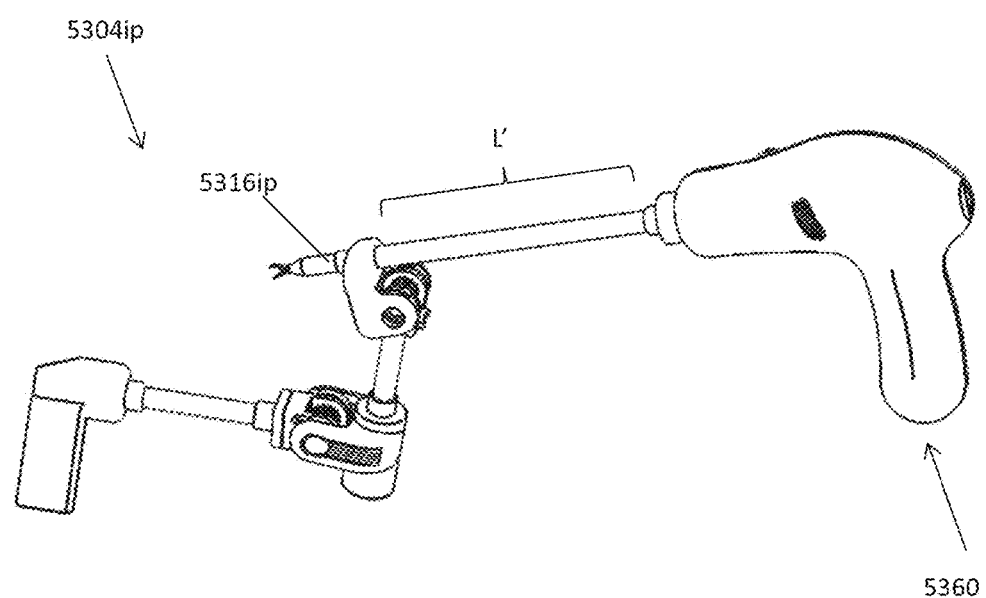
FIG. 53B is a simplified schematic side view of an input device arm including an extended handle, according to some embodiments of the invention.

In some embodiments, an input device includes adjustable scaling, where, for example, user movement (e.g. user hand movement) is scaled by different amounts Handle Slides to Change Distance from Handle to Gripper FIG. 53A is a simplified schematic side view of an input device arm 5304ip including a handle 5360, according to some embodiments of the invention. FIG. 53B is a simplified schematic side view of an input device arm 5304ip including an extended handle 5360, according to some embodiments of the invention. In some embodiments, a separation of handle 5360 from segment 5316ip is increased (e.g. from separation L illustrated in FIG. 53A to separation L' illustrated in FIG. 53B), meaning user movements of the handle translate to smaller movements of segment 5316ip.

In some embodiments, possible amount of separation of the handle is continuous from a minimum to a maximum and, for example, a user selects the amount of separation. Alternatively, in some embodiments, discrete amounts of separation of the handle are provided by input device arm 11av094ip.

Exemplary Input Device Connecting Portions

FIGS. 54A-54B are simplified schematic side views of a portion of an input device arm 5404ip including a connection 5408ip between input device segments 5412ip, 5415ip, in different configurations, according to some embodiments of the invention.

As described elsewhere in this document (e.g. as described regarding FIG. 48C, FIG. 49A), in some embodiments, input device segments are rotatable around a segment long axis, for example, rotation of second segment 5412ip about a segment central long axis, in a direction D1 transfers the portion of input device arm 5404ip illustrated in FIG. 54A to the configuration illustrated in FIG. 54B.

In some embodiments, one or more connection between adjacent input device arm segments includes a pivot connection. In some embodiments, flexion of adjacent segments with respect to each other is about pivot connections. For example, first segment 5412ip rotating around pivot connection 5408ip in a direction D2 transfers the portion of the input device arm 5404ip illustrated in FIG. 54B to the configuration illustrated in FIG. 54C.

Exemplary Measurement of Input Device Movement

In some embodiments, sensor/s mounted on and/or within the input device measure input device movement, and this measured movement is used to control movement of the surgical device.

In some embodiments, one or more portion of an input device includes a sensor. In some embodiments, one or more input device segment includes a sensor which measures rotation of the segment. In some embodiments, the input device includes one or more sensor which senses an extent of flexion of one or more input device joint.

Referring back to FIG. 54A, in some embodiments, motion sensors are mounted on input device connecting portions. In some embodiments, one or more sensor senses rotation of first segment 5412ip around pivot axis 5470, sensor/s, for example, producing a signal corresponding to flexion of first segment 5412ip with respect to segment 5404ip. In some embodiments one or more sensor senses rotation of second segment 5412ip about a segment long axis (not illustrated in FIG. 54A).

In some embodiments, a connecting portion includes two brackets, a bracket connected and flexing with each segment, the brackets connected together at a pivot point around.

In an exemplary embodiment, connecting portion 5408ip includes an external bracket 5472 coupled to first segment 5412ip, which pivots around an internal bracket 5474. In some embodiments, second segment 5412ip is coupled to internal bracket 5474 and is rotatable within internal bracket 5474.

In an exemplary embodiment, segment 5404ip is coupled to a shaft gear 5476 where shaft gear 5476 rotates with segment 5416ip, within inner bracket 5474, for example, shaft gear 5476 sliding within inner bracket 5474 when segment 10av16ip rotates. Outer bracket 5472 includes first and second gears 5478, 5479. In some embodiments, first and second gears 5478, 5479 which rotate with flexion of second segment 5412ip with respect to first segment 5412ip.

In some embodiments, shaft gear 5476 interfaces with first and second gears 5478, 5479, rotation of shaft gear 5476 about segment 5404ip long axis causing first gear 5478 and second gear 5479 to rotate in different rotational directions about axis 5470. In some embodiments, flexion of segments 5412ip, 5414ip with respect to each other causes first and second gears 5478, 5479 to rotate in the same rotational direction around axis 5470.

In some embodiments, connecting portion 5408ip includes two sensors. For example, in an exemplary embodiment, a first sensor 5482 connected to (e.g. mounted on and/or within) outer bracket 5472 senses rotation (e.g. direction and/or amount of rotation) of first gear 5478 and a second sensor 5484 senses rotation of second gear 5479. In some embodiments, two sensors, each sensor sensing rotation of one of first and second gears 5478, 5479 provides sufficient information to measure both flexion of segments with respect to each other 5412ip, 5416ip, where both gears 10av78, 5479 rotate in the same direction and rotation of second segment 5474 around a segment long axis where gears 10av78, 5479 rotate in different directions.

Alternatively, in some embodiments, each input device arm segment includes at least one sensor sensing rotation of the segment and additional sensor/s sense flexion between segments.

In an exemplary embodiment, sensors 5482, 5484 are magnetic differential encoders (e.g. rotor encoder/s), where, for example, a sensor senses a position of a magnet mounted on the gear. Other motion sensors, e.g. optical encoders are envisioned and encompassed by the invention.

In some embodiments, each connection between each adjacent segment pair of the input device includes a connecting portion as described with respect to FIG. 54A. In some embodiments, sensor outputs from more than one connecting portion are used to determine flexion and/or rotation at of segment/s, for example, in the circumstance where segments concurrently flex and rotate.

Referring back to FIG. 51, in some embodiments position sensors include electrical connectors 5164. Where connectors 5164, for example, transmit signal/s from position sensors (e.g. wirelessly and/or connectors are connected using wires and/or cables).

Exemplary Input Device Locking Mechanism/s

In some embodiments, an input device includes one or more locking mechanism. In some embodiments, a user locks one or more portion of an input device.

For example, in some embodiments, during a procedure, a user desires one or more surgical device portion to remain stationary while other segment/s are moved, the user locks corresponding input device portion/s in position and then continues to move other portions of the surgical device, using the input device.

For example, in some embodiments, upon a safety alert, a user manually and/or a system automatically locks one or more portion of the input device, for example preventing further movement of the surgical device. In some embodiments, locking is into a last position. In some embodiments, locking is into a homing position (e.g. input device moves into a homing position and then locks in that position).

For example, in some embodiments, when a user lets go and/or looses grasp on and/or takes a break from controlling the input device, one or more portion of the input device is manually and/or automatically locked in position. For example, in some embodiments, an input device includes one or more sensor detecting an amount (e.g. area of contact and/or strength and/or pressure of contact) of user contact with the input device (e.g. pressure sensor). In some embodiments, upon detection (e.g. by comparison of sensor signal/s with a threshold, where the threshold is e.g. stored in a memory) of a loss of contact and/or insufficient contact, the input device is automatically locked (e.g. a processor receiving sensor signals generates and/or sends command signals to input device locking mechanism/s).

In some embodiments, a single locking mechanism, when in a locked configuration, prevents rotation of a segment and flexion between adjacent segments. In some embodiments, a locking mechanism is located at a connection between two segments.

Figure 55A:
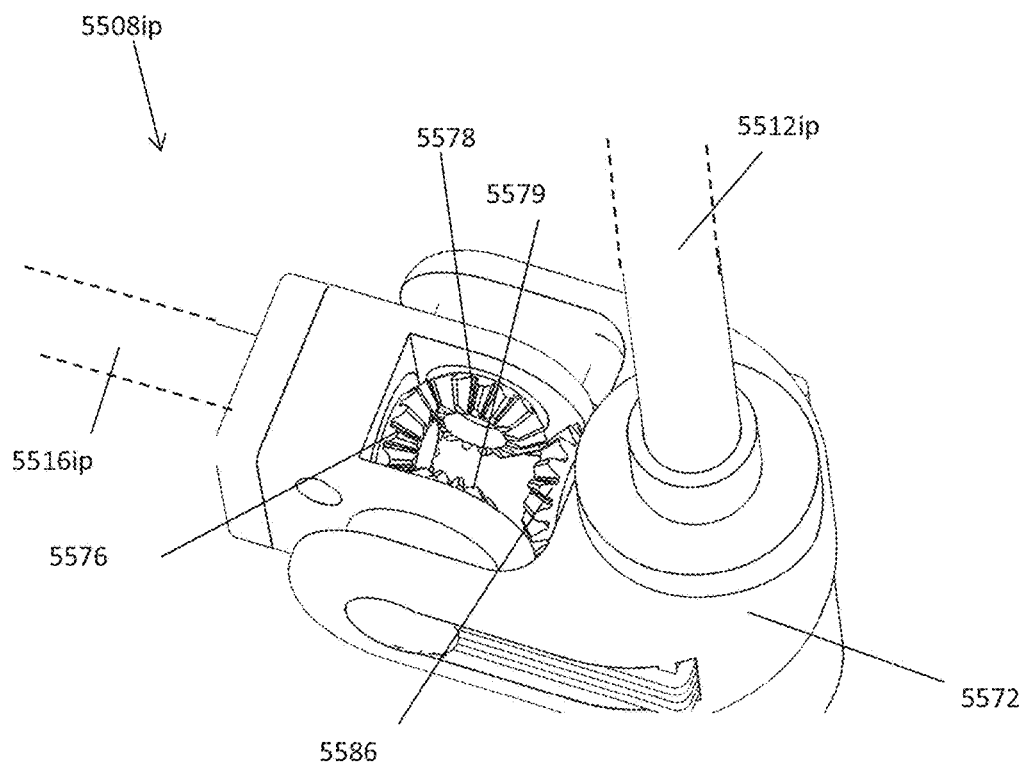
FIG. 55A is a simplified schematic side view of an input device arm connecting portion including a locking element in an unlocked configuration, according to some embodiments of the invention.
Figure 55B:
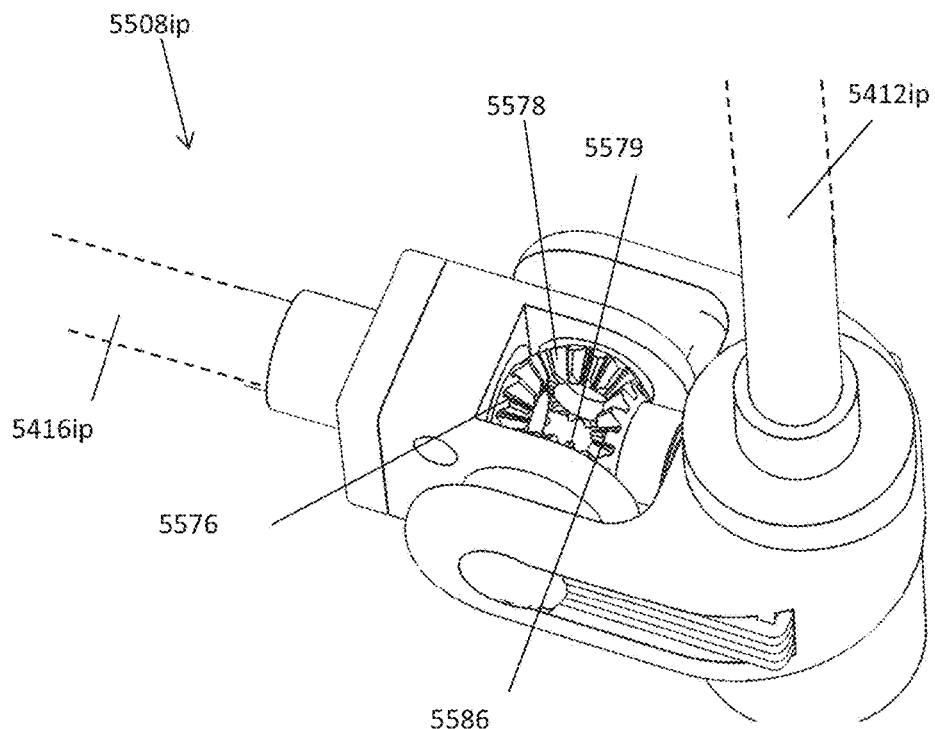
FIG. 55B is a simplified schematic side view of a portion of an input device arm connecting portion including a locking element in a locked configuration, according to some embodiments of the invention.

In some embodiments, a locking mechanism includes one or more element which prevents rotation of one or more of gears 5476, 5478, 5479 FIG. 55A is a simplified schematic side view of an input device arm connecting portion 5508*ip* including a locking element in an unlocked configuration, according to some embodiments of the invention. FIG. 55B is a simplified schematic side view of a portion of an input device arm connecting portion 5508*ip* including a locking element in a locked configuration, according to some embodiments of the invention.

In an exemplary embodiment, a locking element 5586 locks first and second gears 5578, 5579 e.g. preventing rotation of the gears 5578, 5579. In some embodiments, locking element 5586 is connected to outer bracket 5572.

Referring to FIG. 55B, where locking element 5586 is in a locked configuration. In some embodiments, locking element 5586 includes a gear fixed to outer bracket 5572 that prevents first and second gears 5578, 5579 from rotating. In some embodiments, stationary first and second gears 5578, 5579 prevent shaft gear 5576, (and, in some embodiments, segment 5516*ip*) from rotating.

In some embodiments, locking element is moved between locked and unlocked configurations manually, for example, by a user pushing the element manually. In some embodiments, an actuator moves locking element 5586 (e.g. automatically and/or upon receipt of a user input).

In some embodiments, a single locking mechanism (e.g. 5586) at each connecting portion is able to lock rotation and flexion of all input device segments. A potential advantage being reduced size and/or complexity of the input device arms.

Alternatively, in some embodiments, each connecting portion includes more than one locking mechanism, for example, a mechanism to prevent rotation of a segment and another mechanism to prevent flexion of the segment.

A potential advantage of a gear locking element is the high resistive ability of the lock, providing a secure lock. However, gear locking, in some embodiments, provides a discrete number of locking positions.

Figure 56:
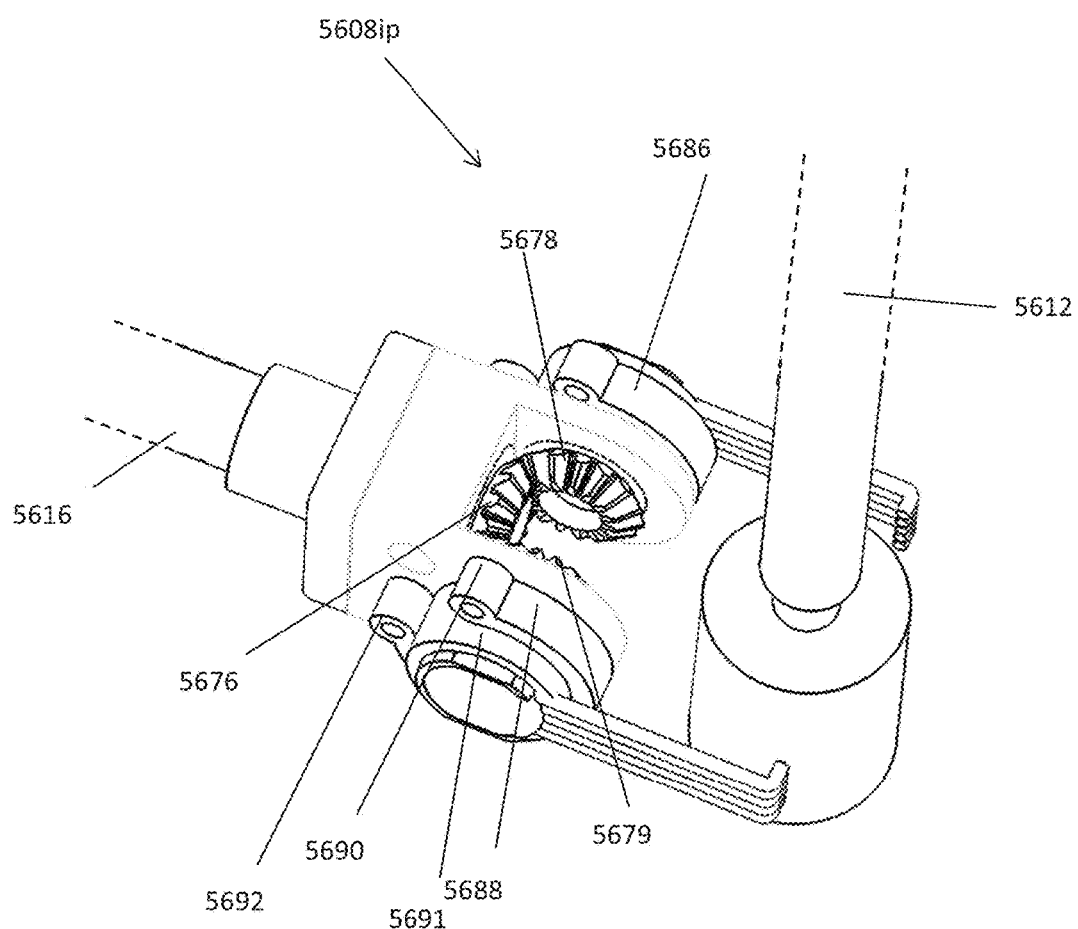
FIG. 56 is a simplified schematic side view of an input device arm connecting portion including a locking mechanism, according to some embodiments of the invention.
Figure 57:
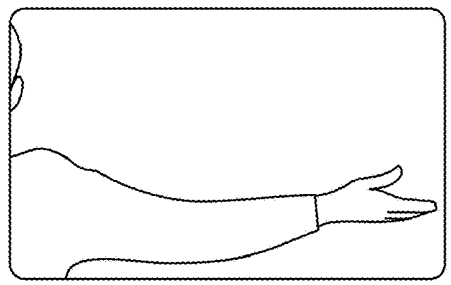
FIG. 57 is a series of photographic illustrations showing movement of a user and of a device arm, according to some embodiments of the invention.
Figure 57:
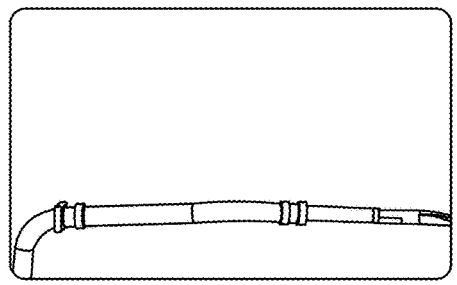
Figure 57:
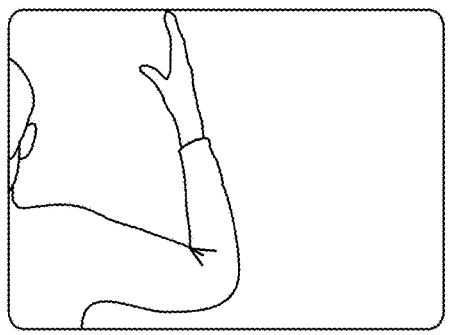
Figure 57:
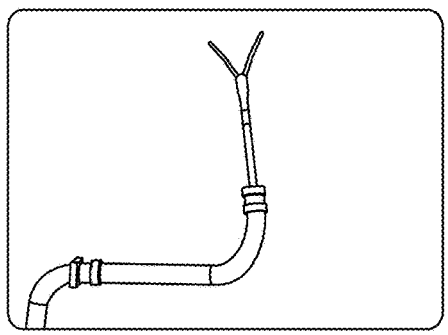
Figure 57:
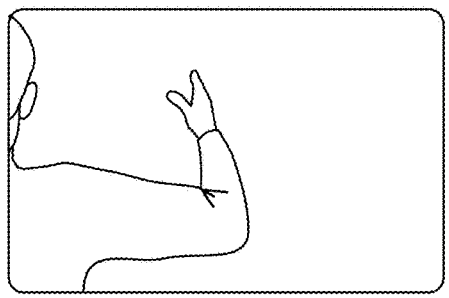
Figure 57:
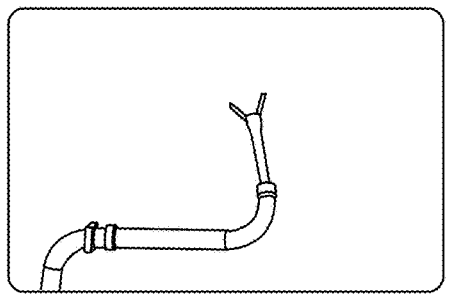
Figure 57:
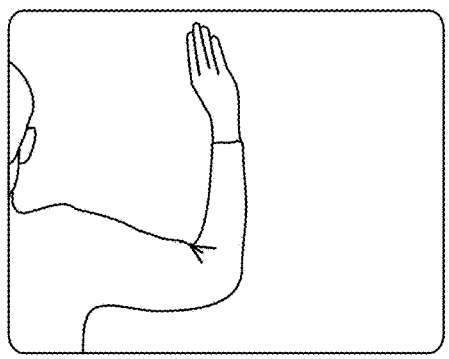
Figure 57:
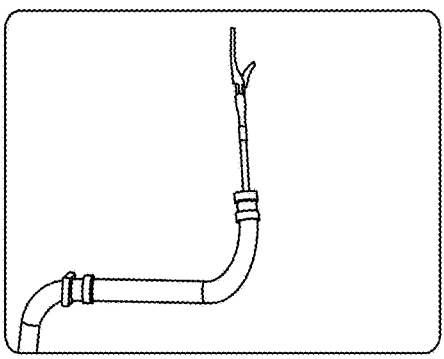

FIG. 56 is a simplified schematic side view of an input device arm connecting portion 5608*ip* including a locking mechanism, according to some embodiments of the invention. In some embodiments, a locking mechanism prevents rotation of at least one of gears 5676, 5678, 5679.

In some embodiments, a first locking element 5686 is used to prevent rotation of first gear 5678. In some embodiments, first locking element 6286 is an element which is tightened around a shaft (not visible in FIG. 56) connected to first gear 5678 and increased friction between locking element 6286 and the shaft, when, for example, locking element 5686 is tightened around the shaft.

In an exemplary embodiment, each of first and second gears 5678, 5679 is lockable using first and second locking elements 5686, 5688 respectively. A potential benefit of locking two of the gears, is increased strength of locking. In some embodiments, shaft gear 5676 is also locked by a locking mechanism.

In an exemplary embodiment, second locking element 5688 has a shape which partially surrounds a shaft connected to second gear 5679 and second gear is locked in position by pulling locking element ends 5690, 5692 towards each other e.g. by pulling wire/s (not illustrated) attached to ends 5690, 5692. A potential benefit of locking elements 5688, 5690 is the ability to lock the joint in any position (e.g. continuous locking). However, locking strength, in some embodiments, is limited by the frictional force between the locking element (e.g. 5688) and the portion onto which the locking element is tightened (e.g. axle 5691).

Exemplary Control by Mimicking User Body Movement

In some embodiments, movement of one or more portion (e.g. joint) of a device arm is controlled by measured movement of a corresponding portion in a user arm (e.g. a device joint movement controls movement of the corresponding device joint). In some embodiments, the anatomical name used in this document for a device portion is the name of a corresponding portion in a user when user movement is used to control the device.

In some embodiments, a position of segments of a device arm with respect to each other (angles between segment long axes) is controlled by a position of segments of a user arm with respect to each other (e.g. positions of the device arm and user arm are matched).

In some embodiments, device and arm position (angles between segment long axes) are aligned in an initialization process and position matching and/or control is maintained by movement control. For example, if the device arm and user arm start in the same position and user movements are accurately mapped to the device, the arms remain in a matched position. In an exemplary embodiment, both movement of the device and position of device segments are controlled by measured user movement. Referring to FIG.

58, images B1-B4 illustrate a device arm where the arm and device position are controlled by measurements of a user arm (images A1-A4).

Figure 58:
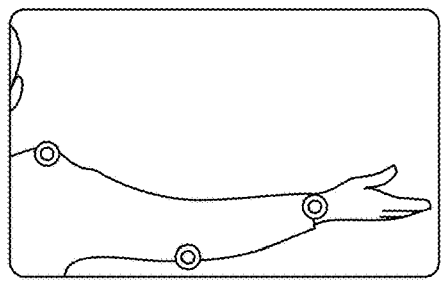
FIG. 58 illustrates control of a device arm using motion capture technology, according to some embodiments of the invention.
Figure 58:
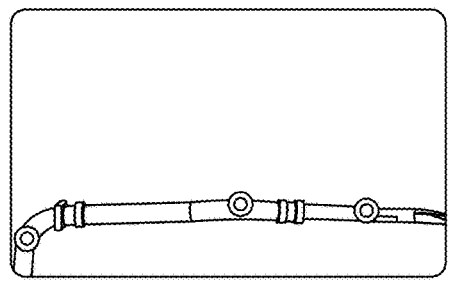
Figure 58:
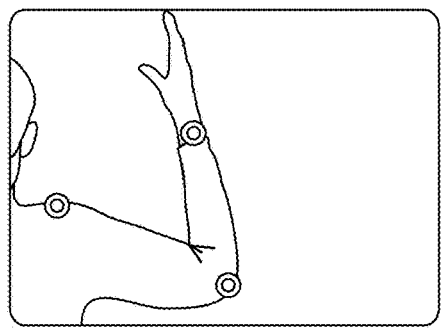
Figure 58:
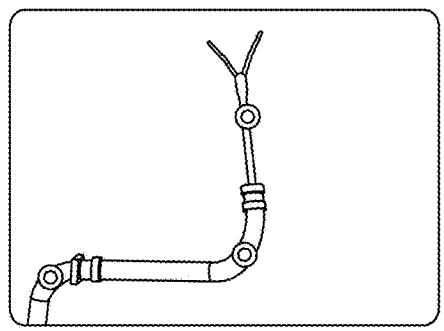
Figure 58:
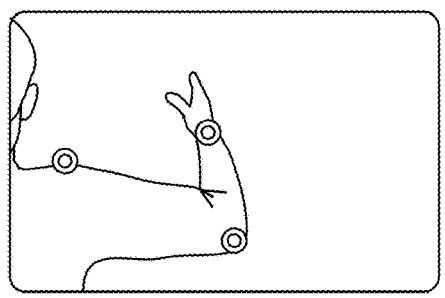
Figure 58:
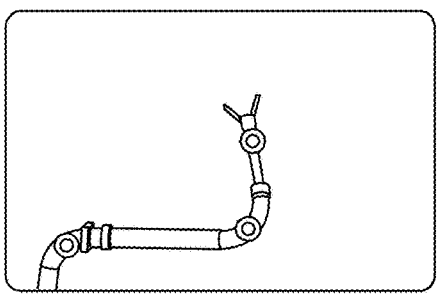
Figure 58:
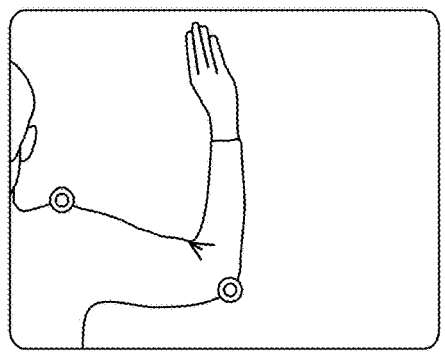
Figure 58:
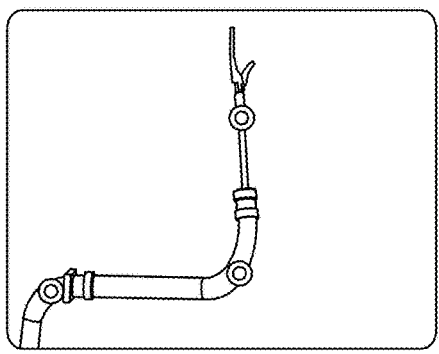

FIG. 58 is a series of photographic illustrations showing movement of a user and of a device arm, according to some embodiments of the invention.

A1 shows an outstretched user arm and B1 shows a device arm mimicking this arm orientation with approximately 180° between a long axis of the device humerus and a long axis of the device radius. In order to move from the position in A1 to that in A2, the user bends their arm at the elbow (elbow flexion). B2 shows the device arm mimicking this arm orientation with approximately 90° between the humerus long axis and the radius long axis. In order to move from the position in A2 to that in A3, the user rotates their humerus in a forwards (of the user) direction (medial rotation).

B3 shows the device arm mimicking this arm orientation by rotating the device humerus by approximately 90°. In order to move from the position in A3 to that in A4, the user rotates their hand, such that their palm is facing forwards of the user (wrist pronation). B3 shows the device arm mimicking this arm orientation by clockwise rotation of the radius by approximately 90°.

Optionally, in some embodiments, a device camera position with e.g. respect to device arms is controlled by a user head position e.g. with respect to user arms. In some embodiments, device camera position is selectively controlled by user head movement, for example, allowing a user to turn their head e.g. to view a display, without moving the device camera. In some embodiments, mimicking of a user head position is within a range of positions. In some embodiments head movements are filtered before being used to control the camera (e.g. rapid and/or unexpected user head positions are not mimicked by the device camera).

Exemplary Measurement of User Movement

In some embodiments, for example, in order for a user to control the device, user arm movement is measured, (e.g. by measuring position and/or orientation of arm portion/s repetitively). In some embodiments, measurement is using motion capture technology (e.g. using one or more infrared motion detection camera). FIG. 58 illustrates control of a device arm using motion capture technology, according to some embodiments of the invention. In FIG. 58, measured joint positions are illustrated as white circles on images A1-A4.

In some embodiments, images of one or more user arm are captured. In some embodiments, measurement includes extracting the position and/or movement of joints, e.g. position and/or movement of joints in 3D space, position and/or movement of joints with respect to each other. In some embodiments, joints are modeled as points and/or regions in space, which are, for example, extracted from images.

Alternatively or additionally, in some embodiments, one or more other arm parameter is measured, for example, movement of one or more segment, angles between segments. For example, in some embodiments, one or more segment is modeled by a segment long axis line in space, which line is, e.g., extracted from images. For example, in some embodiments, angles between segments and/or change in angles between segments, are measured (e.g. extracted from images).

In some embodiments, measurement of user arm position is assisted by placing markers onto the user (e.g. reflective markers), for example, at the joint, as is known in the art of motion capture. In an exemplary embodiment, markers are 4 mm spheres. In an exemplary embodiment, Kinect™ motion capture technology is used.

Additionally, or alternatively, in some embodiments, one or more sensor, for example, affixed to the user measures user body position and/or motion (e.g. a position sensor, a motion sensor).

Figure 59A:
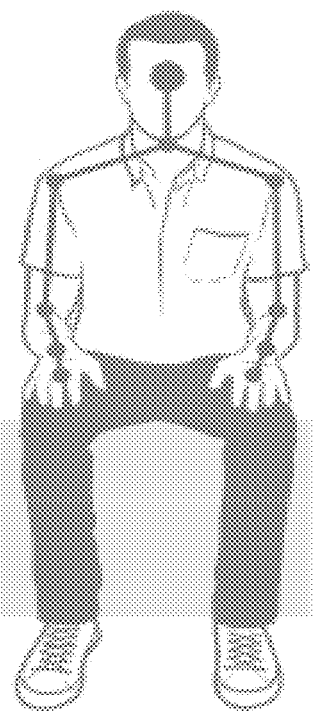
FIG. 59A and FIG. 59B are simplified schematic illustrations of body points the position and/or movement of which are measured, according to some embodiments of the invention.
Figure 59B:
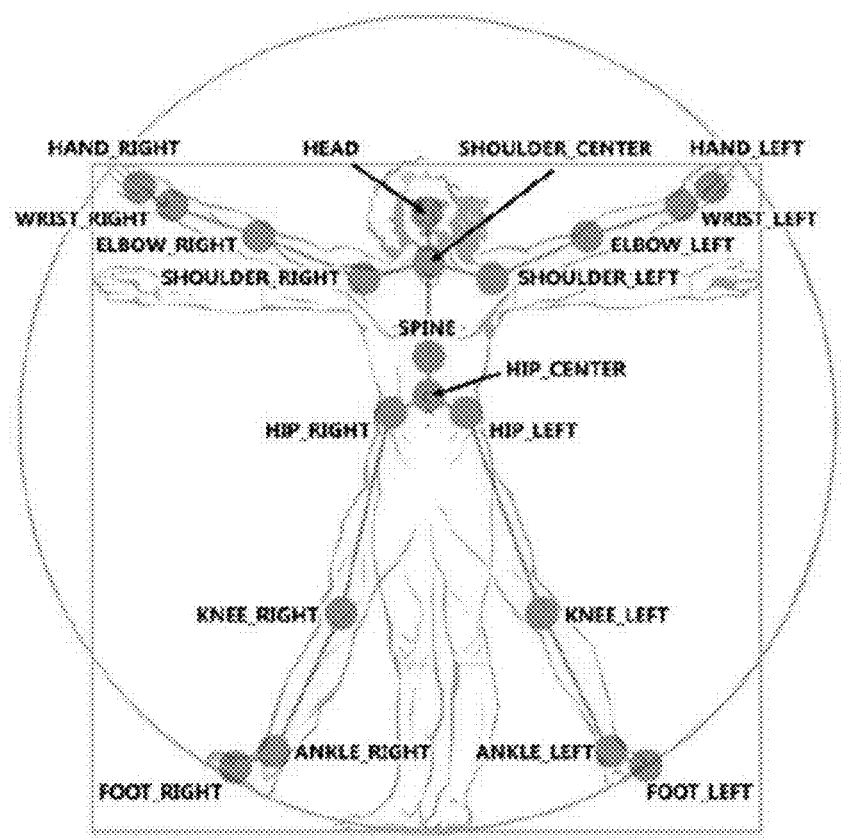

FIG. 59A and FIG. 59B are simplified schematic illustrations of body points the position and/or movement of which are measured, according to some embodiments of the invention. In some embodiments, upper body points (e.g. position of joints) are measured, for example, as illustrated in FIG. 59A. In some embodiments, body points including points on the upper body (e.g. including the head) and/or lower body are measured, for example, as illustrated in FIG. 59B.

In some embodiments, a user holds a tool avatar (e.g. scissors, grasper) and measurements of tool position and/or orientation and/or movement and/or actuation (e.g. opening, closing) are measured (e.g. using motion capture) and used to control a device tool (e.g. hand tool). In some embodiments, a measured orientation of a tool avatar is used to measure user wrist rotation. In some embodiments, a tool avatar includes a reflective coating to aid motion capture.

Exemplary User Motion Control Positions, e.g. Seated or Standing

In some embodiments, a user controls a surgical device with user body motion when the user is in a seated position. In some embodiments, the user is standing. Other exemplary positions include such as leaning on a support (e.g. desk and/or wall). In some embodiments, motion detection (e.g. implemented by a processor e.g. processor 4216, FIG. 42) is tailored depending on the user position (e.g. if the user is seated or standing).

As is described in more detail below, in some embodiments, transition between a seated and a standing position is used to change mode of the system In some embodiments, detection of whether a user is seated or standing is based on a measured height difference between a measured position of the spine and/or a measured distance between the center of the hips to the feet, and/or distances between other body parts.

Exemplary Mapping of Measured User Movement

In some embodiments, measurements of user limb/s are mapped to the device for control of the device. In some embodiments, user arm portions (e.g. segments and/or joints) are mapped to corresponding device portions. In some embodiments, mapping is automatic and extracted measurement of movement of a portion is automatically mapped to the anatomic equivalent (e.g. radius to radius, humerus to humerus) for control. Alternatively, in some embodiments, a mapping of measured user segments to device segments is defined by the user, before and/or during use of the device. For example, in some embodiments a user sets control of a device shoulder joint by the user hand segment, for example, for ease of control e.g. when the shoulder joint is near a delicate tissue portion.

In some embodiments, e.g. once a user arm portion is mapped to a device arm portion, measured movement of the user portion is mapped for control of movement of the device portion.

In some embodiments, one or more ratio between device arm segments are approximately the same as human ratios (e.g. a length of a radius segment is 20% shorter than a length of a humerus segment) and, for example, one or more part of a mapping between measured user arm movements and device arm movement is a scale. For example, in some embodiments, the device segments lengths are approximately a scaled down version of human arm segments lengths and user arm movements are, for example, scaled down to the device for control of the device.

For example, in some embodiments, a device arm has a length (excluding the torso) which is a tenth of a user arm length (excluding the torso), where length is measured as a long axis length of the arm (both user and device) when straight, from where the humerus meets the torso to the distal tip of the hand tool and/or radius. Then, in some embodiments, if, for example a distal end of the user radius is moved 10 cm in an x direction, then the distal end of the device radius is correspondingly moved 1 cm in the x direction.

In an exemplary embodiment, movement of user joints is measured. From the joint measurements angles and/or changes in angle between user segments are calculated. In some embodiments, the calculated angles and/or changes in angle are used to control device, segment movement, for example, a 10° increase in angle between two user arm segments corresponding to a 10° increase in angle between the corresponding segments in the device arm, the distance moved by the device segments being scaled correctly.

In some embodiments, measured movements of different portions of a user are mapped for device control using different mappings. For example, in some embodiments, a mapping for control of a device end effectors is a different mapping that that for control of other device portions, e.g. for reduced movement of some device portions.

In some embodiments, for example, as different human arms have different ratios between segments, a device is calibrated to an individual user (e.g. before the user starts using the device). In some embodiments, a user arm length is measured by measuring a length of user arm segments when the user's arm is straight. For example, when a user arm is held straight, measured joint positions (e.g. in 3D space) provide lengths of segments between the joints. In some embodiments, prior to using the device in treatment, the system performs an automatic calibration between a user arm (or arms) and a device arm (or arms).

In some embodiments, human arms and device arms have different segment ratios (e.g. device, is crab-like with a longer radius than humerus) and, for example, the device is moved with relative movements (as described elsewhere). For example, in some embodiments, a device with different ratio segments is controlled by moving a device end effectors according to position and/or movement of a user hand, while using measured user elbow and shoulder joint position and/or movement as a starting point for robotics control of other device joints.

In some embodiments, device control includes more than one mapping mode. In a first mode, for example, for rough positioning movements, the device mimics user segment angles with a 1:1 mapping. In an alternative mode, for example, for fine work (e.g. surgery once the device is positioned), larger user gestures are used to control fine device movements, for example, in some embodiments a 20° deflection of a user's humerus about a shoulder joint results in a 2° deflection of a device humerus.

In some embodiments, a user selects a fine work mode by moving arms to a designated position, e.g. to an arm rest.

Exemplary Initialization

In some embodiments, during initializing, the user matches user arm and/or input device arm position (arm position e.g. as defined above) to a surgical device arm position (optionally for two user arms and two device arms, each user arm corresponding to a device arm).

For example, in some embodiments, the user views an image of the device, and moves their arm/s (and/or input device arms) to copy an orientation of the surgical device arm. In some embodiments, the user receives feedback e.g. visual on the display and/or audio, to guide matching of the user arm/s (and/or input device arms) to the surgical device arm. In some embodiments, the user matches two arms simultaneously.

In some embodiments, a surgical device arm position is matched to a user arm position (and/or to an input device arm position). For example, once a user arm (and/or an input device arm) is in a desired position, the surgical device arm moves (e.g. automatically) into a position where positions of surgical device arm joints and/or angles of segments with respect to each other and/or orientation of the device arm mimic the user arm (and/or the input device arm). In some embodiments, when initializing a device-user arm pair, one portion of the surgical device arm remains static in space (e.g. the torso/s and/or the end effecter/s) and the other portion/s move to initialize the surgical device to user position (and/or input device position). In some embodiments, a user defines the static portion.

Optionally, initializing of a surgical device arm is automatic, for example, by using robotics (e.g. kinematics and/or motion constraints).

In some embodiments, for example, before insertion of the surgical device into a body, a surgical device is initialized to a specific user anatomy. For example, one or more segment length is adjustable. For example, in some embodiments, one or more segment length is adjusted, e.g. so that segment ratios are the same as a user's limb segment ratio. For example, in some embodiments, one or more segment length is adjusted, e.g. so that the segment and/or a ration of two segment lengths matches that of an input device.

In some embodiments, for example, if mapping of movement of the surgical device is not fully accurate, during use (e.g. during a treatment and/or surgery), the surgical device arms are re-initialized after a time duration and/or number of movements and/or distance moved.

In some embodiments, a user origin (and/or an input device origin) for measurement of user orientation and/or a device origin are set. For example, in some embodiments, a device orientation in space is matched to a user orientation in space (and/or an input device orientation in space).

In some embodiments, a system including surgical arm/s is able to recognize when the arm/s are in a straight and/or initialized position. For example, the arm/s include sensor/s and a processor receiving the sensor signal/s infers a position from the signal/s, in some embodiments, identifying if the arm/s are straight.

In some embodiments, for example, before a treatment is carried out using a surgical device, a surgical device and input device are initialized. In some embodiments, initializing of an input device to a surgical device includes aligning structural configurations (e.g. angles between long axes of segments) of the input and surgical devices. In some embodiments, for example, once structural configurations are aligned (e.g. during initialization and/or re-initialization) a sensors initial point is set.

In some embodiments, surgical device arms are initialized to a straight position, segment long axes are parallel (e.g. collinear). In some embodiments, surgical device arms are provided in a straight position e.g. factory calibrated to a straight position. In some embodiments, a jig is used to straighten surgical device arm/s.

In some embodiments, for example, before a surgical system (e.g. system 4250 illustrated in FIG. 42) is used, input device arm/s are initialized using a jig. For example, in an exemplary embodiment, a jig is used to straighten input device arm/s to match straight surgical device arm/s.

Figure 60A:
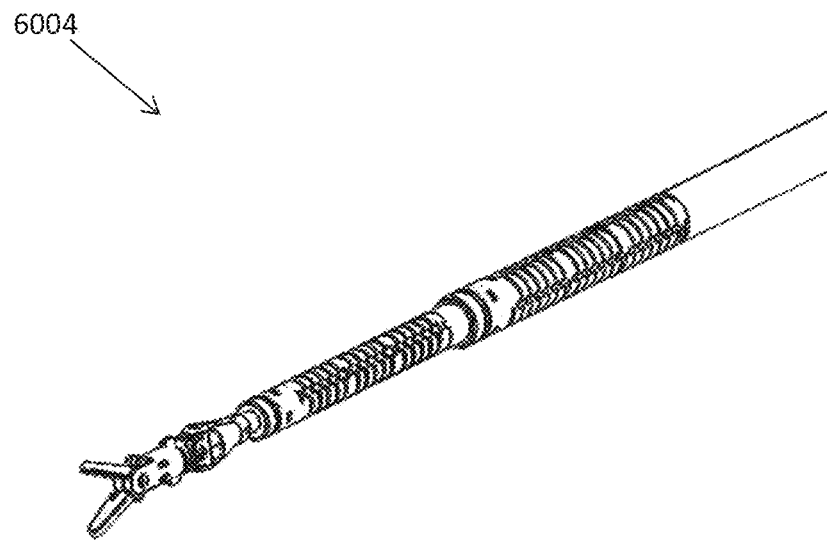
FIG. 60A is a simplified schematic side view of a surgical device arm in a straight configuration, according to some embodiments of the invention.
Figure 60B:
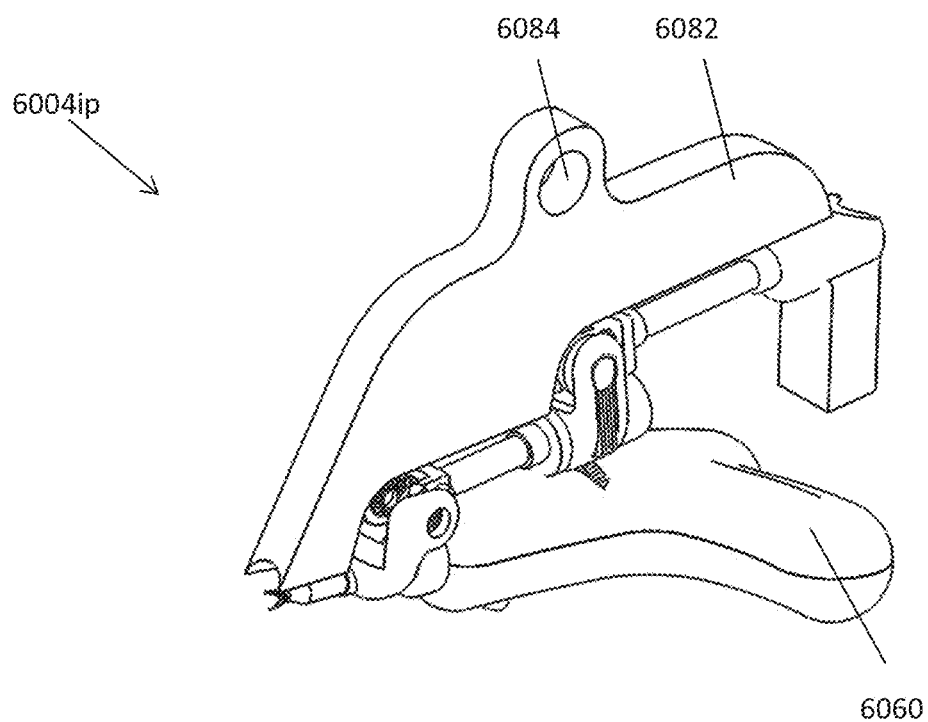
FIG. 60B is a simplified schematic side view of an input device arm straightened by a jig, according to some embodiments of the invention.

FIG. 60A is a simplified schematic side view of a surgical device arm in a straight configuration, according to some embodiments of the invention. FIG. 60B is a simplified schematic side view of an input device arm straightened by a jig 6082, according to some embodiments of the invention.

In some embodiments, jig 6082 includes one or more element shaped to straighten input device arm 6004*ip* when the jig is pressed against the input arm. In some embodiments, jig 6082 includes one or more hollow into which at least a portion of input device arm 6004*ip* fits.

In some embodiments, jig 6082 includes a hole or handle 6084, for example, to aid a user holding and/or carrying and/or using the jig.

Exemplary Re-Initialization

In some embodiments, the surgical device does not include any motion sensors and/or does not provide feedback as to the configuration (e.g. angles between segments etc.) of the surgical device.

In some embodiments, surgical device arm/s and input device arm/s are re-initialized (e.g. matching angles between long axes). In some embodiments, re-initialization is carried out in the event of system error/s, for example mechanical problem/s in the surgical and/or input device arms and/or electrical problems (e.g. in motor/s and/or sensors.

Figure 61:
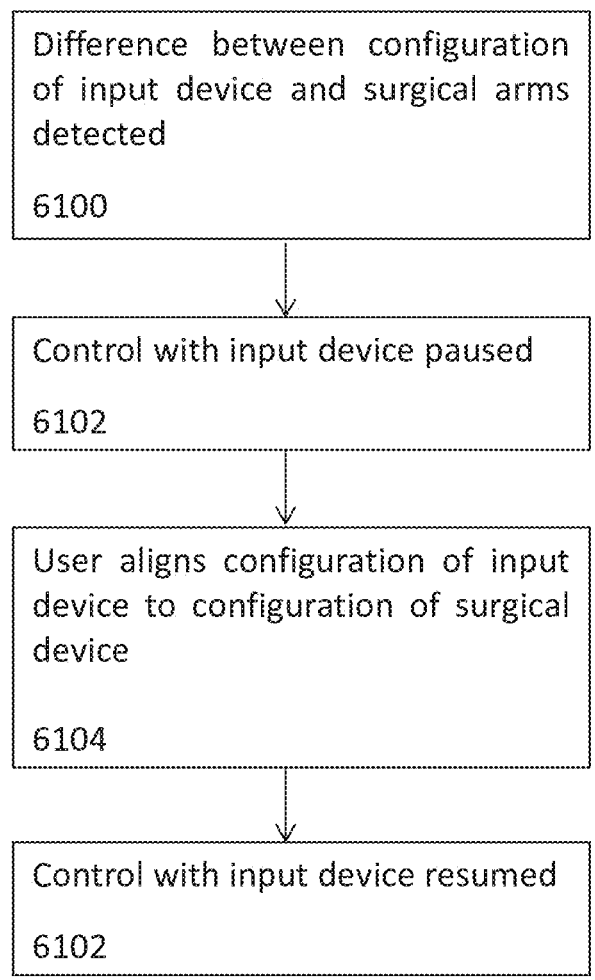
FIG. 61 is a flow chart of a method of re-initialization, according to some embodiments of the invention.

FIG. 61 is a flow chart of a method of re-initialization, according to some embodiments of the invention.

Figure 62A:
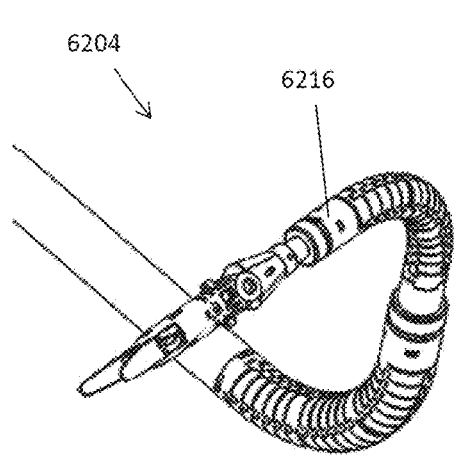
FIG. 62A is a simplified schematic side view of a surgical device arm 6204, according to some embodiments of the invention.
Figure 62B:
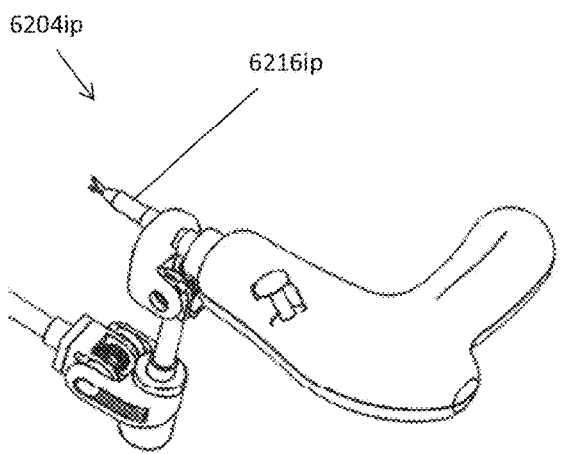
FIG. 62B is a simplified schematic side view of an input device arm 6204*ip* unaligned to the surgical device arm of FIG. 62A, according to some embodiments of the invention.
Figure 62C:
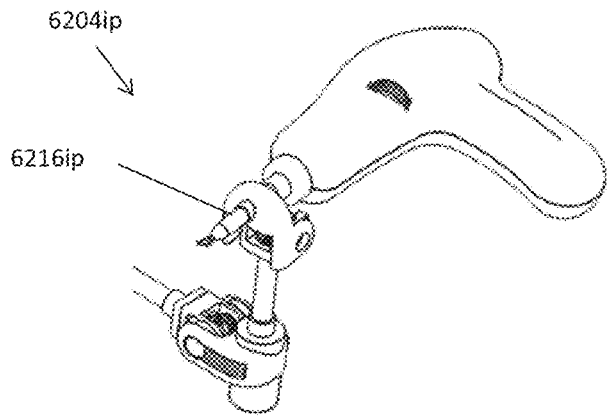
FIG. 62C is a simplified schematic side view of an input device arm realigned to the surgical device arm of FIG. 62A, according to some embodiments of the invention.

FIG. 62A is a simplified schematic side view of a surgical device arm 6204, according to some embodiments of the invention. FIG. 62B is a simplified schematic side view of an input device arm 6204*ip* unaligned to the surgical device arm of FIG. 62A, according to some embodiments of the invention. FIG. 62C is a simplified schematic side view of an input device arm 6204*ip* realigned to the surgical device arm of FIG. 62A, according to some embodiments of the invention.

At 6100, in some embodiments, a difference between a configuration of the surgical device and that of an input object (e.g. input device and/or user body portions) is detected.

In some embodiments, a user detects the difference, for example visually identifying a difference in the configuration of surgical arms (e.g. as viewed using an image inserted with the surgical device and/or a model of the surgical arms displayed on a display).

In some embodiments, the surgical system automatically detects the difference, for example, based on a discrepancy between sensed input object configuration and a model of surgical device configuration (e.g. based on motor movements of the surgical device).

For example, referring to FIGS. 62A-62B, which illustrate a 90° difference in orientation of an input device radius 6216*ip* with respect to the orientation of a surgical device arm radius 6216.

At 6102, in some embodiments, once a difference (e.g. a difference over a threshold value, for example, determined by processor 4216, FIG. 42) between an input object and surgical device configuration is detected, control of surgical device movement by the input device is paused, for example, by a user manually inputting a "pause" instruction into a user interface and/or automatic pausing (e.g. initiated by processor 4216, FIG. 42).

At 6102, a configuration of the input object is aligned to that of the surgical device.

For example, referring to FIG. 62A and FIG. 62C, where an orientation of input device radius 6216*ip* has been aligned to the orientation of surgical device radius 6216.

In some embodiments, alignment is by a user manually moving the input object (e.g. the user manually moves an input device, the user moves the user's body), optionally where the user is guided by displayed images (e.g. actual and/or modeled image of the surgical device) and/or instructions.

In some embodiments, at least a portion of an input device is automatically aligned, for example, by actuator/s on the input device (e.g. controlled by a processor) and/or by a separate aligning device.

In some embodiments, an input device is used to calibrate a processor associated with actuation of the surgical device with the surgical device arms. For example, in some embodiments, calibration is performed upon a mis-match (e.g. due to a mechanical problem and/or loss of power) between a real orientation of surgical device arm/s and an orientation of arms stored in a memory (e.g. orientation of arms derived from, for example, actuation control signal/s). In some embodiments, a user aligns surgical device arm/s to the a stored arm configuration using an input object (e.g. input device).

At 6102, in some embodiments, after the input device and surgical device are realigned, control of movement of the surgical device by movement of the input device is resumed.

In some embodiments, initialization and/or alignment of an input device arm is used in changing which input device arm controls which surgical device arm. For example, in some embodiments, an input device includes fewer arms than there are surgical arms, for example, in some embodiments, five surgical device arms are controlled using an input device with two arms.

In some embodiments, when a user changes which surgical device arm is controlled by an input device arm, in some embodiments, the respective arms are aligned and/or initialized, for example, in some embodiments, the input device arm automatically moving to a position of the new surgical device to be controlled.

In some embodiments, more than one surgical device is controlled using an input device and/or mechanical arms inserted through different incisions are controlled by an input device. For example, in some embodiments, an input device controlling movement of mechanical arm/s which have been inserted into a patient transvaginally is then used to control mechanical arm/s which have been inserted into the same patient (e.g. concurrently inserted) through an incision in the abdomen (e.g. through an incision in the umbilicus).

In some embodiments, more than one input device (and/or input object e.g. measured user body movement) is used to control one or more surgical devices, for example, enabling more than one surgeon to operate on a patient e.g. at the same time e.g. sequentially.

Alternatively or additionally to moving the input device, in some embodiments, aligning the input device and surgical device includes moving one or more portion of the surgical device.

Additionally or alternatively, in some embodiments, re-initialization (e.g. as described in this section) is between one or more portion of a surgical device and one or more portion of a user's body (e.g. where measured movement of a user body is used to control movement of portion/s of the surgical device).

Exemplary Filtering

Optionally, in some embodiments, measured user movements and/or desired device movement mapped from user movements are filtered (e.g. to remove undesired and/or damaging movements) before the device is moved. Additionally or alternatively, in some embodiments, measured movement of an input device is filtered, for example, before the device is moved according to the movement of the input device.

In some embodiments, movements are filtered to remove large movements. Where, for example, in some embodiments, large movements are movements taking the device out of a defined working area (e.g. the abdomen) and/or are movements of more than a sum of the humerus and radius long axis lengths. In some embodiments, movements are filtered to remove sudden movements, For example, measured sudden movement is slowed and/or removed. In some embodiments, tremors (e.g. fast small movements, e.g. movements which map to less than 20%, or 10%, or 5% of a radius long axis length where the movement duration is less than 0.1 s or less than 0.05 s or less than 0.01 s) are removed.

In some embodiments, movements are filtered to remove movement to a disallowed and/or damaging region. For example, in some embodiments, the device is prevented from moving into a disallowed region for example, an organ. In some embodiments, a user attempting to move the device into a disallowed region receives an alarm and/or alert, e.g. through the display, an audio alert, through force feedback of an avatar, through feedback (e.g. vibration and/or visual feedback (e.g. illuminated and/or flashing light)) of a device coupled to a user (e.g. the input device provides feedback).

In some embodiments, disallowed regions are marked (e.g. by a user), for example, before treatment (e.g. surgery) with the device commences.

For example, in some embodiments, a user delineates disallowed regions e.g. by instructing a surgical device to move to define edges of an allowed region and saving (e.g. in a memory) indications of the allowed region. For example, in some embodiments, a user moves (e.g. using an input device and/or measured user movement) a surgical device through a boundary (and/or to individual boundary points) where the boundary line/s and/or points are saved.

In some embodiments, disallowed regions are identified in and/or marked on collected images, e.g. images collected by an imager (e.g. camera) inserted into the patient (e.g. with the surgical device) and/or images collected by additional imager/s (e.g. CT, MRI, ultrasound etc.). In some embodiments, disallowed regions identified from images prior to treatment are mapped to images collected during treatment to generate disallowed regions for filtering.

For example, in an exemplary embodiment, a user falls, user arm movement is filtered to remove the fall, and the surgical device pauses movement.

In some embodiments, an anatomical map for example, specified by a user and/or from imaging e.g. CT, MRI includes disallowed regions. In some embodiments, if a user attempts to move the surgical device to a disallowed region and/or moves the surgical device near to a disallowed region, an alarm is initiated e.g. audio alarm, display alarm.

Exemplary System Modes

In some embodiments, a system (e.g. system 4250 FIG. 42 and/or system 850 FIG. 8 and/or system 4550 FIG. 45) includes a plurality of operation modes (also herein termed "states").

Figure 63A:
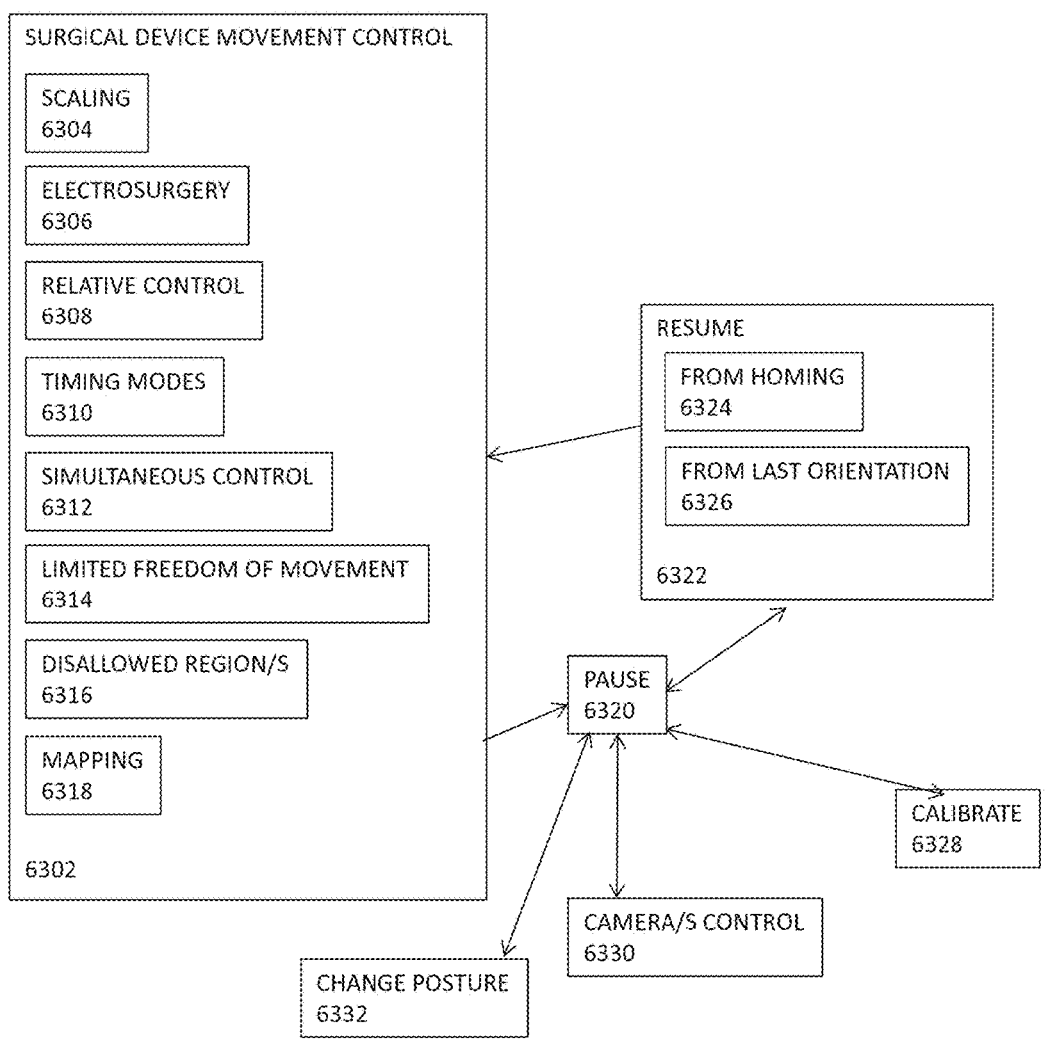
FIG. 63A is a simplified schematic of exemplary system modes, according to some embodiments of the invention.

FIG. 63A is a simplified schematic of exemplary system modes, according to some embodiments of the invention.

In some embodiments, a system includes a device movement control mode 6302 where movement of an input object (e.g. input device and/or measured user body movement) controls movement of the surgical device. In some embodiments, (e.g. as described in more detail below) there is more than one device movement state. In some embodiments, the system is in more than one mode concurrently (e.g. system is in more than one surgical device movement control mode currently), e.g. in some embodiments a fine motion mode and a relative motion mode run concurrently.

Exemplary surgical device movement control modes 6302 are described below in more detail and include, for example, scaling mode/s 6304, electrosurgery modes 6306 where one or more portion of a surgical device is electrically charged, relative control mode/s 6308, timing mode/s, simultaneous control mode/s 6310, disallowed region/s mode/s 6312, mapping mode/s 6318 where input object movements are mapped and/or filtered before being used to control movement of the surgical device.

In some embodiments, modes are selected by a user using one or more user interface. In some embodiments, modes are selected by a user using gestures (e.g. as described in more detail below).

In some embodiments, the system includes a pause mode 6320, where control of movement of the surgical device is paused. In some embodiments, pause mode 6304 is entered before selection of another mode e.g. in some embodiments, a pause mode is entered before transfer between and/or select and/or de-select surgical device movement control modes 6302.

In some embodiments, the system includes one or more resume mode 6322 (e.g. as described in more detail below).

In some embodiments, the system includes one or more calibration mode, where for example, one or more portion of the system is calibrated and/or initialized.

In some embodiments, the system includes one or more camera control mode, where 6330 for example, camera/s inserted with the surgical device arms are controlled. In some embodiments, camera/s are controlled with one or more of the surgical device movement control modes 6302 e.g. camera/s position controlled with relative control mode/s and/or timing modes, disallowed region mode/s etc. In some embodiments, camera control mode/s 6330 include imaging modes e.g. zoom.

In some embodiments, the system includes modes for different user postures, e.g. user is sitting or standing. Optionally, in some embodiments, gesture control is different in different user postures.

Exemplary Surgical Device Motion Control Modes

In some embodiments, a system includes a user motion control mode, where a user controls movement of a surgical device by motion of the user's body. In some embodiments, a system includes an input device control mode, where a user controls movement of a surgical device by moving an input device. In some embodiments, a system includes a combined user motion control and input device control mode where, for example, movement of one or more portion of a surgical device is controlled by movement of an input device and one or more portion of the surgical device is controlled by measured user body movement.

Exemplary Pause Mode

In some embodiments, there are various situations where device mimicking of user movement is paused and/or adjusted.

In some embodiments, a system includes a pause state, where, for example, user body movement and/or movement of an input device does not effect movement of the surgical device.

In some embodiments, a user selectively pauses surgical device mimicking of user movement and/or movement control by an input device (e.g. through a user interface). For example, if a user wants to take a break (e.g. due to muscle fatigue) and/or wants to change to a more comfortable position, the user pauses mimicking of user movement and/or movement control by an input device. In some embodiments, a user pauses the device in order to (e.g. prior to) transfer to a different mode.

In some embodiments, a user selectively pauses one or more arm and then selectively resumes control of one or more arm using user arm movement (and/or movement control by an input device). In some embodiments, a user controls more than two arms using pausing and selecting of arms. For example, a user controlling movement of two arms (e.g. using user arm movements), pauses one or both arms, and then selects two arms one or more of which are optionally different from the initial two arms to resume movement.

In some embodiments, a user pauses a portion of a device, for example, in order to use device freedom of movement which is more than human freedom of movement (and/or to use device freedom of movement which is more than the freedom of movement of an input device being used).

For example, in some embodiments, a user rotates a user segment until the user can no longer rotate the segment. The user then pauses the device, repositions the segment such that the user can continue rotating the segment, e.g. turning by the segment over.

For example, in some embodiments, a user pauses mimicking of user hand motion for rotation of a device hand through more degrees than possible with a user hand, e.g. to use the hand as a drill and/or screwdriver.

In some embodiments, a user pauses control with a user input device in order to switch input devices (e.g. to use a different scaled input device, e.g. to use an input device with a different number of limbs, for example upon inserting and/or removing a device tool and/or arm).

In some embodiments, a user pauses mimicking for one or more arm, for example in order to switch between methods of control (e.g. as described below).

Optionally, after resuming mimicking, the device and/or user arm is initialized e.g. as described previously.

Exemplary Resume Mode

In some embodiments, after a surgical device is paused, there are different types of resume mode, where movement control of the surgical device is resumed. For example, in some embodiments, upon entering a pause mode (and/or upon resumption of control when leaving a pause mode), a surgical device arm and/or an input device arm move to a homing position (e.g. straighten); the system is in a homing mode.

For example, in some embodiments, for the system to move out of a pause mode, user body portion/s and/or input device portion/s are aligned to surgical device limb/s.

For example, in some embodiments, after entering a pause mode, control is resumed with relative control (e.g. as describe in the section below "Exemplary relative movement mode"). Optionally, to enter a relative control mode after a pause mode, a relative movement mode is selected e.g. with a user interface and/or with a user gesture.

Exemplary Scaling Modes

In some embodiments, a system has different modes whereby a same size user movement (measured user body movement and/or user movement of an input device) results in different sized surgical device movements. In some embodiments, a user transfers between different scale modes (where user movement is scaled by different amounts). For example, in some embodiments, a user performs large initial surgical movements (e.g. incisions) using a first scale mode and then transfers to a fine work mode where user movements are scaled down when performed by the surgical device e.g. for suturing.

Exemplary Timing, Delay, Modes

In some embodiments, a system includes different modes for timing of control movements (e.g. measured movement of user device body portion/s and/or user movement of an input device) resulting in corresponding movement of the surgical device.

In some embodiments, movement of the device (e.g. device arm) is substantially at the same time as movement of the user arms and/or the input device arms (e.g. with a delay of less than 2 seconds, or less than 1 second, or less than 0.5 seconds, or less than 0.1 seconds).

Alternatively, in some embodiments, movement of the device (e.g. device arm) is delayed, for example, a user makes a movement, then optionally authorizing the movement for control of movement of the device.

In some embodiments, the device moves according to measurements of user joints at the same speed as the user movement. Alternatively, in some embodiments, the device moves at a different speed (e.g. slower).

In some embodiments, a user selects an amount of delay and/or speed change (e.g. through a user interface and/or with a user body gesture).

In some embodiments, a user performs control movement/s (e.g. by moving an input device and/or user body movement) to control movement of the surgical device, but user control movement/s are stored and used to control surgical device movement/s after a time delay.

For example, in an exemplary embodiment, a user records user control movements (e.g. in a memory, for example where the memory is accessible by processor 4216, FIG. 42). After recording, in some embodiments, the user (or a different user), initiates control of the surgical device using the pre-recorded movement/s.

In some embodiments, a user controls movement of a surgical device by selecting from a list of pre-programmed movements and/or movement sequences.

In some embodiments, a user recording a sequence of control movements selects (e.g. through a user interface) one or more break point within the sequence. In some embodiments, when a control movement sequence including one or more break points is performed by a surgical device, the surgical device pauses at each break point (e.g. for a time period and/or until receipt of a "resume movement" command from a user).

In some embodiments, a representation of a recorded movement and/or movement sequence is displayed to a user controlling a surgical device (e.g. using an input device and/or with user body movement), for example, assisting and/or instructing the user as to how to carry out a procedure. In some embodiments, a representation of a deviation of user movement/s from the recorded movement/s is displayed.

Exemplary Relative Movement Mode

Optionally, measured movement of one or more portion of the user's body and/or portion of an input device controls a portion of the surgical device, without that portion of the surgical device having the same position as the measured portion/s, where surgical device position is the orientation of segments relative to each other.

For example, in some embodiments, relative movement of one or more segment is controlled by user movement (e.g. one or more portion of a device arm is not initialized to a user arm position). For example, a portion of a device arm is bent (e.g. angle between device radius and device humerus is less than 180°), and the user arm is straight (angle between user radius and user humerus is 180°), but bending of the user radius with respect to the user humerus results in movement of the device radius with respect to the device humerus, e.g. in some embodiments, by the same number of degrees.

For example, in an exemplary embodiment, one or more device arm is outstretched (e.g. to access a target within the body) for example with an angle of 90° or more between the humerus and support section, and (e.g. to provide the user with a comfortable working arm position) a corresponding user humerus segment is held downwards (e.g. at the user sides), for example with angles of less than 70° between the humerus and support section. Relative motion of user hand and/or radius and/or wrist then control movement of the device hand, radius and wrist respectively.

Exemplary Simultaneous Movement Mode

In some embodiments, measurement of user joints is of more than one limb (e.g. both user arms, an arm and a leg, two arms and one or more leg) simultaneously. In some embodiments, measurement of movement of more than one input device limb is simultaneous.

Optionally, surgical device arms are then moved simultaneously, for example according to the measurement. A potential advantage being the ability of two or more device arms to work together, for example, to grasp a portion of tissue together, for example, to pass an object from one hand tool to another etc.

In some embodiments, movement of a user arm and movement of a user hand and/or tool avatar are measured simultaneously. Optionally, a surgical device arm is moved and a device hand tool is actuated (e.g. opening, closing) simultaneously. A potential advantage user control of a position and/or orientation of a tool and use of the tool simultaneously e.g. similar to traditional surgery.

Exemplary Limit to Freedom of Movement Mode

In some embodiments, in a restricted freedom of movement mode, movement of an input device and/or surgical device is limited where, for example, rotation of one or more joint is restricted in direction and/or amount and/or flexion of one or more joint is restricted. In some embodiments, a user specifies the limits of freedom of movement of one or more joint. In some embodiments, a system includes a human freedom of movement mode, where freedom of movement of a portion of the surgical device and/or input device is restricted to that of a corresponding body part (e.g. a surgical device arm and/or an input device arm is limited to mapped freedom of movement of that of a human arm).

Generally, human freedom of movement (e.g. for arms) includes limits to the angles of rotation and flexion of segments. Optionally, in some embodiments, the device is restricted to human freedom of movement e.g. during one or more control mode.

Exemplary Control of Transfer Between Modes and/or Mode Selection

In some embodiments, a system is transferred between modes and/or modes are selected through a user interface (e.g. button/s and/or touch screen and/or computer terminal and/or voice recognition unit etc.).

Alternatively, or additionally, in some embodiments, a user selects a mode and/or transfers from one mode to another by performing a gesture, which is recognized by the system.

In some embodiments, a gesture is a single user movement, for example, a user raises a user leg, for example, a user transfers position (e.g. between sitting and standing). In some embodiments, a gesture is with one user body portion (e.g. a limb—e.g. raising of a user leg). In some embodiments, a gesture involves movement and/or positioning of more than one body portion, for example, an exemplary gesture being a user crossing user legs.

In some embodiments, a gesture involves more than one sequential movement, for example, a user raising a user leg and then lowering the leg again. A further exemplary sequential gesture includes: Raising one or the arms so that the humerus is at an angle of approximately 45° with respect to the floor and then lowering the raised arm back down wards to the hip (performing an angle of 90° with the same humerus). This gesture is, for example used to initiate and/or resume the movement of the laparoscopic arms.

In some embodiments, the user changes mode (e.g. initiates a pause mode) by moving one or more body portion to a designated position and/or to a designated object. For example, in some embodiments, a user pauses control of device arms by resting user arms on an arm-rest (e.g. a designated arm rest).

Exemplary Initiation of Movement Control, Becoming an Operator

In some embodiments, the system stores one or more identifier for each user (e.g. in a memory, for example where the memory is accessible by processor e.g. processor 4216, FIG. 42). In some embodiments, a user identifier includes user body dimension (e.g. a skeleton built from relative joint positions). In some embodiments, only users with stored and/or allowed skeletons are able to operate the device. For example, in some embodiments, a user enters a field of view of system cameras and/or performs an initial gesture (e.g. initiation gesture), and the system checks if position of detected body portion/s match a stored skeleton before allowing the user to control the surgical device.

In some embodiments, a user which performs an initiation gesture becomes the operator.

In some embodiments, a user becomes an operator upon detection of the user sitting, e.g. at a control chair and/or sitting in a control zone.

Figure 63B:
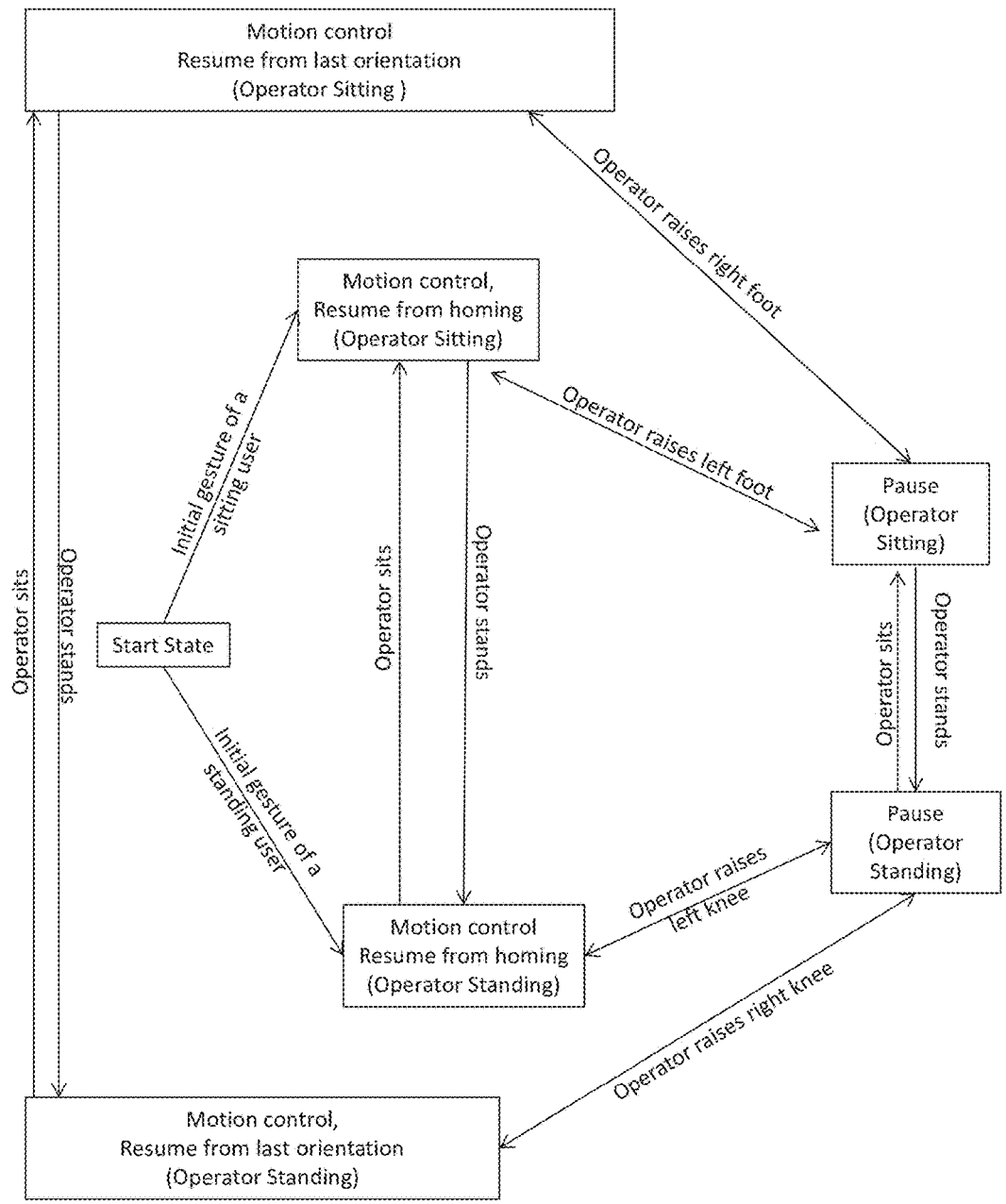
FIG. 63B is a simplified schematic illustration of exemplary states and gestures for transition between states, according to some embodiments of the invention.

FIG. 63B is a simplified schematic illustration of exemplary states and gestures for transition between states, according to some embodiments of the invention. In some embodiments, a user decides whether or not to sit or stand (e.g. upon starting to use the system and/or during use of the system) and the system is controllable by a user both in a seated and in a standing position.

In some embodiments, a system is in an initial "start state" before an operator starts using a system. In some embodiments, an initial gesture transfers the system from a "start state" into a state where the user controls the surgical device movements by an initial gesture. In some embodiments, depending on a user position (e.g. sitting or standing), different initial gestures transfer the user from the start state into a control state.

In some embodiments, for example, depending on whether the user is seated or standing, the user performs a different gesture to transfer system states (e.g. from control into a pause mode). For example, in some embodiments (e.g.

in a standing position lifting a leg transfers the system state between modes. In some embodiments, when a user is seated, the same transfer is performed, for example, by a user crossing their legs. Potentially this assists ease of user control as crossing legs while standing may be awkward as may be lifting a user leg while seated.

In some embodiments, a user tailors and/or defines user control movements and/or gestures (e.g. according to user comfort and/or in the situation where, for example a user is lacking a limb).

In some embodiments, depending on the gesture performed, the system resumes using a different type of resume mode (e.g. different types of resume mode as described above).

FIG. 63B shows exemplary transfer between resume and pause states, for two different resume states for different user positions (e.g. standing and sitting). In some embodiments, a user is able to change a user position (e.g. between standing and sitting) while the system is paused and/or when the system is controlled by user body movements (and/or movement of an input device).

In some embodiments, a user moves a left leg to transfer between a motion control state and a pause state where a seated user, for example lifts a left foot to transfer and a standing user, for example lifts a left knee to transfer. For example, in some embodiments, a seated user repetitively transfers to and from a pause mode and a motion control mode by lifting and lowering a left foot repetitively. In some embodiments, moving the left leg transfers between pause state and a motion control state where resumption of control after the pause is from a homing position (homing mode).

In some embodiments, a user moves a right leg to transfer between a motion control state and a pause state where a seated user, for example lifts a right foot to transfer and a standing user, for example lifts a right knee to transfer. In some embodiments, moving the right leg transfers between pause state and a motion control state where control resumes without the surgical device moving during and/or at initiation of entry into the pause mode.

Exemplary Determining of Gestures

In some embodiments, at one or more point in user use of a system, for example, upon a user starting use of the system, upon a user changing position (e.g. from seated to standing) one or more position of one or more body part is measured and, in some embodiments, recorded.

In some embodiments, gesture recognition uses recorded user body part position/s (and/or stored average position for the body part). For example, in an exemplary embodiment, when a user sits down, the height of one or more user foot is measured and/or recorded (e.g. in a memory). In some embodiments, a recorded foot height is used to determine whether a measured foot height and/or change in foot height relates to whether an operator has performed a "raise foot" gesture. In a motion control mode, for example, when a leg and/or foot is used to control motion of a portion of a surgical device (e.g. a device limb), a pre-recorded seated foot position is used to determine if a user's foot has moved and/or is used to quantify amount of movement of the user's foot.

Exemplary Control of Surgical Device Hand Tools

For example, as described above (e.g. in the section titled "Exemplary user interface/s"), a user controls a hand tool (also herein termed end effecter) using a user interface.

In some embodiments, a user controls a hand tool by moving portion/s of an input device, where the portions correspond to portion/s of the hand tool.

Alternatively, or additionally, in some embodiments, one or more hand tool (also herein termed "end effecter") is controlled by measured movement of user hand/s. In some embodiments, actuation (e.g. opening and closing) of a hand tool is controlled by relative position of a user's fingers and/or thumb. In some embodiments, closing of a tool is when two or more points and/or surfaces of the tool are brought closer together (e.g. flat surfaces of scissor blades are slid into contact and/or close proximity). In some embodiments, opening of a tool is when two or more points and/or surfaces of the tool are moved further apart.

In some embodiments, a user controls a position and/or movement of a hand tool, (e.g. by positioning the distal end of the radius using user arm movements, e.g. as described above) and simultaneously actuates the hand tool (e.g. controls opening and closing of a hand tool).

In an exemplary embodiment, a hand tool is closed when distal ends of a user thumb and finger/s are brought together and/or opened when distal ends of user thumb and finger/s are moved apart.

FIG. 64A is a simplified schematic of an open user hand, according to some embodiments of the invention. FIG. 64B is a simplified schematic of a portion of a device arm including a hand tool where the hand tool is in an open position, according to some embodiments of the invention.

FIG. 64C is a simplified schematic of a closed user hand, according to some embodiments of the invention. FIG. 64D is a simplified schematic of a portion of a device arm including a hand tool where the hand tool is in a closed position, according to some embodiments of the invention. In some embodiments, transition of the device hand tool from the open position illustrated in FIG. 64B to the position illustrated in FIG. 64D is achieved by movement of the user's hand from the position illustrated in FIG. 64A to the user hand position illustrated in FIG. 64B.

In some embodiments, rotation of a user hand is measured by detecting the relative position of distal ends of user thumb and/or one or more fingers. In some embodiments, the device hand rotation about a hand long axis rotation is controlled by measured mapped user hand rotation.

In some embodiments, a user performs a "short-cut" motion to initiate a movement or sequence of device arm and/or hand movements (e.g. a gesture), e.g. movements to tie a suture knot, repetitive rotation for screwing and/or drilling.

FIG. 65 is a series of photographic illustrations showing exemplary control of a device hand using measured user hand position, according to some embodiments of the invention. In some embodiments, position and/or movement of user fingertips and thumb is captured using motion capture technology, where captured positions are illustrated as white circles on image A.

In some embodiments, mapped measured orientation and/or movement of a tool avatar held by the user controls the orientation and/or movement of a device hand tool. In some embodiments, a tool avatar is a miniature model of the user hand tool. In some embodiments, a tool avatar includes portions which the user manipulates with the hand grasping the avatar, to actuate the tool avatar: For example, in some embodiments, a scissors hand tool is controlled by a user holding a pair of scissors.

For example, in some embodiments, a user holds a pair of scissors the motion and/or opening and closing of which is mimicked by a device scissors hand tool (e.g. using motion capture of one or more part of the scissors). In some embodiments, a hand tool avatar includes markers and/or is coated, at least partially, in reflective material, for example, to aid motion capture.

In some embodiments, the hand tool avatar is part of a device avatar, as described above.

Optionally, in some embodiments, the avatar provides force feedback of tissue to the user. For example, a scissors avatar resists opening and closing corresponding to the resistance of tissue being cut by device hand tool scissors. For example, a scissors or gripper performing electrosurgery.

In some embodiments, a tool avatar provides force feedback to a user, for example providing the user information as to device tool conditions. For example, the device includes one or more pressure sensor, the data from which is used to provide feedback, e.g. through one or more actuator, to a user. For example, in an exemplary embodiment, a scissors avatar provides resistance to a user opening and closing of the scissors reflecting the resistance of tissue that a corresponding device scissors hand tool is cutting.

General

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of providing feedback during surgery to a user controlling, via an input device, motor-actuated-movement of a surgical device limb, the surgical device limb comprising at least two spaced apart joints, said method comprising:
  introducing said surgical device limb into the body through an incision or a natural body orifice such that said at least two spaced apart joints are inside the body;
  controlling movement of said at least two spaced apart joints, when inside the body, via said input device;
  identifying one or more disallowed anatomical regions in the patient's body in which movement of said surgical device limb should be avoided;
  calculating a position of at least one of said two spaced apart joints with respect to said one or more disallowed anatomical regions based on at least one of: data obtained by position sensors, data obtained from captured images, and motor control signals;
  wherein said calculating is not based on contact with tissue of said one or more disallowed anatomical regions; and
  upon said user attempting movement of at least one of said joints of said surgical device limb to said one or more disallowed anatomical regions, providing feedback to said user via said input device, said feedback including at least one of force feedback, visual feedback, and audible feedback.

2. The method according to claim 1, wherein said identifying comprises collecting images by an imager inserted into the patient's body.

3. The method according to claim 1, wherein said identifying comprises producing an anatomical map according to CT and/or MRI scans of the patient.

4. The method according to claim 1, wherein said input device comprises input arms and wherein said feedback is in the form of force resistance in response to the user's manipulation of said input arms.

5. The method according to claim 4, wherein said avatar input arm is shaped to reflect a shape of said surgical device limb.

6. The method according to claim 1, comprising moving said surgical device limb within the patient's body to define edges of an allowed region, and saving indications of said allowed region to a system memory.

7. The method according to claim 1, comprising filtering movements of said surgical device limb according to said identified disallowed anatomical regions.

8. The method according to claim 7, wherein said filtering prevents accidental movement of said surgical device limb when an undesired movement of said input device is performed.

9. The method according to claim 1, further comprising measuring at least one of a position and orientation of said input device.

10. A surgical system comprising:
    a surgical device sized and shaped for insertion into a human body through an incision or a natural body orifice, said surgical device comprising at least one articulated limb, said limb comprising a plurality of sequentially coupled surgical device portions defining at least two spaced apart joints;
    an input device, comprising at least one articulated limb, said limb comprising a plurality of sequentially coupled input device portions; said input device configured to control motor-actuated movement of said at least two spaced apart joints of said surgical device when said at least two spaced apart joints are inside the body;
    a memory which stores one or more boundary lines defining one or more anatomical regions in which movement of each of said sequentially coupled surgical device portions is allowed; and
    a controller which limits movement of one or more portions of said surgical device articulated limb based on said one or more stored boundary lines and based on a position of at least one of said two spaced apart joints, said position calculated based on at least one of: data obtained by position sensors, data obtained from captured images, and motor control signals.

11. The system according to claim 10, further comprising an imager insertable into the patient body, said imager configured to collect images for identifying said one or more boundary lines.

12. The system according to claim 10, comprising at least one of an audio alarm and a display alarm for alarming a user that said surgical device or a portion thereof is being moved in proximity to said one or more boundary lines.

13. The system according to claim 10, wherein said position sensors comprises one or both of a pressure sensor and a motion sensor for indicating a position of said surgical device inside the patient's body.

14. The system according to claim 10, wherein said memory stores a map of disallowed anatomical regions.

15. The system according to claim 10, wherein said input device comprises one or more sensors for detecting user contact with said input device.

16. The system according to claim 15, wherein said surgical device comprises one or more locks for limiting movement of said surgical device upon said detecting loss of contact or insufficient contact.

17. The system according to claim 10, comprising a control mode in which movement of said surgical device, including angles of rotation and a degree of flexion of said at least two joints, is restricted to human freedom of movement of corresponding human arm segments.

18. The system according to claim 10, wherein said controller is configured to filter signals received from said input device.

19. The system according to claim 18, wherein said controller is configured to filter signals to remove one or more of: large user movements, sudden movements of the user, and tremors of the user.

20. The system according to claim 18, wherein said controller is configured to filter signals to remove movements into or adjacent disallowed anatomical regions.

21. The system according to claim 10, wherein a maximal diameter of said surgical device limb is 10 mm.

22. The system according to claim 10, including a motor unit for actuating movement of said articulated surgical device limb, and wherein said position sensors are configured within said motor unit.

* * * * *